(12) United States Patent
Bissantz et al.

(10) Patent No.: US 9,656,971 B2
(45) Date of Patent: May 23, 2017

(54) COMT INHIBITORS

(71) Applicant: Hoffmann-La Roche Inc., Little Falls, NJ (US)

(72) Inventors: Caterina Bissantz, Village-Neuf (FR); René Bonnafous, Rixheim (FR); Bernd Buettelmann, Schopfheim (DE); Roland Jakob-Roetne, Inzlingen (DE); Christian Lerner, Binningen (CH); Markus Rudolph, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/752,177

(22) Filed: Jun. 26, 2015

(65) Prior Publication Data

US 2016/0002177 A1 Jan. 7, 2016

Related U.S. Application Data

(63) Continuation of application No. PCT/EP2013/077885, filed on Dec. 23, 2013.

(30) Foreign Application Priority Data

Dec. 27, 2012 (EP) .................... 12199491

(51) Int. Cl.
| | | |
|---|---|---|
| C07D 239/88 | (2006.01) | |
| C07D 471/04 | (2006.01) | |
| C07D 417/10 | (2006.01) | |
| C07D 417/04 | (2006.01) | |
| C07D 413/04 | (2006.01) | |
| C07D 409/04 | (2006.01) | |
| C07D 409/06 | (2006.01) | |
| C07D 409/14 | (2006.01) | |
| C07D 405/04 | (2006.01) | |
| C07D 403/04 | (2006.01) | |
| C07D 401/04 | (2006.01) | |
| C07D 401/10 | (2006.01) | |
| C07D 401/12 | (2006.01) | |
| C07D 403/10 | (2006.01) | |
| C07D 401/06 | (2006.01) | |

(52) U.S. Cl.
CPC ......... *C07D 239/88* (2013.01); *C07D 401/04* (2013.01); *C07D 401/06* (2013.01); *C07D 401/10* (2013.01); *C07D 401/12* (2013.01); *C07D 403/04* (2013.01); *C07D 403/10* (2013.01); *C07D 405/04* (2013.01); *C07D 409/04* (2013.01); *C07D 409/06* (2013.01); *C07D 409/14* (2013.01); *C07D 413/04* (2013.01); *C07D 417/04* (2013.01); *C07D 417/10* (2013.01); *C07D 471/04* (2013.01)

(58) Field of Classification Search
CPC .. C07D 239/88; C07D 401/04; C07D 401/06; C07D 401/10; C07D 401/12; C07D 403/04; C07D 403/10; C07D 405/04; C07D 409/04; C07D 409/06; C07D 409/14; C07D 413/04; C07D 417/04; C07D 417/10; C07D 471/04
See application file for complete search history.

(56) References Cited

FOREIGN PATENT DOCUMENTS

| WO | WO 2004/031161 A1 | 4/2004 |
|---|---|---|
| WO | 2005/058228 A2 | 6/2005 |
| WO | WO 2007/147217 A1 | 12/2007 |
| WO | WO 2010/071944 A1 | 7/2010 |
| WO | 2011/109254 A1 | 9/2011 |
| WO | WO 2011/109261 A1 | 9/2011 |
| WO | WO 2011/109267 A1 | 9/2011 |

OTHER PUBLICATIONS

Dempcy et al., Biochemistry, vol. 30, No. 34, 1991 8480-8487.*
International Search Report issued in International Application No. PCT/EP2013/077885, dated Mar. 18, 2014, in 2 pages.

* cited by examiner

*Primary Examiner* — Rebecca Anderson
(74) *Attorney, Agent, or Firm* — Genentech, Inc.; Mark D. Kafka

(57) ABSTRACT

The present invention relates to compounds of formula

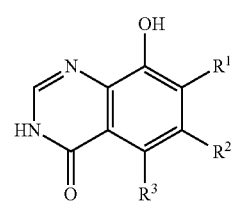

I wherein the substituents are described in claim 1 and to the pharmaceutically acceptable salts thereof.
These compounds inhibit the enzyme catechol-O-methyltransferase (COMT). The compounds may be used for the treatment of Parkinson's disease, depression, cognitive impairment and motor symptoms, resistant depression, cognitive impairment, mood and negative symptoms of schizophrenia.

3 Claims, No Drawings

COMT INHIBITORS

CROSS-REFERENCE TO RELATED APPLICATIONS

This application is a continuation application of International Application No. PCT/EP2013/077885, filed on Dec. 23, 2013, which claims priority to European Patent Application No. 12199491.7, filed on Dec. 27, 2012.

The present invention relates to compounds of formula

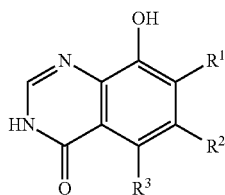

I wherein
$R^1$ is hydrogen, methyl, Br, F or Cl;
$R^2$ is hydrogen, lower alkyl, Br, I, $C_{3-6}$-cycloalkyl, C(O)O-lower alkyl, C(O)NH-lower alkyl substituted by halogen, C(O)(morpholine) or is
3,4-dihydro-naphthalen-2-yl, optionally substituted by lower alkyl
1,2,3,4-tetrahydro-naphthalen-2-yl,
2,3-dihydro-benzofuran-6-yl,
1-methyl-2,3-dihydro-1H-indolin-5-yl,
1-methylindolin-5-yl,
tetrahydro-pyran-4-yl,
3,6-dihydro-2H-pyran-4-yl,
2-isopropyl-1,2,3-tetrahydro-isoquinolin-5-yl,
2,3-dihydro-benzo[1,4]dioxin-6-yl,
benzo-[1,3]-dioxol-5-yl
1,2,3,4-tetrahydro-isoquinolin-7-yl, optionally substituted by lower alkyl,
cyclohexenyl,
morpholinyl, 4-methyl-piperazinyl,
naphalen-1-yl, naphtalen-2-yl,
or is $(CHR)_n$-phenyl, optionally substituted by one to five substituents $R^4$,
wherein
$R^4$ is F, Cl, CN, $CH_2$—CN, lower alkyl, hydroxy, lower alkyl substituted by hydroxy, lower alkoxy, $(CH_2)_{1,2}$-lower alkoxy, S-lower alkyl, $(CH_2)_{1,2}$—S-lower alkyl, —$CH_2)_{1,2}$—$S(O)_2$-lower alkyl, —$S(O)_2$-lower alkyl, —$S(O)_2$-di-lower alkyl amino, —$S(O)_2$-piperidinyl, lower alkyl substituted by halogen, —N═N-phenyl, di-lower alkyl amino, $(CH_2)_{1,2}$-di-lower alkyl amino, $(CH_2)_2$—NH-lower alkyl, NHC(O)-lower alkyl, lower alkoxy substituted by halogen, $CH(CH_3)C(O)O$-lower alkyl, O-phenyl, O-benzyl, phenyl optionally substituted by $CF_3$, $SF_5$, benzyl, CO)-lower alkyl, CO)-phenyl, C(O)-morpholinyl, C(O)-4-methyl-piperazinyl, C(O)-di-oxo-thiomorpholinyl, C(O)-piperidinyl optionally substituted by F, CO)—NH—$(CH_2)_2$-morpholinyl, C(O)—NR—$(CH_2)_2$—$NR_2$, C(O)—N-di-lower alkyl, $CH_2$—O—$(CH_2)_2$-4-methyl-piperazinyl, $CH_2$—O—$(CH_2)_2$— di-alkyl amino, $CH_2$—O—$(CH_2)_2$— pyrrolidinyl, $CH_2$—O—$(CH_2)_2$-morpholinyl, $CH_2$—O—$(CH_2)_2$-piperidinyl optionally substituted by lower alkyl substituted by halogen or by lower alkyl, $(CH_2)_{3,4}$-pyrrolidinyl, $(CH_2)_{2,3}$-di-lower alkyl amino, morpholinyl, $CH_2$-morpholinyl, $CH_2$-piperazin substituted by lower alkyl, —$S(O)_2$— piperazin substituted by lower alkyl, $CH_2$—O—C(O)— piperazin substituted by lower alkyl, pyrazolyl or $(CH_2)_{1,2}$-lower alkoxy;
R is hydrogen, lower alkyl or hydroxyl;
n is 0, 1, 2 or 3;
or $R^2$ is
C(O)-phenyl, optionally substituted by lower alkyl;
or is —O-phenyl optionally substituted by F;
or is CH═CH-phenyl, optionally substituted by lower alkyl;
or is C≡C-phenyl;
or $R^2$ is
is heteroaryl, selected from the group consisting of pyrazolyl, thiazolyl, pyridinyl, pyrimidinyl, imidazolyl, isoxazolyl, isothiazolyl, thiophenyl, 1-thia-3,4-diazolyl, imidazo[1,2-a]pyridinyl, indazolyl, quinolinyl or isoquinolinyl, and which groups are optionally substituted by $R^5$,
wherein
$R^5$ is halogen, lower alkyl, lower alkoxy, lower alkyl substituted by halogen, lower alkoxy substituted by halogen, hydroxy, $(CH_2)_{1,2}$-lower alkoxy, $CH_2$-di-lower alkyl amino, di-lower alkyl amino, morpholinyl, piperazinyl, pyrrolidin-1-yl, C(O)-piperidinyl, C(O)-4-methyl-piperazinyl, phenyl optionally substituted by halogen, pyridinyl, $S(O)_2N(CH_3)_2$, C(O)O-lower alkyl, NHC(O)-lower alkyl,
or is C(O)-heteroaryl, selected from pyridinyl or thiophenyl, wherein the heteroaryl groups are optionally substituted by lower alkyl,
n is 0, 1, 2 or 3;
$R^3$ is hydrogen, methyl, Br, F, Cl, $CF_3$, nitro, amino, cyano, NHC(O)-phenyl, or is 1-methyl-1,2,3,6-tetrahydropyridinyl, or is pyridinyl, optionally substituted by methyl or morpholinyl, or is phenyl optionally substituted by methyl, $SO_2CH_3$, $CF_3$, CN, F or C(O)Ndi-lower alkyl;
with the proviso that $R^1$ and $R^3$ are not simultaneously chloro and $R^1$, $R^2$ and $R^3$ are not simultaneously hydrogen, and to the pharmaceutically acceptable salts thereof.

Similar compounds have been described in WO2007/147217, which are used for the treatment of glioma brain tumors.

WO 2004/031161 and WO 2007/118276 disclose 8-hydroxy-4(3H)-quinazolinones for the treatment of neurological conditions, for example Alzheimer's disease and Parkinson's disease and for the treatment of age-related macular degeneration. The specific compounds of the present invention are not disclosed.

The compounds of formula I possess valuable pharmacological properties. In particular, these compounds inhibit the enzyme catechol-O-methyltransferase (COMT), a magnesium-dependent enzyme which catalyzes the transfer of the methyl group of S-adenosylmethionine to a catechol substrate, whereby the corresponding methyl ethers are formed. Suitable substrates which can be O-methylated by COMT and which can thus be deactivated are, for example, extraneuronal catecholamines and exogeneously-administered therapeutically active substances having a catechol structure.

The compounds of formula I above can accordingly be used in the prevention or control of illnesses in which a deactivation of extraneuronal catecholamines by COMT plays a role, for example, in the prevention or control of depressions. In this case the compounds of formula I above can be used as individual compounds or in combination with other therapeutically active substances which favorably influence the course of the illness. The compounds of formula I can, however, also be used as co-medications with other therapeutically active substances. In addition the compounds of formula I are COMT inhibitors that lack the potential toxicity associated with nitrocatechol containing compounds (K. S. Smith, P. L. Smith, T. N. Heady, J. M. Trugman, W. D. Harman, T. L. Macdonald, Chem. Res. Toxicol. 2003, 16, 123-128; M. d'Ischia, C. Costantini, Bioorganic & Medicinal Chemistry 1995, 3, 923-927).

The compounds of formula I can also be used for the control of illnesses with therapeutically active substances which have a catechol structure. The treatment of Parkinson's disease and of parkinsonism with L-dopa, a therapeutically active substance having the catechol structure, can be mentioned as an example. In such cases the compounds of formula I can be used in the form of a co-medication or as combination preparations.

Numerous documents describe the current knowledge on COMT-inhibition, for example—in the field of depression Fava, M., J. F. Rosenbaum, A. R. Kolsky, J. E. Alpert, A. A. Nierenberg, M. Spillmann, C. Moore, P. Renshaw, T. Bottiglieri, G. Moroz, and G. Magni. Open study of the catechol-O-methyltransferase inhibitor tolcapone in major depressive disorder. J Clin Psychopharmacol 1999, 19, 329.

—in the field of schizophrenia:

D. R. Weinberger, M. F. Egan, A. Bertolino, J. H. Callicott, V. S. Mattay, B. K. Lipska, K. F. Berman, T. E. Goldberg, Prefrontal neurons and the genetics of schizophrenia, Biol. Psychiatry 2001, 50, 825;

M. F. Egan, T. E. Goldberg, B. S. Kolachana, J. H. Callicott, C. M. Mazzanti, R. E. Straub, D. Goldman, D. R. Weinberger, Effect of COMT Val108/158 Met genotype on frontal lobe function and risk for schizophrenia, Proc. Natl. Acad. Sci. USA 2001, 98, 6917;

P. Bitsios, P. Roussos, Tolcapone, COMT polymorphisms and pharmacogenomic treatment of schizophrenia, Pharmacogenomics 2011, 12, 559.

—in the field of Parkinson's disease

Two COMT inhibitors are marketed for improvement of levodopa therapy, Tasmar/Tolcapone, M. C. Kurth, C. H. Adler, M. St. Hilaire, C. Singer, C. Waters, P. LeWitt, D. A. Chernik, E. E. Dorflinger, K. Yoo, Tolcapone improves motor function and reduces levodopa requirement in patients with Parkinson's disease experiencing motor fluctuations: A multicenter, double-blind, randomized, placebo-controlled trial, Neurology, 1997, 48, 81;

O. Gershanik, M. Emre, G. Bernhard, D. Sauer, Efficacy and safety of levodopa with entacapone in Parkinson's disease patients suboptimally controlled with levodopa alone, in daily clinical practice: an international, multicentre, open-label study, Progress in Neuro-Psychopharmacology & Biological Psychiatry, 2003, 27, 963;

M. Gasparini, E. Fabrizio, V. Bonifati, G. Meco, Cognitive improvement during Tolcapone treatment in Parkinson's disease, J. Neural. Transm. 1997, 104, 887.

—in the field of cognition improvement

H. M. Lachman, D. F. Papolos, T. Saito, Y. M. Yu, C. L. Szumlanski, R. M. Weinshilboum, Human catechol-O-methyltransferase pharmacogenetics: description of a functional polymorphism and its potential application to neuropsychiatric disorders, Pharmacogenetics 1996, 6, 243;

A. K. Malhotra, L. J. Kestler, C. Mazzanti, J. A. Bates, T. Goldberg, D. Goldman, A functional polymorphism in the COMT gene and performance on a test of prefrontal cognition, Am. J. Psychiatry 2002, 159, 652;

J. Savitz, M. Solms, R. Ramesar, The molecular genetics of cognition: dopamine, COMT and BDNF, Genes, Brain and Behavior 2006, 5, 311.

The COMT inhibitors tolcapone and entacapone are clinically approved for Parkinson's disease (PD) with the classical L-Dopa substitution therapy. They inhibit peripherally O-methylation and deactivation of the administered L-Dopa. Tolcapone has a brain/plasma ratio of ~0.01 and has been used as a tool compound to study the central effects of COMT inhibition in clinical trials and in animal experiments. Tolcapone has been shown to have anti-depressant activity in the rat anhedonia model and in an open clinical trial in 21 patients with major depressive disorder (MDD) treated for 8 weeks at 400 mg b.i.d. Although this indicates that COMT inhibition may be a potential treatment for MDD, no follow up placebo-controlled studies were performed with tolcapone because of the safety concerns regarding liver toxicity. It is interesting to note that during a safety study with tolcapone in PD patients there was a reduction, although not significant, in the incidence of depression compared to placebo. A number of non-motor symptoms in PD, such as depression, are now recognised as being clinically important and treatment of these symptoms would greatly improve the quality of life for patients. So far there have been no trials with COMT inhibitors in PD using an index of depression as an outcome measure. A deficiency in dopaminergic transmission may play a role in the depressive state of MDD and PD. Moreover, the reduced mood and negative symptoms which are part of the symptomatology of schizophrenia may be related to hypoactivity in the prefrontal cortex. COMT inhibition in the brain increases dopamine concentrations selectively at the synapses in the prefrontal cortex because of the very low expression of high affinity dopamine transporters in this area, which otherwise control dopamine levels. COMT inhibition should therefore increase dopaminergic neurotransmission in the prefrontal cortex without affecting normal (or exaggerated) dopamine activity in other brain regions. Moreover, COMT in the brain is a unique target for the treatment of disorders associated with dysfunction of the prefrontal cortex, such as cognitive impairment in PD, cognitive impairment associated with schizophrenia, attention deficit hyperactivity disorder (ADHD), frontotemporal dementia, impulsivity. Since both tolcapone and entacapone have their limitations due to pharmacokinetics, efficacy, safety, there is a need for new COMT inhibitors with improvements in these parameters.

The current project aims to target COMT inhibition in the brain in order to treat:

(1). Parkinson's disease: depression, cognitive impairment and motor symptoms;

(2). Treatment-resistant depression (TRD);

(3). Cognitive impairment, mood and negative symptoms of schizophrenia.

A centrally acting COMT inhibitor would be first in class. COMT inhibition is safe since no target related toxicities have been evident from the broad use of tolcapone and entacapone.

Therefore, the object of the present invention was to identify compounds that are COMT inhibitors. It has been found that the compounds of formula I are active in this area and they may therefore be used for the treatment of Parkinson's disease, depression, cognitive impairment and motor symptoms, resistant depression, cognitive impairment, mood and negative symptoms of schizophrenia.

The present invention relates to specific novel compounds of formula I, to the processes for their production, as well as to the use of compound of formula I in the treatment or prevention of disorders, relating to Parkinson's disease, depression, cognitive impairment and motor symptoms, resistant depression, cognitive impairment, mood and negative symptoms of schizophrenia, and to pharmaceutical compositions containing the novel compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "lower alkyl substituted by halogen" denotes a lower alkyl group as defined above, wherein at least one hydrogen atom is replaced by a halogen atom. The preferred group is $CF_3$.

The term "lower alkoxy substituted by halogen" denotes a lower alkoxy group as defined above, wherein at least one hydrogen atom is replaced by a halogen atom. The preferred group is $OCF_3$.

The term "cycloalkyl" denotes a cyclic alkyl group, containing 3 to 6 carbon ring atoms.

The term "halogen" denotes chlorine, bromine, fluorine or iodine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula I, wherein $R^1$ and $R^3$ are hydrogen and $R^2$ is $(CHR)_n$-phenyl, optionally substituted by one to five substituents $R^4$, or is C(O)-phenyl, optionally substituted by lower alkyl, or is O-phenyl optionally substituted by F, or is CH=CH-phenyl, optionally substituted by lower alkyl, or is C≡C-phenyl, for example the following compounds 6-Benzyl-8-hydroxyquinazolin-4(3H)-one
6-(2-Fluorobenzyl)-8-hydroxyquinazolin-4(3H)-one
8-Hydroxy-6-(3-methylbenzyl)quinazolin-4(3H)-one
8-Hydroxy-6-(2-methoxybenzyl)quinazolin-4(3H)-one
8-Hydroxy-6-(3-methoxybenzyl)quinazolin-4(3H)-one
8-Hydroxy-6-phenethylquinazolin-4(3H)-one
(E)-8-Hydroxy-6-styrylquinazolin-4(3H)-one
(E)-8-Hydroxy-6-(4-methylstyryl)quinazolin-4(3H)-one
8-Hydroxy-6-isobutylquinazolin-4(3H)-one
8-Hydroxy-6-(phenylethynyl)quinazolin-4(3H)-one
8-Hydroxy-6-(3-isopropoxyphenyl)quinazolin-4(3H)-one
8-Hydroxy-6-(2-methoxy-5-(trifluoromethyl)phenyl)quinazolin-4(3H)-one
4-Chloro-3-(8-hydroxy-4-oxo-3,4-dihydroquinazolin-6-yl)benzonitrile
8-hydroxy-6-(3,4,5-trifluorophenyl)quinazolin-4(3H)-one
(E)-6-(5-(Dimethylamino)-2-(phenyldiazenyl)phenyl)-8-hydroxyquinazolin-4(3H)-one
8-Hydroxy-6-(4-methyl-4'-(trifluoromethyl)biphenyl-2-yl)quinazolin-4(3H)-one
8-Hydroxy-6-(2,3,4-trifluoro-phenyl)-3H-quinazolin-4-one
(rac.) Methyl 2-(2-(8-hydroxy-4-oxo-3,4-dihydroquinazolin-6-yl)biphenyl-4-yl)propanoate
8-Hydroxy-6-(perfluorophenyl)quinazolin-4(3H)-one
6-(5-tert-Butyl-2-methoxyphenyl)-8-hydroxyquinazolin-4(3H)-one
8-Hydroxy-6-(2-methoxy-5-methylphenyl)quinazolin-4(3H)-one
6-(2,5-Dichlorophenyl)-8-hydroxyquinazolin-4(3H)-one
8-Hydroxy-6-(3-(morpholinomethyl)phenyl)quinazolin-4(3H)-one
6-(2-Chloro-5-methanesulfonyl-phenyl)-8-hydroxy-3H-quinazolin-4-one
8-Hydroxy-6-(hydroxy(p-tolyl)methyl)quinazolin-4(3H)-one
8-Hydroxy-6-(4-methylbenzoyl)quinazolin-4(3H)-one
8-Hydroxy-6-(hydroxy(phenyl)methyl)quinazolin-4(3H)-one
6-Benzoyl-8-hydroxy-3H-quinazolin-4-one
8-Hydroxy-6-(3-(methoxymethyl)phenyl)quinazolin-4(3H)-one
6-(2-Benzylphenyl)-8-hydroxyquinazolin-4(3H)-one
6-(2-Benzoylphenyl)-8-hydroxyquinazolin-4(3H)-one
6-(4-Pentafluorosulfanylphenyl)-8-hydroxyquinazolin-4(3H)-one
N-(2-(Diisopropylamino)ethyl)-4-(8-hydroxy-4-oxo-3,4-dihydroquinazolin-6-yl)-N-isopropyl-3-(methoxymethyl)benzamide 2,2,2-trifluoroacetate
8-Hydroxy-6-(4-((4-isopropylpiperazin-1-yl)methyl)-2-(methoxymethyl)phenyl)quinazolin-4(3H)-one tetrakis(2,2,2-trifluoroacetate)
4-(8-Hydroxy-4-oxo-3,4-dihydroquinazolin-6-yl)-3-(methoxymethyl)benzyl 4-isopropylpiperazine-1-carboxylate bis(2,2,2-trifluoroacetate)
8-Hydroxy-6-[3-(4-methyl-piperazine-1-sulfonyl)-phenyl]-3H!-quinazolin-4-one;
6-(2-Acetylphenyl)-8-hydroxyquinazolin-4(3H)-one
8-Hydroxy-6-(2-(2-hydroxypropan-2-yl)phenyl)quinazolin-4(3H)-one
8-Hydroxy-6-(2-(methylsulfanylmethyl-phenyl)-3H-quinazolin-4-one 2,2,2-trifluoroacetate
8-Hydroxy-6-(2-(methylsulfonylmethyl)phenyl)quinazolin-4(3H)-one 2,2,2-trifluoroacetate
8-Hydroxy-6-(2-(2-(methylsulfonyl)ethyl)phenyl)quinazolin-4(3H)-one 2,2,2-trifluoroacetate
8-Hydroxy-6-(2-((2-(1-(2,2,2-trifluoroethyl)piperidin-4-yl)ethoxy)methyl)phenyl)quinazolin-4(3H)-one 2,2,2-trifluoroacetate
8-Hydroxy-6-(2-((2-(4-(2,2,2-trifluoroethyl)piperazin-1-yl)ethoxy)methyl)phenyl)quinazolin-4(3H)-one 2,2,2-trifluoroacetate
6-(4-Fluorophenyl)-8-hydroxyquinazolin-4(3H)-one
6-(4-Fluoro-2-methylphenyl)-8-hydroxyquinazolin-4(3H)-one
8-Hydroxy-6-phenylquinazolin-4(3H)-one
8-Hydroxy-6-(4-hydroxyphenyl)quinazolin-4(3H)-one
8-Hydroxy-6-p-tolylquinazolin-4(3H)-one
6-(4-Chlorophenyl)-8-hydroxyquinazolin-4(3H)-one
6-(2-Chlorophenyl)-8-hydroxyquinazolin-4(3H)-one
6-(2,4-Difluorophenyl)-8-hydroxyquinazolin-4(3H)-one
8-Hydroxy-6-(4-methoxy-phenyl)-3H-quinazolin-4-one
8-Hydroxy-6-(4-pyrazol-1-yl-phenyl)-3H-quinazolin-4-one
8-Hydroxy-6-(4-morpholin-4-yl-phenyl)-3H-quinazolin-4-one
8-Hydroxy-6-(2-trifluoromethoxy-phenyl)-3H-quinazolin-4-one
8-Hydroxy-6-(3-morpholinophenyl)quinazolin-4(3H)-one
6-(4-Dimethylamino-phenyl)-8-hydroxy-3H-quinazolin-4-one
6-(3-Dimethylamino-phenyl)-8-hydroxy-3H-quinazolin-4-one
6-(3-Chloro-phenyl)-8-hydroxy-3H-quinazolin-4-one 6-(2-((Dimethylamino)methyl)phenyl)-8-hydroxyquinazolin-4(3H)-one
8-Hydroxy-6-(3-(methylsulfonyl)phenyl)quinazolin-4(3H)-one
6-(2-Fluoro-4-(methylsulfonyl)phenyl)-8-hydroxyquinazolin-4(3H)-one
N-(2-(8-Hydroxy-4-oxo-3,4-dihydroquinazolin-6-yl)phenyl)acetamide
8-Hydroxy-6-(2-methoxyphenyl)quinazolin-4(3H)-one
4-(8-Hydroxy-4-oxo-3,4-dihydroquinazolin-6-yl)-N-(2-morpholinoethyl)benzamide
N-(2-(Dimethylamino)ethyl)-4-(8-hydroxy-4-oxo-3,4-dihydroquinazolin-6-yl)benzamide
8-Hydroxy-6-(3-(morpholine-4-carbonyl)phenyl)quinazolin-4(3H)-one
6-(4-Fluorophenoxy)-8-hydroxyquinazolin-4(3H)-one
8-Hydroxy-6-[3-(4-methyl-piperazine-1-carbonyl)-phenyl]-3H-quinazolin-4-one
6-[3-(1,1-Dioxo-1λ$^6$-thiomorpholine-4-carbonyl)-phenyl]-8-hydroxy-3H-quinazolin-4-one
8-Hydroxy-6-[2-(4-methyl-piperazine-1-carbonyl)-phenyl]-3H-quinazolin-4-one
6-[2-(1,1-Dioxo-1λ$^6$-thiomorpholine-4-carbonyl)-phenyl]-8-hydroxy-3H-quinazolin-4-one
6-[3-(4,4-Difluoro-piperidine-1-carbonyl)-phenyl]-8-hydroxy-3H-quinazolin-4-one
6-[4-(4,4-Difluoro-piperidine-1-carbonyl)-phenyl]-8-hydroxy-3H-quinazolin-4-one
2-(8-Hydroxy-4-oxo-3,4-dihydroquinazolin-6-yl)benzonitrile
2-(2-(8-Hydroxy-4-oxo-3,4-dihydroquinazolin-6-yl)phenyl)acetonitrile
6-(2-(Dimethylamino)phenyl)-8-hydroxyquinazolin-4(3H)-one
8-Hydroxy-6-o-tolylquinazolin-4(3H)-one
6-(2-Ethoxy-4-fluorophenyl)-8-hydroxyquinazolin-4(3H)-one
8-Hydroxy-6-(2-(methylsulfonyl)phenyl)quinazolin-4(3H)-one
6-(5-Fluoro-2-methylphenyl)-8-hydroxyquinazolin-4(3H)-one
6-(Biphenyl-2-yl)-8-hydroxyquinazolin-4(3H)-one
6-(4-Chloro-2-ethoxyphenyl)-8-hydroxyquinazolin-4(3H)-one
6-(2-Ethylphenyl)-8-hydroxyquinazolin-4(3H)-one
6-(2-((Diisopropylamino)methyl)phenyl)-8-hydroxyquinazolin-4(3H)-one
8-Hydroxy-6-(2-(methoxymethyl)phenyl)quinazolin-4(3H)-one
8-Hydroxy-6-(2-(trifluoromethyl)phenyl)quinazolin-4(3H)-one
8-Hydroxy-6-(2-phenoxyphenyl)quinazolin-4(3H)-one
8-Hydroxy-6-(2-(methylthio)phenyl)quinazolin-4(3H)-one
8-Hydroxy-6-(2-morpholinophenyl)quinazolin-4(3H)-one
6-(2-Ethoxyphenyl)-8-hydroxyquinazolin-4(3H)-one
2-(8-Hydroxy-4-oxo-3,4-dihydroquinazolin-6-yl)-N,N-diisopropylbenzamide
6-(2-(Benzyloxy)phenyl)-8-hydroxyquinazolin-4(3H)-one
6-(2-Butoxyphenyl)-8-hydroxyquinazolin-4(3H)-one
6-(3-Dimethylaminomethyl-phenyl)-8-hydroxy-3H-quinazolin-4-one
8-Hydroxy-6-[2-methoxymethyl-4-(4-methyl-piperazine-1-carbonyl)-phenyl]-3H-quinazolin-4-one
8-Hydroxy-6-(2-(2-(methylamino)ethyl)phenyl)quinazolin-4(3H)-one
8-Hydroxy-6-[2-methoxymethyl-5-(4-methyl-piperazine-1-carbonyl)-phenyl]-3H-quinazolin-4-one;
6-(2-(2-(Dimethylamino)ethyl)phenyl)-8-hydroxyquinazolin-4(3H)-one
8-Hydroxy-6-[2-methoxymethyl-3-(4-methyl-piperazine-1-carbonyl)-phenyl]-3H-quinazolin-4-one
8-Hydroxy-6-[2-(2-morpholin-4-yl-ethoxymethyl)-phenyl]-3H-quinazolin-4-one
8-Hydroxy-6-[2-(2-morpholin-4-yl-ethoxymethyl)-phenyl]-3H-quinazolin-4-one;
8-Hydroxy-6-(2-((2-(pyrrolidin-1-yl)ethoxy)methyl)phenyl)quinazolin-4(3H)-one
8-Hydroxy-6-[2-(2-pyrrolidin-1-yl-ethoxymethyl)-phenyl]-3H-quinazolin-4-one;
8-Hydroxy-6-(2-((2-(4-methylpiperazin-1-yl)ethoxy)methyl)phenyl)quinazolin-4(3H)-one
6-(2-(2-(Dimethylamino)ethoxy)methyl)phenyl)-8-hydroxyquinazolin-4(3H)-one
8-Hydroxy-6-(2-(3-(pyrrolidin-1-yl)propyl)phenyl)quinazolin-4(3H)-one
6-(2-(3-(Dimethylamino)propyl)phenyl)-8-hydroxyquinazolin-4(3H)-one
6-(3-(2-(Dimethylamino)ethyl)phenyl)-8-hydroxyquinazolin-4(3H)-one
8-Hydroxy-6-(2-(4-(pyrrolidin-1-yl)butyl)phenyl)quinazolin-4(3H)-one
8-Hydroxy-6-(2-(propylsulfonyl)phenyl)quinazolin-4(3H)-one
2-(8-Hydroxy-4-oxo-3,4-dihydro-quinazolin-6-yl)-N,N-dimethyl-benzenesulfonamide
8-Hydroxy-6-[2-(piperidine-1-sulfonyl)-phenyl]-3H-quinazolin-4-one or
8-Hydroxy-6-(2-((2-(1-methylpiperidin-4-yl)ethoxy)methyl)phenyl)quinazolin-4(3H)-one.

One further embodiment of the invention are compounds of formula I, wherein R$^2$ is hydrogen, lower alkyl, Br, I, C$_{3-6}$-cycloalkyl, C(O)O-lower alkyl, C(O)NH-lower alkyl substituted by halogen, 3,4-dihydro-naphthalen-2-yl, optionally substituted by lower alkyl, 1,2,3,4-tetrahydronaphthalen-2-yl, 2,3-dihydro-benzofuran-6-yl, 1-methyl-2,3-dihydro-1H-indolin-5-yl, 1-methylindolin-5-yl, tetrahydro-pyran-4-yl, 3,6-dihydro-2H-pyran-4-yl, 2-isopropyl-1,2,3-tetrahydro-isoquinolin-5-yl, 2,3-dihydro-benzo[1,4]dioxin-6-yl, benzo-[1,3]-dioxol-5-yl or 1,2,3,4-tetrahydro-isoquinolin-7-yl, optionally substituted by lower alkyl, cyclohexenyl, morpholinyl, 4-methyl-piperazinyl, naphthalene-1-yl or naphthalene-2-yl,
for example the following compounds
5-Bromo-8-hydroxyquinazolin-4(3H)-one
Methyl 8-hydroxy-4-oxo-3,4-dihydroquinazoline-6-carboxylate
8-Hydroxy-6-(morpholine-4-carbonyl)quinazolin-4(3H)-one
8-Hydroxy-4-oxo-N-(2,2,3,3,3-pentafluoropropyl)-3,4-dihydroquinazoline-6-carboxamide
8-Hydroxy-4-oxo-N-(2,2,2-trifluoroethyl)-3,4-dihydroquinazoline-6-carboxamide
Ethyl 8-hydroxy-4-oxo-3,4-dihydroquinazoline-6-carboxylate
6-(3,4-Dihydro-naphthalen-2-yl)-8-hydroxy-3H-quinazolin-4-one
(rac.) 8-Hydroxy-6-(1,2,3,4-tetrahydronaphthalen-2-yl)quinazolin-4(3H)-one
6-Ethyl-8-hydroxyquinazolin-4(3H)-one 2,2,2-trifluoroacetate
8-Hydroxy-6-isopropylquinazolin-4(3H)-one
8-Hydroxy-6-isobutylquinazolin-4(3H)-one
6-Cyclopentyl-8-hydroxyquinazolin-4(3H)-one 6-(5,8-dimethyl-3,4-dihydro-naphthalen-2-yl)-8-hydroxy-3H-quinazolin-4-one
6-(2,3-Dihydrobenzofuran-6-yl)-8-hydroxyquinazolin-4(3H)-one
8-Hydroxy-6-(1-methylindolin-5-yl)quinazolin-4(3H)-one
6-Bromo-8-hydroxy-5-(trifluoromethyl)quinazolin-4(3H)-one
8-Hydroxy-5-(trifluoromethyl)quinazolin-4(3H)-one
6-Bromo-8-hydroxy-5-nitro-3H-quinazolin-4-one
8-Hydroxy-6-(tetrahydro-2H-pyran-4-yl)quinazolin-4(3H)-one 2,2,2-trifluoroacetate
6-(3,6-Dihydro-2H-pyran-4-yl)-8-hydroxyquinazolin-4(3H)-one
6-Bromo-8-hydroxy-5-(2-methylpyridin-4-yl)quinazolin-4(3H)-one
8-Hydroxy-6-(2-isopropyl-1,2,3,4-tetrahydroisoquinolin-5-yl)quinazolin-4(3H)-one 2,2,2-trifluoroacetate
6-Bromo-5-chloro-8-hydroxyquinazolin-4(3H)-one
7-Fluoro-5-(4-fluorophenyl)-8-hydroxyquinazolin-4(3H)-one
6-Bromo-8-hydroxyquinazolin-4(3H)-one
6-Bromo-8-hydroxy-7-methylquinazolin-4(3H)-one
8-Hydroxy-6-iodo-3H-quinazolin-4-one
6-Chloro-8-hydroxyquinazolin-4(3H)-one
8-Hydroxy-5-methylquinazolin-4(3H)-one
5-Chloro-8-hydroxyquinazolin-4(3H)-one
5-(4-Fluorophenyl)-8-hydroxyquinazolin-4(3H)-one
8-Hydroxy-6-(naphthalen-2-yl)quinazolin-4(3H)-one
8-Hydroxy-6-(naphthalen-1-yl)quinazolin-4(3H)-one
8-Hydroxy-6-(1,2,3,4-tetrahydroisoquinolin-7-yl)quinazolin-4(3H)-one
8-Hydroxy-6-(3-(morpholine-4-carbonyl)phenyl)quinazolin-4(3H)-one
6-(2,3-Dihydrobenzo[b][1,4]dioxin-6-yl)-8-hydroxyquinazolin-4(3H)-one
6-(Benzo[d][1,3]dioxol-5-yl)-8-hydroxyquinazolin-4(3H)-one
6-Cyclohexenyl-8-hydroxyquinazolin-4(3H)-one
8-Hydroxy-6-morpholinoquinazolin-4(3H)-one
8-Hydroxy-6-(4-methyl-piperazin-1-yl)-3H-quinazolin-4-one
6-Bromo-5-fluoro-8-hydroxyquinazolin-4(3H)-one
5-Fluoro-8-hydroxyquinazolin-4(3H)-one
6-Bromo-7-fluoro-5-(4-fluoro-phenyl)-8-hydroxy-3H-quinazolin-4-one or
6-Bromo-7-chloro-8-hydroxyquinazolin-4(3H)-one.

One further embodiment of the invention are compounds of formula I, wherein $R^1$ and $R^3$ are hydrogen and $R^2$ is heteroaryl, selected from the group consisting of pyrazolyl, thiazolyl, pyridinyl, pyrimidinyl, imidazolyl, isoxazolyl, isothiazolyl, thiophenyl, 1-thia-3,4-diazolyl, imidazo[1,2-a]pyridinyl, indazolyl, quinolinyl or isoquinolinyl, and which groups are optionally substituted by $R^5$, or is C(O)-heteroaryl, selected from pyridinyl or thiophenyl, wherein the heteroaryl groups are optionally substituted by lower alkyl, for example the following compounds 8-Hydroxy-6-(1-(2-methoxyethyl)-1H-pyrazol-5-yl)quinazolin-4(3H)-one
8-Hydroxy-6-(4-(methoxymethyl)-2-methylthiazol-5-yl)quinazolin-4(3H)-one
8-Hydroxy-6-(1-(2-methoxyethyl)-1H-pyrazol-4-yl)quinazolin-4(3H)-one
6-(6-(Dimethylamino)pyridin-3-yl)-8-hydroxyquinazolin-4(3H)-one
8-Hydroxy-6-(6-morpholinopyridin-2-yl)quinazolin-4(3H)-one
8-Hydroxy-6-(6-(pyrrolidin-1-yl)pyridin-2-yl)quinazolin-4(3H)-one
8-Hydroxy-6-(5-methylthiazol-2-yl)quinazolin-4(3H)-one
8-Hydroxy-6-(1-methyl-1H-imidazol-2-yl)quinazolin-4(3H)-one
8-Hydroxy-6-nicotinoylquinazolin-4(3H)-one
8-Hydroxy-6-(1-methyl-1H-imidazol-4-yl)quinazolin-4(3H)-one
8-Hydroxy-6-(5-methyl-3-phenylisoxazol-4-yl)quinazolin-4(3H)-one
4-(8-Hydroxy-4-oxo-3,4-dihydroquinazolin-6-yl)-N,N-dimethyl-1H-imidazole-1-sulfonamide
6-(3,5-Dimethylisoxazol-4-yl)-8-hydroxyquinazolin-4(3H)-one
8-Hydroxy-6-(1-methyl-1H-imidazol-5-yl)quinazolin-4(3H)-one
Ethyl 2-(8-hydroxy-4-oxo-3,4-dihydroquinazolin-6-yl)-4-methyl-1H-imidazole-5-carboxylate
Methyl 5-(8-hydroxy-4-oxo-3,4-dihydroquinazolin-6-yl)-4-methylthiophene-2-carboxylate
8-Hydroxy-6-(1-methyl-3-(trifluoromethyl)-1H-pyrazol-4-yl)quinazolin-4(3H)-one
8-Hydroxy-6-(5-methyl-1,3,4-thiadiazol-2-yl)quinazolin-4(3H)-one
Methyl 2-(8-hydroxy-4-oxo-3,4-dihydroquinazolin-6-yl)thiazole-4-carboxylate
8-Hydroxy-6-(2-methylthiazol-4-yl)quinazolin-4(3H)-one
8-Hydroxy-6-(imidazo[1,2-a]pyridin-3-yl)quinazolin-4(3H)-one
6-(1,2-Dimethyl-1H-imidazol-5-yl)-8-hydroxyquinazolin-4(3H)-one
Methyl 4-(8-hydroxy-4-oxo-3,4-dihydroquinazolin-6-yl)-1-methyl-1H-pyrazole-3-carboxylate
8-Hydroxy-6-(5-(pyridin-2-yl)thiophen-2-yl)quinazolin-4(3H)-one
8-Hydroxy-6-(thiazol-5-yl)quinazolin-4(3H)-one
8-Hydroxy-6-(thiazol-4-yl)quinazolin-4(3H)-one
8-Hydroxy-6-(isothiazol-4-yl)quinazolin-4(3H)-one
8-Hydroxy-6-isonicotinoylquinazolin-4(3H)-one
8-Hydroxy-6-(5-methylthiophene-2-carbonyl)quinazolin-4(3H)-one
6-(1,5-Dimethyl-3-(trifluoromethyl)-1H-pyrazol-4-yl)-8-hydroxyquinazolin-4(3H)-one
8-Hydroxy-6-(1-methyl-1H-indazol-5-yl)quinazolin-4(3H)-one
8-Hydroxy-6-(3-methyl-5-(piperidine-1-carbonyl)thiophen-2-yl)quinazolin-4(3H)-one
8-Hydroxy-6-[3-methyl-5-(4-methyl-piperazine-1-carbonyl)-thiophen-2-yl]-3H-quinazolin-4-one
N-(5-(8-Hydroxy-4-oxo-3,4-dihydroquinazolin-6-yl)-6-(methoxymethyl)pyridin-2-yl)pivalamide
8-Hydroxy-6-(2-(methoxymethyl)pyridin-3-yl)quinazolin-4(3H)-one bis(2,2,2-trifluoroacetate)
8-Hydroxy-6-(2-methylpyridin-4-yl)quinazolin-4(3H)-one
8-Hydroxy-6-(2-methylpyridin-3-yl)quinazolin-4(3H)-one
6-(6-Bromo-pyridin-3-yl)-8-hydroxy-3H-quinazolin-4-one
6-(2,5-Dimethyl-2H-pyrazol-3-yl)-8-hydroxy-3H-quinazolin-4-one
6-[1-(4-Fluoro-phenyl)-1H-pyrazol-4-yl]-8-hydroxy-3H-quinazolin-4-one
8-Hydroxy-6-(pyrimidin-5-yl)quinazolin-4(3H)-one 2,2,2-trifluoroacetate
8-Hydroxy-6-(2-methyl-5-trifluoromethyl-2H-pyrazol-3-yl)-3H-quinazolin-4-one
6-(2-((Dimethylamino)methyl)phenyl)-8-hydroxyquinazolin-4(3H)-one
8-Hydroxy-6-(1-methyl-1H-indazol-4-yl)quinazolin-4(3H)-one 6-(2,4-Dimethoxypyrimidin-5-yl)-8-hydroxyquinazolin-4(3H)-one
8-Hydroxy-6-(2-methoxypyridin-3-yl)quinazolin-4(3H)-one
8-Hydroxy-6-(6-methoxypyridin-3-yl)quinazolin-4(3H)-one
8-Hydroxy-6-(4-methylthiophen-3-yl)quinazolin-4(3H)-one
6-(2,5-Dimethylthiophen-3-yl)-8-hydroxyquinazolin-4(3H)-one
8-Hydroxy-6-(6-methylpyridin-3-yl)quinazolin-4(3H)-one
8-Hydroxy-6-(quinolin-8-yl)quinazolin-4(3H)-one
8-Hydroxy-6-(isoquinolin-4-yl)quinazolin-4(3H)-one
6-(2,4-Dimethylthiazol-5-yl)-8-hydroxyquinazolin-4(3H)-one
8-Hydroxy-6-(1-methyl-1H-pyrazol-4-yl)quinazolin-4(3H)-one
8-Hydroxy-6-(2-hydroxypyridin-3-yl)quinazolin-4(3H)-one
8-Hydroxy-6-(1-methyl-1H-pyrazol-5-yl)quinazolin-4(3H)-one
8-Hydroxy-6-(6-morpholinopyridin-3-yl)quinazolin-4(3H)-one
6-(6-(Dimethylamino)pyridin-2-yl)-8-hydroxyquinazolin-4(3H)-one
8-Hydroxy-6-(6-(piperazin-1-yl)pyridin-3-yl)quinazolin-4(3H)-one
8-Hydroxy-6-(2-(piperazin-1-yl)pyridin-4-yl)quinazolin-4(3H)-one
6-(1,4-Dimethyl-1H-imidazol-2-yl)-8-hydroxyquinazolin-4(3H)-one
6-(2,6-Dimethyl-pyridin-3-yl)-8-hydroxy-3H-quinazolin-4-one
8-Hydroxy-6-(4-methyl-2-phenylthiazol-5-yl)quinazolin-4(3H)-one
8-Hydroxy-6-(5-methyl-1-phenyl-1H-pyrazol-4-yl)quinazolin-4(3H)-one
8-Hydroxy-6-(3-methyl-1H-pyrazol-4-yl)quinazolin-4(3H)-one
6-(1,5-Dimethyl-1H-pyrazol-4-yl)-8-hydroxyquinazolin-4(3H)-one
8-Hydroxy-6-(2-(2,2,2-trifluoroethoxy)pyridin-3-yl)quinazolin-4(3H)-one
8-Hydroxy-6-(3-methylpyridin-4-yl)quinazolin-4(3H)-one or
8-Hydroxy-6-(1-methyl-3-(4-methylpiperazine-1-carbonyl)-1H-pyrazol-5-yl)quinazolin-4(3H)-one.

One further embodiment of the invention are compounds of formula I, wherein $R^1$ is methyl, Br, F or Cl, for example the following compounds
5,7-Dibromo-6-(4-fluorophenyl)-8-hydroxyquinazolin-4(3H)-one
5,7-Difluoro-8-hydroxy-6-phenylquinazolin-4(3H)-one
7-bromo-6-(4-fluorophenyl)-8-hydroxy-5-p-tolylquinazolin-4(3H)-one
6-Bromo-8-hydroxy-7-methylquinazolin-4(3H)-one
7-Fluoro-6-(4-fluorophenyl)-8-hydroxyquinazolin-4(3H)-one
7-Chloro-6-(4-fluorophenyl)-8-hydroxyquinazolin-4(3H)-one or
6-Bromo-7-chloro-8-hydroxyquinazolin-4(3H)-one.

One further embodiment of the invention are compounds of formula I, wherein $R^3$ is methyl, Br, F, Cl, $CF_3$, nitro, amino, cyano, NHC(O)-phenyl, or is 1-methyl-1,2,3,6-tetrahydropyridinyl, or is pyridinyl, optionally substituted by methyl or morpholinyl, or is phenyl optionally substituted by methyl, $SO_2CH_3$, $CF_3$, CN, F or C(O)Ndi-lower alkyl, for example the following compounds;

5-Bromo-8-hydroxyquinazolin-4(3H)-one
5,7-Dibromo-6-(4-fluorophenyl)-8-hydroxyquinazolin-4(3H)-one
5,7-Difluoro-8-hydroxy-6-phenylquinazolin-4(3H)-one
6-Bromo-8-hydroxy-5-(trifluoromethyl)quinazolin-4(3H)-one
8-Hydroxy-5-(trifluoromethyl)quinazolin-4(3H)-one
6-(4-Fluorophenyl)-8-hydroxy-5-(trifluoromethyl)quinazolin-4(3H)-one
6-Bromo-8-hydroxy-5-nitro-3H-quinazolin-4-one
6-(4-Fluorophenyl)-8-hydroxy-5-phenylquinazolin-4(3H)-one
6-(4-Fluorophenyl)-8-hydroxy-5-p-tolylquinazolin-4(3H)-one
7-bromo-6-(4-fluorophenyl)-8-hydroxy-5-p-tolylquinazolin-4(3H)-one
6-(4-Fluorophenyl)-8-hydroxy-5-(3-(methylsulfonyl)phenyl)quinazolin-4(3H)-one
6-(4-Fluorophenyl)-8-hydroxy-5-(3-(trifluoromethyl)phenyl)quinazolin-4(3H)-one
6-(4-Fluorophenyl)-8-hydroxy-4-oxo-3,4-dihydro quinazoline-5-carbonitrile
N,N-Diethyl-4-(6-(4-fluorophenyl)-8-hydroxy-4-oxo-3,4-dihydro quinazolin-5-yl)benzamide
6-(4-Fluorophenyl)-8-hydroxy-5-(pyridin-4-yl)quinazolin-4(3H)-one
6-(4-Fluorophenyl)-8-hydroxy-5-(4-(methylsulfonyl)phenyl)quinazolin-4(3H)-one
6-(4-Fluorophenyl)-8-hydroxy-5-(2-methylpyridin-4-yl)quinazolin-4(3H)-one
6-(4-Fluorophenyl)-8-hydroxy-5-(2-morpholinopyridin-4-yl)quinazolin-4(3H)-one
6-(4-Fluorophenyl)-8-hydroxy-5-(1-methyl-1,2,3,6-tetrahydropyridin-4-yl)quinazolin-4(3H)-one
4-[6-(4-Fluoro-phenyl)-8-hydroxy-4-oxo-3,4-dihydro-quinazolin-5-yl]-benzonitrile
5-Chloro-6-(4-fluorophenyl)-8-hydroxyquinazolin-4(3H)-one
5,6-Bis(4-fluorophenyl)-8-hydroxyquinazolin-4(3H)-one
6-Bromo-8-hydroxy-5-(2-methylpyridin-4-yl)quinazolin-4(3H)-one
6-Bromo-5-chloro-8-hydroxyquinazolin-4(3H)-one
5-Chloro-8-hydroxy-6-(2-(methylsulfonylmethyl)phenyl)quinazolin-4(3H)-one
5-Chloro-8-hydroxy-6-(2-((2-(1-(2,2,2-trifluoroethyl)piperidin-4-yl)ethoxy)methyl)phenyl)quinazolin-4(3H)-one 2,2,2-trifluoroacetate
5-Bromo-6-(4-fluorophenyl)-8-hydroxyquinazolin-4(3H)-one
7-Fluoro-5,6-bis(4-fluorophenyl)-8-hydroxyquinazolin-4(3H)-one
7-Fluoro-5-(4-fluorophenyl)-8-hydroxyquinazolin-4(3H)-one
8-Hydroxy-5-methylquinazolin-4(3H)-one
5-Chloro-8-hydroxyquinazolin-4(3H)-one
5-(4-Fluorophenyl)-8-hydroxyquinazolin-4(3H)-one
5-Fluoro-6-(4-fluorophenyl)-8-hydroxyquinazolin-4(3H)-one
6-Bromo-5-fluoro-8-hydroxyquinazolin-4(3H)-one
5-Fluoro-8-hydroxyquinazolin-4(3H)-one
5-Fluoro-8-hydroxy-6-(2-methylpyridin-3-yl)quinazolin-4(3H)-one
6-Bromo-7-fluoro-5-(4-fluoro-phenyl)-8-hydroxy-3H-quinazolin-4-one
6-(4-Fluoro-phenyl)-8-hydroxy-5-nitro-3H-quinazolin-4-one
5-Amino-6-(4-fluorophenyl)-8-hydroxyquinazolin-4(3H)-one N-(6-(4-Fluorophenyl)-8-hydroxy-4-oxo-3,4-dihydroquinazolin-5-yl)benzamide or 5-Chloro-8-hydroxy-6-(2-hydroxymethyl-phenyl)-3H-quinazolin-4-one.

The preparation of compounds of formula I of the present invention may be carried out in sequential or convergent synthetic routes. Syntheses of the compounds of the invention are shown in the following schemes 1 to 39. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 39, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

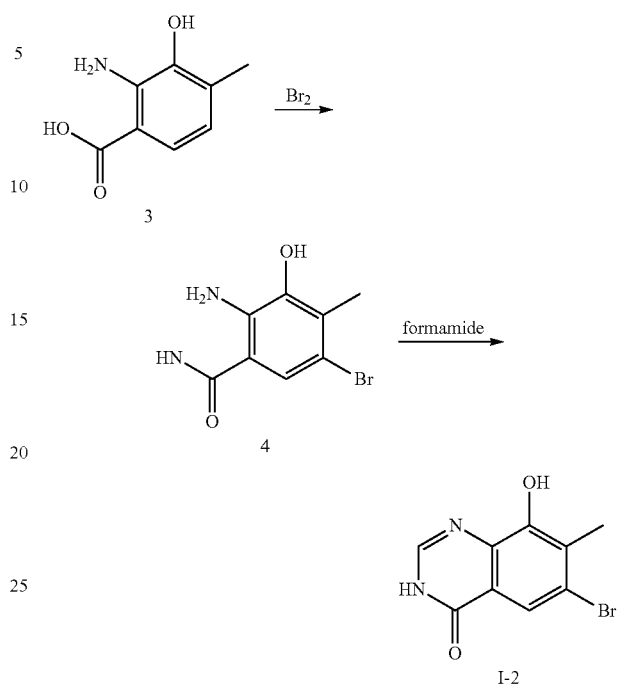

A halogen atom can be introduced by halogenation such as by treatment of benzoic acid derivative 3 with bromine and then cyclized by treatment with formamide as illustrated in Scheme 2 for the synthesis of bromide I-2.

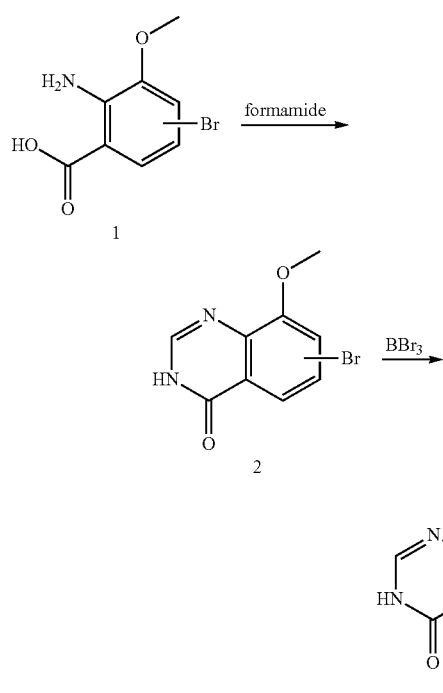

Halogenated compounds of formula I-1 can be prepared according to Scheme 1: A suitably substituted 3-methoxy-2-aminobenzoic acid 1 is cyclized with formamide to form a methoxyquinazolinone of formula 2. The methoxy group is then cleaved with boron tribromide, HBr or another suitable reagent to form a hydroxyquinazolinone of formula I-1. The hydroxy group may also be protected with another protecting group instead of methyl ether.

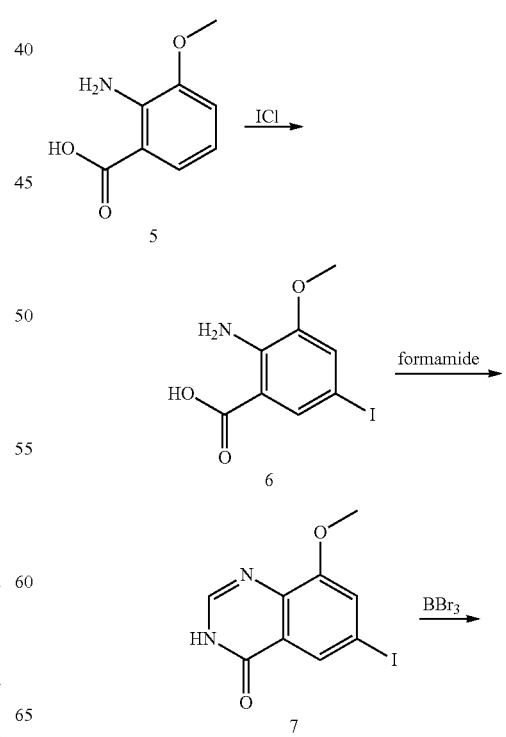

-continued

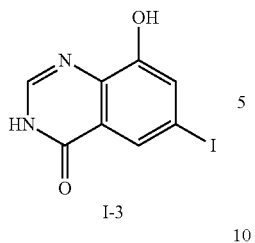
I-3

Benzoic acid derivative 5 can be converted to iodide 6 by treatment with a suitable iodination agent such as ICl. Intermediate 6 can be cyclized by treatment with formamide to ether 7, which can be deprotected to give iodo-hydroxyquinazolinone I-3. (Scheme 3)

Scheme 4

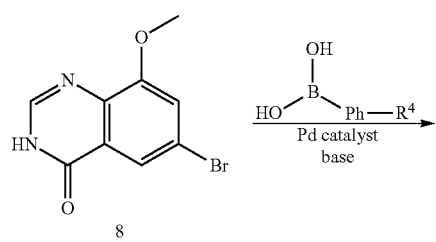
8

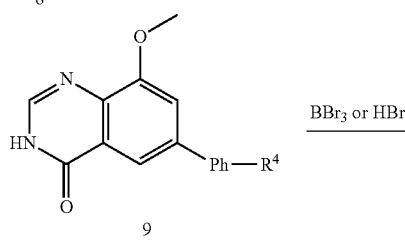
9

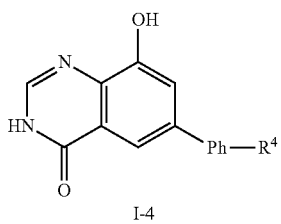
I-4

Halogenated methoxyquinazolinones such as bromide 8 can be reacted with boronic acids and esters in presence of a suitable palladium catalyst and a base to give biaryls of formula 9. (Scheme 4) The methoxy group is then cleaved with boron tribromide, HBr or another suitable reagent to form a hydroxyquinazolinone of formula I-4. The hydroxy group may also be protected with another protecting group instead of methyl ether.

Scheme 5

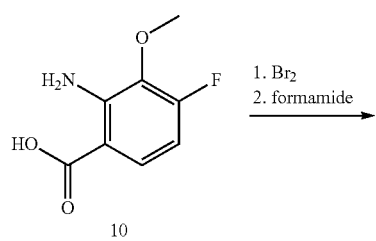
10

-continued

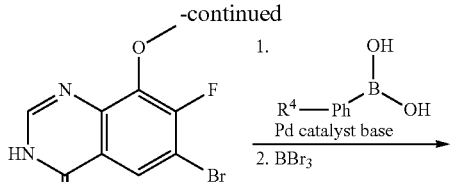
11

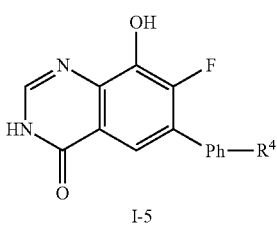
I-5

A halogen atom can be introduced by halogenation such as by treatment of 3-methoxy-2-aminobenzoic acid 10 with bromine as illustrated in Scheme 5 for the synthesis of bromo-methoxyquinazolinone 11. Bromo-methoxyquinazolinone 11 can further converted to biaryls of formula I-5.

Scheme 6

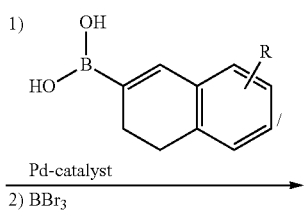
8

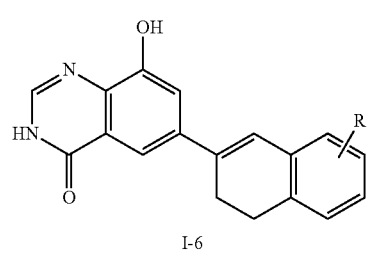
I-6

R is hydrogen or lower alkyl,

As illustrated in Scheme 6, this process can also be used to prepare alkenes of formula I-6.

Scheme 7

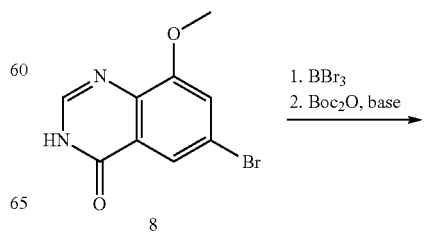
8

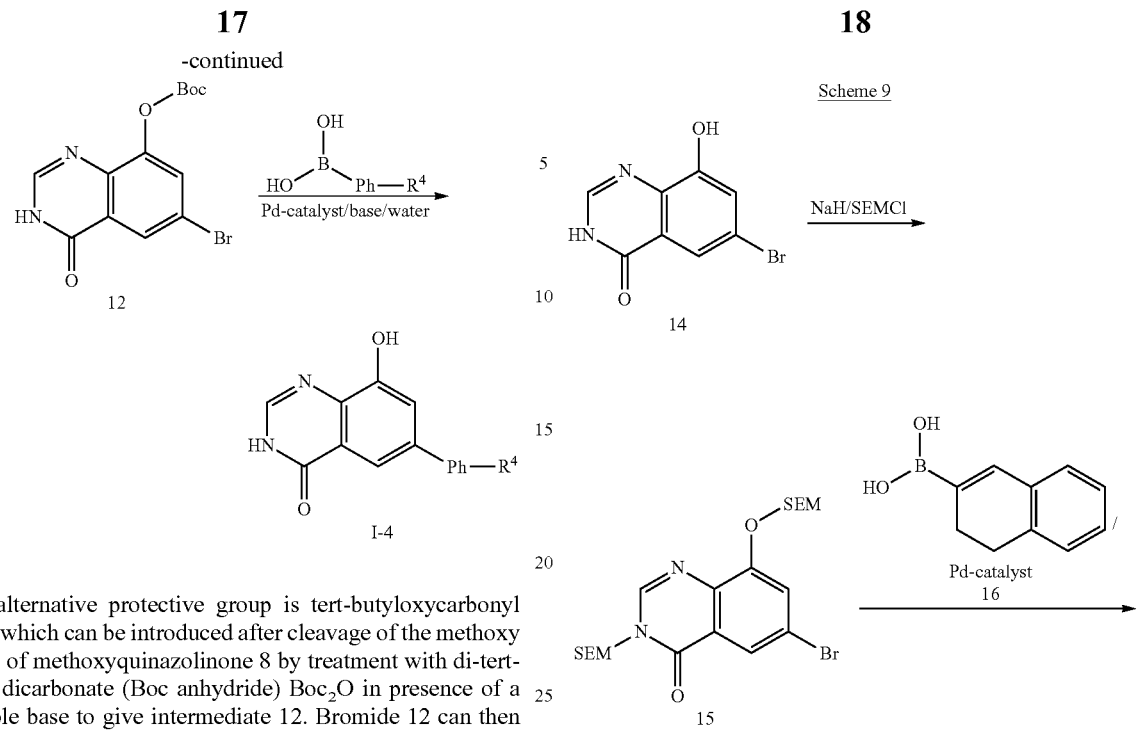

One alternative protective group is tert-butyloxycarbonyl (boc) which can be introduced after cleavage of the methoxy group of methoxyquinazolinone 8 by treatment with di-tert-butyl dicarbonate (Boc anhydride) $Boc_2O$ in presence of a suitable base to give intermediate 12. Bromide 12 can then be transformed to biaryls of formula I-4. (Scheme 7)

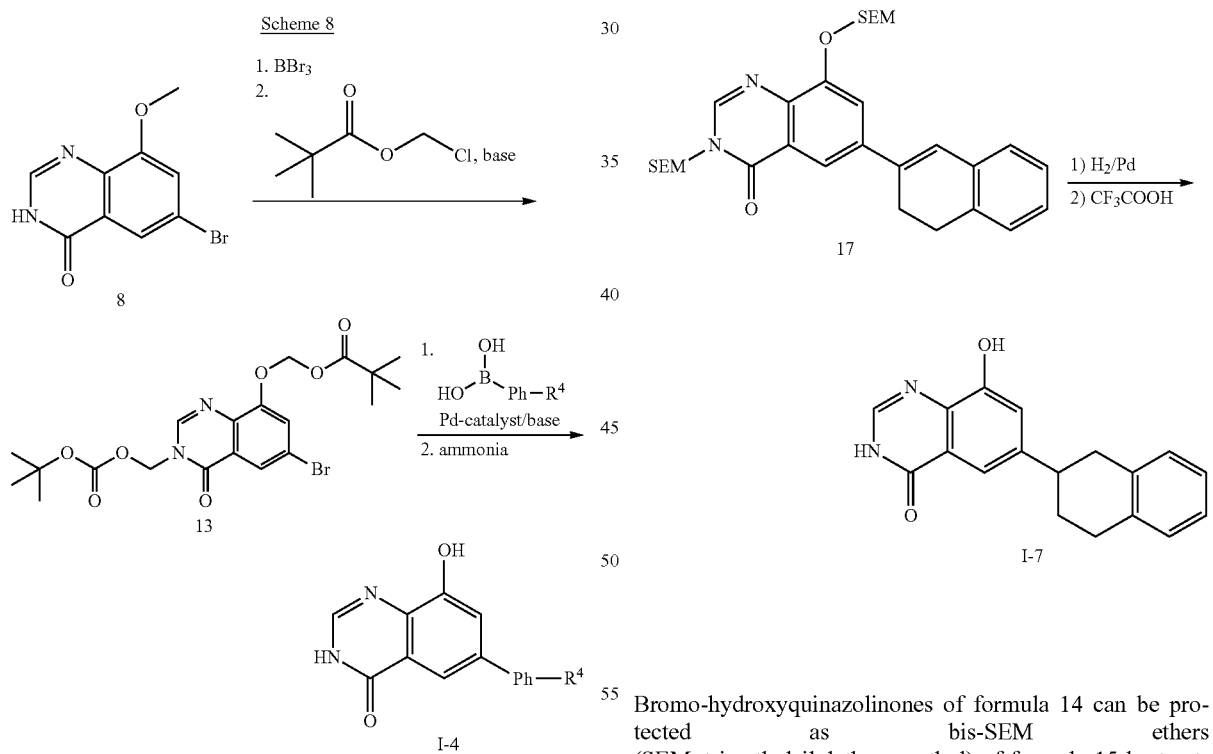

Another alternative protective group is pivaloyl oxymethyl (POM), which can be introduced after cleavage of the methoxy group from 8 in presence of a suitable base to give bromide 13. Bromide 13 can then be transformed by treatment with boronic acids in presence of a suitable palladium catalyst and base, followed by deprotection under suitable conditions such as treatment with ammonia to biaryls of formula I-4. (Scheme 8)

Bromo-hydroxyquinazolinones of formula 14 can be protected as bis-SEM ethers (SEM=trimethylsilylethoxymethyl) of formula 15 by treatment with SEM-Cl in presence of a suitable base such as sodium hydride as illustrated in Scheme 9. Intermediate 15 can then be transformed to alkenes of formula 17 by treatment with a boronic acid of formula 16 in presence of a suitable palladium catalyst. Alkenes of formula 17 can be reduced to alkanes with hydrogen in presence of palladium and deprotected under acidic conditions such as by treatment with trifluoroacetic acid to give compounds of formula I-7. (Scheme 9)

Scheme 10

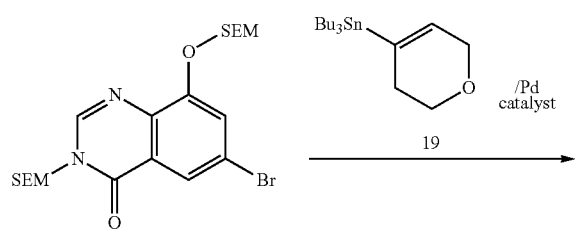

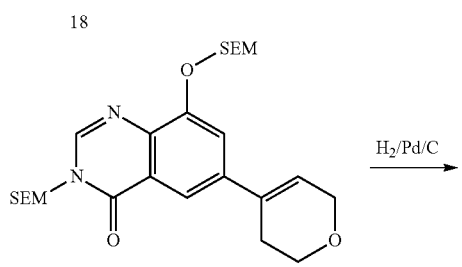

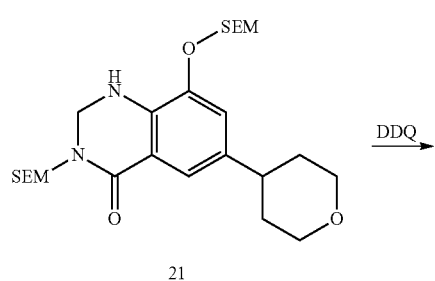

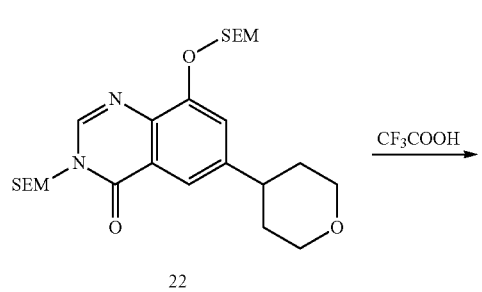

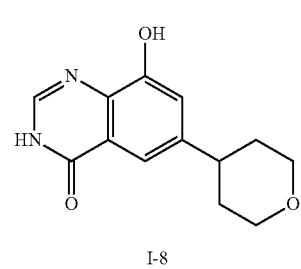

Bromide 18 can be treated with stannane 19 in presence of a suitable palladium catalyst to give intermediate 20. Hydrogenation in presence of palladium and oxidation with a suitable oxidizing agent such as DDQ gives intermediate 22, which can be deprotected to hydroxyquinazolinone I-8. (Scheme 10)

Scheme 11

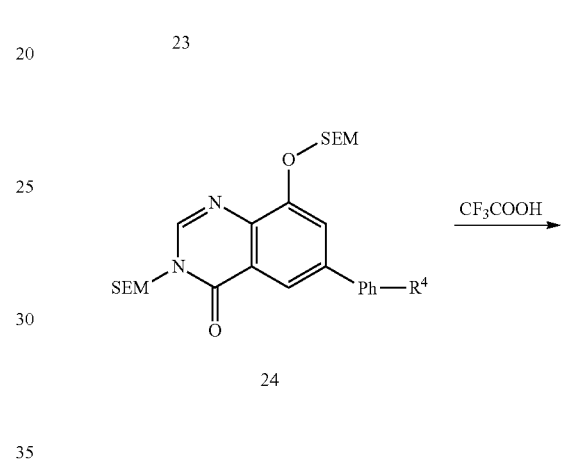

Bromide 23 can be treated with boronic acids or boronic esters in presence of a suitable palladium catalyst and base, typically in presence of water, (Suzuki coupling), or organotin compounds in presence of a suitable palladium catalyst (Stille coupling) and deprotected to give compounds of formula I-4 as shown in Scheme 11.

Scheme 12

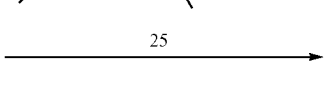

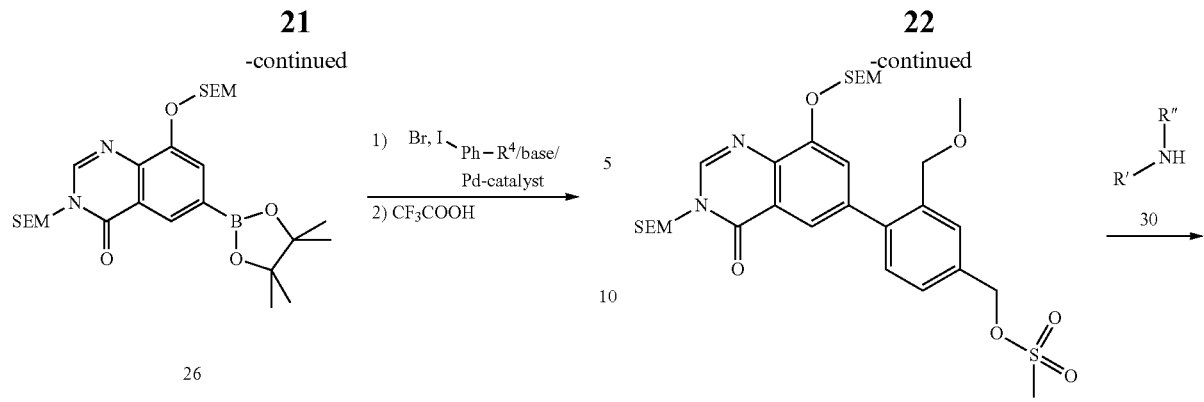

Bromide 23 can be converted to boronic acid esters of formula 26 by treatment with 25 in presence of a suitable base and palladium catalyst (Scheme 12). Intermediate 26 can be treated with aryliodides or bromides in presence of a suitable base and palladium catalyst to give after deprotection biaryls of formula I-4.

Scheme 13

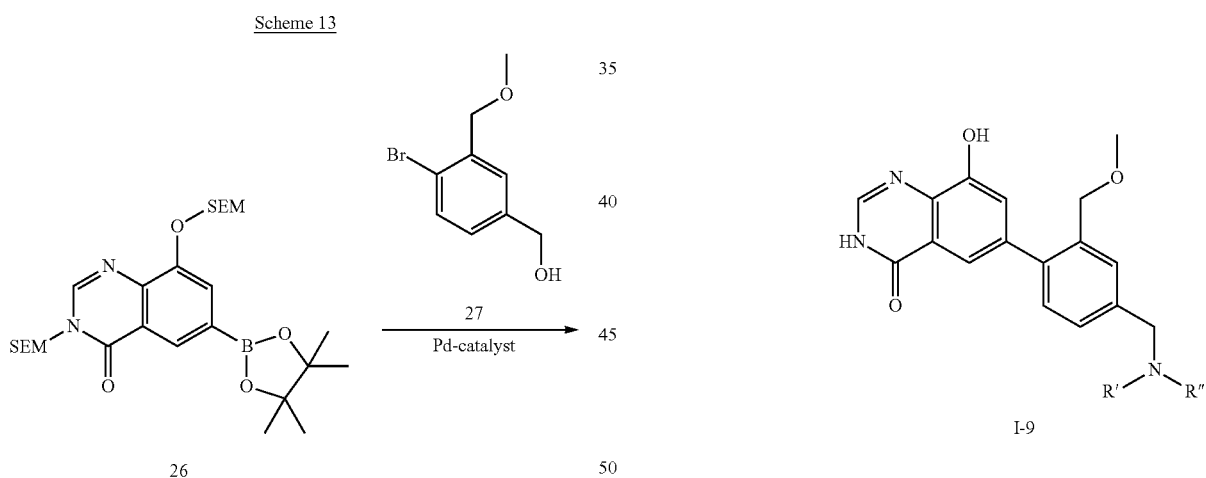

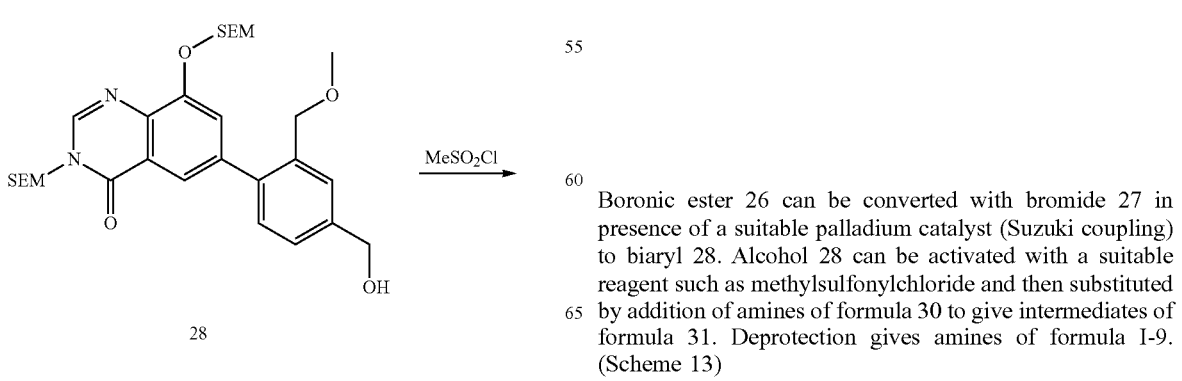

R' and R" are lower alkyl

Boronic ester 26 can be converted with bromide 27 in presence of a suitable palladium catalyst (Suzuki coupling) to biaryl 28. Alcohol 28 can be activated with a suitable reagent such as methylsulfonylchloride and then substituted by addition of amines of formula 30 to give intermediates of formula 31. Deprotection gives amines of formula I-9. (Scheme 13)

Scheme 14
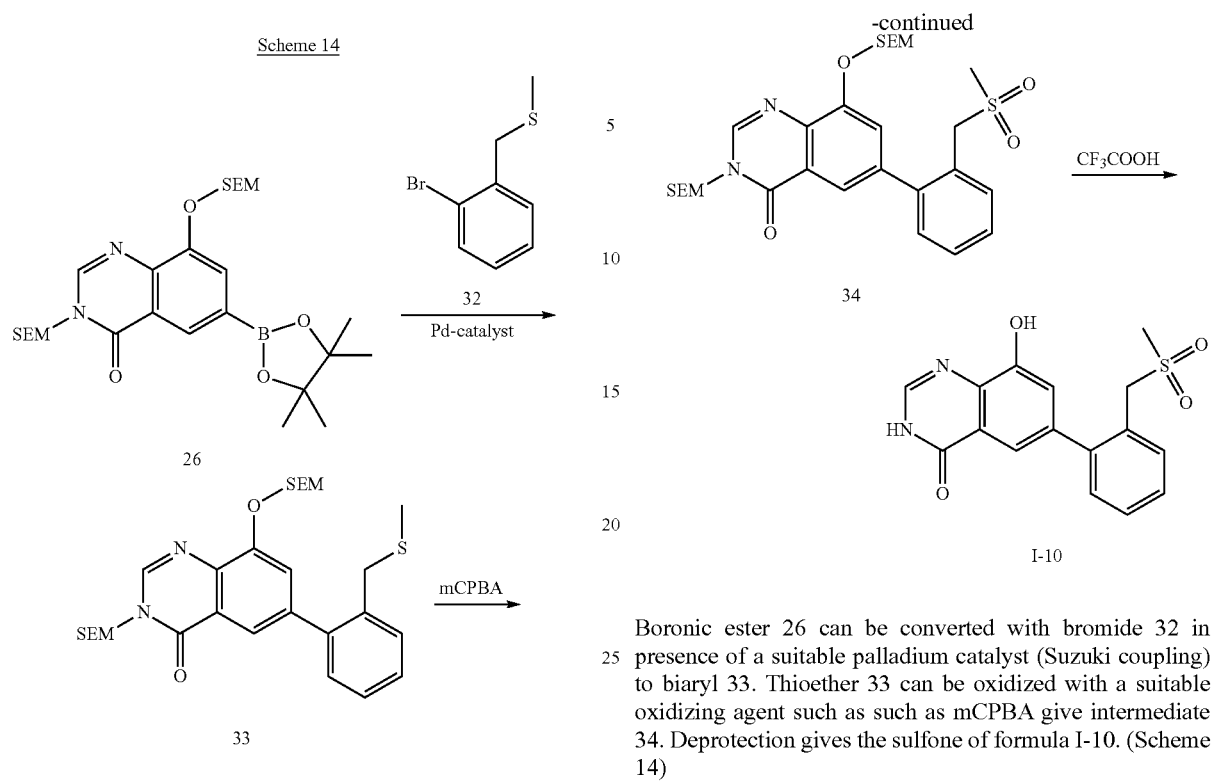
Boronic ester 26 can be converted with bromide 32 in presence of a suitable palladium catalyst (Suzuki coupling) to biaryl 33. Thioether 33 can be oxidized with a suitable oxidizing agent such as such as mCPBA give intermediate 34. Deprotection gives the sulfone of formula I-10. (Scheme 14)
Scheme 15
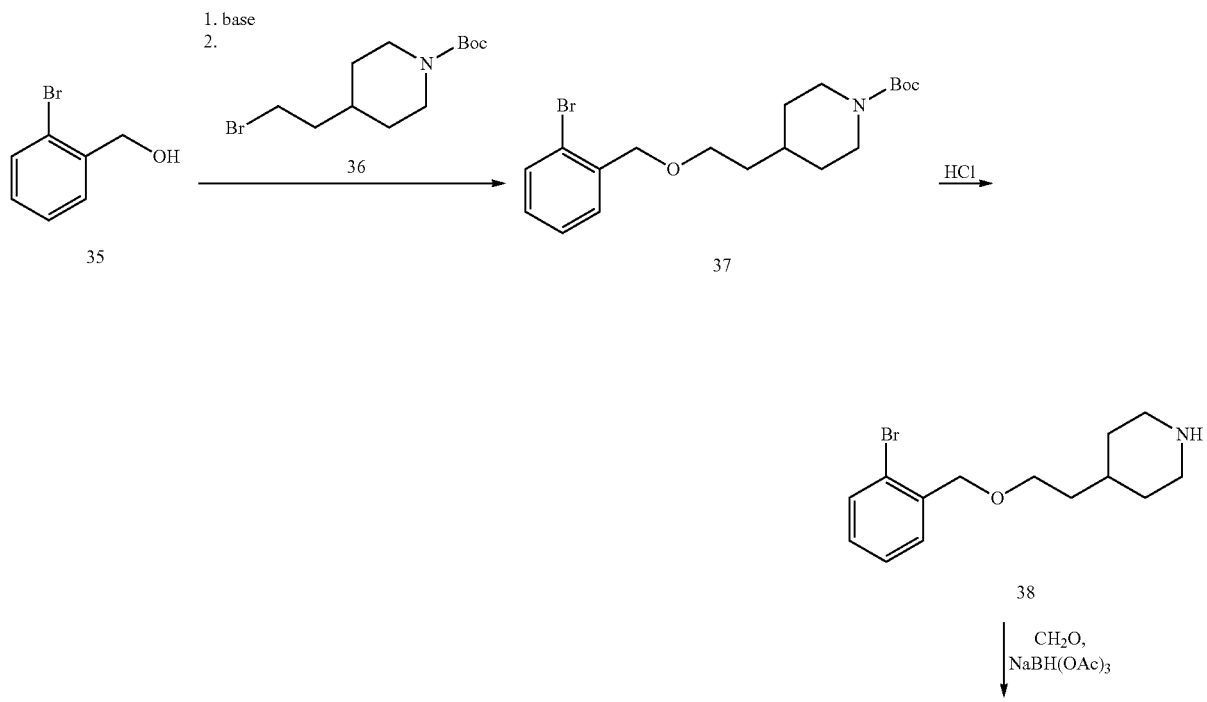

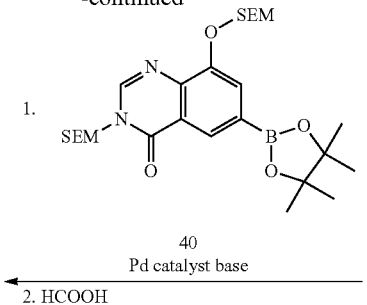

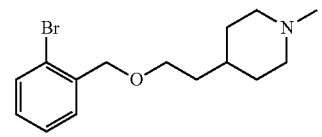

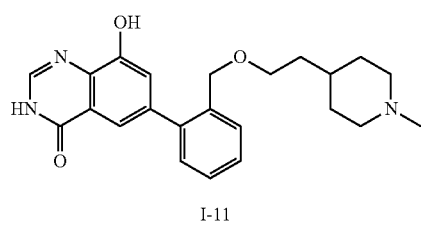

I-11

39

Alcohol 35 can be converted to ether 37 by treatment with a suitable base and bromide 36. Amine 38 can be prepared from 37 by deprotection with a suitable reagent such as hydrochloric acid or trifluoroacetic acid. Treatment of amine 38 with formaldehyde and a suitable reducing agent such as NaBH(OAc)₃ gives amine 39, which can be converted by treatment with boronic ester 40 in presence of a suitable palladium catalyst and base (Suzuki coupling), followed by deprotection to give amine I-11. (Scheme 15)

Scheme 16

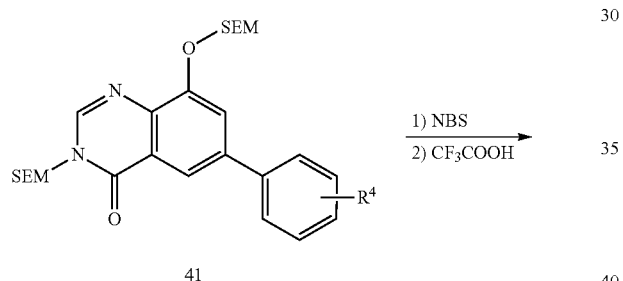

41

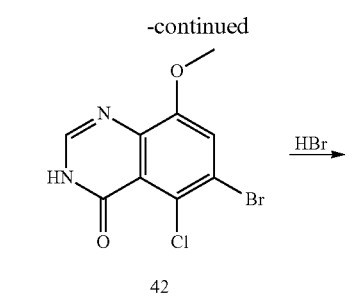

42

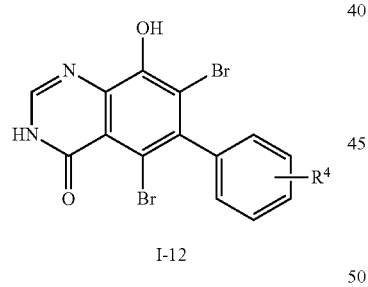

I-12

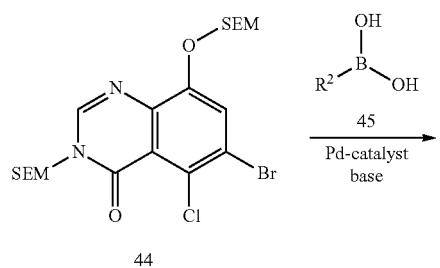

43

Biaryls of formula 41 can be brominated by treatment with a suitable halogenating agent such as NBS and deprotected to give compounds of formula I-12. (Scheme 16)

Scheme 17

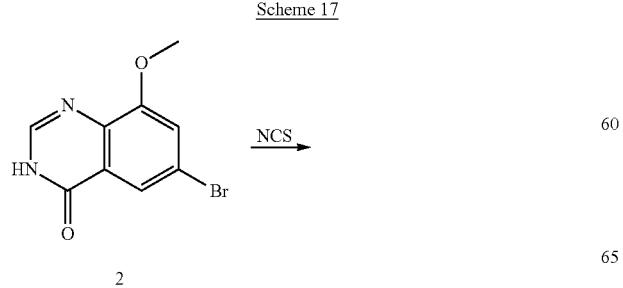

2

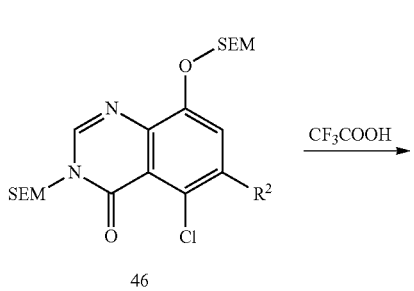

46

-continued

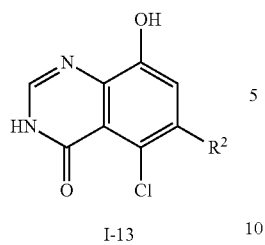

I-13

Bromide 2 can be chlorinated with a suitable chlorination agent such as NCS to give intermediate 42, which can be deprotected and then protected by treatment with SEM-Cl in presence of a suitable base to give intermediate 44. Treatment of 44 with a boronic acid of formula 45 in presence of a palladium catalyst and a suitable base (Suzuki coupling) gives biaryls of formula 46, which after deprotection give biaryls of formula I-13. (Scheme 17)

-continued

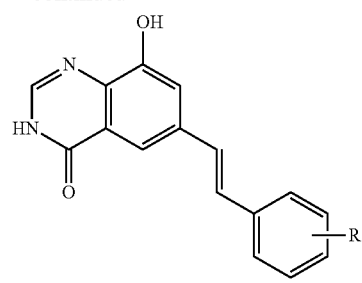

I-15

R is hydrogen or lower alkyl.

Bromide 15 can be treated with alkenes of formula 48 in presence of a suitable palladium catalyst (Heck coupling) and deprotected to give alkenes of formula I-15 as shown in Scheme 19.

Scheme 18

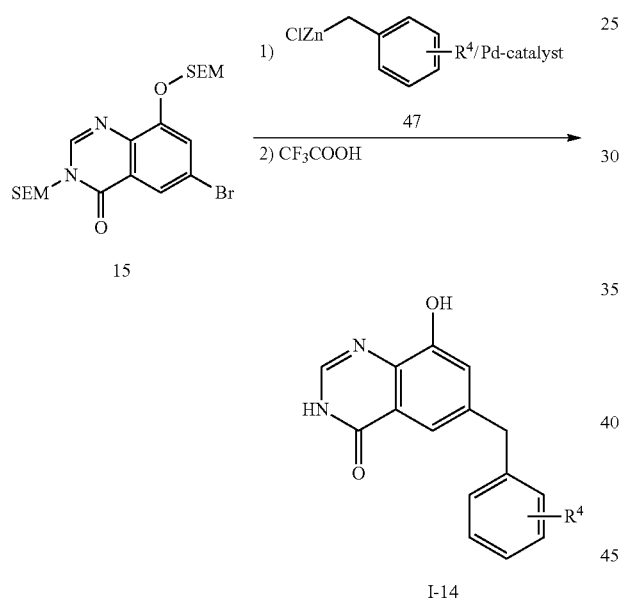

I-14

Bromide 15 can be treated with organozinc reagents of formula 47 in presence of a suitable palladium catalyst (Negishi coupling) and deprotected to give compounds of formula I-14 as shown in Scheme 18.

Scheme 20

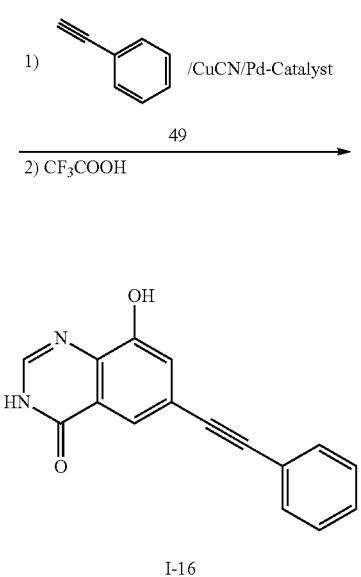

I-16

Bromide 15 can be treated with alkines of formula 49 in presence of a suitable palladium catalyst (Sonogashira coupling) and deprotected to give alkines of formula I-16 as shown in Scheme 20.

Scheme 19

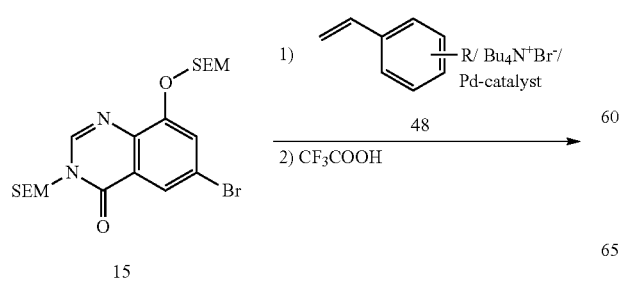

Scheme 21

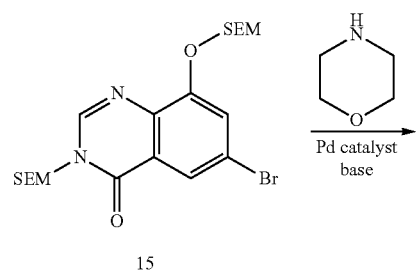

Scheme 22

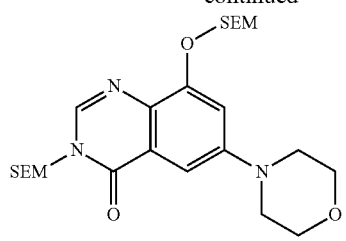
50

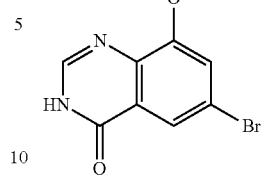
2

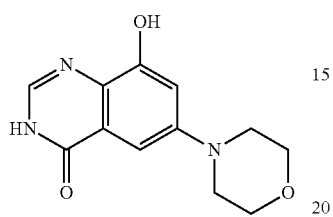
I-17

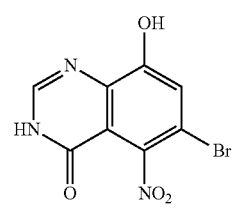
I-18

Bromide 15 can be treated with amines (for example morpholine) in presence of a suitable palladium catalyst and base (Buchwald-Hartwig coupling) and deprotected to give amines of formula I-17 as shown in Scheme 21.

Methoxyquinazolinone 2 may be nitrated by addition of nitric acid in the presence of sulfuric acid or with other suitable nitrating agents. The methoxy group is then cleaved with boron tribromide, HBr or another suitable reagent to form hydroxyquinazolinone I-18.

Scheme 23

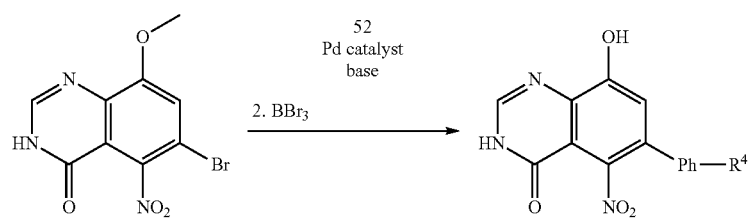
51    I-19

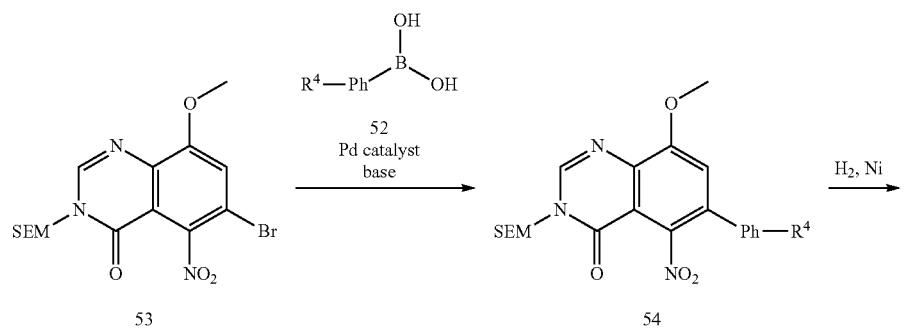
53    54

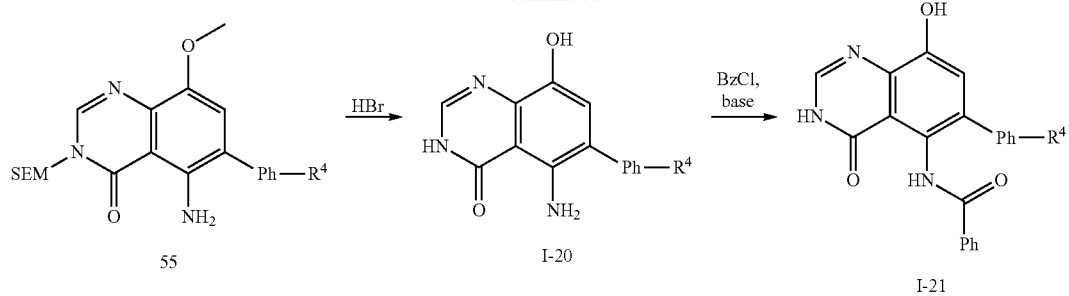

Nitroaryl 51 can be converted to hydroxyquinazolinone I-19 by treatment with arylboronic acids of formula 52 in presence of a suitable palladium catalyst and base (Suzuki coupling) followed by deprotection (Scheme 23). Treatment of 51 with SEM-Cl and a suitable base gives intermediate 53, which can be converted to biaryls of formula 54 by treatment with arylboronic acids of formula 52 in presence of a suitable palladium catalyst and base (Suzuki coupling). Hydrogenation in presence of a suitable catalyst such as Raney nickel gives intermediates of formula 55, which can be deprotected to give anilines of formula I-20. Anilines of formula I-20 can be treated with acid chlorides such as benzoyl chloride in presence of a suitable base to give amides of formula I-21.

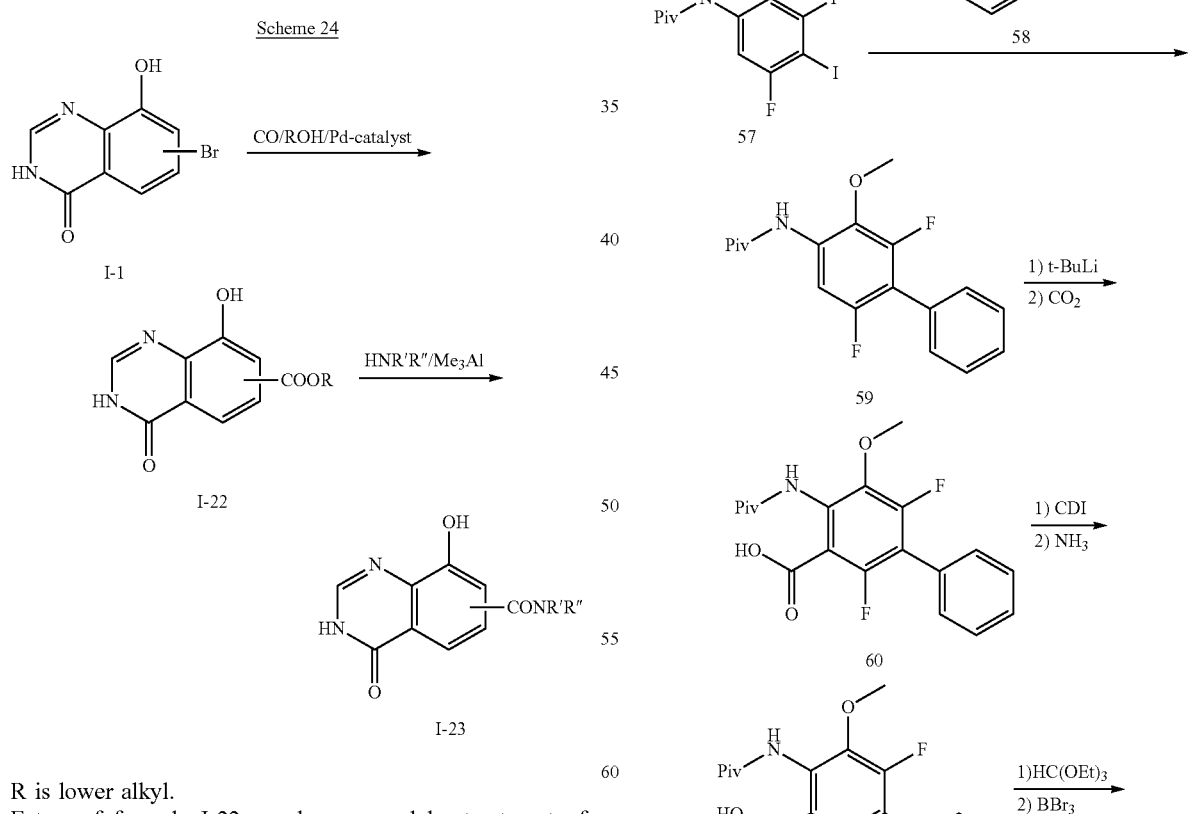

R is lower alkyl.

Esters of formula I-22 can be prepared by treatment of bromides of formula I-1 with carbon monoxide in presence of a suitable palladium catalyst and alcohol. Esters of formula I-22 can then be converted to amides of formula I-23 by treatment with suitable amines in presence of a suitable lewis acid such as trimethylaluminum. (Scheme 24)

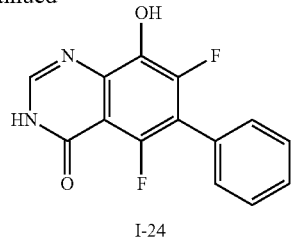

I-24

Treatment of difluoride 56 with pivaloyl chloride, followed by deprotonation with a suitable strong base such as LDA and iodination gives intermediate 57. Treatment of 57 with phenylboronic acid in presence of a palladium catalyst and base gives biaryl 59. Carboxylic acid 60 can be prepared from 59 by deprotonation with a strong base such as t-BuLi, followed by treatment with carbon dioxide. Carboxylic acid 60 can be converted to amide 61 by activation with a suitable reagent such as CDI, followed by treatment with ammonia. Hydroxyquinazolinone I-24 can be prepared from 61 by cyclization with $HC(OEt)_3$, followed by deprotection. (Scheme 25)

converted to nitrile 64 by treatment with copper cyanide followed by bromination. Nitrile 64 can be hydrolyzed to amide 65. Cyclization with $HC(OEt)_3$ followed by deprotection gives hydroxyquinazolinone I-25. (Scheme 26)

Scheme 26

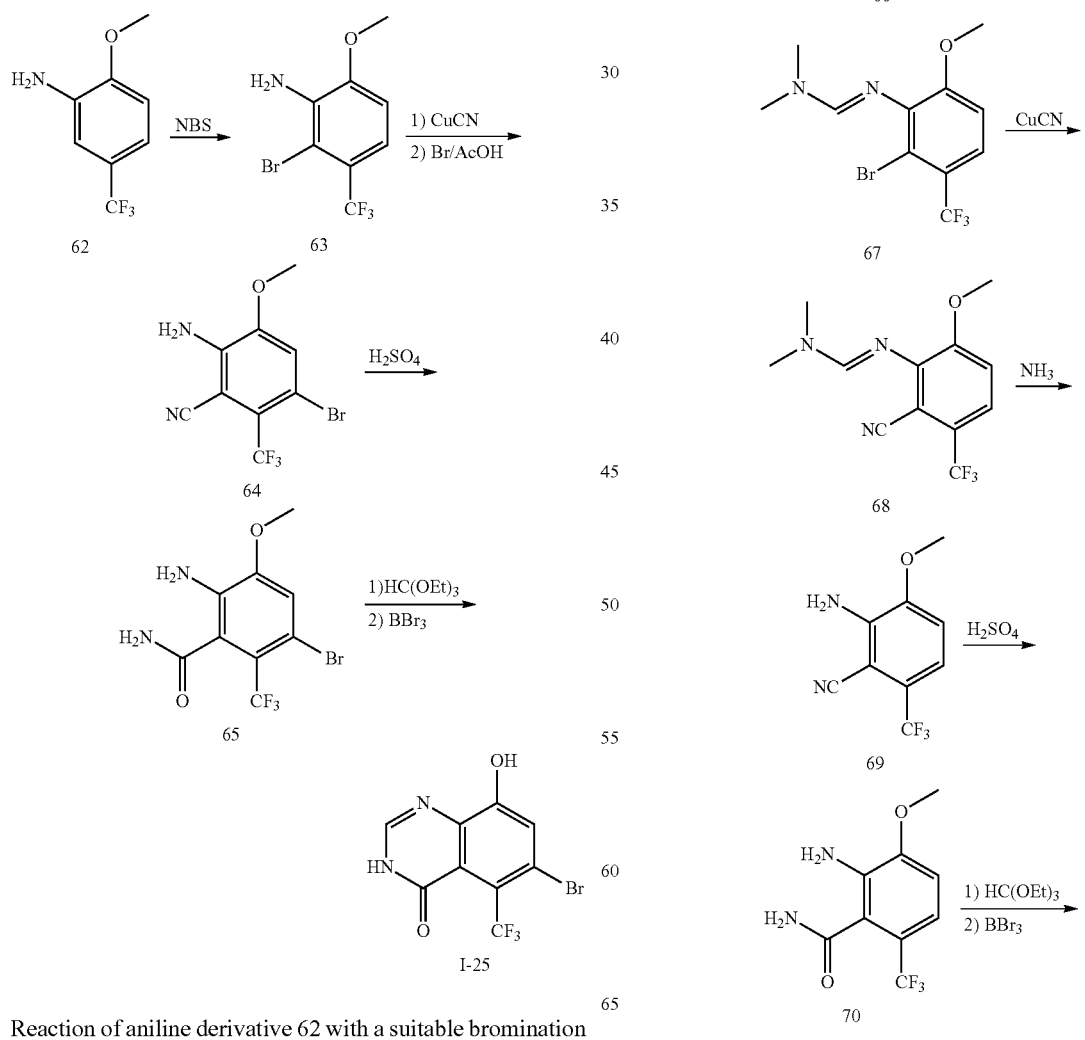

Reaction of aniline derivative 62 with a suitable bromination agent such as NBS gives intermediate 63, which can be Scheme 27

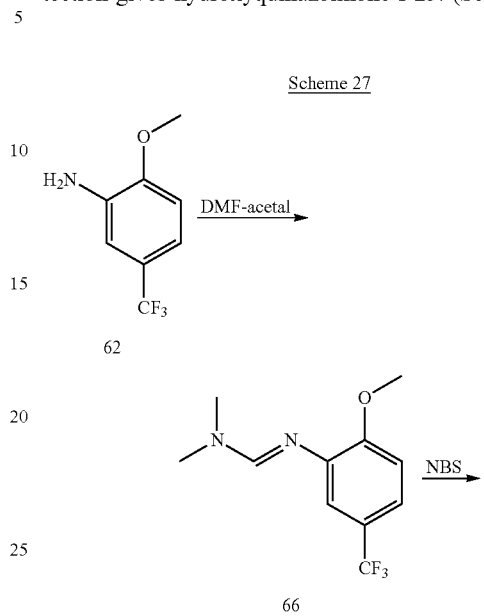

-continued

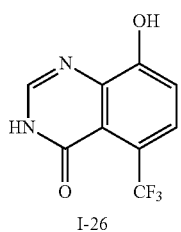

I-26

Aniline derivative 62 can be converted by treatment with DMF-acetal to intermediate 66, which can be brominated with a suitable reagent such as NBS to bromide 67. Treatment of 67 with copper cyanide gives nitrile 68, which can be deprotected by addition of ammonia to 69. Nitrile 69 can be hydrolyzed to amide 70. Cyclization with $HC(OEt)_3$ followed by deprotection gives hydroxyquinazolinone I-26. (Scheme 27)

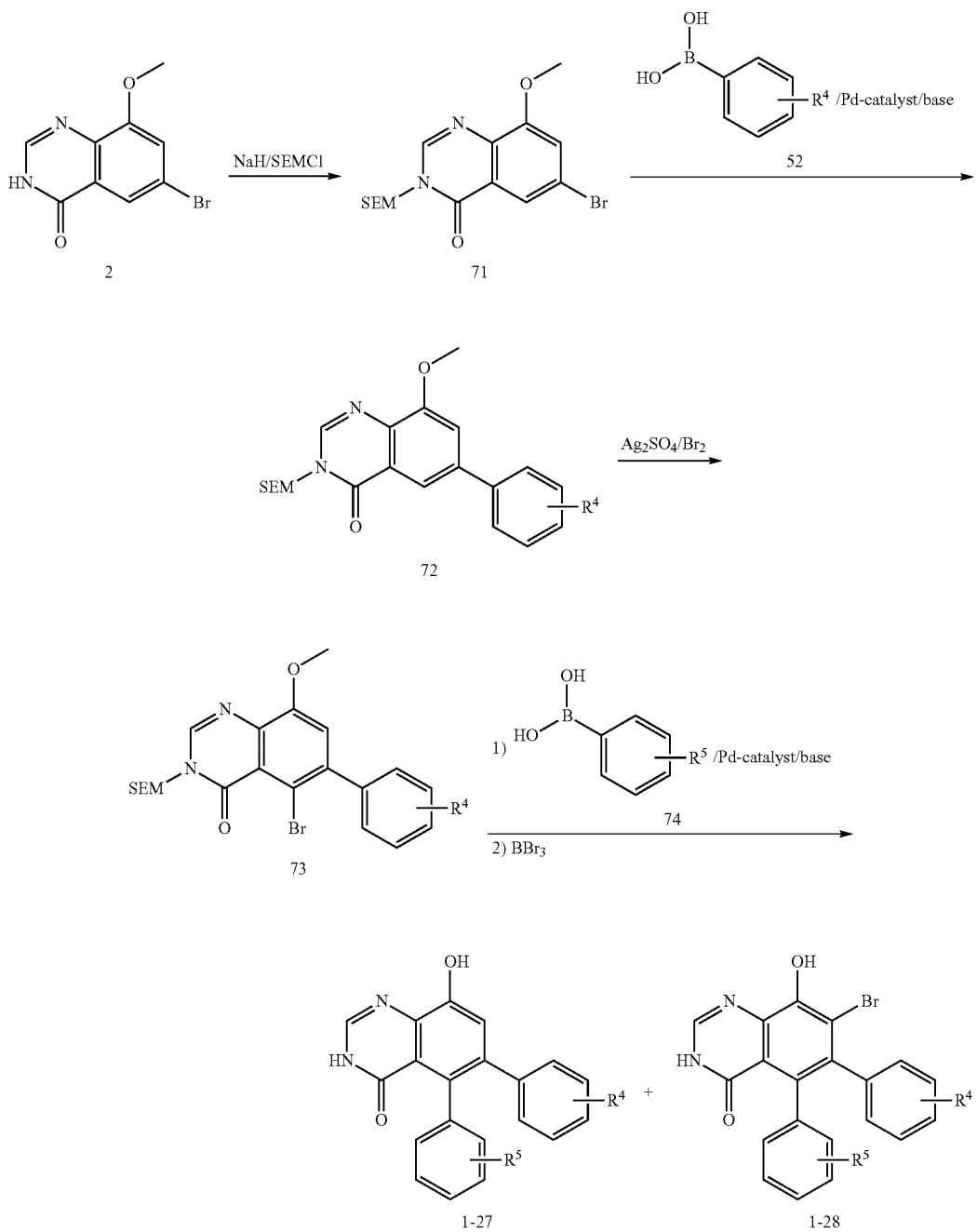

Bromide 2 can be protected by treatment with SEM-Cl and a suitable base to give intermediate 71. Treatment with boronic acids of formula 52 in presence of a suitable palladium catalyst and base (Suzuki coupling) gives biaryls of formula 72. Bromination in presence of silver salts gives bromides of formula 73, which can be treated with boronic acids in presence of a palladium catalyst and suitable base, followed by deprotection to give hydroxyquinazolinones of formula I-27 and I-28. (Scheme 28)

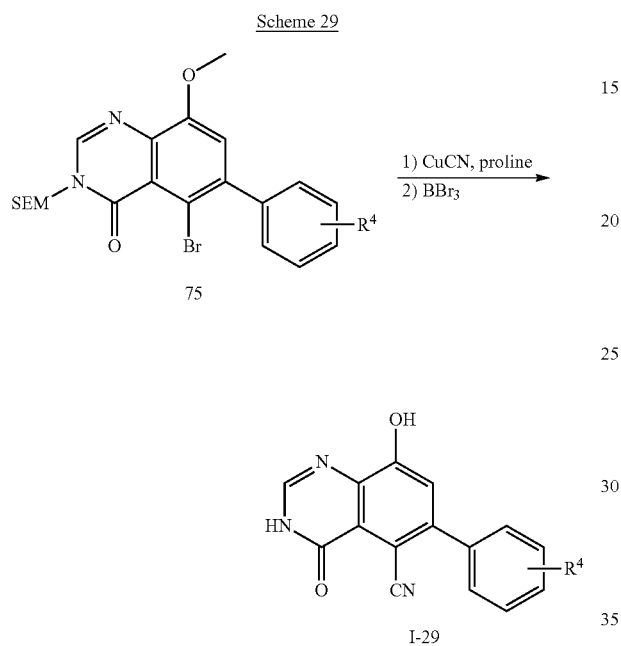

Bromides of formula 75 can be converted to hydroxyquinazolinones of formula I-29 by treatment with copper cyanide in presence of proline, followed by deprotection. (Scheme 29)

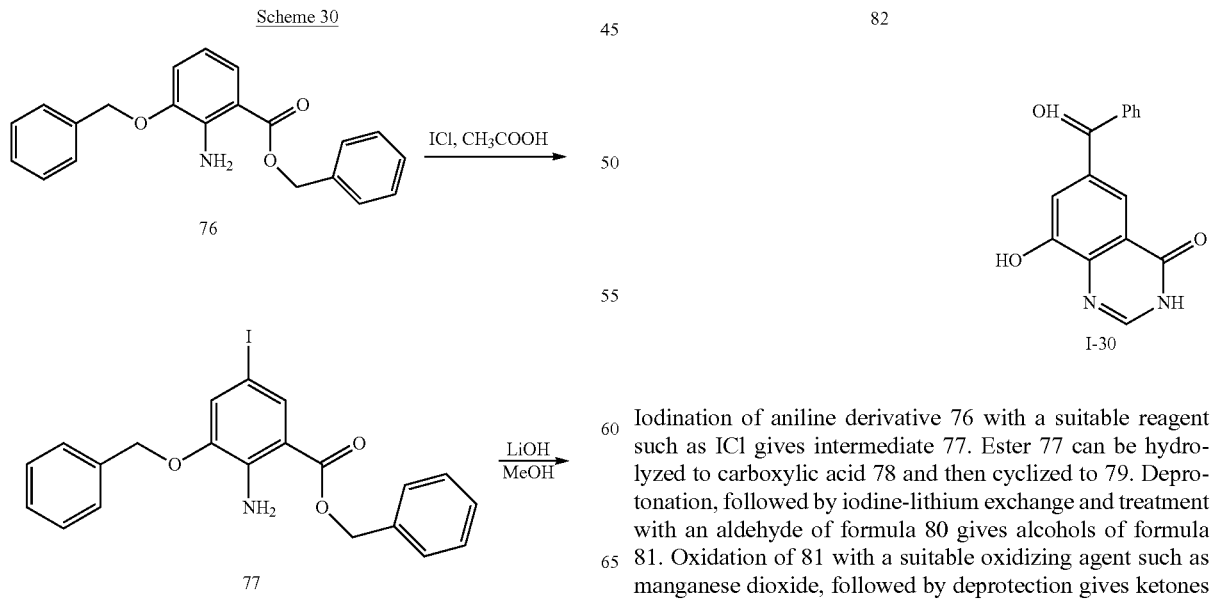

Iodination of aniline derivative 76 with a suitable reagent such as ICl gives intermediate 77. Ester 77 can be hydrolyzed to carboxylic acid 78 and then cyclized to 79. Deprotonation, followed by iodine-lithium exchange and treatment with an aldehyde of formula 80 gives alcohols of formula 81. Oxidation of 81 with a suitable oxidizing agent such as manganese dioxide, followed by deprotection gives ketones of formula I-30. (Scheme 30)

Scheme 31

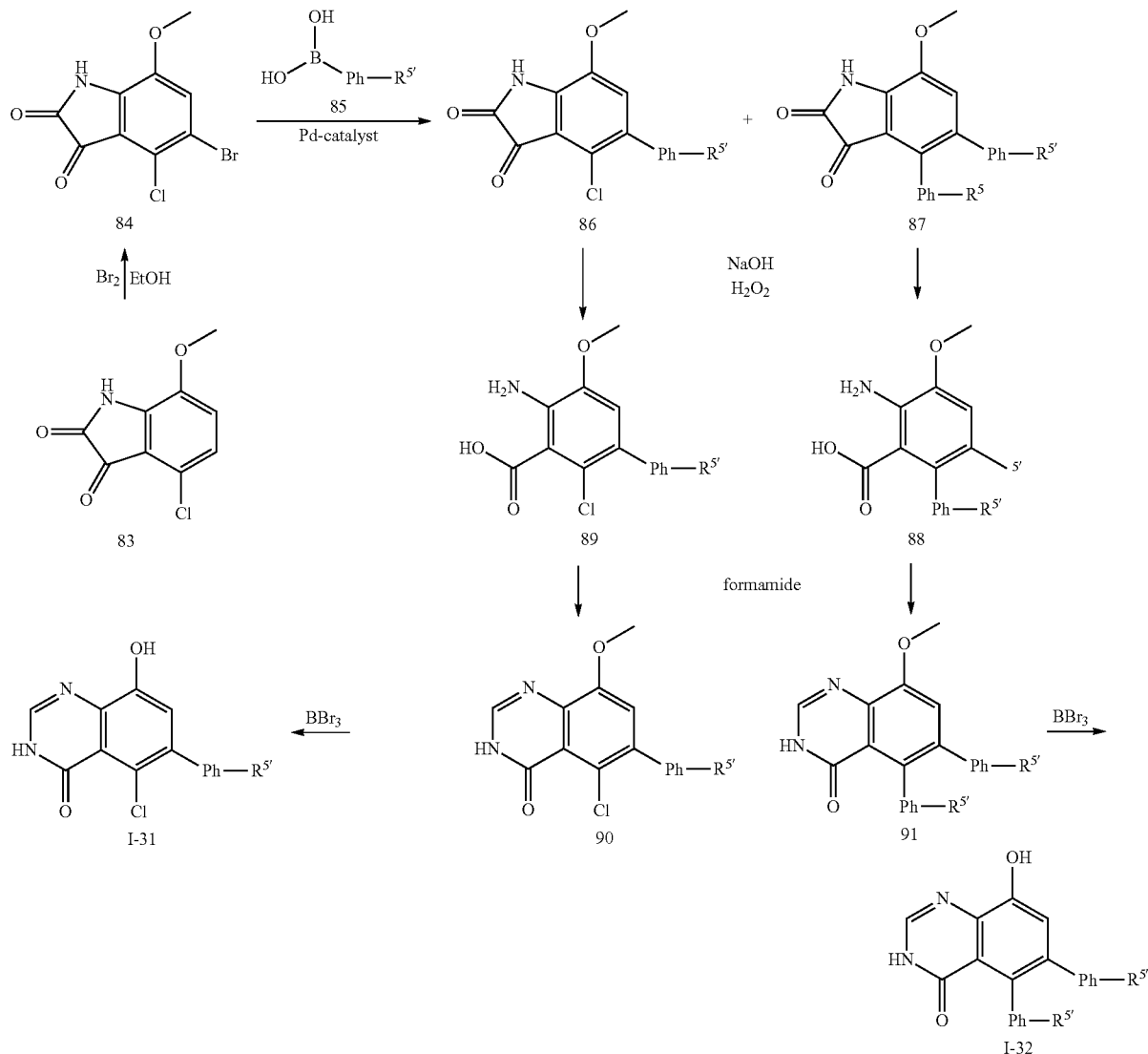

R[5'] is lower alkyl, SO$_2$-lower alkyl, lower alkyl substituted by halogen, CN, F or C(O)N(lower alkyl)$_2$.

Bromination of isatin derivative 83 gives bromide 84. Treatment with boronic acids of formula 85 in presence of a palladium catalyst and suitable base (Suzuki coupling) gives biaryls of formula 86 and 87. Oxidation with a suitable oxidizing agent such as hydrogen peroxide gives carboxylic acids 89 and 88, which can be cyclized with formamide and then deprotected to hydroxyquinazolinones I-31 and I-32. (Scheme 31)

Scheme 32

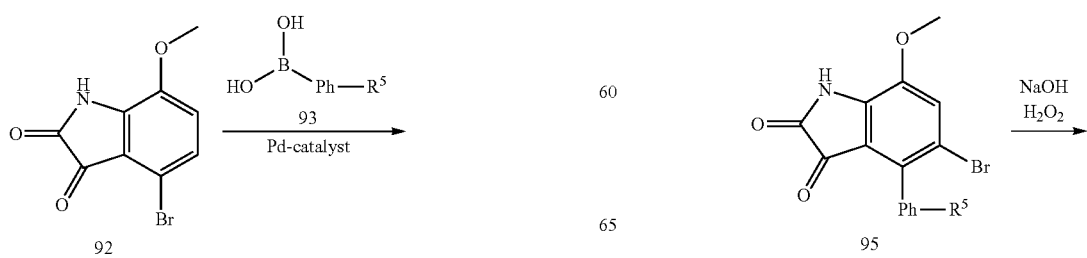

-continued

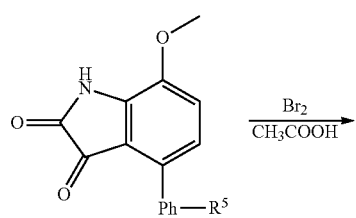

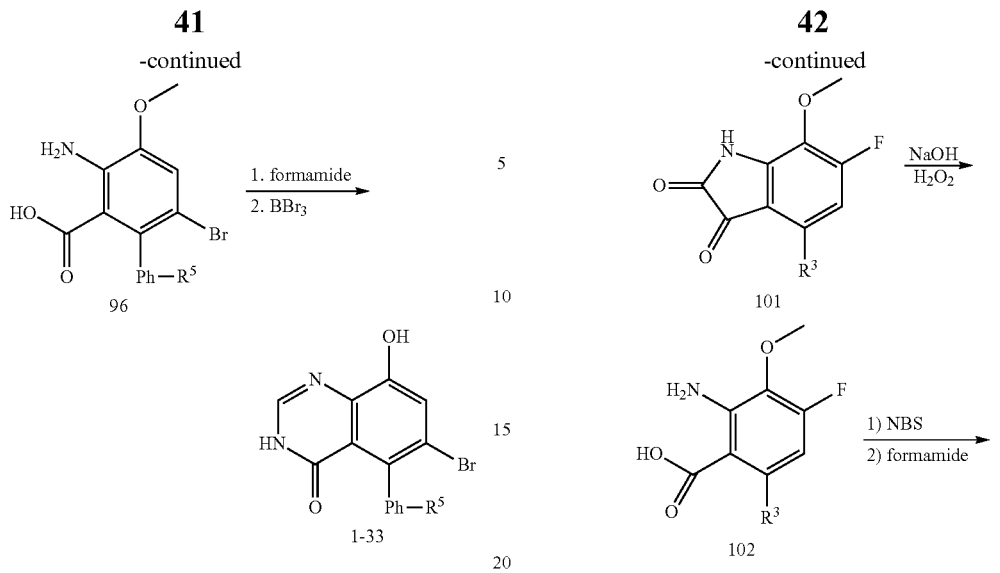

Bromides 92 can be converted to biaryls of formula 94 by treatment with boronic acids of formula 93 in presence of a palladium catalyst and base (Suzuki coupling). Bromination, for example by treatment with bromine in trifluoroacetic acid, gives bromides of formula 95. Oxidation with a suitable oxidizing agent such as hydrogen peroxide gives carboxylic acids of formula 96, which can be cyclized by treatment with formamide and deprotected to hydroxyquinazolinones of formula I-33. (Scheme 32)

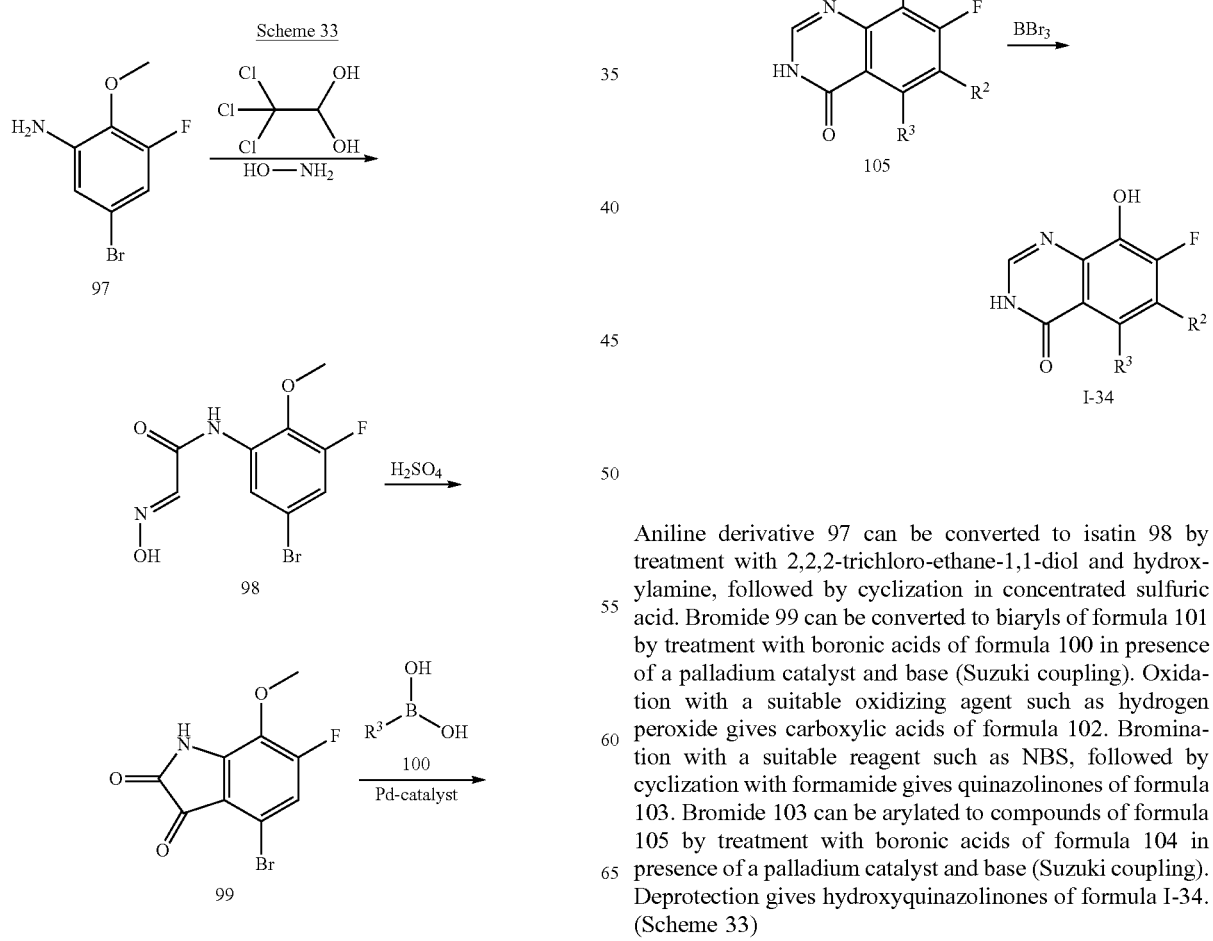

Aniline derivative 97 can be converted to isatin 98 by treatment with 2,2,2-trichloro-ethane-1,1-diol and hydroxylamine, followed by cyclization in concentrated sulfuric acid. Bromide 99 can be converted to biaryls of formula 101 by treatment with boronic acids of formula 100 in presence of a palladium catalyst and base (Suzuki coupling). Oxidation with a suitable oxidizing agent such as hydrogen peroxide gives carboxylic acids of formula 102. Bromination with a suitable reagent such as NBS, followed by cyclization with formamide gives quinazolinones of formula 103. Bromide 103 can be arylated to compounds of formula 105 by treatment with boronic acids of formula 104 in presence of a palladium catalyst and base (Suzuki coupling). Deprotection gives hydroxyquinazolinones of formula I-34. (Scheme 33)

Scheme 34

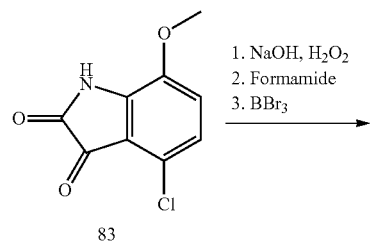

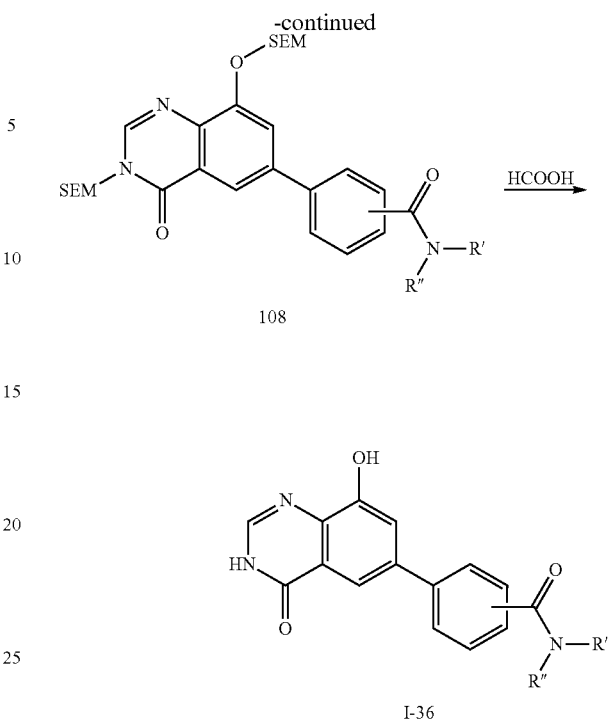

Isatin derivative 83 can be oxidized with a suitable reagent such as hydrogen peroxide, cyclized with formamide and then deprotected to give hydroxyquinazolinone I-35. (Scheme 34)

Scheme 35

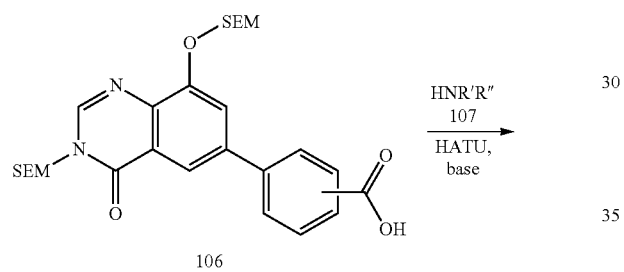

Carboxylic acid derivatives of formula 106 can be coupled with amines of formula 107 in presence of a suitable coupling reagent such as HATU and a suitable base to give amides of formula 108. Amides of formula 108 can be deprotected to hydroxyquinazolinones of formula I-36. (Scheme 35)

Scheme 36

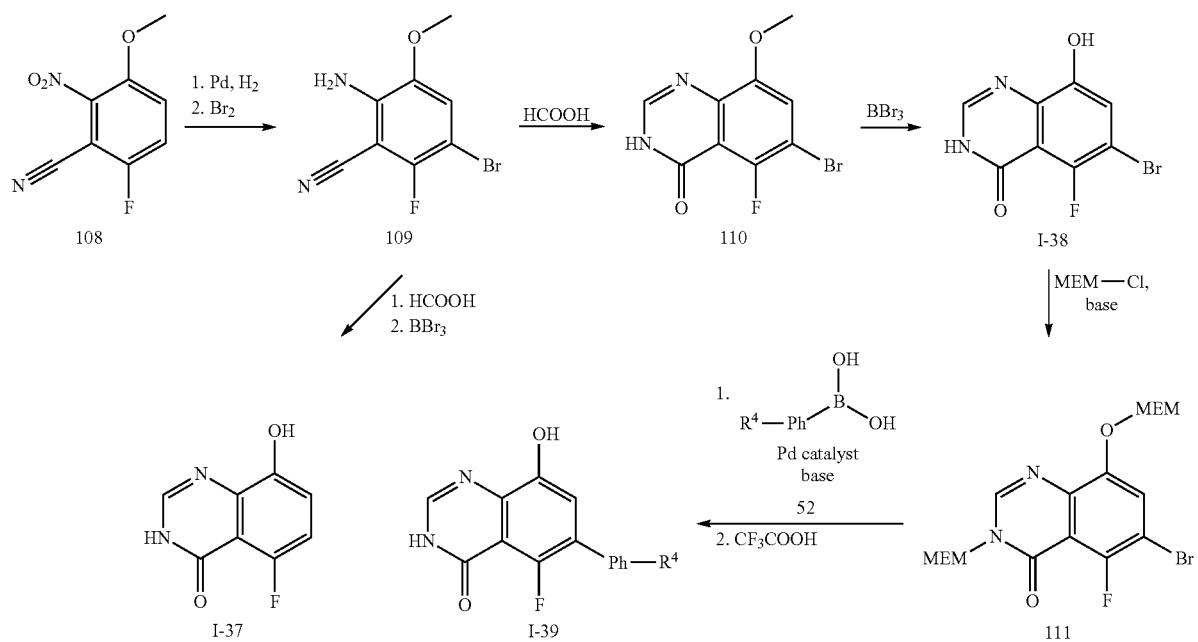

Nitroaryl 108 can be reduced with a suitable reducing agent such as hydrogen in presence of palladium and then brominated to give bromide 109. Bromide 109 can be cyclizied with formic acid and then deprotected to give hydroxyquinazolinone I-38. Bromide 109 can be cyclizied with formic acid and then deprotected to give hydroxyquinazolinone I-37. Treatment with MEM-Cl and a suitable base gives intermediate 111. Biaryls of formula I-39 can be prepared from 111 by treatment with boronic acids of formula 52 in presence of a suitable palladium catalyst and base, followed by deprotection. (Scheme 36)

Alcohols of formula 112 can be converted to bromides of formula 113 by treatment with carbon tetrabromide in presence of triphenylphosphine. Bromides 113 can be converted to amines of formula 114 by treatment with amines of formula HNR'R" in presence of a suitable base. Deprotection gives hydroxyquinazolinones of formula I-40. (Scheme 35)

Scheme 37

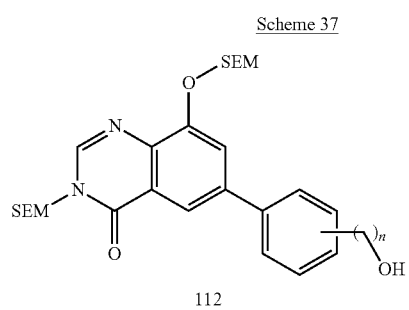

112

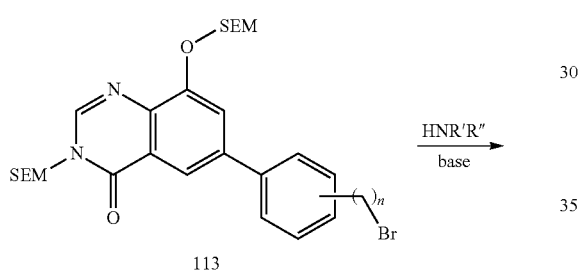

113

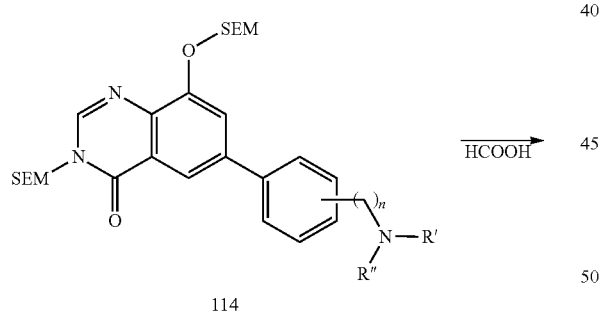

114

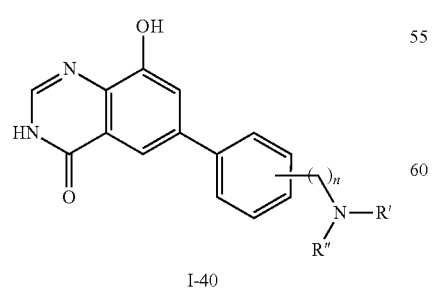

I-40

R' and R" are lower alkyl.

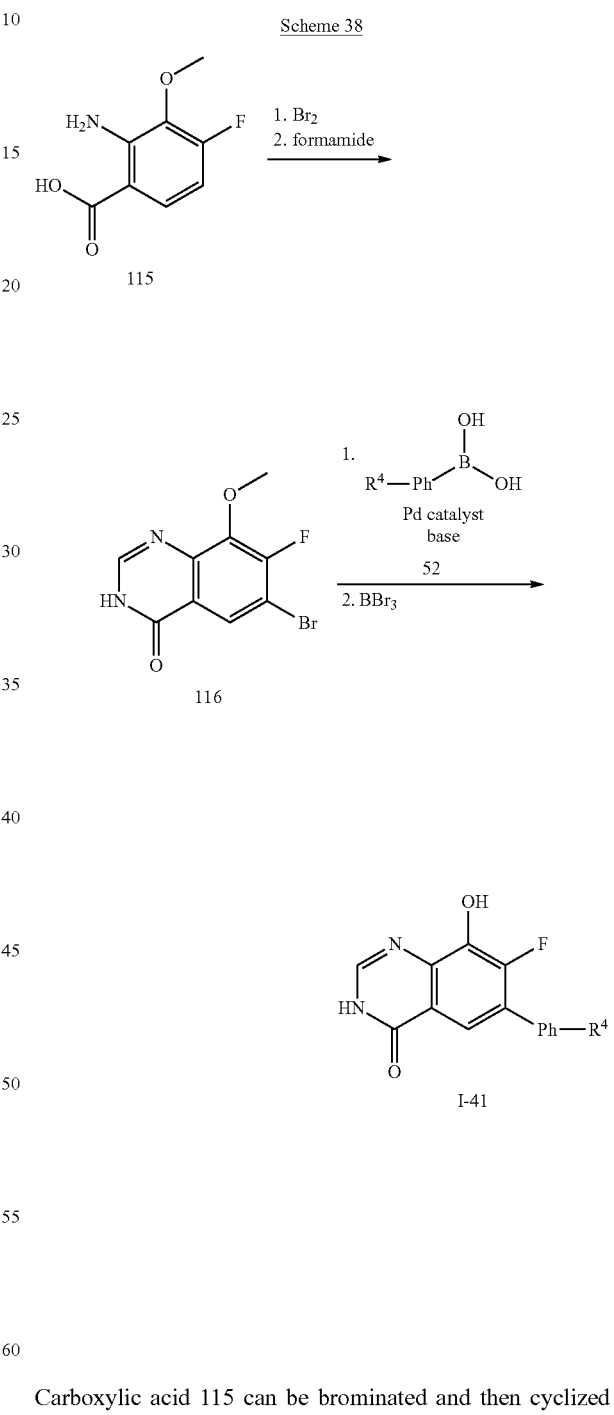

Carboxylic acid 115 can be brominated and then cyclized with formamide to give bromide 116. Biaryls of formula I-41 can be prepared from 116 by treatment with boronic acids of formula 52 in presence of a suitable palladium catalyst and base (Suzuki coupling), followed by deprotection.

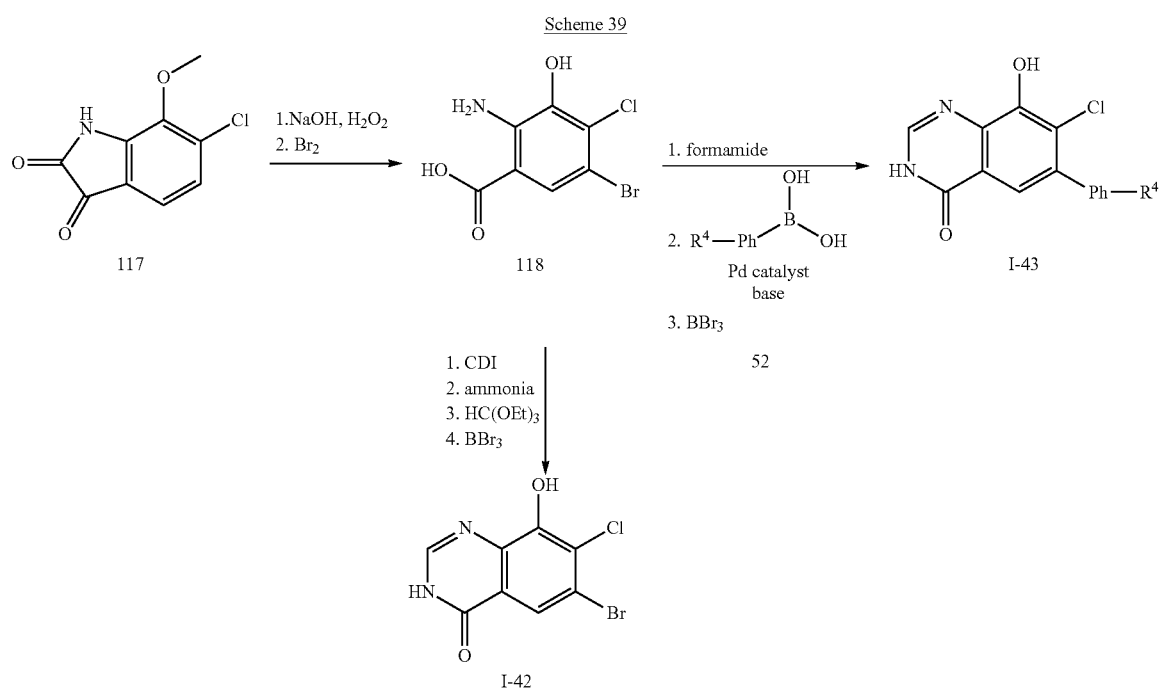

Scheme 39

Isatin derivative 117 can be oxidized with a suitable oxidizing agent such as hydrogen peroxide and then brominated to carboxylic acid 118. Cyclization with formamide and reaction with boronic acids in presence of a suitable palladium catalyst and base (Suzuki coupling), followed by deprotection gives biaryls of formula I-43. Treatment of acid 118 with CDI, followed by ammonia, cyclization and deprotection gives hydroxyquinazolinone I-42. (Scheme 39)

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as COMT inhibitors.

The compounds were investigated in accordance with the test given hereinafter.

COMT-Fluorescence Assay (published in WO2012/013614)

Assay Principle

The fluorescence assay for the identification of COMT inhibitors is based on the fact that the substrate which is a 4-Nitrocatechol labeled with the fluorescence dye Alexa Fluor 488 undergoes a specific intramolecular interaction resulting in a decreased fluorescence of Alexa Fluor 488. This intramolecular interaction is disturbed if the 4-Nitrocatechol is methylated. Therefore methylation of the 4-Nitrocatechol-Alexa Fluor 488 substrate by COMT via the transfer of the methyl group of S-Adenosylmethionine (SAM) to the substrate leads to an increase of fluorescence intensity. This increase of fluorescence intensity can be followed in a kinetic measurement. The slope in the linear range of the kinetic is calculated. An inhibitor compound decreases the slope.

Materials

Plates: 384-well microtiter plate, Corning black with flat clear bottom, non binding surface, polystyrene (ref. 3655)

Reagent and Buffer Stock Solutions:

Buffer stock solutions: 0.1 M Phosphate buffer pH 7.6 ($Na_2HPO_4$ Fluka 71644, $NaH_2PO_4$ Merck 6346.0500), stored at 4° C.

580 mM $MgCl_2$ (Merck 1.0833.0250), stored at RT

1M CaCl$_2$ stored at 4° C.
65 mM DTT (Sigma D-0632), stored at −20° C.
Rec. human COMT: preparations from Daniel Schlatter
  46 µM, aliquots stored at −80° C.
4-Nitrocatechol-Alexa488: prepared in house, 1.3 mM in DMSO, stored at RT (dark)
S-Adenosyl-methionine: 10 mM in H$_2$O (Sigma-Aldrich A2804), stored at −20° C.

Profiling Method
Reagent and Buffer Solutions:
Assaybuffer (endconc.): 40 mM Phosphate buffer pH 7.6
  2.88 mM MgCl$_2$
  0.9 mM DTT
  0.25 mM CaCl$_2$
Compound dilutions: dilutions in 100% DMSO (Sigma 41640), 6.25% final DMSO concentration in assay
Rec. human COMT: 80 nM in assay buffer, 25 nM final assay concentration
4-Nitrocatechol-Alexa488/SAM:
  320 nM 4-Nitrocatechol-Alexa488 and 800 nM SAM in assay buffer
  200 nM final assay concentration 4-Nitrocatechol-Alexa488
  500 nM final assay concentration SAM
Method

| | | |
|---|---|---|
| 10 µl | hCOMT (Multidrop) | |
| 2 µl | Cmpd. (100% DMSO) (Biomek FX) | |
| 1 min | mixing by shaking (Variomag Teleshake 1500 rpm) | |
| 20 l | SAM/4-Nitrocatechol-Alexa488 Mix (Multidrop) | |
| 5 min | mixing by shaking (Variomag Teleshake 1500 rpm) | |
| readout | kinetic readout (every 60 s, 180 times, reader at RT) (exc. 475(40) nm, em. 535(45) nm; intensity 7.5%; exposure 1 s) | |

Signal [rfu/min]=slope from linear range of the kinetic

HTS Method
Reagent and Buffer Solutions:
Assay buffer (end conc.): 40 mM Phosphate buffer pH 7.6
  2.88 mM MgCl$_2$
  0.9 mM DTT
  0.25 mM CaCl$_2$
Compound dilutions: dilutions in 100% DMSO (Sigma 41640), 6.25% final DMSO concentration in assay
Rec. human COMT: 75 nM in assay buffer, 25 nM final assay concentration
4-Nitrocatechol-Alexa488/SAM:
  430 nM 4-Nitrocatechol-Alexa488 and 1070 nM SAM in assay buffer
  200 nM final assay concentration 4-Nitrocatechol-Alexa488
  500 nM final assay concentration SAM
Method

| | | |
|---|---|---|
| 10 µl | hCOMT | |
| 6 µl | Cmpd. (from prediluted compound plate in water with 31% DMSO) | |
| 1 min | mixing by shaking (Variomag Teleshake 1500 rpm) | |
| 14 µl | SAM/4-Nitrocatechol-Alexa488 Mix | |
| 1 min | mixing by shaking (Variomag Teleshake 1500 rpm) followed by mixing with Biomek FX 10 times, 18 µl | |
| 15 min | incubation #1 at room temperature | |
| readout | start-point on plate::vision reader (exc. 475(40) nm, em. 535(45) nm; intensity 7.5%; exposure 1 s) | |
| 40 min | incubation #2 at room temperature | |
| readout | end-point on plate::vision reader (exc. 475(40) nm, em. 535(45) nm; intensity 7.5%; exposure 1 s) | |

Signal [rfu/min]=(rfu(end-point)−rfu(startpoint))/incubation_time_#2

TABLE 1

List of examples and IC$_{50}$ (uM) data of novel compounds

| Example | IC$_{50}$ |
|---|---|
| 1 | 0.50 |
| 2 | 0.03 |
| 3 | 4.21 |
| 4 | 0.17 |
| 5 | 0.66 |
| 6 | 0.02 |
| 7 | 0.01 |
| 8 | 0.10 |
| 9 | 1.33 |
| 10 | 1.09 |
| 11 | 1.25 |
| 12 | 1.47 |
| 13 | 1.00 |
| 14 | 4.90 |
| 15 | 1.20 |
| 16 | 0.56 |
| 17 | 1.10 |
| 18 | 0.90 |
| 19 | 0.08 |
| 20 | 0.09 |
| 21 | 0.10 |
| 22 | 0.20 |
| 23 | 0.01 |
| 24 | 0.01 |
| 25 | 0.02 |
| 26 | 0.19 |
| 27 | 0.04 |
| 28 | 0.04 |
| 29 | 2.80 |
| 30 | 1.40 |
| 31 | 0.02 |
| 32 | 2.00 |
| 33 | 0.02 |
| 34 | 0.17 |
| 35 | 1.30 |
| 36 | 0.08 |
| 37 | 0.03 |
| 38 | 0.03 |
| 39 | 0.02 |
| 40 | 0.01 |
| 41 | 0.16 |
| 42 | 1.03 |
| 43 | 0.04 |
| 44 | 0.11 |
| 45 | 0.03 |
| 46 | 0.01 |
| 47 | 0.06 |
| 48 | 0.05 |
| 49 | 0.02 |
| 50 | 0.01 |
| 51 | 0.26 |
| 52 | 0.01 |
| 53 | 0.02 |
| 54 | 0.06 |
| 55 | 0.01 |
| 56 | 0.01 |
| 57 | 0.01 |
| 58 | 0.01 |
| 59 | 0.04 |
| 60 | 0.02 |
| 61 | 0.13 |
| 62 | 0.01 |
| 63 | 0.04 |
| 64 | 0.01 |

TABLE 1-continued

List of examples and IC$_{50}$ (uM) data of novel compounds

| Example | IC$_{50}$ |
|---|---|
| 65 | 4.83 |
| 66 | 0.10 |
| 67 | 7.45 |
| 68 | 0.06 |
| 69 | 1.04 |
| 70 | 0.02 |
| 71 | 0.02 |
| 72 | 0.03 |
| 73 | 0.04 |
| 74 | 0.25 |
| 75 | 0.51 |
| 76 | 4.60 |
| 77 | 0.05 |
| 78 | 0.32 |
| 79 | 0.15 |
| 80 | 0.09 |
| 81 | 0.01 |
| 82 | 0.04 |
| 83 | 0.06 |
| 84 | 0.11 |
| 85 | 0.17 |
| 86 | 0.03 |
| 87 | 0.23 |
| 88 | 0.12 |
| 89 | 0.02 |
| 90 | 0.02 |
| 91 | 0.10 |
| 92 | 0.06 |
| 93 | 0.16 |
| 94 | 0.09 |
| 95 | 0.97 |
| 96 | 0.03 |
| 97 | 0.01 |
| 98 | 0.04 |
| 99 | 0.10 |
| 100 | 0.05 |
| 101 | 0.01 |
| 102 | 0.001 |
| 103 | 0.01 |
| 104 | 0.01 |
| 105 | 0.07 |
| 106 | 0.02 |
| 107 | 0.02 |
| 108 | 0.08 |
| 109 | 0.02 |
| 110 | 0.02 |
| 111 | 0.02 |
| 112 | 0.17 |
| 113 | 3.60 |
| 114 | 0.04 |
| 115 | 0.05 |
| 116 | 0.18 |
| 117 | 0.04 |
| 118 | 0.01 |
| 119 | 0.61 |
| 120 | 0.09 |
| 121 | 0.03 |
| 122 | 0.01 |
| 123 | 0.01 |
| 124 | 0.2 |
| 125 | 0.02 |
| 126 | 0.14 |
| 127 | 0.02 |
| 128 | 0.02 |
| 129 | 0.03 |
| 130 | 0.03 |
| 131 | 0.04 |
| 132 | 0.02 |
| 133 | 0.02 |
| 134 | 0.01 |
| 135 | 0.01 |
| 136 | 3.21 |
| 137 | 0.06 |
| 138 | 0.02 |
| 139 | 0.29 |
| 140 | 5.04 |
| 141 | 0.01 |
| 142 | 0.01 |
| 143 | 0.81 |
| 144 | 0.05 |
| 145 | 0.07 |
| 146 | 0.02 |
| 147 | 0.02 |
| 148 | 0.01 |
| 149 | 0.01 |
| 150 | 0.00 |
| 151 | 0.16 |
| 152 | 0.07 |
| 153 | 0.19 |
| 154 | 0.02 |
| 155 | 1.38 |
| 156 | 0.01 |
| 157 | 0.02 |
| 158 | 0.03 |
| 159 | 0.55 |
| 160 | 0.08 |
| 161 | 0.05 |
| 162 | 0.03 |
| 163 | 0.04 |
| 164 | 0.02 |
| 165 | 0.03 |
| 166 | 0.06 |
| 167 | 0.26 |
| 168 | 0.03 |
| 169 | 0.04 |
| 170 | 0.02 |
| 171 | 0.08 |
| 172 | 0.02 |
| 173 | 0.05 |
| 174 | 0.07 |
| 175 | 0.02 |
| 176 | 0.02 |
| 177 | 0.04 |
| 178 | 0.01 |
| 179 | 0.09 |
| 180 | 0.27 |
| 181 | 0.02 |
| 182 | 0.03 |
| 183 | 0.07 |
| 184 | 0.02 |
| 185 | 0.02 |
| 186 | 0.03 |
| 187 | 0.71 |
| 188 | 1.27 |
| 189 | 0.84 |
| 190 | 1.29 |
| 191 | 0.03 |
| 192 | 0.02 |
| 193 | 1.28 |
| 194 | 0.73 |
| 195 | 0.01 |
| 196 | 0.12 |
| 197 | 2.53 |
| 198 | 0.01 |
| 199 | 0.02 |
| 200 | 0.01 |
| 201 | 0.02 |
| 202 | 0.02 |
| 203 | 0.01 |
| 204 | 0.02 |
| 205 | 0.17 |
| 206 | 0.03 |
| 207 | 0.02 |
| 208 | 0.05 |
| 209 | 0.37 |
| 210 | 0.03 |
| 211 | 0.07 |
| 212 | 0.87 |
| 213 | 0.03 |
| 214 | 0.64 |
| 215 | 0.07 |
| 216 | 0.04 |

TABLE 1-continued

List of examples and IC$_{50}$ (uM) data of novel compounds

| Example | IC$_{50}$ |
|---|---|
| 217 | 0.05 |
| 218 | 1.40 |
| 219 | 0.02 |
| 220 | 0.02 |
| 221 | 0.03 |
| 222 | 0.06 |
| 223 | 0.02 |
| 224 | 0.22 |
| 225 | 0.06 |
| 226 | 1.03 |
| 227 | 0.05 |
| 228 | 0.05 |
| 229 | 0.054 |
| 230 | 0.02 |
| 231 | 0.01 |
| 232 | 0.31 |
| 233 | 1.17 |
| 234 | 0.98 |
| 235 | 0.03 |
| 236 | 0.02 |
| 237 | 0.02 |
| 238 | 0.03 |
| 239 | 0.05 |
| 240 | 0.03 |
| 241 | 0.03 |
| 242 | 0.22 |
| 243 | 0.13 |
| 244 | 0.15 |
| 245 | 0.73 |
| 246 | 1.59 |
| 247 | 0.05 |
| 248 | 0.10 |
| 249 | 3.23 |
| 250 | 1.14 |
| 251 | 0.74 |
| 252 | 0.03 |
| 253 | 0.10 |
| 254 | 1.40 |
| 255 | 0.12 |
| 256 | 0.036 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD).

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

| Example | Structure |
|---|---|
| 1 | 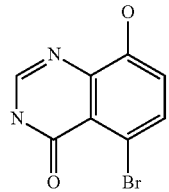 |
| 2 | 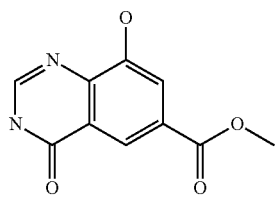 [SMILES: COC(=O)c1cc(O)c2nc[nH]c(=O)c2c1] |
| 3 | 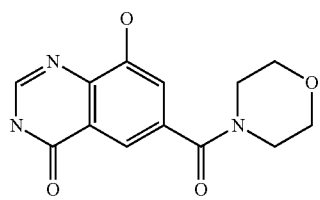 [SMILES: O=C(c1cc(O)c2nc[nH]c(=O)c2c1)N1CCOCC1] |
| 4 | 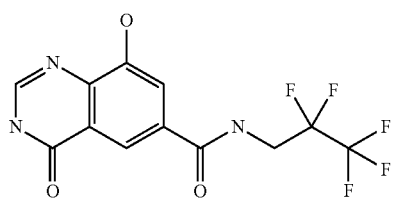 [SMILES: O=C(NCC(F)(F)C(F)(F)F)c1cc(O)c2nc[nH]c(=O)c2c1] |
| 5 | 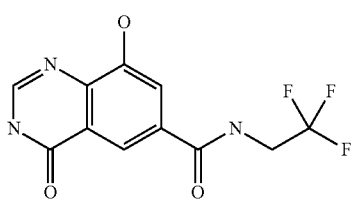 [SMILES: O=C(NCC(F)(F)F)c1cc(O)c2nc[nH]c(=O)c2c1] |
| 6 | 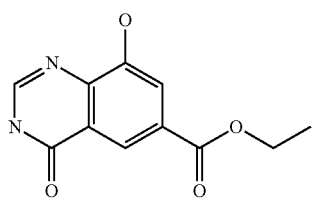 [SMILES: CCOC(=O)c1cc(O)c2nc[nH]c(=O)c2c1] |
| 7 | 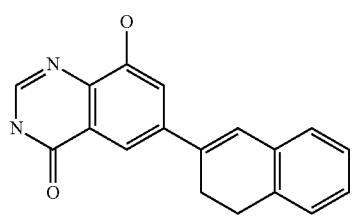 [SMILES: O=c1[nH]cnc2c(O)cc(C3=Cc4ccccc4CC3)cc12] |
-continued
| Example | Structure |
|---|---|
| 8 | 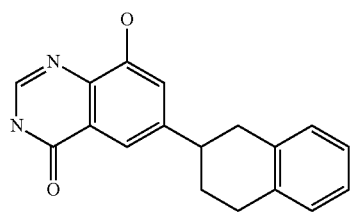 [SMILES: O=c1[nH]cnc2c(O)cc(C3CCc4ccccc4C3)cc12] |
| 9 | 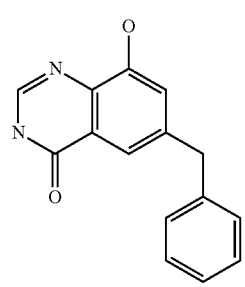 [SMILES: O=c1[nH]cnc2c(O)cc(Cc3ccccc3)cc12] |
| 10 | 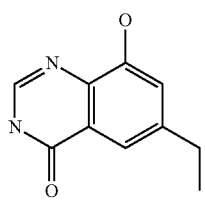 |
| 11 | 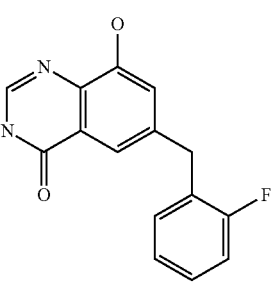 [SMILES: O=c1[nH]cnc2c(O)cc(Cc3ccccc3F)cc12] |
| 12 | 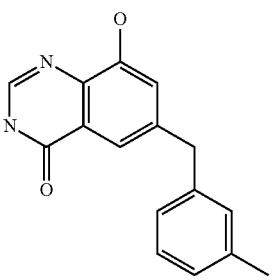 [SMILES: Cc1cccc(Cc2cc(O)c3nc[nH]c(=O)c3c2)c1] |
| 13 | 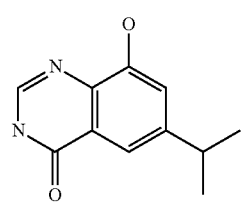 |

-continued
| Example | Structure |
|---|---|
| 14 | 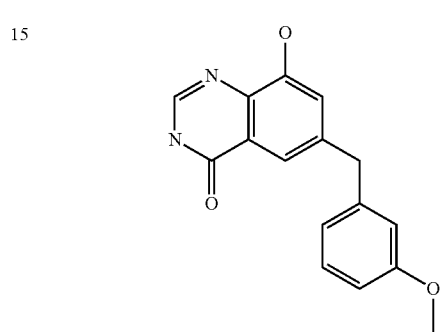 |
| 15 | 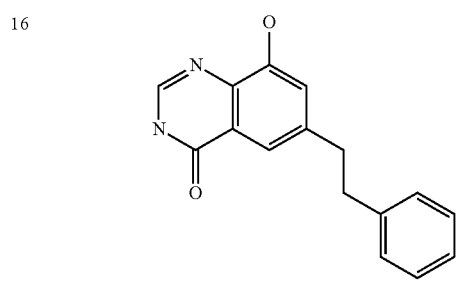 |
| 16 | 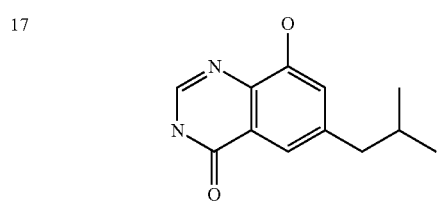 |
| 17 | 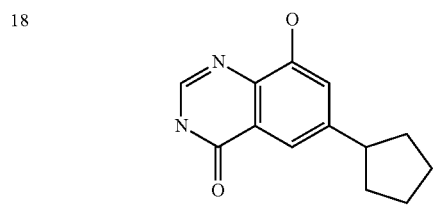 |
| 18 | 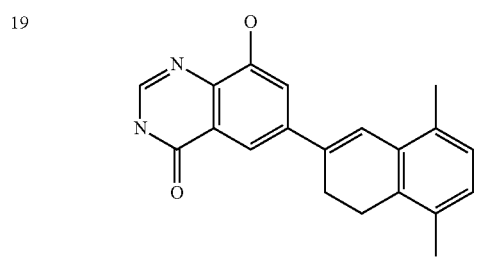 |
| 19 | 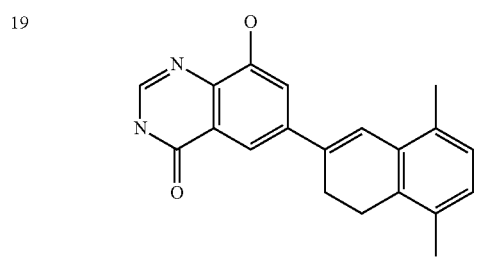 |
-continued
| Example | Structure |
|---|---|
| 20 | 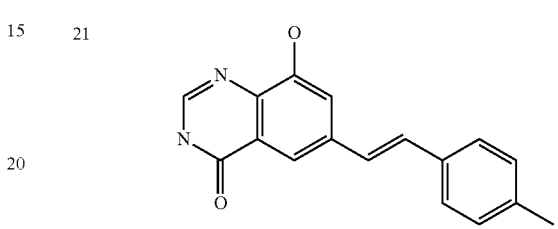 |
| 21 | 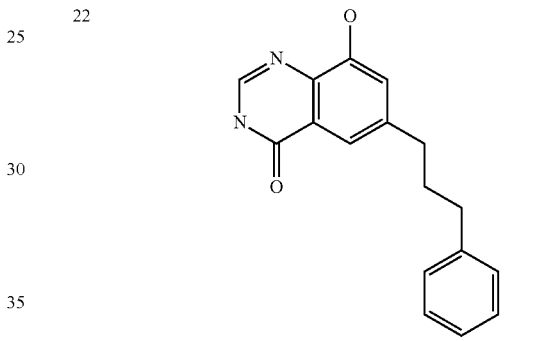 |
| 22 | 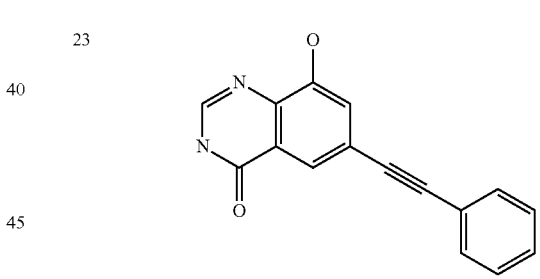 |
| 23 | 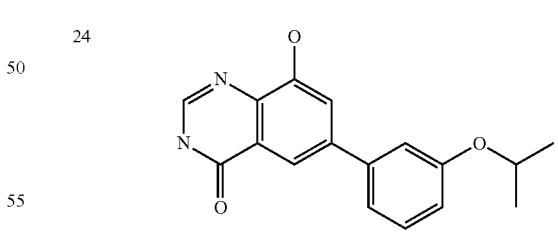 |
| 24 | 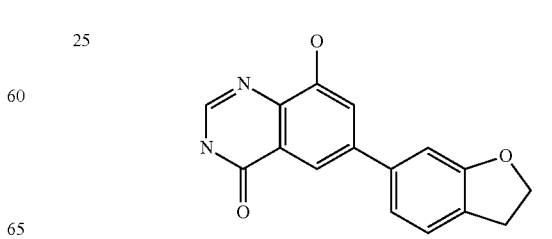 |
| 25 | 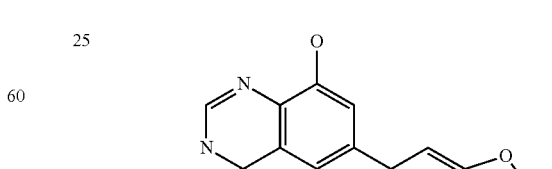 |

| Example | Structure |
|---|---|
| 26 | 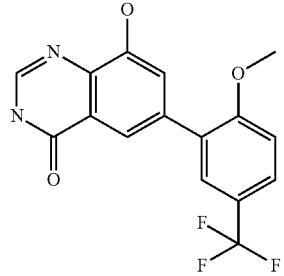 [SMILES: COc1ccc(C(F)(F)F)cc1-c1cc(O)c2nc[nH]c(=O)c2c1] |
| 27 | 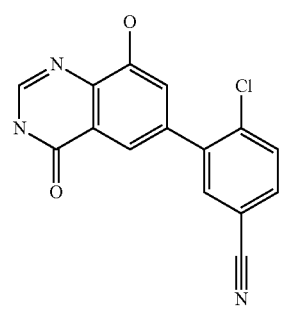 [SMILES: N#Cc1ccc(Cl)c(-c2cc(O)c3nc[nH]c(=O)c3c2)c1] |
| 28 | 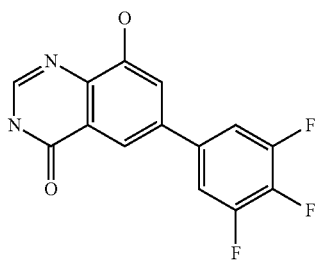 [SMILES: O=c1[nH]cnc2c(O)cc(-c3cc(F)c(F)c(F)c3)cc12] |
| 29 | 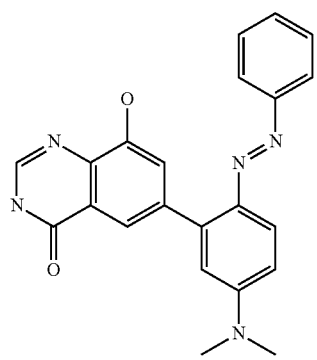 [SMILES: CN(C)c1ccc(/N=N/c2ccccc2)c(-c2cc(O)c3nc[nH]c(=O)c3c2)c1] |
| 30 | 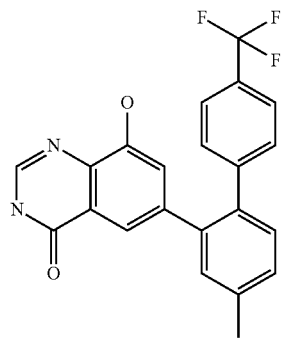 [SMILES: Cc1ccc(-c2ccc(C(F)(F)F)cc2)c(-c2cc(O)c3nc[nH]c(=O)c3c2)c1] |
| Example | Structure |
|---|---|
| 31 | 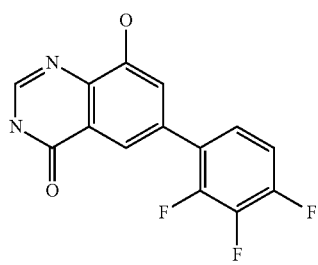 [SMILES: O=c1[nH]cnc2c(O)cc(-c3ccc(F)c(F)c3F)cc12] |
| 32 | 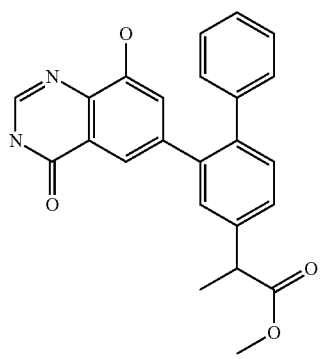 [SMILES: COC(=O)C(C)c1ccc(-c2ccccc2)c(-c2cc(O)c3nc[nH]c(=O)c3c2)c1] |
| 33 | 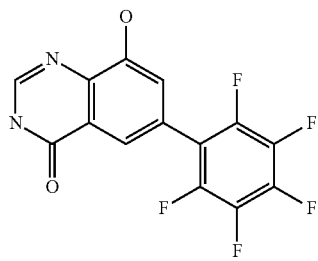 [SMILES: O=c1[nH]cnc2c(O)cc(-c3c(F)c(F)c(F)c(F)c3F)cc12] |
| 34 | 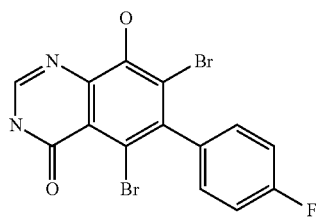 [SMILES: O=c1[nH]cnc2c(O)c(Br)c(-c3ccc(F)cc3)c(Br)c12] |
| 35 | 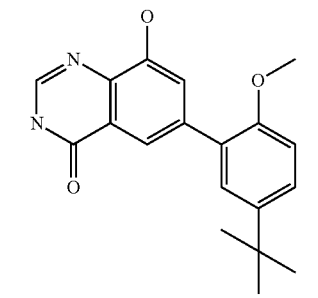 [SMILES: COc1ccc(C(C)(C)C)cc1-c1cc(O)c2nc[nH]c(=O)c2c1] |

-continued
| Example | Structure |
|---|---|
| 36 | 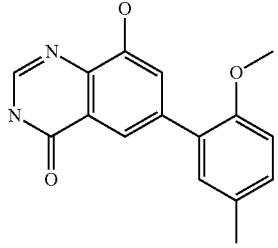 [SMILES: COc1ccc(C)cc1-c1cc(O)c2nc[nH]c(=O)c2c1] |
| 37 | 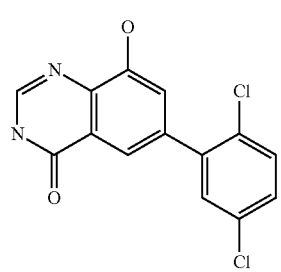 [SMILES: O=c1[nH]cnc2c(O)cc(-c3cc(Cl)ccc3Cl)cc12] |
| 38 | 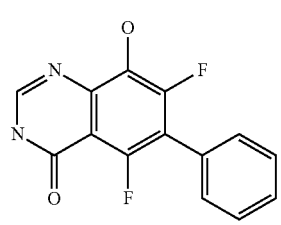 [SMILES: O=c1[nH]cnc2c(O)c(F)c(-c3ccccc3)c(F)c12] |
| 39 | 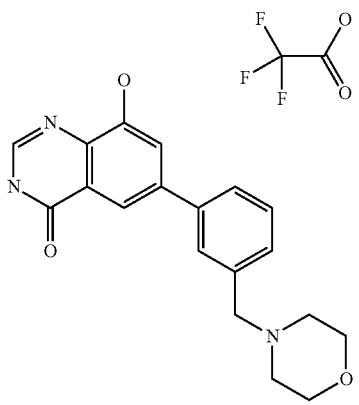 [SMILES: O=c1[nH]cnc2c(O)cc(-c3cccc(CN4CCOCC4)c3)cc12 ; O=C(O)C(F)(F)F] |
| 40 | 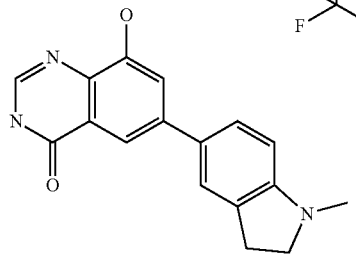 |
-continued
| Example | Structure |
|---|---|
| 41 | 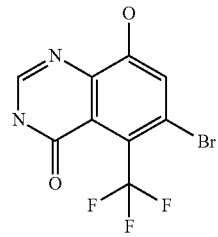 [SMILES: O=c1[nH]cnc2c(O)cc(Br)c(C(F)(F)F)c12] |
| 42 | 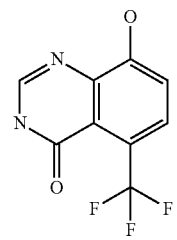 [SMILES: O=c1[nH]cnc2c(O)ccc(C(F)(F)F)c12] |
| 43 | 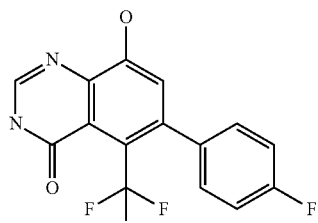 |
| 44 | 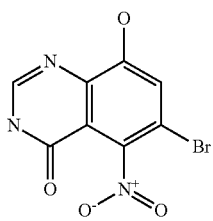 [SMILES: O=c1[nH]cnc2c(O)cc(Br)c([N+](=O)[O-])c12] |
| 45 | 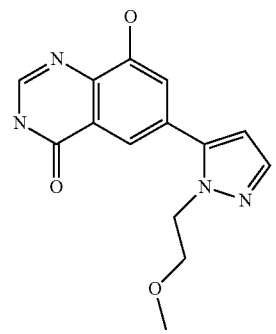 [SMILES: COCCn1nccc1-c1cc(O)c2nc[nH]c(=O)c2c1] |
| 46 | 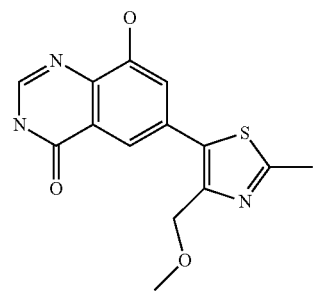 [SMILES: COCc1nc(C)sc1-c1cc(O)c2nc[nH]c(=O)c2c1] |

-continued

| Example | Structure |
|---|---|
| 47 | (quinazolinone with pyrazole substituted by 2-methoxyethyl) |
| 48 | (quinazolinone with 2-chloro-5-methylsulfonylphenyl) |
| 49 | (quinazolinone with 4-fluorophenyl and phenyl) |
| 50 | (quinazolinone with 4-fluorophenyl and 4-methylphenyl) |

-continued

| Example | Structure |
|---|---|
| 51 | (bromo quinazolinone with 4-fluorophenyl and 4-methylphenyl) |
| 52 | (quinazolinone with 4-fluorophenyl and 3-methylsulfonylphenyl) |
| 53 | (quinazolinone with 4-fluorophenyl and 3-trifluoromethylphenyl) |
| 54 | (cyano quinazolinone with 4-fluorophenyl) |

-continued
| Example | Structure |
|---|---|
| 55 | 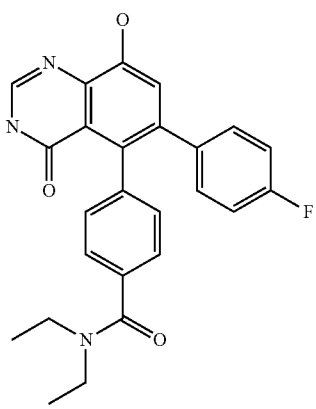 [SMILES: CCN(CC)C(=O)c1ccc(-c2c(-c3ccc(F)cc3)cc(O)c3nc[nH]c(=O)c23)cc1] |
| 56 | 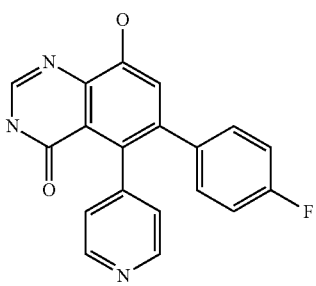 [SMILES: O=c1[nH]cnc2c(O)cc(-c3ccc(F)cc3)c(-c3ccncc3)c12] |
| 57 | 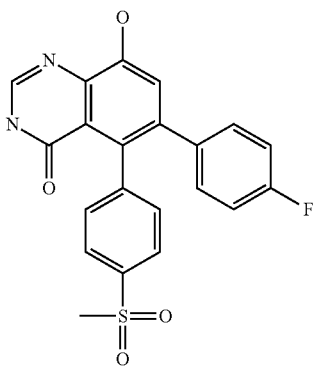 [SMILES: CS(=O)(=O)c1ccc(-c2c(-c3ccc(F)cc3)cc(O)c3nc[nH]c(=O)c23)cc1] |
| 58 | 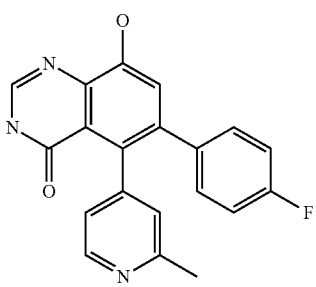 [SMILES: Cc1cc(-c2c(-c3ccc(F)cc3)cc(O)c3nc[nH]c(=O)c23)ccn1] |
-continued
| Example | Structure |
|---|---|
| 59 | 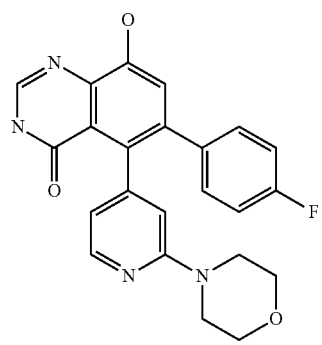 [SMILES: O=c1[nH]cnc2c(O)cc(-c3ccc(F)cc3)c(-c3ccnc(N4CCOCC4)c3)c12] |
| 60 | 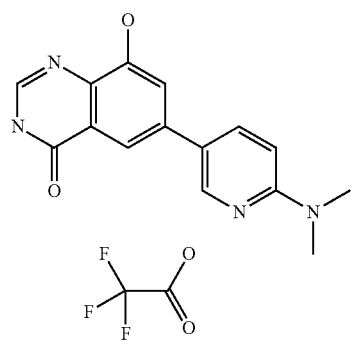 [SMILES: CN(C)c1ccc(-c2cc(O)c3nc[nH]c(=O)c3c2)cn1 ; O=C(O)C(F)(F)F] |
| 61 | 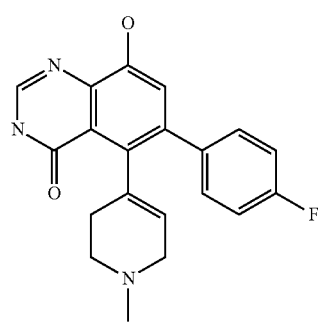 [SMILES: CN1CC=C(c2c(-c3ccc(F)cc3)cc(O)c3nc[nH]c(=O)c23)CC1] |
| 62 | 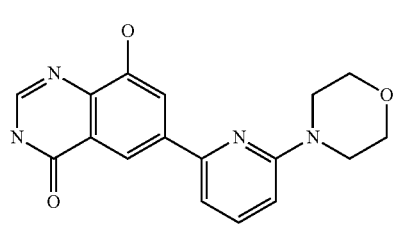 [SMILES: O=c1[nH]cnc2c(O)cc(-c3cccc(N4CCOCC4)n3)cc12] |
| 63 | 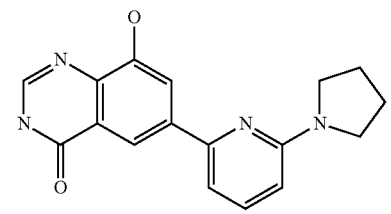 [SMILES: O=c1[nH]cnc2c(O)cc(-c3cccc(N4CCCC4)n3)cc12] |

-continued
| Example | Structure |
|---|---|
| 64 | 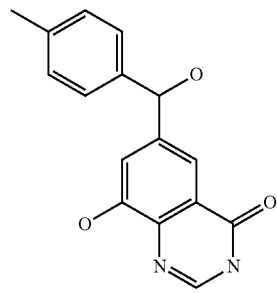 [SMILES: Cc1ccc(C(O)c2cc(O)c3nc[nH]c(=O)c3c2)cc1] |
| 65 | 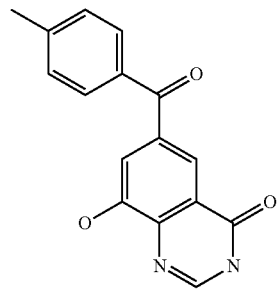 [SMILES: Cc1ccc(C(=O)c2cc(O)c3nc[nH]c(=O)c3c2)cc1] |
| 66 | 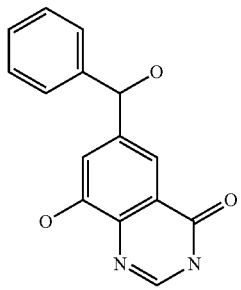 [SMILES: O=c1[nH]cnc2c(O)cc(C(O)c3ccccc3)cc12] |
| 67 | 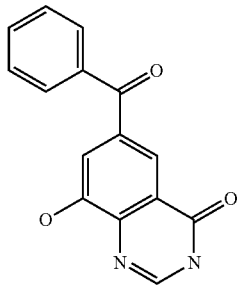 [SMILES: O=C(c1ccccc1)c1cc(O)c2nc[nH]c(=O)c2c1] |
| 68 | 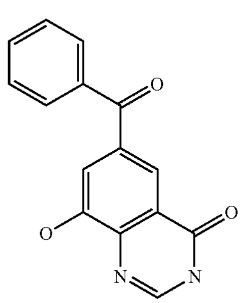 |
-continued
| Example | Structure |
|---|---|
| 69 | 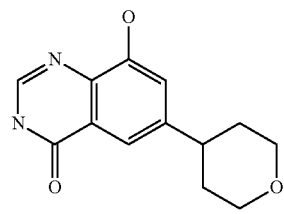 [SMILES: O=c1[nH]cnc2c(O)cc(C3CCOCC3)cc12] |
| 70 | 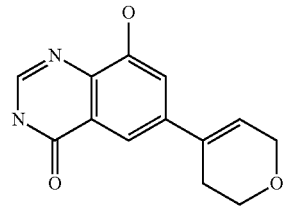 |
| 71 | 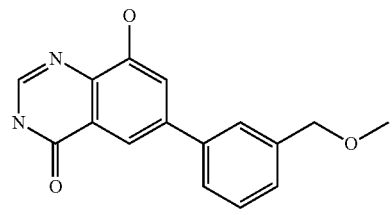 [SMILES: COCc1cccc(-c2cc(O)c3nc[nH]c(=O)c3c2)c1] |
| 72 | 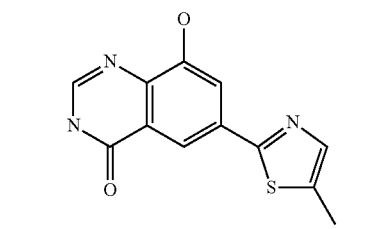 [SMILES: Cc1cnc(-c2cc(O)c3nc[nH]c(=O)c3c2)s1] |
| 73 | 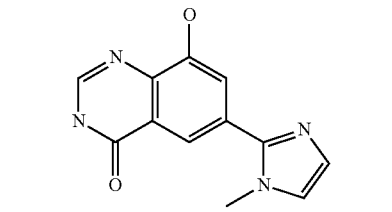 [SMILES: Cn1ccnc1-c1cc(O)c2nc[nH]c(=O)c2c1] |
| 74 | 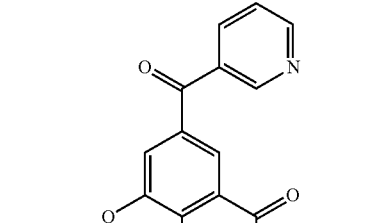 |

-continued
| Example | Structure |
|---|---|
| 75 | 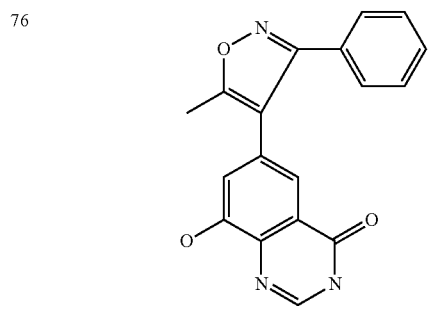 |
| 76 | 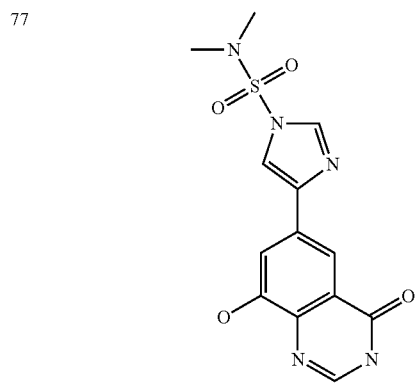 |
| 77 | 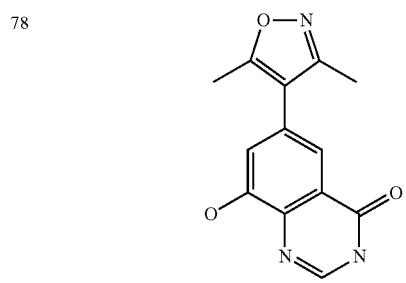 |
| 78 | 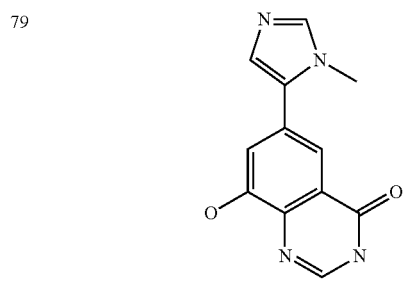 |
| 79 | 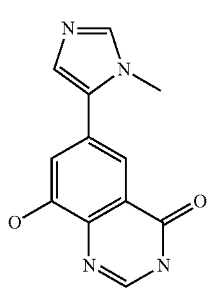 [SMILES: Cn1cncc1-c1cc(O)c2nc[nH]c(=O)c2c1] |
-continued
| Example | Structure |
|---|---|
| 80 | 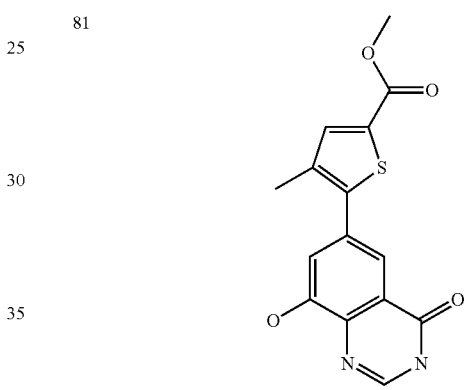 |
| 81 | 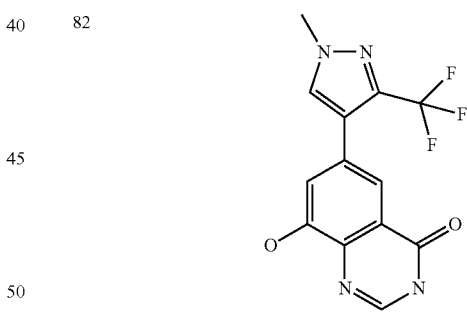 |
| 82 | 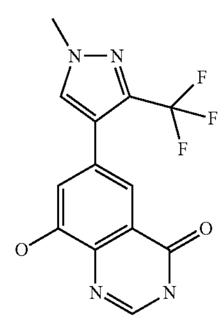 [SMILES: Cn1cc(-c2cc(O)c3nc[nH]c(=O)c3c2)c(C(F)(F)F)n1] |
| 83 | 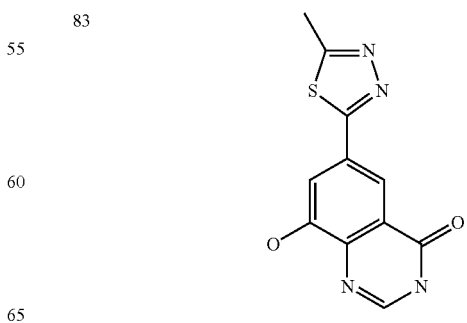 |

-continued
| Example | Structure |
|---|---|
| 84 | 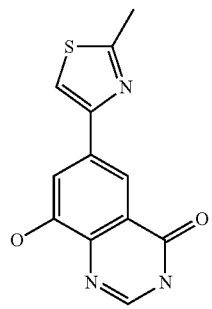 [SMILES: Cc1nc(-c2cc(O)c3nc[nH]c(=O)c3c2)cs1] |
| 85 | 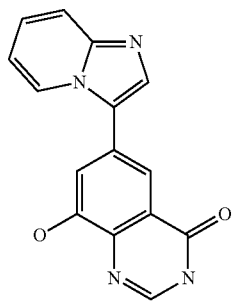 [SMILES: O=c1[nH]cnc2c(O)cc(-c3cnc4ccccn34)cc12] |
| 86 | 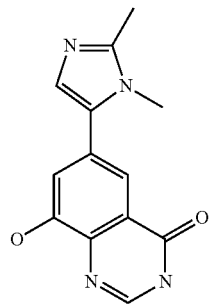 [SMILES: Cc1ncc(-c2cc(O)c3nc[nH]c(=O)c3c2)n1C] |
| 87 | 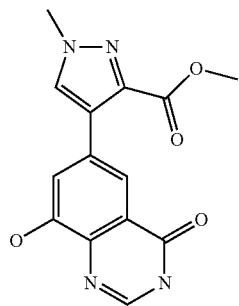 |
| 88 | 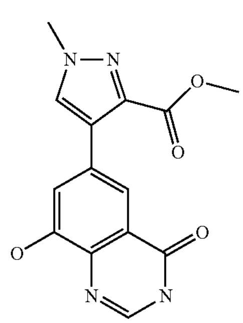 [SMILES: COC(=O)c1nn(C)cc1-c1cc(O)c2nc[nH]c(=O)c2c1] |
-continued
| Example | Structure |
|---|---|
| 89 | 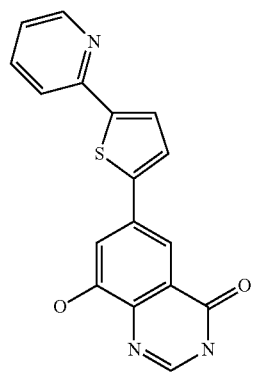 [SMILES: O=c1[nH]cnc2c(O)cc(-c3ccc(-c4ccccn4)s3)cc12] |
| 90 | 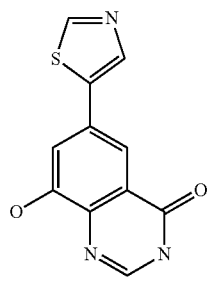 [SMILES: O=c1[nH]cnc2c(O)cc(-c3cncs3)cc12] |
| 91 | 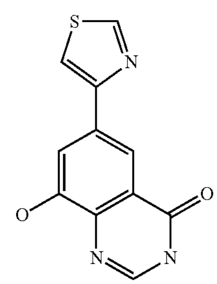 [SMILES: O=c1[nH]cnc2c(O)cc(-c3cscn3)cc12] |
| 92 | 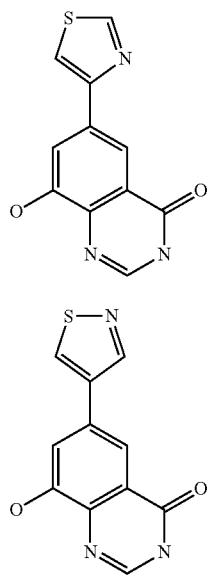 |
| 93 | 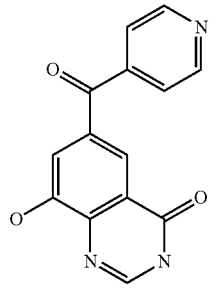 [SMILES: O=C(c1ccncc1)c1cc(O)c2nc[nH]c(=O)c2c1] |

-continued
| Example | Structure |
|---|---|
| 94 | 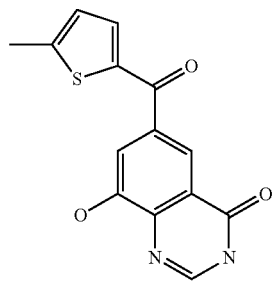 [SMILES: Cc1ccc(C(=O)c2cc(O)c3nc[nH]c(=O)c3c2)s1] |
| 95 | 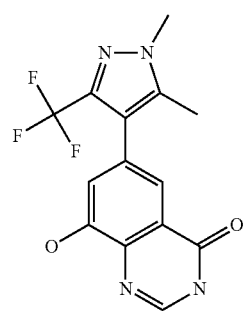 [SMILES: Cc1c(-c2cc(O)c3nc[nH]c(=O)c3c2)c(C(F)(F)F)nn1C] |
| 96 | 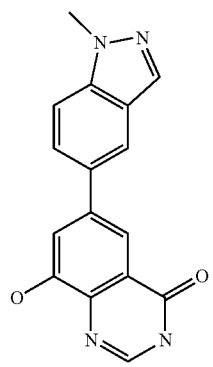 [SMILES: Cn1ncc2cc(-c3cc(O)c4nc[nH]c(=O)c4c3)ccc21] |
| 97 | 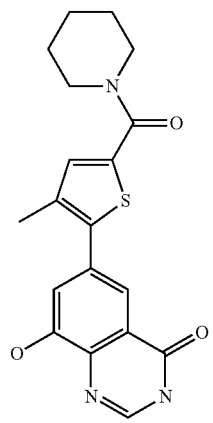 [SMILES: Cc1cc(C(=O)N2CCCCC2)sc1-c1cc(O)c2nc[nH]c(=O)c2c1] |
-continued
| Example | Structure |
|---|---|
| 98 | 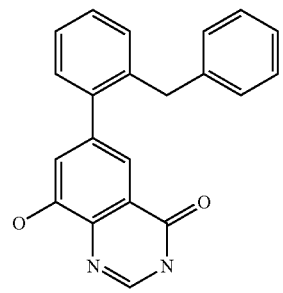 [SMILES: O=c1[nH]cnc2c(O)cc(-c3ccccc3Cc3ccccc3)cc12] |
| 99 | 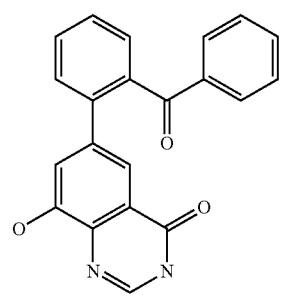 [SMILES: O=C(c1ccccc1)c1ccccc1-c1cc(O)c2nc[nH]c(=O)c2c1] |
| 100 | 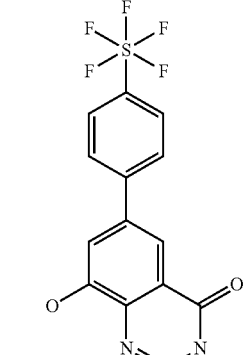 |
| 101 | 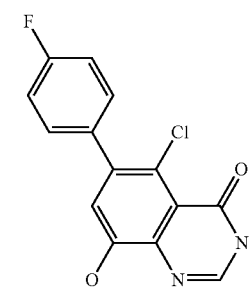 [SMILES: O=c1[nH]cnc2c(O)cc(-c3ccc(F)cc3)c(Cl)c12] |
| 102 | 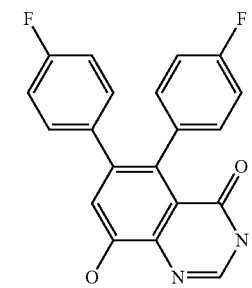 [SMILES: O=c1[nH]cnc2c(O)cc(-c3ccc(F)cc3)c(-c3ccc(F)cc3)c12] |

-continued
| Example | Structure |
|---|---|
| 103 | 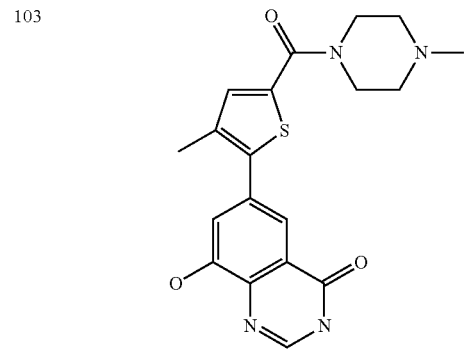 |
| 104 | 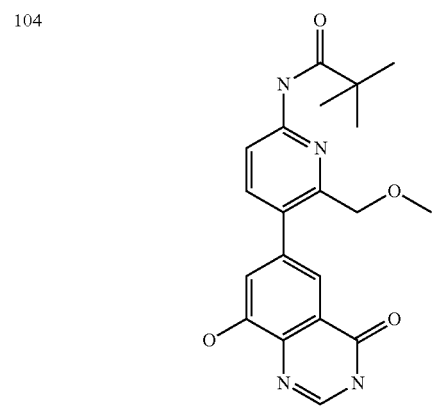 |
| 105 | 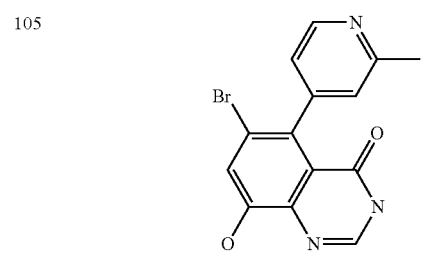 |
| 106 | 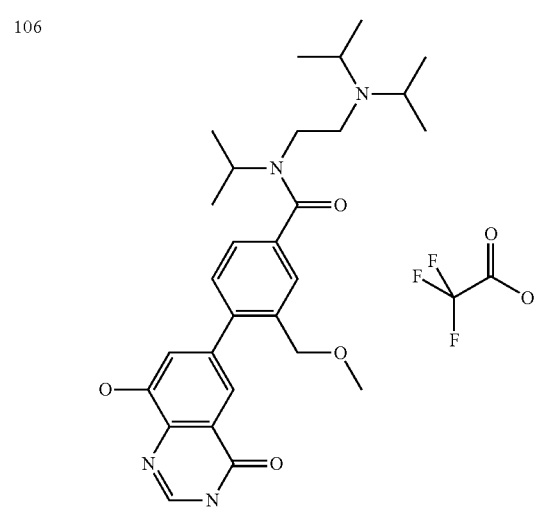 |
-continued
| Example | Structure |
|---|---|
| 107 | 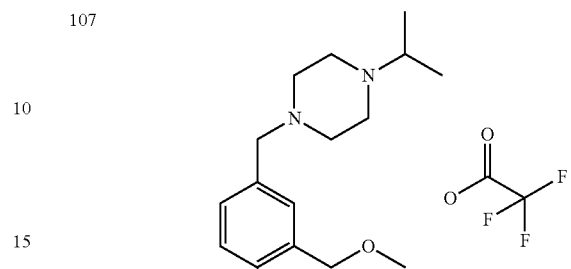 |
| 108 | 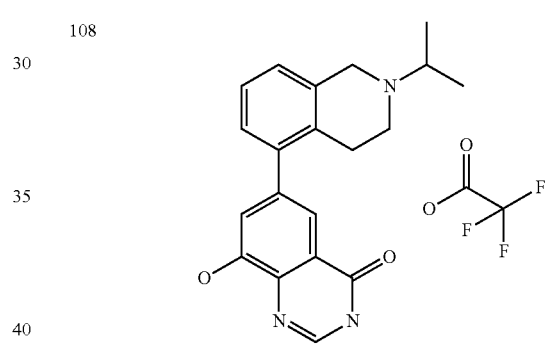 |
| 109 | 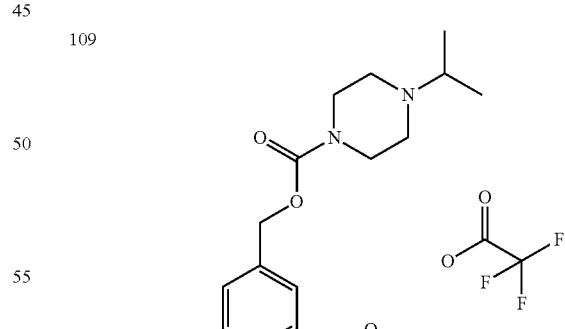 |

| Example | Structure |
|---|---|
| 110 | 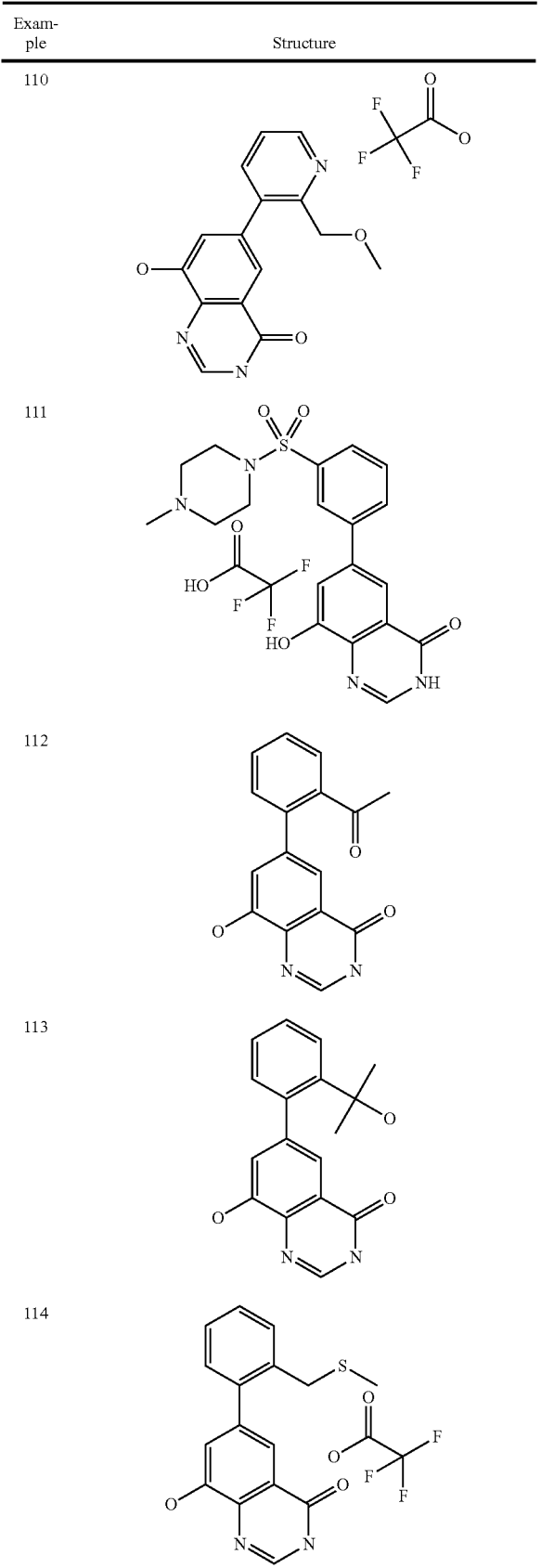 |
| 111 | |
| 112 | |
| 113 | |
| 114 | |
| Example | Structure |
|---|---|
| 115 | 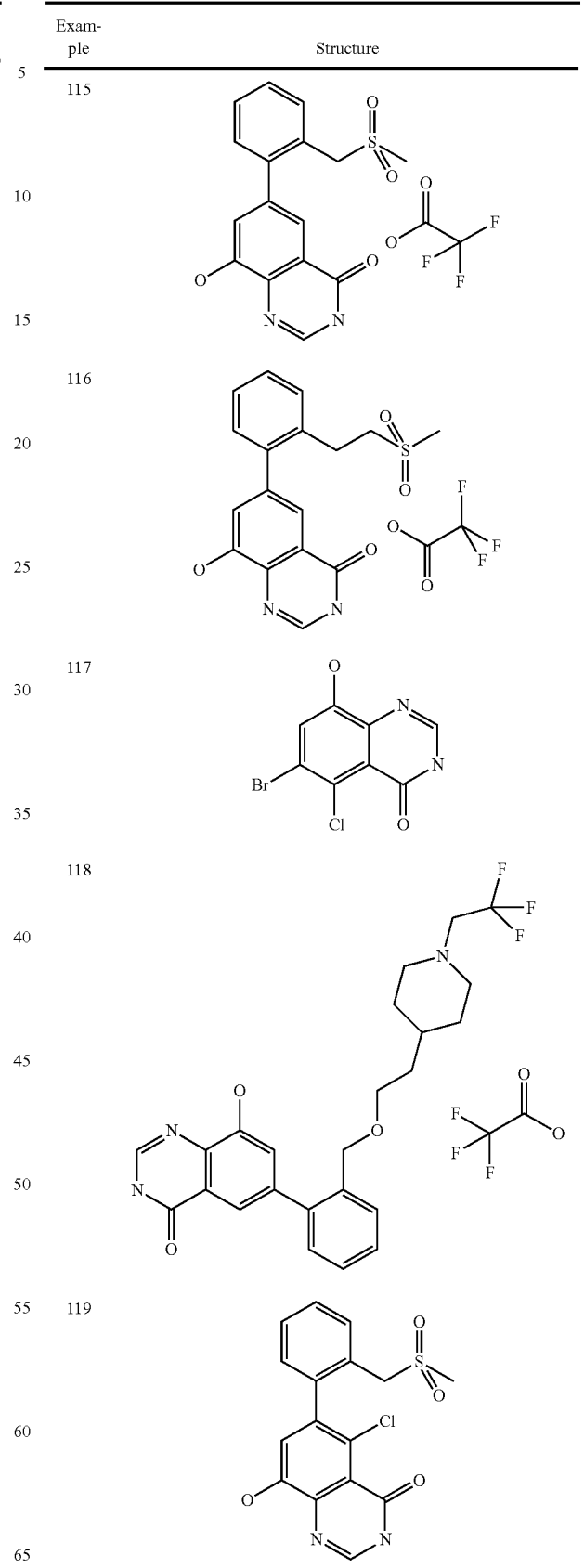 |
| 116 | |
| 117 | |
| 118 | |
| 119 | |

-continued
| Example | Structure |
|---|---|
| 120 | 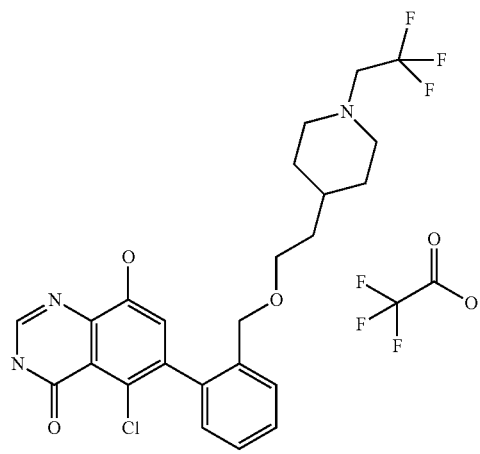 [SMILES: O=c1[nH]cnc2c(O)cc(-c3ccccc3COCCC3CCN(CC(F)(F)F)CC3)c(Cl)c12 ; O=C(O)C(F)(F)F] |
| 121 | 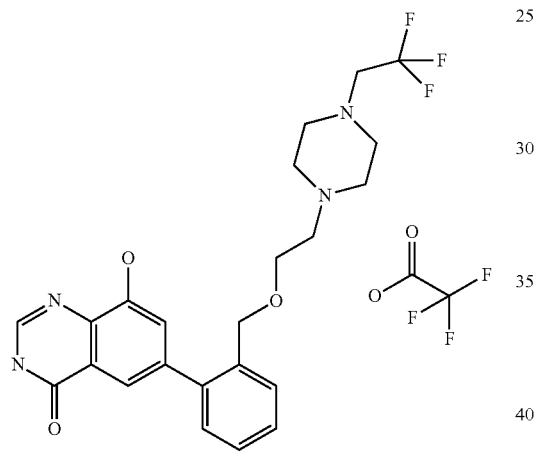 |
| 122 | 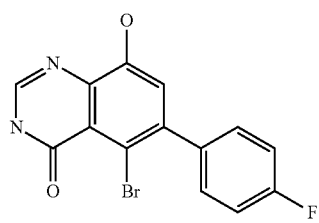 [SMILES: O=c1[nH]cnc2c(O)cc(-c3ccc(F)cc3)c(Br)c12] |
| 123 | 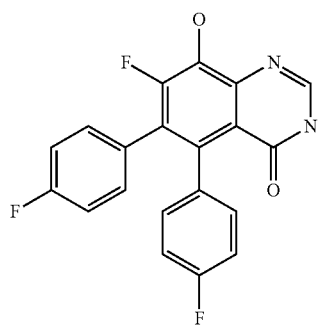 [SMILES: O=c1[nH]cnc2c(O)c(F)c(-c3ccc(F)cc3)c(-c3ccc(F)cc3)c12] |
-continued
| Example | Structure |
|---|---|
| 124 | 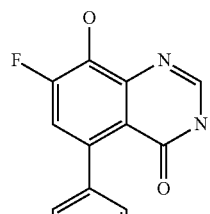 |
| 125 | 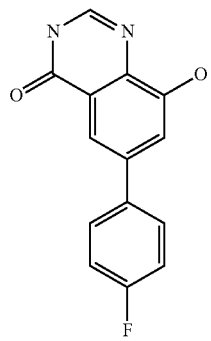 [SMILES: O=c1[nH]cnc2c(O)cc(-c3ccc(F)cc3)cc12] |
| 126 | 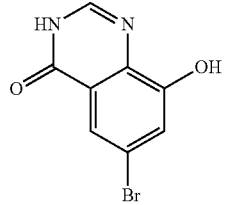 [SMILES: O=c1[nH]cnc2c(O)cc(Br)cc12] |
| 127 | 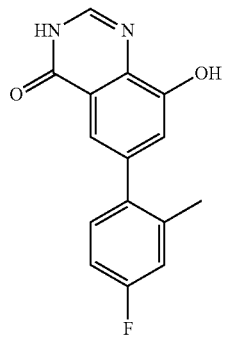 [SMILES: Cc1cc(F)ccc1-c1cc(O)c2nc[nH]c(=O)c2c1] |
| 128 | 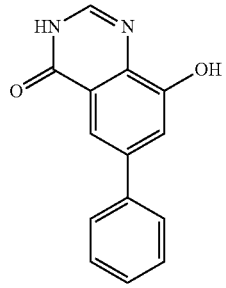 [SMILES: O=c1[nH]cnc2c(O)cc(-c3ccccc3)cc12] |

| Example | Structure |
|---|---|
| 129 | 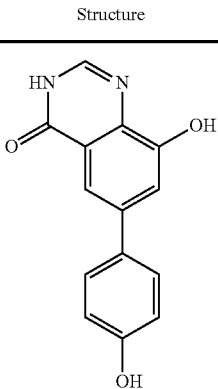 |
| 130 | 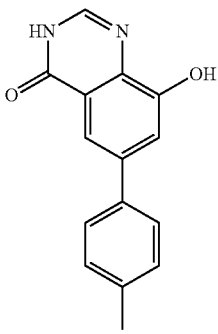 [SMILES: Cc1ccc(-c2cc(O)c3nc[nH]c(=O)c3c2)cc1] |
| 131 | 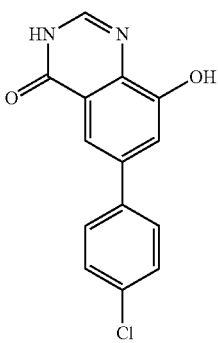 [SMILES: O=c1[nH]cnc2c(O)cc(-c3ccc(Cl)cc3)cc12] |
| 132 | 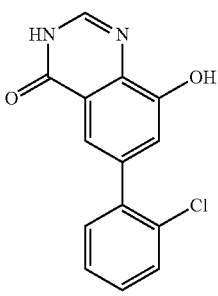 [SMILES: O=c1[nH]cnc2c(O)cc(-c3ccccc3Cl)cc12] |
| 133 | 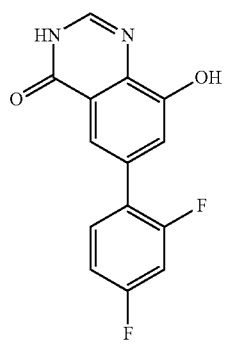 [SMILES: O=c1[nH]cnc2c(O)cc(-c3ccc(F)cc3F)cc12] |
| 134 | 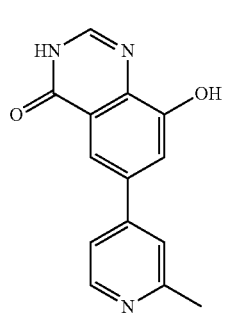 [SMILES: Cc1cc(-c2cc(O)c3nc[nH]c(=O)c3c2)ccn1] |
| 135 | 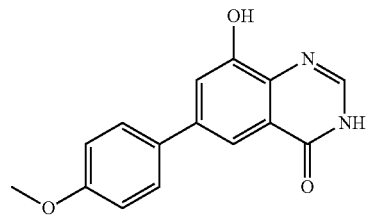 [SMILES: COc1ccc(-c2cc(O)c3nc[nH]c(=O)c3c2)cc1] |
| 136 | 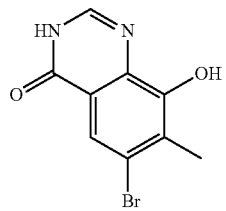 |
| 137 | 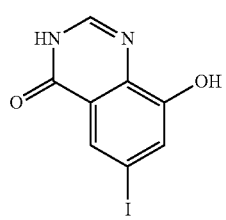 [SMILES: O=c1[nH]cnc2c(O)cc(I)cc12] |

| Example | Structure |
|---|---|
| 138 | 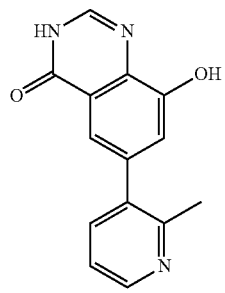 [SMILES: Cc1ncccc1-c1cc(O)c2nc[nH]c(=O)c2c1] |
| 139 | 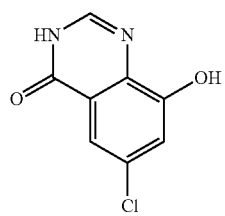 |
| 140 | 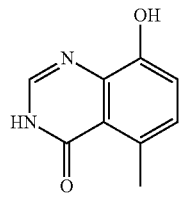 |
| 141 | 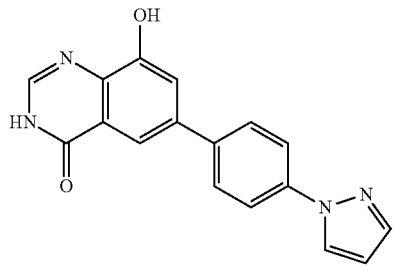 [SMILES: O=c1[nH]cnc2c(O)cc(-c3ccc(-n4cccn4)cc3)cc12] |
| 142 | 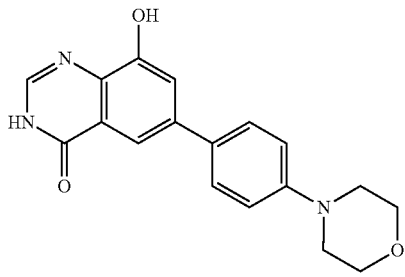 [SMILES: O=c1[nH]cnc2c(O)cc(-c3ccc(N4CCOCC4)cc3)cc12] |
| 143 | 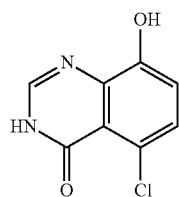 |
| 144 | 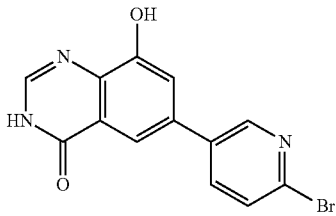 [SMILES: O=c1[nH]cnc2c(O)cc(-c3ccc(Br)nc3)cc12] |
| 145 | 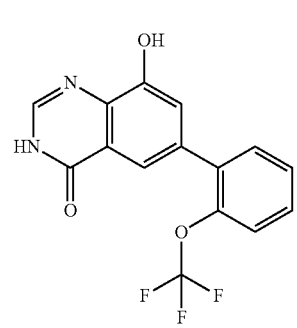 [SMILES: O=c1[nH]cnc2c(O)cc(-c3ccccc3OC(F)(F)F)cc12] |
| 146 | 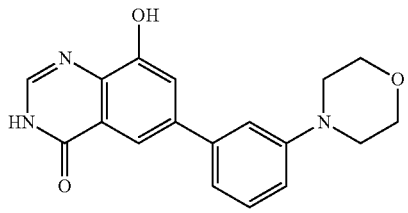 [SMILES: O=c1[nH]cnc2c(O)cc(-c3cccc(N4CCOCC4)c3)cc12] |
| 147 | 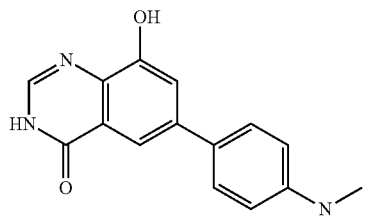 |
| 148 | 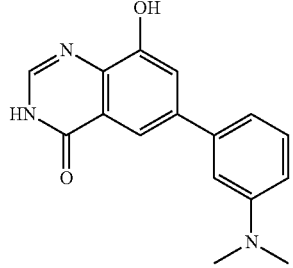 [SMILES: CN(C)c1cccc(-c2cc(O)c3nc[nH]c(=O)c3c2)c1] |
| 149 | 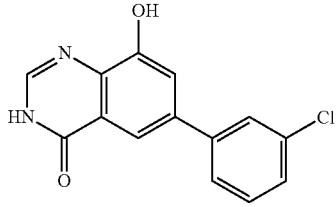 [SMILES: O=c1[nH]cnc2c(O)cc(-c3cccc(Cl)c3)cc12] |

-continued
| Example | Structure |
|---|---|
| 150 | 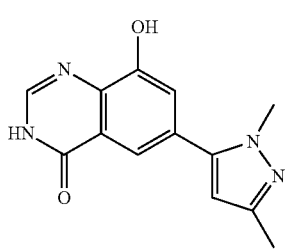 [SMILES: Cc1cc(-c2cc(O)c3nc[nH]c(=O)c3c2)n(C)n1] |
| 151 | 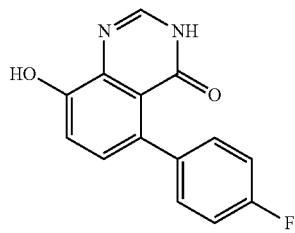 [SMILES: O=c1[nH]cnc2c(O)ccc(-c3ccc(F)cc3)c12] |
| 152 | 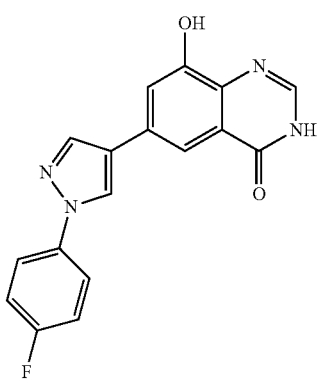 [SMILES: O=c1[nH]cnc2c(O)cc(-c3cnn(-c4ccc(F)cc4)c3)cc12] |
| 153 | 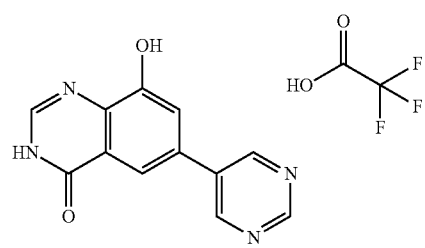 [SMILES: O=c1[nH]cnc2c(O)cc(-c3cncnc3)cc12 ; O=C(O)C(F)(F)F] |
| 154 | 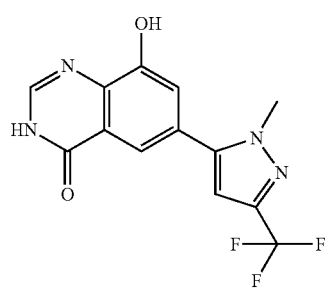 [SMILES: Cn1nc(C(F)(F)F)cc1-c1cc(O)c2nc[nH]c(=O)c2c1] |
-continued
| Example | Structure |
|---|---|
| 155 | 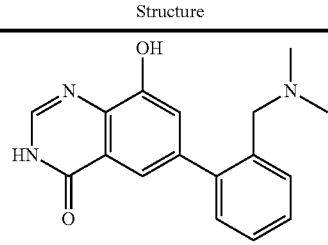 |
| 156 | 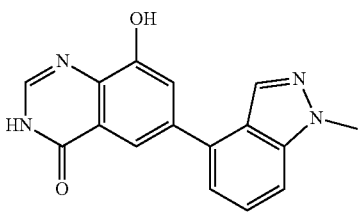 [SMILES: Cn1ncc2c(-c3cc(O)c4nc[nH]c(=O)c4c3)cccc21] |
| 157 | 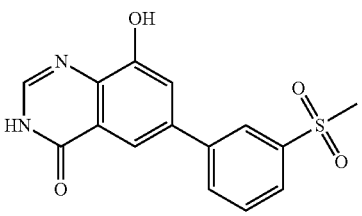 [SMILES: CS(=O)(=O)c1cccc(-c2cc(O)c3nc[nH]c(=O)c3c2)c1] |
| 158 | 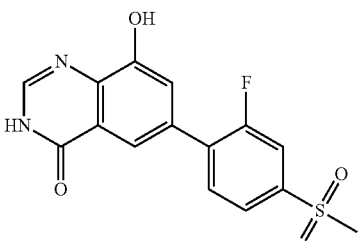 |
| 159 | 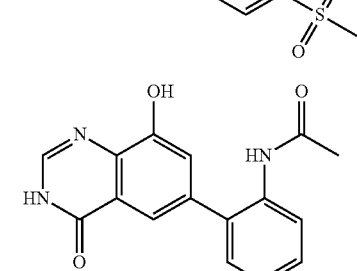 |
| 160 | 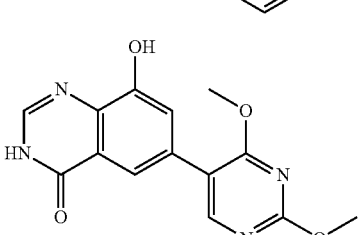 |
| 161 | 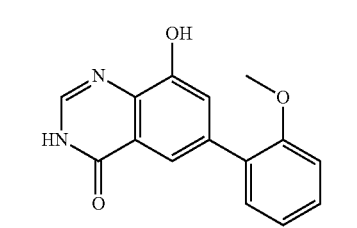 [SMILES: COc1ccccc1-c1cc(O)c2nc[nH]c(=O)c2c1] |

| Example | Structure |
|---|---|
| 162 | 2-methoxypyridin-3-yl substituted 8-hydroxyquinazolin-4(3H)-one |
| 163 | 6-methoxypyridin-3-yl substituted 8-hydroxyquinazolin-4(3H)-one |
| 164 | 4-methylthiophen-3-yl substituted 8-hydroxyquinazolin-4(3H)-one |
| 165 | 2,5-dimethylthiophen-3-yl substituted 8-hydroxyquinazolin-4(3H)-one |
| 166 | 6-methylpyridin-3-yl substituted 8-hydroxyquinazolin-4(3H)-one |
| 167 | quinolin-8-yl substituted 8-hydroxyquinazolin-4(3H)-one |
| 168 | isoquinolin-4-yl substituted 8-hydroxyquinazolin-4(3H)-one |
| 169 | naphthalen-2-yl substituted 8-hydroxyquinazolin-4(3H)-one |
| 170 | naphthalen-1-yl substituted 8-hydroxyquinazolin-4(3H)-one |
| 171 | 1,2,3,4-tetrahydroisoquinolin-6-yl substituted 8-hydroxyquinazolin-4(3H)-one |
| 172 | 4-(2-morpholinoethylcarbamoyl)phenyl substituted 8-hydroxyquinazolin-4(3H)-one |
| 173 | 4-(2-(dimethylamino)ethylcarbamoyl)phenyl substituted 8-hydroxyquinazolin-4(3H)-one |
| 174 | 1,2,3,4-tetrahydroisoquinolin-7-yl substituted 8-hydroxyquinazolin-4(3H)-one |

-continued
| Example | Structure |
|---|---|
| 175 | 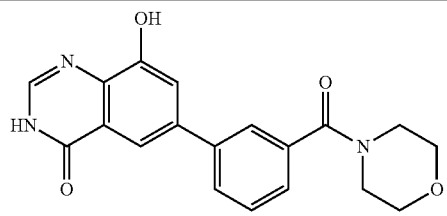 [SMILES: O=C(c1cccc(-c2cc(O)c3nc[nH]c(=O)c3c2)c1)N1CCOCC1] |
| 176 | 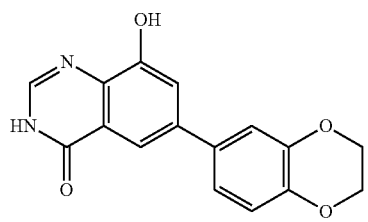 [SMILES: O=c1[nH]cnc2c(O)cc(-c3ccc4c(c3)OCCO4)cc12] |
| 177 | 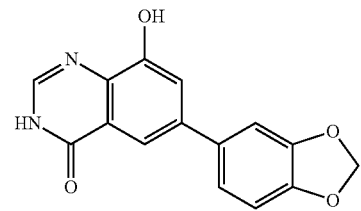 [SMILES: O=c1[nH]cnc2c(O)cc(-c3ccc4c(c3)OCO4)cc12] |
| 178 | 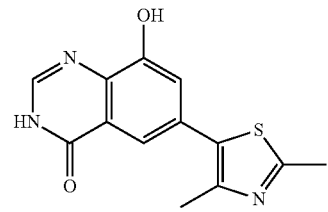 [SMILES: Cc1nc(C)c(-c2cc(O)c3nc[nH]c(=O)c3c2)s1] |
| 179 | 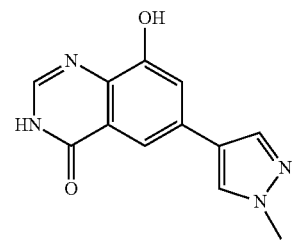 [SMILES: Cn1cc(-c2cc(O)c3nc[nH]c(=O)c3c2)cn1] |
| 180 | 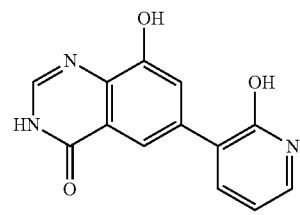 [SMILES: O=c1[nH]cnc2c(O)cc(-c3cccnc3O)cc12] |
| 181 | 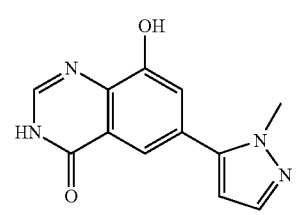 [SMILES: Cn1nccc1-c1cc(O)c2nc[nH]c(=O)c2c1] |
-continued
| Example | Structure |
|---|---|
| 182 | 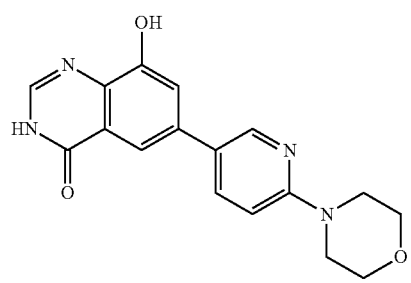 [SMILES: O=c1[nH]cnc2c(O)cc(-c3ccc(N4CCOCC4)nc3)cc12] |
| 183 | 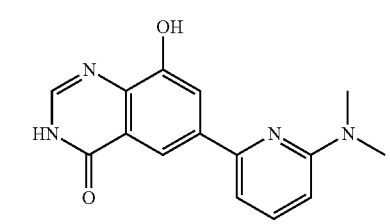 [SMILES: CN(C)c1cccc(-c2cc(O)c3nc[nH]c(=O)c3c2)n1] |
| 184 | 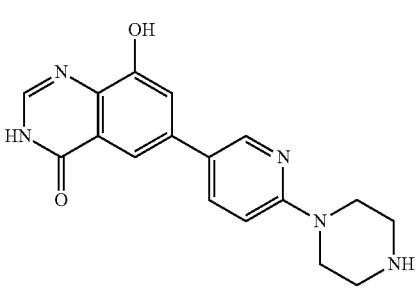 [SMILES: O=c1[nH]cnc2c(O)cc(-c3ccc(N4CCNCC4)nc3)cc12] |
| 185 | 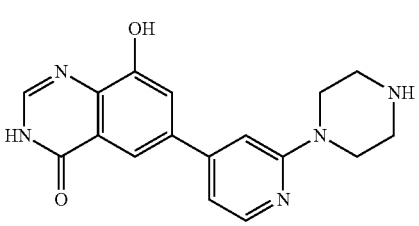 [SMILES: O=c1[nH]cnc2c(O)cc(-c3ccnc(N4CCNCC4)c3)cc12] |
| 186 | 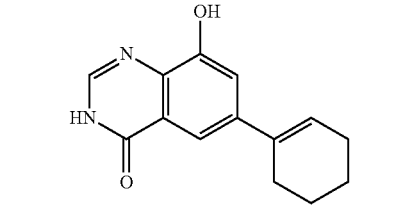 [SMILES: O=c1[nH]cnc2c(O)cc(C3=CCCCC3)cc12] |
| 187 | 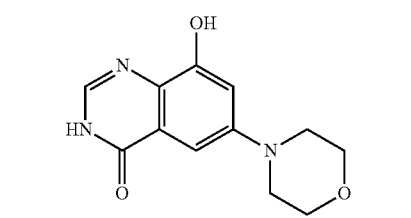 [SMILES: O=c1[nH]cnc2c(O)cc(N3CCOCC3)cc12] |

-continued
| Example | Structure |
|---|---|
| 188 | 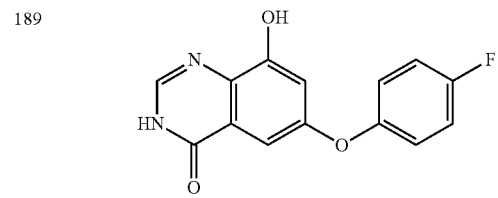 |
| 189 | 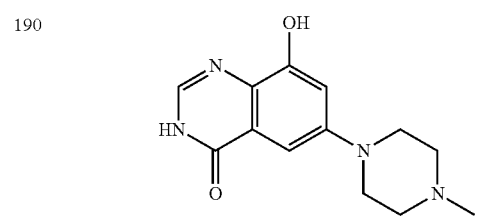 |
| 190 | 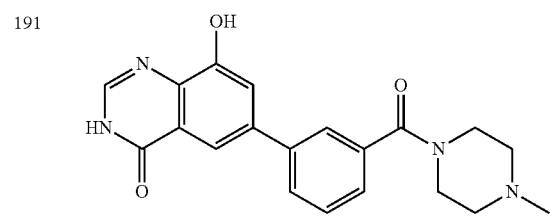 |
| 191 | 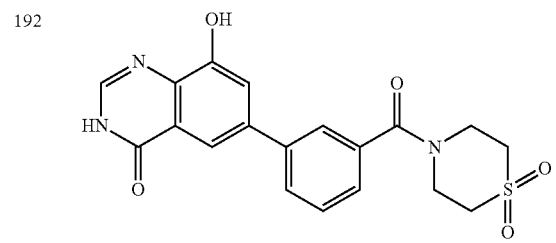 |
| 192 | 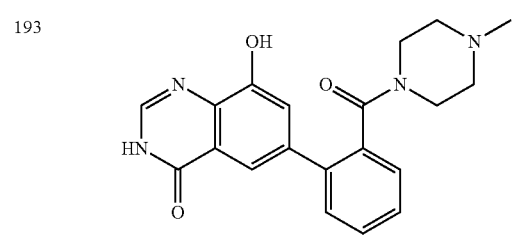 |
| 193 | 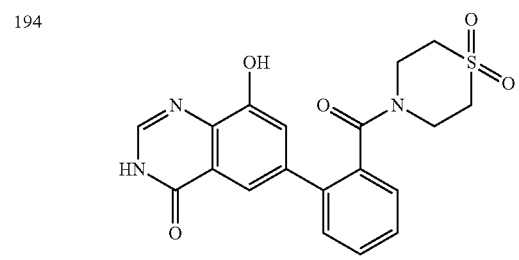 |
| 194 | 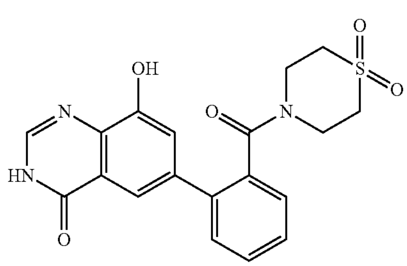 [SMILES: O=C(c1ccccc1-c1cc(O)c2nc[nH]c(=O)c2c1)N1CCS(=O)(=O)CC1] |
-continued
| Example | Structure |
|---|---|
| 195 | 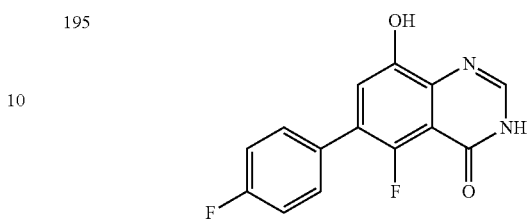 |
| 196 | 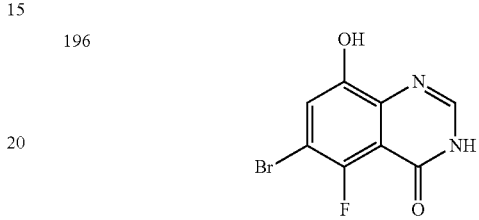 |
| 197 | 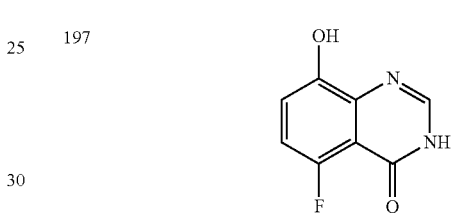 |
| 198 | 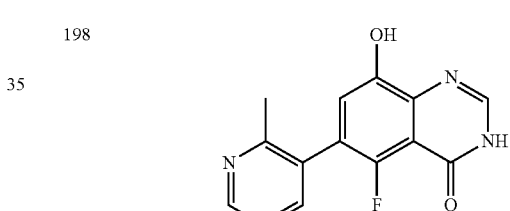 |
| 199 | 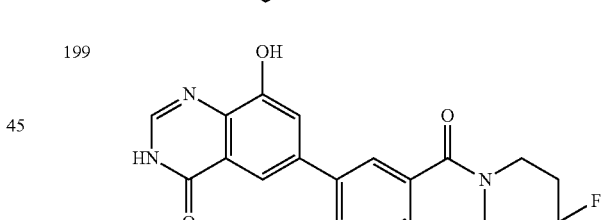 |
| 200 | 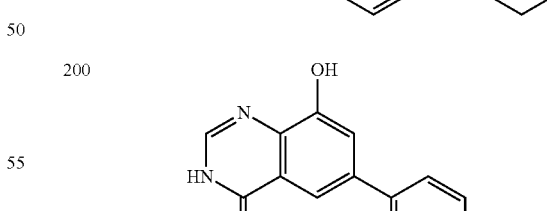 |
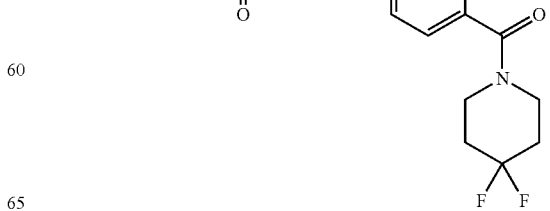

-continued

| Example | Structure |
|---------|-----------|
| 201 | 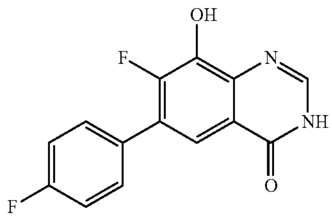 [SMILES: O=c1[nH]cnc2c(O)c(F)c(-c3ccc(F)cc3)cc12] |
| 202 | 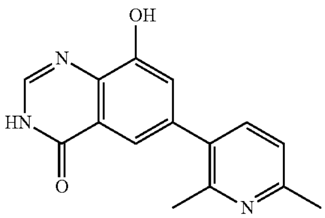 [SMILES: Cc1ccc(-c2cc(O)c3nc[nH]c(=O)c3c2)c(C)n1] |
| 203 | 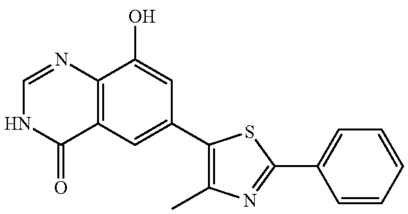 [SMILES: Cc1nc(-c2ccccc2)sc1-c1cc(O)c2nc[nH]c(=O)c2c1] |
| 204 | 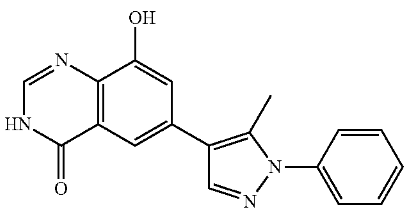 [SMILES: Cc1c(-c2cc(O)c3nc[nH]c(=O)c3c2)cnn1-c1ccccc1] |
| 205 | 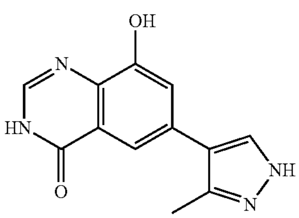 [SMILES: Cc1n[nH]cc1-c1cc(O)c2nc[nH]c(=O)c2c1] |
| 206 | 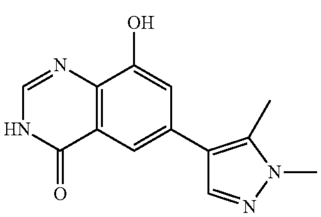 [SMILES: Cc1c(-c2cc(O)c3nc[nH]c(=O)c3c2)cnn1C] |
| 207 | 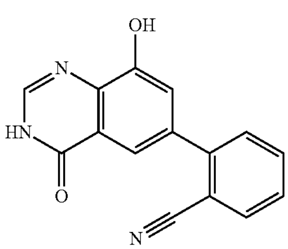 [SMILES: N#Cc1ccccc1-c1cc(O)c2nc[nH]c(=O)c2c1] |
| 208 | |
| 209 | |
| 210 | |
| 211 | |
| 212 | |
| 213 | |

| Example | Structure |
|---|---|
| 214 | 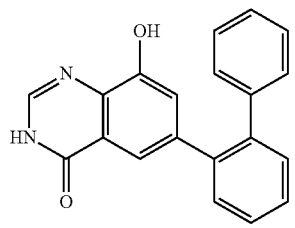 [SMILES: O=c1[nH]cnc2c(O)cc(-c3ccccc3-c3ccccc3)cc12] |
| 215 | 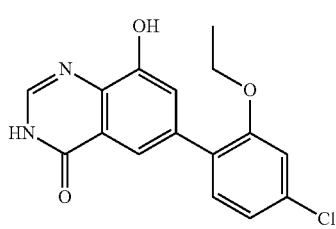 [SMILES: CCOc1cc(Cl)ccc1-c1cc(O)c2nc[nH]c(=O)c2c1] |
| 216 | 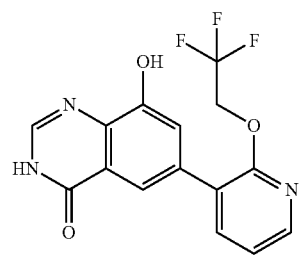 [SMILES: O=c1[nH]cnc2c(O)cc(-c3cccnc3OCC(F)(F)F)cc12] |
| 217 | 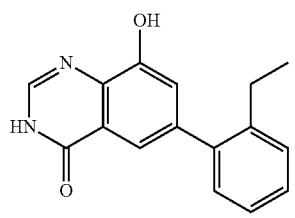 [SMILES: CCc1ccccc1-c1cc(O)c2nc[nH]c(=O)c2c1] |
| 218 | 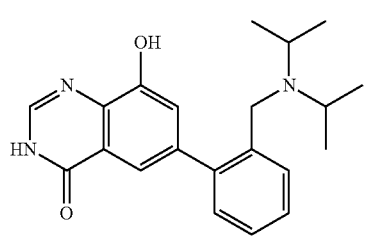 [SMILES: CC(C)N(Cc1ccccc1-c1cc(O)c2nc[nH]c(=O)c2c1)C(C)C] |
| 219 | 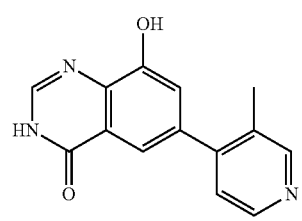 [SMILES: Cc1cnccc1-c1cc(O)c2nc[nH]c(=O)c2c1] |
| 220 | 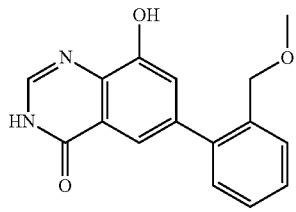 |
| 221 | 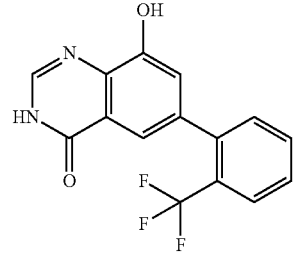 [SMILES: O=c1[nH]cnc2c(O)cc(-c3ccccc3C(F)(F)F)cc12] |
| 222 | 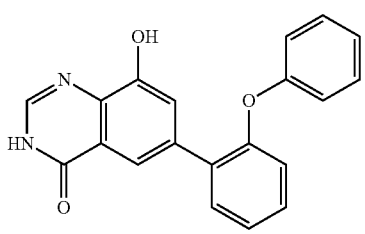 [SMILES: O=c1[nH]cnc2c(O)cc(-c3ccccc3Oc3ccccc3)cc12] |
| 223 | 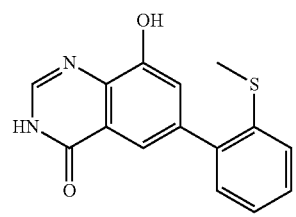 [SMILES: CSc1ccccc1-c1cc(O)c2nc[nH]c(=O)c2c1] |
| 224 | 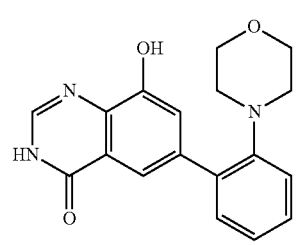 [SMILES: O=c1[nH]cnc2c(O)cc(-c3ccccc3N3CCOCC3)cc12] |
| 225 | 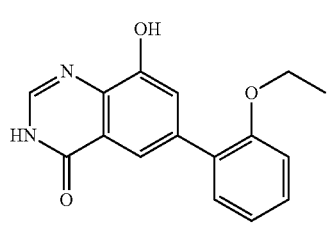 [SMILES: CCOc1ccccc1-c1cc(O)c2nc[nH]c(=O)c2c1] |

| Example | Structure |
|---|---|
| 226 | 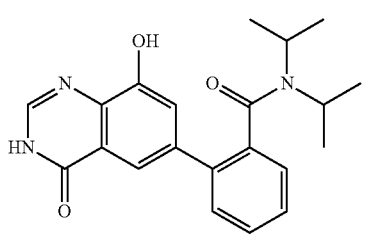 [SMILES: CC(C)N(C(=O)c1ccccc1-c1cc(O)c2nc[nH]c(=O)c2c1)C(C)C] |
| 227 | 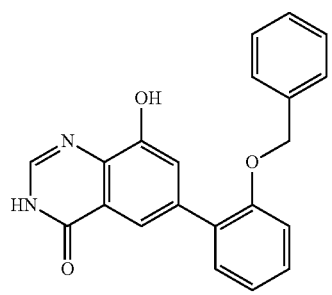 [SMILES: O=c1[nH]cnc2c(O)cc(-c3ccccc3OCc3ccccc3)cc12] |
| 228 | 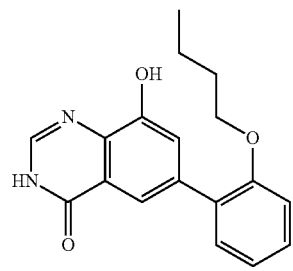 [SMILES: CCCCOc1ccccc1-c1cc(O)c2nc[nH]c(=O)c2c1] |
| 229 | 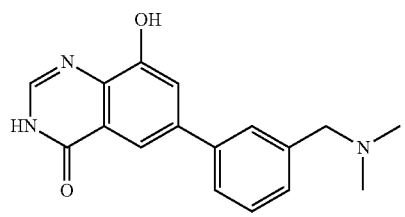 [SMILES: CN(C)Cc1cccc(-c2cc(O)c3nc[nH]c(=O)c3c2)c1] |
| 230 | 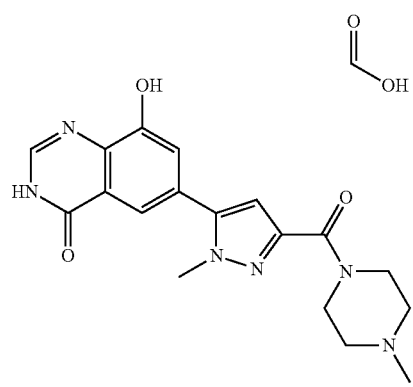 [SMILES: CN1CCN(C(=O)c2cc(-c3cc(O)c4nc[nH]c(=O)c4c3)n(C)n2)CC1 ; O=CO] |
| Example | Structure |
|---|---|
| 231 | 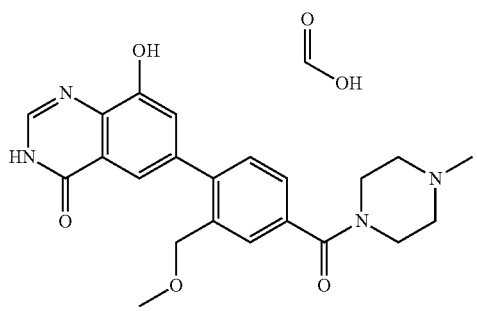 [SMILES: COCc1cc(C(=O)N2CCN(C)CC2)ccc1-c1cc(O)c2nc[nH]c(=O)c2c1 ; O=CO] |
| 232 | 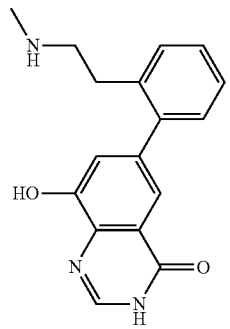 [SMILES: CNCCc1ccccc1-c1cc(O)c2nc[nH]c(=O)c2c1] |
| 233 | 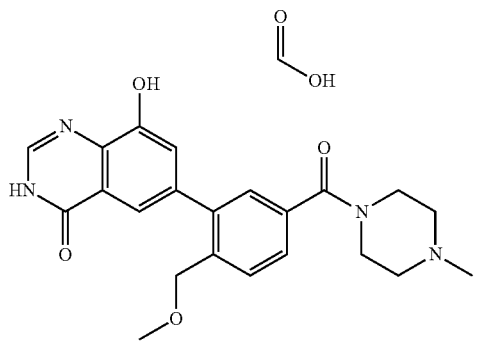 [SMILES: O=CO ; COCc1ccc(C(=O)N2CCN(C)CC2)cc1-c1cc(O)c2nc[nH]c(=O)c2c1] |
| 234 | 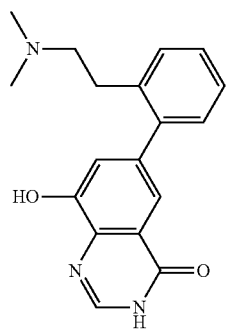 [SMILES: CN(C)CCc1ccccc1-c1cc(O)c2nc[nH]c(=O)c2c1] |

| Example | Structure |
|---|---|
| 235 | 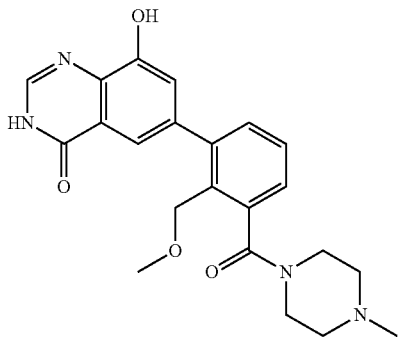 [SMILES: COCc1c(C(=O)N2CCN(C)CC2)cccc1-c1cc(O)c2nc[nH]c(=O)c2c1] |
| 236 | 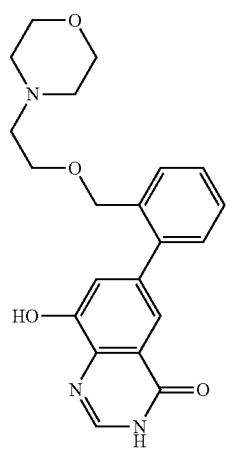 [SMILES: O=c1[nH]cnc2c(O)cc(-c3ccccc3COCCN3CCOCC3)cc12] |
| 237 | 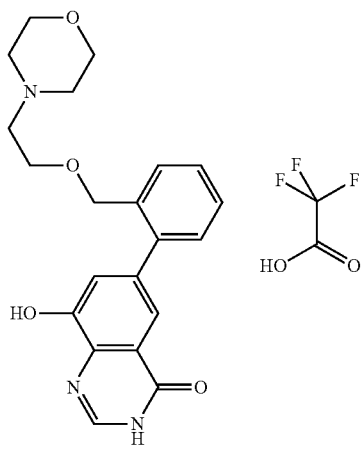 [SMILES: O=c1[nH]cnc2c(O)cc(-c3ccccc3COCCN3CCOCC3)cc12 ; O=C(O)C(F)(F)F] |
| 238 | 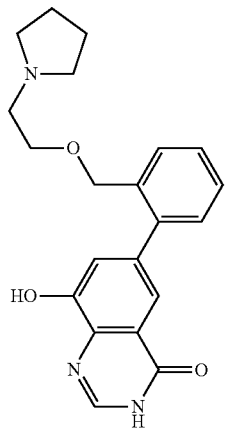 [SMILES: O=c1[nH]cnc2c(O)cc(-c3ccccc3COCCN3CCCC3)cc12] |
| 239 | 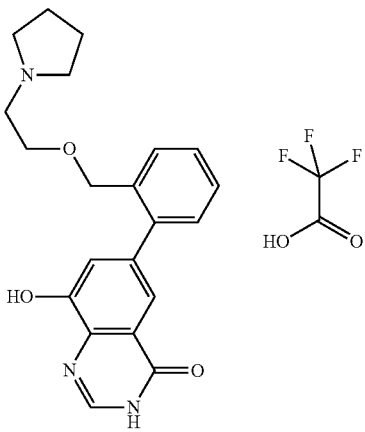 [SMILES: O=c1[nH]cnc2c(O)cc(-c3ccccc3COCCN3CCCC3)cc12 ; O=C(O)C(F)(F)F] |
| 240 | 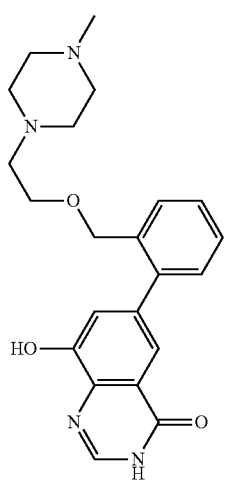 [SMILES: CN1CCN(CCOCc2ccccc2-c2cc(O)c3nc[nH]c(=O)c3c2)CC1] |

-continued
| Example | Structure |
|---|---|
| 241 | 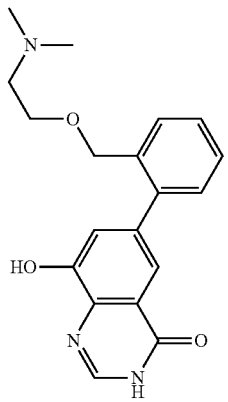 [SMILES: CN(C)CCOCc1ccccc1-c1cc(O)c2nc[nH]c(=O)c2c1] |
| 242 | 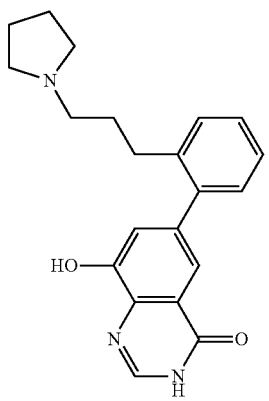 [SMILES: O=c1[nH]cnc2c(O)cc(-c3ccccc3CCCN3CCCC3)cc12] |
| 243 | 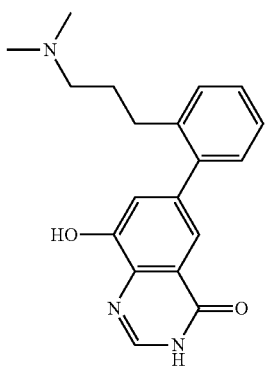 [SMILES: CN(C)CCCc1ccccc1-c1cc(O)c2nc[nH]c(=O)c2c1] |
| 244 | 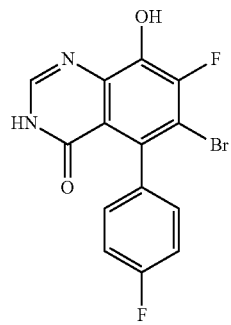 [SMILES: O=c1[nH]cnc2c(O)c(F)c(Br)c(-c3ccc(F)cc3)c12] |
-continued
| Example | Structure |
|---|---|
| 245 | 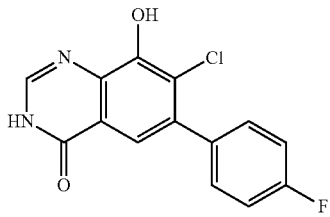 [SMILES: O=c1[nH]cnc2c(O)c(Cl)c(-c3ccc(F)cc3)cc12] |
| 246 | 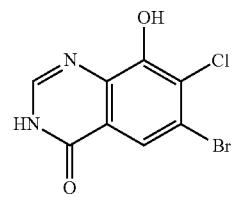 [SMILES: O=c1[nH]cnc2c(O)c(Cl)c(Br)cc12] |
| 247 | 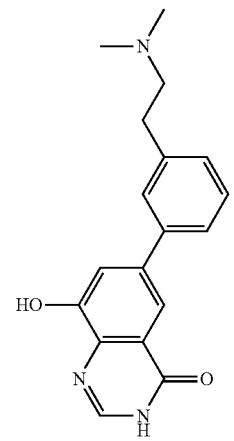 [SMILES: CN(C)CCc1cccc(-c2cc(O)c3nc[nH]c(=O)c3c2)c1] |
| 248 | 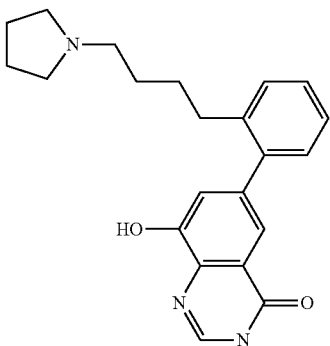 |
| 249 | 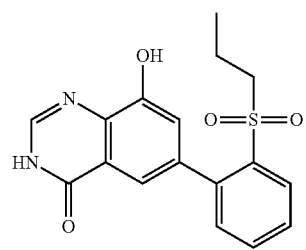 |

| Example | Structure |
|---|---|
| 250 | *(structure: 6-(2-(N,N-dimethylsulfamoyl)phenyl)-8-hydroxyquinazolin-4(3H)-one)* |
| 251 | *(structure: 8-hydroxy-6-(2-(piperidin-1-ylsulfonyl)phenyl)quinazolin-4(3H)-one)* |
| 252 | *(structure: 6-(4-fluorophenyl)-8-hydroxy-5-nitroquinazolin-4(3H)-one)* |
| 253 | *(structure: 5-amino-6-(4-fluorophenyl)-8-hydroxyquinazolin-4(3H)-one, HBr salt)* |
| 254 | *(structure: N-(6-(4-fluorophenyl)-8-hydroxy-4-oxo-3,4-dihydroquinazolin-5-yl)benzamide)* |
| 255 | *(structure: 5-chloro-6-(2-(hydroxymethyl)phenyl)-8-hydroxyquinazolin-4(3H)-one)* |

| Example | Structure |
|---|---|
| 256 | *(structure: 6-(2-((2-(1-methylpiperidin-4-yl)ethoxy)methyl)phenyl)-8-hydroxyquinazolin-4(3H)-one)* |

EXAMPLE 1

5-Bromo-8-hydroxyquinazolin-4(3H)-one a) 5-Bromo-8-methoxyquinazolin-4(3H)-one

A suspension of 2-amino-6-bromo-3-methoxybenzoic acid (CAS Registry No. 67303-48-4) (5.0 g, 20.3 mmol) in formamide (20 ml) was stirred at 150° C. for 16 hours. After cooling to 90° C. water (100 ml) was added and the dark brown precipitate was filtered, triturated with methanol (20 ml) and dried. The title compound was isolated as a brown solid (3.6 g, 60%).
MS: m/e=254.9/252.9 [M−H]⁻.

b) 5-Bromo-8-hydroxyquinazolin-4(3H)-one

A suspension of 5-bromo-8-methoxyquinazolin-4(3H)-one (85 mg, 0.33 mmol) and boron tribromide (1.67 ml of a 1M solution in dichloromethane, 1.67 mmol) was stirred at room temperature for 22 hours. Then the reaction mixture was cooled in an ice bath and methanol (1 ml) was added. After evaporation of all volatiles the residue was triturated with water. An analytical sample of the title compound was obtained by preparative HPLC: Gemini Axia 5μ C18A 110A 100×30 mm. Gradient (0.1% formic acid in water)/methanol=10/90 to 40/60. The title compound was obtained as a white solid (0.01 g, 12%). MS: m/e=240.8 [M−H]⁻

EXAMPLE 2

Methyl 8-hydroxy-4-oxo-3,4-dihydroquinazoline-6-carboxylate a) 6-Bromo-8-methoxy-3H-quinazolin-4-one A suspension of 2-amino-5-bromo-3-methoxybenzoic acid hydrobromide (CAS Registry No. 864293-44-7) (85.5 g, 261 mmol) in formamide (300 ml) was stirred at 150° C. for 12 hours. After cooling to room temperature water (1 l) was added and the precipitate was filtered, triturated with water and dried. The title compound was isolated as an off-white solid (59.4 g, 89%).
MS: m/e=255.0/257.0 [M+H]$^+$.

b) 6-Bromo-8-hydroxy-3H-quinazolin-4-one

A solution of 6-bromo-8-methoxy-3H-quinazolin-4-one (45 g, 176 mmol) in a mixture of aqueous hydrobromic acid (135 ml of a 48% solution), hydrobromic acid in acetic acid (190 ml of a 32% solution) and acetic acid (190 ml) was stirred at 130° C. for 4 days. The reaction mixture was allowed to reach room temperature and filtered. The precipitate was dried thoroughly and the title compound was isolated as an off-white solid (39.3 g, 93%). MS: m/e=238.9/240.9 [M–H]$^-$.

c) Methyl 8-hydroxy-4-oxo-3,4-dihydroquinazoline-6-carboxylate

An autoclave containing a mixture of 6-bromo-8-hydroxy-3H-quinazolin-4-one (0.50 g, 2.1 mmol), bis(diphenylphosphino)ferrocene-palladium(II)dichloride dichloromethane complex (75 mg, 0.092 mmol), triethylamine (317 mg, 3.1 mmol), methanol (50 ml) and ethyl acetate (50 ml) was charged with carbon monoxide (70 bar) and heated to 110° C. for 18 hours. The reaction mixture was allowed to reach room temperature and filtered. The precipitate was dried and the title compound was isolated as a white solid (0.29 g, 63%). MS: m/e=219.0 [M–H]$^-$.

EXAMPLE 3

8-Hydroxy-6-(morpholine-4-carbonyl)quinazolin-4(3H)-one

To a solution of morpholine (95 mg, 1.1 mmol) in dioxane (10 ml) 0.8 ml of a 2M solution of trimethylaluminum in toluene (1.6 mM) was added dropwise. After stirring at room temperature for 45 minutes methyl 8-hydroxy-4-oxo-3,4-dihydroquinazoline-6-carboxylate (60 mg, 0.27 mmol) was added and the resulting mixture was stirred at 90° C. for 16 hours. At room temperature dichloromethane and saturated aqueous Seignette salt solution was added and stirring was continued for 30 minutes. The organic phase was adsorbed on silica and chromatographed (silica gel, dichloromethane/methanol=97:3 to 92:8). After trituration with diisopropyl-ether the title compound was isolated as a white solid. (0.02 g, 21%). MS: m/e=276.1 [M+H]$^+$.

EXAMPLE 4

8-Hydroxy-4-oxo-N-(2,2,3,3,3-pentafluoropropyl)-3,4-dihydroquinazoline-6-carboxamide In analogy to example 3, 2,2,3,3,3-pentafluoropropan-1-amine (instead of morpholine) was reacted with trimethylaluminum and methyl 8-hydroxy-4-oxo-3,4-dihydroquinazoline-6-carboxylate. After workup the title compound was isolated as a white solid (0.02 g, 20%). MS: m/e=336.0 [M–H]$^-$.

EXAMPLE 5

8-Hydroxy-4-oxo-N-(2,2,2-trifluoroethyl)-3,4-dihydroquinazoline-6-carboxamide

In analogy to example 3, 2,2,2-trifluoroethanamine (instead of morpholine) was reacted with trimethylaluminum and methyl 8-hydroxy-4-oxo-3,4-dihydroquinazoline-6-carboxylate. After workup the title compound was isolated as a white solid (2.1 mg, 2%). MS: m/e=285.9 [M–H]$^-$.

EXAMPLE 6

Ethyl 8-hydroxy-4-oxo-3,4-dihydroquinazoline-6-carboxylate

In analogy to example 2c, a mixture of 6-bromo-8-hydroxy-3H-quinazolin-4-one, bis(diphenylphosphino)ferrocene-palladium(II)dichloride dichloromethane complex, triethylamine, ethyl acetate, ethanol (instead of methanol) was reacted with carbon monoxide. After workup the title compound was isolated as an off-white solid (63%). MS: m/e=232.9 [M–H]$^-$.

EXAMPLE 7

6-(3,4-Dihydro-naphthalen-2-yl)-8-hydroxy-3H-quinazolin-4-one a) 6-Bromo-8-(2-trimethylsilanyl-ethoxymethoxy)-3-(2-trimethylsilanyl-ethoxymethyl)-3H-quinazolin-4-one With cooling in an ice-bath, sodium hydride (415 mg of a 60% dispersion in mineral oil, 10.4 mmol) was added in small portions to a solution of 6-bromo-8-hydroxy-3H-quinazolin-4-one (example 2b, 1.0 g, 4.2 mmol) in dimethylformamide (15 ml). After 10 minutes 2-(trimethylsilyl)ethoxymethyl chloride (1.7 g, 10.4 mmol) was added dropwise. The mixture was stirred at 80° C. for 30 minutes. After evaporation of the solvent the residue was partitioned (ethyl acetate/water). The organic phase was dried (Na$_2$SO$_4$) concentrated and chromatographed (silica gel, heptane/ethyl acetate=100:00 to 85:15) to furnish the title compound as a white solid (2.08 g, 47%). MS: m/e=503.1/501.2 [M+H]$^+$.

b) 6-(3,4-Dihydronaphthalen-2-yl)-8-((2-(trimethylsilyl)ethoxy)methyl)-3-((2-(trimethylsilyl)ethoxy)methyl)quinazolin-4(3H)-one A mixture of 6-bromo-8-(2-trimethylsilanyl-ethoxymethoxy)-3-(2-trimethylsilanyl-ethoxymethyl)-3H-quinazolin-4-one (0.46 g, 0.92 mmol), bis(diphenylphosphino)ferrocene-palladium(II)dichloride (0.10 g, 0.14 mmol), 3,4-dihydronaphthalen-2-ylboronic acid (CAS Registry No. 864293-44-7) (0.21 g, 1.2 mmol) and potassium carbonate (0.26 g, 1.84 mmol) in dimethylformamide (20 ml) and water (1 ml) was stirred at 100° C. for 90 minutes. After filtration all volatiles were evaporated and the residue was dissolved in dichloromethane, adsorbed on silica and chromatographed (silica gel, heptane/ethyl acetate=100:00 to 70:30) to furnish the title compound as a light yellow oil (0.40 g, 79%). MS: m/e=551.4 [M+H]$^+$.

c) 6-(3,4-Dihydro-naphthalen-2-yl)-8-hydroxy-3H-quinazolin-4-one

Trifluoroacetic acid (3 ml) was added to a solution of 6-(3,4-dihydronaphthalen-2-yl)-8-((2-(trimethylsilyl)ethoxy)methoxy)-3-((2-(trimethylsilyl)ethoxy)methyl)quinazolin-4(3H)-one (0.13 g, 0.24 mmol) in dichloromethane (10 ml). After 3 hours at room temperature all volatiles were evaporated and the residue was dissolved in methanol (10 ml) and stirred for 1 hour. Evaporation of the solvent left an oil that was triturated with ether to provide the title compound as a white solid (0.04 g, 42%). MS: m/e=288.8 [M−H]⁻.

EXAMPLE 8

(rac.) 8-Hydroxy-6-(1,2,3,4-tetrahydronaphthalen-2-yl)quinazolin-4(3H)-one a) (rac.) 6-(1,2,3,4-Tetrahydronaphthalen-2-yl)-8-((2-(trimethylsilyl)ethoxy)methoxy)-3-((2-(trimethylsilyl)ethoxy)methyl)quinazolin-4(3H)-one To a solution of 6-(3,4-dihydronaphthalen-2-yl)-8-((2-(trimethylsilyl)ethoxy)methoxy)-3-((2-(trimethylsilyl)ethoxy)methyl)quinazolin-4(3H)-one (example 7b) (0.22 g, 0.44 mmol) in ethyl acetate (10 ml) was added palladium on charcoal (0.05 g of a 10% dispersion). The mixture was stirred at room temperature under hydrogen atmosphere for 16 hours. After filtration and removal of all volatiles the residue was adsorbed on silica and chromatographed (silica gel, heptane/ethyl acetate=100:0 to 70:30) to furnish the title compound as a colorless oil (0.10 g, 45%. MS: m/e=553.5 [M+H]⁺.

b) (rac.) 8-Hydroxy-6-(1,2,3,4-tetrahydronaphthalen-2-yl)quinazolin-4(3H)-one

In analogy to example 7c, (rac.) 6-(1,2,3,4-tetrahydronaphthalen-2-yl)-8-((2-(trimethylsilyl)ethoxy)methoxy)-3-((2-(trimethylsilyl)ethoxy)methyl)quinazolin-4(3H)-one (instead of 6-(3,4-dihydro-naphthalen-2-yl)-8-hydroxy-3H-quinazolin-4-one) was reacted with trifluoroacetic acid. After workup the title compound was isolated as an off-white solid (45%).
MS: m/e=293.0 [M+H]⁺.

EXAMPLE 9

6-Benzyl-8-hydroxyquinazolin-4(3H)-one

A mixture of 6-bromo-8-(2-trimethylsilanyl-ethoxymethoxy)-3-(2-trimethylsilanyl-ethoxymethyl)-3H-quinazolin-4-one (example 7a) (0.25 g, 0.5 mmol), bis(triphenylphosphine)palladium(II)dichloride (0.018 g, 0.025 mmol) and benzylzinc bromide (1.1 ml of a 0.5 M solution in THF) and THF (1 ml) was stirred at 50° C. for 30 minutes. The mixture was extracted with ethyl acetate and sat. sodium bicarbonate solution. The organic layer was dried (Na₂SO₄), adsorbed on silica and chromatographed (silica gel, heptane/ethyl acetate=100:00 to 75:25) to furnish the SEM protected title compound as an oil. Trifluoroacetic acid (2 ml) was added and the mixture was stirred for 2 hours. After evaporation of all volatiles the oily residue was triturated with ethyl acetate to furnish the title compound as an off-white solid (0.02 g, 18%). MS: m/e=253.3 [M+H]⁺.

EXAMPLE 10

6-Ethyl-8-hydroxyquinazolin-4(3H)-one 2,2,2-trifluoroacetate

A mixture of 6-bromo-8-(2-trimethylsilanyl-ethoxymethoxy)-3-(2-trimethylsilanyl-ethoxymethyl)-3H-quinazolin-4-one (example 7a) (0.1 g, 0.2 mmol), bis(diphenylphosphino)ferrocene-palladium(II)dichloride (0.007 g, 0.01 mmol) and diethylzinc (0.15 ml of a 1.5M solution in toluene) and THF (1 ml) was stirred at room temperature for 4 hours. The mixture was extracted with ethyl acetate and sat. sodium bicarbonate solution. The organic layer was dried (Na₂SO₄), adsorbed on silica and chromatographed (silica gel, heptane/ethyl acetate=100:00 to 75:25) to furnish the SEM protected title compound as an oil. Trifluoroacetic acid (1 ml) was added and the mixture was stirred for 2 hours. After evaporation of all volatiles the oily residue was triturated with ethyl acetate to furnish the title compound as an off-white solid (0.01 g, 33%). MS: m/e=191.1 [M+H]⁺.

EXAMPLE 11

6-(2-Fluorobenzyl)-8-hydroxyquinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and 2-fluorobenzylzinc bromide (instead of benzylzinc bromide). After workup the SEM protected title compound was treated with trifluoroacetic acid to furnish the title compound as a white solid (52%). MS: m/e=271.3 [M+H]⁺.

EXAMPLE 12

8-Hydroxy-6-(3-methylbenzyl)quinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and 3-methylbenzylzinc bromide (instead of benzylzinc bromide). After workup the SEM protected title compound was treated with trifluoroacetic acid to furnish the title compound as a white solid (59%). MS: m/e=267.1 [M+H]⁺.

EXAMPLE 13

8-Hydroxy-6-isopropylquinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and diisopropylzinc (instead of benzylzinc bromide). After workup the SEM protected title compound was treated with trifluoroacetic acid to furnish the title compound as a white solid (25%). MS: m/e=205.1 [M+H]⁺.

EXAMPLE 14

8-Hydroxy-6-(2-methoxybenzyl)quinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and 2-methoxybenzylzinc chloride (instead of benzylzinc bromide). After workup the SEM protected title compound was treated with formic acid (90%) and stirred at 90° C. for 2 hours. After evaporation of all volatiles and trituration with ethyl acetate the title compound was obtained as a white solid (67%). MS: m/e=283.1 [M+H]⁺.

EXAMPLE 15

8-Hydroxy-6-(3-methoxybenzyl)quinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and 3-methoxybenzylzinc chloride (instead of benzylzinc bromide). After workup the SEM protected title compound was treated with formic acid (90%) and stirred at 90° C. for 2 hours. After evaporation of all volatiles and trituration with ethyl acetate the title compound was obtained as a white solid. An analytical sample of the title compound was obtained by preparative HPLC: Gemini Axia 5µ C18A 110A 100×30 mm. Gradient (0.1% formic acid in water)/methanol=10/90 to 40/60. The title compound was obtained as an off-white solid (6%). MS: m/e=283.1 [M+H]⁺.

EXAMPLE 16

8-Hydroxy-6-phenethylquinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and phenethylzinc bromide (instead of benzylzinc bromide). After workup the SEM protected title compound was treated with trifluoroacetic acid to furnish the title compound as a white solid. An analytical sample of the title compound was obtained by preparative HPLC: Gemini Axia 5µ C18A 110A 100×30 mm. Gradient (0.1% formic acid in water)/methanol=10/90 to 40/60. The title compound was obtained as an off-white solid (38%). MS: m/e=267.1 [M+H]⁺.

EXAMPLE 17

8-Hydroxy-6-isobutylquinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and isobutylzinc bromide (instead of benzylzinc bromide). After workup the SEM protected title compound was treated with trifluoroacetic acid to furnish the title compound as a white solid. An analytical sample of the title compound was obtained by preparative HPLC: Gemini Axia 5µ C18A 110A 100×30 mm. Gradient (0.1% formic acid in water)/methanol=10/90 to 40/60. The title compound was obtained as an off-white solid (58%). MS: m/e=219.2 [M+H]'.

EXAMPLE 18

6-Cyclopentyl-8-hydroxyquinazolin-4(3H)-one

A mixture of 6-bromo-8-(2-trimethylsilanyl-ethoxymethoxy)-3-(2-trimethylsilanyl-ethoxymethyl)-3H-quinazolin-4-one (example 7a) (0.2 g, 0.4 mmol), bis(tri-tert-butylphosphine)palladium (O) (0.01 g, 0.02 mmol) and cyclopentylzinc bromide (2.4 ml ml of a 0.5 M solution in THF) and THF (1 ml) was stirred at room temperature for 3 hours. The mixture was extracted with ethyl acetate and sat. sodium bicarbonate solution. The organic layer was dried (Na₂SO₄), adsorbed on silica and chromatographed (silica gel, heptane/ethyl acetate=100:00 to 65:35) to furnish the SEM protected title compound as an oil (0.04 g, 20%) which was dissolved in chloroform (1 ml). Trifluoroacetic acid (1 ml) was added and the mixture was stirred for 2 hours at room temperature. After evaporation of all volatiles the oily residue was purified by preparative HPLC: Gemini Axia 5µ C18A 110A 100×30 mm. Gradient (0.1% formic acid in water)/methanol=10/90 to 40/60. The title compound was obtained as an off-white solid (58%) MS: m/e=231.2 [M+H]⁺.

EXAMPLE 19

6-(5,8-dimethyl-3,4-dihydro-naphthalen-2-yl)-8-hydroxy-3H-quinazolin-4-one

A mixture of 6-bromo-8-(2-trimethylsilanyl-ethoxymethoxy)-3-(2-trimethylsilanyl-ethoxymethyl)-3H-quinazolin-4-one (example 7a) (0.2 g, 0.4 mmol), tetrakis(triphenylphosphine)palladium(O) (0.046 g, 0.04 mmol), 5,8-dimethyl-3,4-dihydronaphthalen-2-ylboronic acid (CAS Registry No. 521917-65-7) (0.12 g, 0.6 mmol), toluene (5 ml) and 1 ml of a 2M aqueous potassium carbonate solution was stirred at 90° C. for 4 hours. The mixture was extracted with ethyl acetate and sat. sodium bicarbonate solution. The organic layer was dried (Na₂SO₄), adsorbed on silica and chromatographed (silica gel, heptane/ethyl acetate=100:00 to 75:25) to furnish the SEM protected title compound as an oil (0.19 g, 83%) which was dissolved in dichloromethane (5 ml). Trifluoroacetic acid (2 ml) was added and the mixture was stirred for 2 hours at room temperature. After evaporation of all volatiles the oily residue was purified by preparative HPLC: Gemini Axia 5µ C18A 110A 100×30 mm. Gradient (0.1% formic acid in water)/methanol=10/90 to 40/60. The title compound was obtained as an off-white solid (9%). MS: m/e=317.1 [M–H]⁻.

EXAMPLE 20

(E)-8-Hydroxy-6-styrylquinazolin-4(3H)-one

A mixture of 6-bromo-8-(2-trimethylsilanyl-ethoxymethoxy)-3-(2-trimethylsilanyl-ethoxymethyl)-3H-quinazolin-4-one (example 7a) (0.1 g, 0.2 mmol), bis(triphenylphosphine)palladium(II)dichloride (0.007 g, 0.01 mmol) styrene (0.031 g, 0.3 mmol), tetrabutylammonium bromide (0.032 g, 0.1 mmol), potassium carbonate (0.055 g, 0.4 mmol) and dimethylformamide (1 ml) was stirred at 140° C. for 2 hours. The mixture was extracted with ethyl acetate and brine. The organic layer was dried (Na₂SO₄), adsorbed on silica and chromatographed (silica gel, heptane/ethyl acetate=100:00 to 65:35) to furnish the SEM protected title compound as a light yellow oil (0.03 g, 29%) which was dissolved in chloroform (5 ml). Trifluoroacetic acid (1 ml) was added and the mixture was stirred for 16 hours at room temperature. After evaporation of all volatiles the title compound was obtained as a yellow solid (0.007 g, 46%). MS: m/e=265.1 [M+H]⁺.

EXAMPLE 21

(E)-8-Hydroxy-6-(4-methylstyryl)quinazolin-4(3H)-one

In analogy to example 20, 6-bromo-8-(2-trimethylsilanyl-ethoxymethoxy)-3-(2-trimethylsilanyl- ethoxymethyl)-3H- quinazolin-4-one (example 7a) was reacted with bis(triphenylphosphine)palladium(II)dichloride, styrene, tetrabutylammonium bromide, potassium carbonate and dimethylformamide. The mixture was stirred at 140° C. for 30 minutes in the microwave oven. After extraction with ethyl acetate and brine the organic layer was dried ($Na_2SO_4$), adsorbed on silica and chromatographed (silica gel, heptane/ethyl acetate=100:00 to 65:35) to furnish the SEM protected title compound as a light yellow oil (0.05 g, 46%) which was dissolved in chloroform (2 ml). Trifluoroacetic acid (0.5 ml) was added and the mixture was stirred for 2 hours at room temperature. After evaporation of all volatiles the oily residue was triturated with ethyl acetate to afford the title compound as an off-white solid (0.009 g, 43%).

MS: m/e=279.1 $[M+H]^+$.

EXAMPLE 22

8-Hydroxy-6-isobutylquinazolin-4(3H)-one

In analogy to example 9, 6-bromo-8-(2-trimethylsilanyl-ethoxymethoxy)-3-(2-trimethylsilanyl-ethoxymethyl)-3H-quinazolin-4-one (example 7a) was reacted with bis(triphenylphosphine)palladium(II)dichloride and 3-phenylpropylzinc bromide (instead of benzylzinc bromide). After workup the SEM protected title compound was treated with trifluoroacetic acid to furnish the title compound as a white solid. MS: m/e=281.1 $[M+H]^+$.

EXAMPLE 23

8-Hydroxy-6-(phenylethynyl)quinazolin-4(3H)-one

A mixture of 6-bromo-8-(2-trimethylsilanyl-ethoxymethoxy)-3-(2-trimethylsilanyl-ethoxymethyl)-3H-quinazolin-4-one (example 7a) (0.2 g, 0.4 mmol), bis(triphenylphosphine)palladium(II)dichloride (0.028 g, 0.04 mmol) ethynylbenzene (0.049 g, 0.5 mmol), copper(II) iodide (0.004 g, 0.02 mmol), triethylamine (0.4 g, 4 mmol) and THF (5 ml) was stirred at 70° C. for 16 hours. The mixture was extracted with ethyl acetate and brine. The organic layer was dried ($Na_2SO_4$), adsorbed on silica and chromatographed (silica gel, heptane/ethyl acetate=100:00 to 80:20) to furnish the SEM protected title compound as an off-white solid (0.2 g, 96%) which was dissolved in dichloromethane (5 ml). Trifluoroacetic acid (1 ml) was added and the mixture was stirred for 16 hours at room temperature. After evaporation of all volatiles and trituration with diisopropylether the title compound was obtained as a light brown solid (0.03 g, 34%). MS: m/e=263.0 $[M+H]^+$.

EXAMPLE 24

8-Hydroxy-6-(3-isopropoxyphenyl)quinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 3-isopropoxyphenylboronic acid (instead of 3,4-dihydronaphthalen-2-ylboronic acid), 2.5 equivalents of 2M aqueous potassium carbonate solution and dioxane (instead of dimethylformamide). The mixture was stirred at 110° C. for 16 hours. After extractive workup and chromatographic purification the SEM protected title compound was isolated as a light yellow oil (82%). In analogy to example 7c, treatment with trifluoroacetic acid and evaporation of all volatiles afforded the title compound which was purified by preparative HPLC: Gemini Axia 5μ C18A 110A 100×30 mm. Gradient (0.1% formic acid in water)/methanol=10/90 to 40/60. The title compound was obtained as a white solid (3%). MS: m/e=295.0 $[M-H]^-$.

EXAMPLE 25

6-(2,3-Dihydrobenzofuran-6-yl)-8-hydroxyquinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with terakis(triphenylphosphine)palladium(O) (instead of bis(diphenylphosphino)ferrocene-palladium(II)dichloride), 2,3-dihydrobenzofuran-6-ylboronic acid (instead of 3,4-dihydronaphthalen-2-ylboronic acid), potassium carbonate and dioxane (instead of dimethylformamide). Extractive workup and chromatographic purification furnished the SEM protected title compound as a light yellow solid (84%). After reaction with 90% formic acid for 2 hours at 90° C., evaporation of all volatiles and trituration with ethyl acetate the title compound was obtained as an off-white solid (62%). MS: m/e=279.1 $[M-H]^-$.

EXAMPLE 26

8-Hydroxy-6-(2-methoxy-5-(trifluoromethyl)phenyl)quinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 2-methoxy-5-(trifluoromethyl)phenylboronic acid (instead of 3,4-dihydronaphthalen-2-ylboronic acid), aqueous 2M potassium carbonate solution and dioxane. Extractive workup and chromatographic purification furnished the SEM protected title compound as a light yellow solid (57%). After reaction with trifluoroacetic acid in chloroform for 2 hours at 90° C., evaporation of all volatiles and trituration with ethyl acetate the title compound was obtained as a white solid (10%). MS: m/e=337.2 $[M+H]^+$.

EXAMPLE 27

4-Chloro-3-(8-hydroxy-4-oxo-3,4-dihydroquinazolin-6-yl)benzonitrile

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 2-chloro-5-cyanophenylboronic acid (instead of 3,4-dihydronaphthalen-2-ylboronic acid), aqueous 2M potassium carbonate solution and dioxane. Extractive workup and chromatographic purification furnished the SEM protected title compound as a light yellow solid (46%). After reaction with trifluoroacetic acid in chloroform for 4 hours at 90° C., evaporation of all volatiles, coevaporation with methanol and trituration with ethyl acetate the title compound was obtained as a light brown solid (49%).

MS: m/e=298.3 $[M+H]^+$.

EXAMPLE 28

8-hydroxy-6-(3,4,5-trifluorophenyl)quinazolin-4 (3H)-one a) 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one A mixture of 6-bromo-8-(2-trimethylsilanyl-ethoxymethoxy)-3-(2-trimethylsilanyl-ethoxymethyl)-3H-quinazolin-4-one (example 7a) (3.0 g, 6 mmol), bis(pinacolato)diboron (3.8 g, 15 mmol), bis(diphenylphosphino)ferrocene-palladium(II)dichloride dichloromethane complex (0.49 g, 0.6 mmol) and potassium acetate (2.94 g, 30 mmol) in dioxane (500 ml) was stirred at 100° C. for 5 hours. After evaporation of all volatiles the residue was adsorbed on silica and chromatographed (silica gel, heptane/ethyl acetate=100:00 to 50:50) and triturated with heptane to furnish the title compound as a white solid (2.8 g, 84%). MS: m/e=549.3 [M+H]$^+$.

b) 6-(3,4,5-trifluorophenyl)-8-((2-trimethylsilyl)ethoxy)methoxy)-3-((2-(trimethylsilyl)ethoxy)methyl)quinazolin-4(3H)-one A solution of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.3 g, 0.55 mmol) and 1,2,3-trifluoro-5-iodobenzene (0.18 g, 0.71 mmol) in dioxane (5 ml) was treated with bis(diphenylphosphino)ferrocene-palladium(II)dichloride (0.04 g, 0.055 mmol). Aqueous 2M potassium carbonate solution (0.5 ml) was added and the reaction mixture was stirred at 100° C. for 16 hours. After extractive workup (ethyl acetate/water) the organic phase was dried (Na$_2$SO$_4$), adsorbed on silica and chromatographed (silica gel, heptane/ethyl acetate=90:10 to 50:50) and triturated with hexane to furnish the title compound as a white solid (0.06 g, 20%). MS: m/e=553.3 [M+H]$^+$.

c) 8-Hydroxy-6-(3,4,5-trifluorophenyl)quinazolin-4 (3H)-one

A solution of 6-(3,4,5-trifluorophenyl)-8-((2-(trimethylsilyl)ethoxy)methoxy)-3-((2-(trimethylsilyl)ethoxy)methyl)quinazolin-4(3H)-one (0.06 g, 0.1 mmol) and trifluoroacetic acid (0.4 ml) in chloroform (1 ml) was stirred at room temperature for 3 hours. Evaporation of all volatiles, coevaporation with methanol and trituration with ethyl acetate afforded the title compound as an off-white solid (0.022 g, 69%). MS: m/e=290.9 [M−H]$^-$.

EXAMPLE 29

(E)-6-(5-(Dimethylamino)-2-(phenyldiazenyl)phenyl)-8-hydroxyquinazolin-4(3H)-one In analogy to example 7b, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 5-(dimethylamino)-2-(phenyldiazenyl)phenylboronic acid (instead of 3,4-dihydronaphthalen-2-ylboronic acid), aqueous 2M potassium carbonate solution and dioxane. Extractive workup and chromatographic purification furnished the SEM protected title compound as a light yellow solid (7%). After reaction with trifluoroacetic acid in chloroform for 2 hours at room temperature, all volatiles were evaporated. Coevaporation with methanol and trituration with ethyl acetate provided the title compound as a black solid (24%). MS: m/e=384.0 [M−H]$^-$.

EXAMPLE 30

8-Hydroxy-6-(4-methyl-4'-(trifluoromethyl)biphenyl-2-yl)quinazolin-4(3H)-one In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), 2-bromo-4-methyl-4'(trifluoromethyl)biphenyl (instead of 1,2,3-trifluoro-5-iodobenzene), bis(diphenylphosphino)ferrocene-palladium(II)dichloride in dioxane (5 ml) was reacted with aqueous 2M potassium carbonate solution (0.5 ml) and the reaction mixture was stirred at 100° C. for 3 days. After extractive workup and chromatographic purification the SEM protected title compound was obtained as a yellow oil (35%). Reaction with trifluoroacetic acid, evaporation and extractive workup (ethyl acetate/water) furnished the title compound as an off-white crystalline solid (28%). MS: m/e=395.0 [M−H]$^-$

EXAMPLE 31

8-Hydroxy-6-(2,3,4-trifluoro-phenyl)-3H-quinazolin-4-one

In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), 1,2,3-trifluoro-4-iodobenzene (instead of 1,2,3-trifluoro-5-iodobenzene), bis(diphenylphosphino)ferrocene-palladium(II)dichloride in dioxane was reacted with aqueous 2M potassium carbonate solution. After extractive workup and chromatographic purification the SEM protected title compound was obtained as a yellow oil (13%). Reaction with trifluoroacetic acid, evaporation and trituration furnished the title compound as a grey solid (12%). MS: m/e=290.8 [M−H]$^-$

EXAMPLE 32

(rac.) Methyl 2-(2-(8-hydroxy-4-oxo-3,4-dihydroquinazolin-6-yl)biphenyl-4-yl)propanoate In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), (rac.) methyl 2-(2-iodobiphenyl-4yl)propanoate (instead of 1,2,3-trifluoro-5-iodobenzene), bis(diphenylphosphino)ferrocene-palladium(II)dichloride in dioxane was reacted with aqueous 2M potassium carbonate. After extractive workup and chromatographic purification the SEM protected title compound was obtained as a yellow oil (26%). Reaction with trifluoroacetic acid, evaporation and trituration furnished the title compound as a light brown solid (68%). MS: m/e=401.1 [M+H]$^+$

EXAMPLE 33

8-Hydroxy-6-(perfluorophenyl)quinazolin-4(3H)-one

In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), 1,2,3,4,5-pentafluoro-6-iodobenzene (instead of 1,2,3-trifluoro-5-iodobenzene), bis(diphenylphosphino)ferrocene-palladium(II)dichloride in dioxane was reacted with aqueous 2M potassium carbonate. After extractive workup and chromatographic purification the SEM protected title compound was obtained as a yellow oil (25%). Reaction with trifluoroacetic acid, evaporation followed by preparative HPLC purification afforded the title compound as a white solid (38%). MS: m/e=327.0 [M−H]⁻

EXAMPLE 34

5,7-Dibromo-6-(4-fluorophenyl)-8-hydroxyquinazolin-4(3H)-one a) 6-(4-Fluorophenyl)-8-((2-(trimethylsilyl)ethoxy)methoxy)-3-((2-(trimethylsilyl)ethoxy)methyl)quinazolin-4(3H)-one In analogy to example 7b, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 4-fluorophenylboronic acid (instead of 3,4-dihydronaphthalen-2-ylboronic acid), 2.5 equivalents of 2M aqueous potassium carbonate solution and dioxane (instead of dimethylformamide). The mixture was stirred at 110° C. for 16 hours. After extractive workup and chromatographic purification the title compound was isolated as a light yellow solid (41%). MS: m/e=517.3 [M+H]⁺ b) 5,7-Dibromo-6-(4-fluorophenyl)-8-hydroxy-3-((2-(trimethylsilyl)ethoxy)methyl)quinazolin-4(3H)-one A solution of 6-(4-Fluorophenyl)-8-((2-(trimethylsilyl)ethoxy)methoxy)-3-((2-(trimethylsilyl)ethoxy)methyl)quinazolin-4(3H)-one (0.36 g, 0.7 mmol) in acetonitrile (2 ml) was treated with N-bromosuccinimide (0.30 g, 1.7 mmol). The mixture was stirred at room temperature for 4 days. The reaction mixture was adsorbed on silica and chromatographed (silica gel, dichloromethane/methanol=100:0 to 90:10). The title compound was isolated as an off-white solid (0.26 g, 69%). MS: m/e=545.0 [M+H]⁺ c) 5,7-Dibromo-6-(4-fluorophenyl)-8-hydroxyquinazolin-4(3H)-one

To a solution of 5,7-dibromo-6-(4-fluorophenyl)-8-hydroxy-3-((2-(trimethylsilyl)ethoxy)methyl)quinazolin-4(3H)-one (0.17 g, 0.31 mmol) in dichloromethane (5 ml) was added trifluoroacetic acid (2 ml). The mixture was stirred at room temperature for 16 hours. After evaporation of all volatiles the residue was coevaporated with toluene. Recrystallization from methanol furnished the title compound as a light brown solid.
MS: m/e=412.8 [M−H]⁻

EXAMPLE 35

6-(5-tert-Butyl-2-methoxyphenyl)-8-hydroxyquinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 5-tert-butyl-2-methoxyphenylboronic acid (instead of 3,4-dihydronaphthalen-2-ylboronic acid), aqueous 2M potassium carbonate solution and dioxane. Extractive workup and chromatographic purification furnished the SEM protected title compound as a white foam (68%). After reaction with trifluoroacetic all volatiles were evaporated. Coevaporation with methanol and trituration with ethyl acetate furnished the title compound as a white solid (40%). MS: m/e=325.0 [M+H]⁺.

EXAMPLE 36

8-Hydroxy-6-(2-methoxy-5-methylphenyl)quinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 2-methoxy-5-methylphenylboronic acid (instead of 3,4-dihydronaphthalen-2-ylboronic acid), aqueous 2M potassium carbonate solution and dioxane. Extractive workup and chromatographic purification furnished the SEM protected title compound as a colorless viscous oil (64%). After reaction with trifluoroacetic all volatiles were evaporated. Coevaporation with methanol and trituration with ethyl acetate furnished the title compound as a white solid (70%). MS: m/e=283.0 [M+H]⁺.

EXAMPLE 37

6-(2,5-Dichlorophenyl)-8-hydroxyquinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 2,5-dichlorophenylboronic acid (instead of 3,4-dihydronaphthalen-2-ylboronic acid), aqueous 2M potassium carbonate solution and dioxane. Extractive workup and chromatographic purification furnished the SEM protected title compound as a light yellow viscous oil (56%). After reaction with trifluoroacetic all volatiles were evaporated. Coevaporation with methanol and trituration with methanol furnished the title compound as a grey solid (74%). MS: m/e=304.9 [M−H]⁻.

EXAMPLE 38

5,7-Difluoro-8-hydroxy-6-phenylquinazolin-4(3H)-one a) N-(3,5-Difluoro-2-methoxyphenyl)pivalamide 3,5-Difluoro-2-methoxyaniline (5.0 g, 31 mmol) was dissolved in THF (50 ml) and triethylamine (3.5 g, 35 mmol)

was added. The mixture was cooled in an ice bath and pivaloyl chloride (4.2 g, 35 mmol) was added dropwise. After 1 hour stirring at 0° C., temperature was allowed to reach 20° C. and stirring was continued for 16 hours. After filtration the organic phase was adsorbed on silica and chromatographed (silica gel, heptane/ethyl acetate=100:00 to 80:20) to furnish the title compound as a colorless liquid (7.2 g, 95%). MS: m/e=244.2 [M+H]$^+$.

b) N-(3,5-Difluoro-4-iodo-2-methoxyphenyl)pivalamide

A solution of N-(3,5-difluoro-2-methoxyphenyl)pivalamide (0.70 g, 2.9 mmol) in THF (30 ml) was cooled to <−75° C. Lithium diisopropylamide (5.6 ml of a 2M solution in cyclohexane/ethylbenzene/tetrahydrofuran, 11.2 mmol) was added dropwise keeping temperature <−70° C. After 2 hours iodine (1.1 g, 4.3 mmol) was added and stirring was continued at 0° C. for 2 hours. The mixture was concentrated, partitioned (ethyl acetate/water) and the organic phase was adsorbed on silica and chromatographed (silica gel, heptane/ethyl acetate=100:00 to 85:25) to furnish the title compound as a light yellow solid (0.83 g, 78%). MS: m/e=368.0 [M−H]$^-$.

c) N-(2,6-Difluoro-3-methoxybiphenyl-4-yl)pivalamide

A mixture of N-(3,5-difluoro-4-iodo-2-methoxyphenyl)pivalamide (0.8 g, 2.2 mmol), bis(diphenylphosphino)ferrocene-palladium(II)dichloride (0.53 g, 0.65 mmol), phenylboronic acid (0.34 g, 2.8 mmol) and potassium carbonate (5 ml of a 2M aqueous solution) in dioxane was stirred at 90° C. for 90 minutes. After filtration all volatiles were evaporated and the residue was partitioned (ethyl acetate/water). The organic phase was adsorbed on silica and chromatographed (silica gel, heptane/ethyl acetate=100:00 to 85:15) to furnish the title compound as a white solid (0.45 g, 65%). MS: m/e=318.0 [M−H]$^-$.

d) 2,6-Difluoro-5-methoxy-4-pivalamidobiphenyl-3-carboxylic acid

A solution of N-(2,6-difluoro-3-methoxybiphenyl-4-yl)pivalamide (0.44 g, 1.4 mmol) in diethyl ether (25 ml) was cooled to <−75° C. tert-Butyllithium (2.2 ml of a 1.6 M solution in heptane, 3.5 mmol) was added dropwise and the reaction mixture was stirred at <−75° C. for 1 hour. Dry ice (5 g) was added and temperature was allowed to reach 20° C. After extractive workup (diethyl ether/water) the aqueous phase was adjusted to pH <7 and partitioned (ethyl acetate/water). The organic layer was dried over Na$_2$SO$_4$ and evaporated to afford the title compound as a white solid (0.30 g, 60%). MS: m/e=362.1 [M−H]$^-$.

e) 2,6-Difluoro-5-methoxy-4-pivalamidobiphenyl-3-carboxamide 2,6-Difluoro-5-methoxy-4-pivalamidobiphenyl-3-carboxylic acid (0.30 g, 0.83 mmol) was dissolved in dimethylformamide (15 ml), carbonyldiimidazole (0.20 g, 1.2 mmol) was added and the reaction mixture was stirred at 60° C. for 2 hours. After cooling to 0° C. aqueous ammonia (10 ml of a 25% solution) was added. The temperature was allowed to reach 20° C. and stirring was continued for 16 hours. All volatiles were evaporated, the residue was dissolved in ethyl acetate and successively washed with 10% aqueous citric acid and 10% aqueous sodium bicarbonate solution. The organic phase was adsorbed on silica and chromatographed (silica gel, dichloromethane/methanol=99:1 to 98:2). The title compound was isolated as a white solid (0.25 g, 84%). MS: m/e=361.2 [M−H]$^-$.

f) 5,7-Difluoro-8-methoxy-6-phenylquinazolin-4(3H)-one

To a suspension of 2,6-difluoro-5-methoxy-4-pivalamidobiphenyl-3-carboxamide (0.067 g, 0.19 mmol) in triethylorthoformate (1 ml) was added p-toluenesulfonic acid (0.0018 g, 0.0092 mmol) and the mixture was stirred at 180° C. for 3 hours. After evaporation of all volatiles the residue was adsorbed on silica and chromatographed (silica gel, dichloromethane/methanol=99:1 to 98:2). The title compound was isolated as a white solid (0.007 g, 13%). MS: m/e=286.8 [M−H]$^-$.

g) 5,7-Difluoro-8-hydroxy-6-phenylquinazolin-4(3H)-one

A mixture of 5,7-difluoro-8-methoxy-6-phenylquinazolin-4(3H)-one (0.031 g, 0.11 mmol), dichloromethane (5 ml) and boron tribromide (0.32 ml of a 1M solution in dichloromethane) was stirred at room temperature for 6 hours. After evaporation of all volatiles the residue was triturated successively with saturated aqueous sodium bicarbonate solution, water and ethyl acetate to provide the title compound as a white solid (0.014 g, 48%). MS: m/e=272.9 [M−H]$^-$.

EXAMPLE 39

8-Hydroxy-6-(3-(morpholinomethyl)phenyl)quinazolin-4(3H)-one 1:1 salt with trifluoroacetate 6-Bromo-8-(2-trimethylsilanyl-ethoxymethoxy)-3-(2-trimethylsilanyl-ethoxymethyl)-3H-quinazolin-4-one (example 7a) (0.50 g, 1 mmol) was reacted with bis(diphenylphosphino)ferrocene-palladium(II)dichloride dichloromethane complex (0.25 g, 0.3 mmol), 4-(3-(4,4,5,5-tetramethyl-1,3,2-dioxaborolan-2-yl)benzyl)morpholine hydrochloride (0.44 g, 1.3 mmol), potassium carbonate (5 ml of a 2M aqueous solution) and dioxane (30 ml). After 2 hours at 90° C. all volatiles were evaporated. Extractive workup (ethyl acetate/water) and drying of the organic phase (Na$_2$SO$_4$) was followed by evaporation of all volatiles. Chromatographed purification (silica gel, dichloromethane/methanol=100:0 to 96:4) furnished the free base of the SEM protected title compound which was isolated as a light brown oil (0.57 g, 95%). This product was dissolved in dichloromethane (10 ml), trifluoroacetic acid (3 ml) was added and the reaction mixture was stirred at room temperature for 3 hours. After evaporation of all volatiles the residue was coevaporated with methanol. The oily residue was triturated with diisopropylether to furnish the title compound as a white solid (0.19 g, 44%). MS: m/e=336.0 [M−H]$^-$.

EXAMPLE 40

8-Hydroxy-6-(1-methylindolin-5-yl)quinazolin-4(3H)-one 1:1 salt with trifluoroacetate In analogy to example 39, 6-Bromo-8-(2-trimethylsilanyl-ethoxymethoxy)-3- (2-trimethylsilanyl-ethoxymethyl)-

3H-quinazolin-4-one (example 7a) was reacted with bis(diphenylphosphino)ferrocene-palladium(II)dichloride dichloromethane complex, 1-methyl-5-(4,4,5,5-tetramethyl1,3,2dioxaborolan-2yl)indoline (instead of 4-(3-(4,4,5,5-tetramethyl-1,3,2-dioxaborolan-2-yl)benzyl)morpholine hydrochloride), potassium carbonate solution and dioxane (30 ml). After chromatographic purification the free base of the SEM protected title compound was isolated (77%) which was reacted with trifluoroacetic acid. After evaporation and trituration the title compound was isolated as a yellow solid (34%). MS: m/e=294.0 [M+H]$^+$.

EXAMPLE 41

6-Bromo-8-hydroxy-5-(trifluoromethyl)quinazolin-4(3H)-one a) 2-Bromo-6-methoxy-3-trifluoromethyl-phenylamine 2-Methoxy-5-(trifluoromethyl)aniline (5.0 g, 26 mmol) was dissolved in tetrachloromethane (100 ml) and cooled in a salt/ice bath. N-bromosuccinimide (5.1 g, 29 mmol) was added in small portions keeping temperature <−10° C. After 1 hour temperature was allowed to reach 0° C. and the reaction mixture was stirred for 1 hour. For workup sodium bisulfite (10% aqueous solution) and ethyl acetate was added and stirring was continued for 30 minutes. The organic phase was adsorbed on silica and chromatographed (silica gel, heptane/ethyl acetate=100:00 to 88:12) to furnish the title compound which was isolated as a red oil (5.7 g, 73%). MS: m/e=269/271 [M]$^+$.

b) 2-Amino-3-methoxy-6-(trifluoromethyl)benzonitrile

A mixture of 2-bromo-6-methoxy-3-trifluoromethyl-phenylamine (4.7 g, 17 mmol, copper(I)cyanide (2.3 g, 26 mmol) and dimethylformamide (15 ml) was stirred at 120° C. for 16 hours. After evaporation of all volatiles the residue was extracted with saturated aqueous ammonium chloride solution and ethyl acetate. The organic phase was adsorbed on silica and chromatographed (silica gel, heptane/ethyl acetate=100:00 to 70:30) to furnish the title compound as a light brown solid (3.8 g, 54%). MS: m/e=215.1 [M−H]$^-$.

c) 2-Amino-5-bromo-3-methoxy-6-(trifluoromethyl)benzonitrile

2-Amino-3-methoxy-6-(trifluoromethyl)benzonitrile (2.0 g, 9.3 mmol) was dissolved in acetic acid (50 ml) and bromine (1.6 g, 10 mmol) was added. The reaction mixture was stirred for 16 hours at room temperature. After evaporation of all volatiles the residue was partitioned (ethyl acetate/water) and the organic phase was adsorbed on silica. Chromatographic purification (silica gel, heptane/ethyl acetate=100:00 to 70:30) furnished the title compound as a white solid (1.0 g, 37%). MS: m/e=294.9/292.7 [M−H]$^-$.

d) 2-Amino-5-bromo-3-methoxy-6-(trifluoromethyl)benzamide

A solution of 2-amino-5-bromo-3-methoxy-6-(trifluoromethyl)benzonitrile (0.2 g, 0.68 mmol) in conc. sulfuric acid (1.5 ml) was stirred at 80° C. for 4 hours, then at room temperature for 16 hours. After addition of ice, sodium bicarbonate was added until pH >7. Extractive workup (ethyl acetate/water) followed by chromatography (silica gel, dichloromethane/methanol=100:0 to 97:3) furnished the title compound which was isolated as a white solid (0.15 g, 73%). MS: m/e=310.9/312.8 [M−H]$^-$.

e) 6-Bromo-8-methoxy-5-(trifluoromethyl)quinazolin-4(3H)-one

A mixture of 2-amino-5-bromo-3-methoxy-6-(trifluoromethyl)benzamide (1.0 g, 3.2 mmol), acetic acid (3 ml) and triethoxymethane (30 ml) was stirred at 80° C. for 150 minutes. Temperature was raised to 120° C. and stirring was continued for 4 hours. The mixture was allowed to reach room temperature and the precipitate was filtered and dried to furnish the title compound as a white solid (0.95 g, 92%). MS: m/e=322.8/320.8 [M−H]$^-$.

f) 6-Bromo-8-hydroxy-5-(trifluoromethyl)quinazolin-4(3H)-one

A suspension of 6-bromo-8-methoxy-5-(trifluoromethyl)quinazolin-4(3H)-one (0.050 g, 0.16 mmol) in dichloromethane (5 ml) was cooled in an ice bath and boron tribromide (0.3 ml of a 1M solution in dichloromethane, 0.3 mmol) was added. After 90 minutes at 0° C. the reaction mixture was allowed to reach room temperature and stirred for 16 hours. All volatiles were evaporated and the residue was triturated with saturated aqueous sodium bicarbonate solution. The precipitate was filtered, washed with water and dried to furnish the title compound as light yellow solid (0.0060 g, 13%). MS: m/e=308.8/306.7 [M−H]$^-$.

EXAMPLE 42

8-Hydroxy-5-(trifluoromethyl)quinazolin-4(3H)-one a) N'-(2-Methoxy-5-(trifluoromethyl)phenyl)-N,N-dimethylformimidamide A mixture of 2-methoxy-5-(trifluoromethyl)aniline (1.91 g, 10 mmol) in dimethylformamidedimethylacetal (3.6 g, 30 mmol) was heated in a bath kept at 130° C. The methanol liberated was allowed to distill off. After 4 hours all volatiles were evaporated and the residue was adsorbed on silica and chromatographed (silica gel, dichloromethane/methanol=100:0 to 95:5). The title compound was isolated as a brown oil (1.7 g, 69%). MS: m/e=247.1 [M+H]$^+$.

b) (E)-N'-(2-Bromo-6-methoxy-3-(trifluoromethyl)phenyl)-N,N-dimethylformimidamide A solution of (E)-N'-(2-methoxy-5-(trifluoromethyl)phenyl)-N,N-dimethylformimidamide (13.7 g, 56 mmol) in chloroform (200 ml) was cooled in an ice bath and N-bromosuccinimide was added in portions maintaining temperature <10° C. After 2 hours the reaction mixture was allowed to reach room temperature and stirred for 16 hours. The precipitate was filtered and chromatographed (silica gel, heptane/ethyl acetate=100:00 to 30:70) to furnish the title compound as a white solid (6.3 g, 35%). MS: m/e=324 [M]$^+$.

c) (E)-N'-(2-Cyano-6-methoxy-3-(trifluoromethyl)phenyl)-N,N-dimethylformimidamide A mixture of (E)-N'-(2-bromo-6-methoxy-3-(trifluoromethyl)phenyl)-N,N-dimethylformimidamide (1.6 g, 5 mmol), copper(I)cyanide (0.67 g, 7.5 mmol) and dimethylformamide (2 ml) was stirred at 120° C. for 12 hours. After dilution with dimethylformamide (20 ml) the mixture was filtered. The organic phase was evaporated and the oily residue was partitioned (ethyl acetate/saturated aqueous ammonium chloride solution). The organic phase was adsorbed on silica and chromatographed (silica gel, heptane/ethyl acetate=100:00 to 0:100). The title compound was isolated as a white solid (0.95 g, 70%). MS: m/e=272.1 [M+H]$^+$.

d) (E)-2-((Dimethylamino)methyleneamino)-3-methoxy-6-(trifluoromethyl)benzamide

In analogy to example 41d, (E)-N'-(2-cyano-6-methoxy-3-(trifluoromethyl)phenyl)-N,N-dimethylformimidamide (instead of 2-amino-5-bromo-3-methoxy-6-(trifluoromethyl)benzonitrile) was reacted with conc. sulfuric acid. After extractive workup and chromatographic purification the title compound was isolated as a white solid (41%). MS: m/e=290.0 [M+H]$^+$.

e) 8-Methoxy-5-(trifluoromethyl)quinazolin-4(3H)-one

A solution of (E)-2-((dimethylamino)methyleneamino)-3-methoxy-6-(trifluoromethyl)benzamide (0.029 g, 0.10 mmol), potassium tert-butanolate (0.017 g, 0.15 mmol) in tert-butanol was stirred at 90° C. for 1 hour. Filtration, washing with water and drying afforded the title compound as a white solid (0.016 g, 66%). MS: m/e=242.9 [M–H]$^-$.

f) 8-Hydroxy-5-(trifluoromethyl)quinazolin-4(3H)-one

In analogy to example 41f, 8-methoxy-5-(trifluoromethyl)quinazolin-4(3H)-one (instead of 6-bromo-8-methoxy-5-(trifluoromethyl)quinazolin-4(3H)-one) was reacted with boron tribromide. Evaporation and trituration with aqueous sodium bicarbonate solution afforded the title compound as white solid (51%). MS: m/e=228.9 [M–H]$^-$.

EXAMPLE 43

6-(4-Fluorophenyl)-8-hydroxy-5-(trifluoromethyl) quinazolin-4(3H)-one a) 6-(4-Fluorophenyl)-8-methoxy-5-(trifluoromethyl)quinazolin-4(3H)-one A mixture of 6-bromo-8-methoxy-5-(trifluoromethyl)quinazolin-4(3H)-one (example 41e) ((0.15 g, 0.46 mmol), bis(diphenylphosphino)ferrocene-palladium(II)dichloride dichloromethane complex (0.11 g, 0.14 mmol), 4-fluorophenylboronic acid (0.085 g, 0.60 mmol) and aqueous potassium carbonate (3 ml of a 2M solution) in dimethylformamide (15 ml) was stirred at 90° C. for 90 minutes. After extractive workup (ethyl acetate/saturated aqueous sodium bicarbonate solution) the organic phase was adsorbed on silica and chromatographed (silica gel, dichloromethane/methanol=100:0 to 95:5). The title compound was isolated as a white solid (0.09 g, 57%). MS: m/e=247.1 [M+H]$^+$.

b) 6-(4-Fluorophenyl)-8-hydroxy-5-(trifluoromethyl) quinazolin-4(3H)-one

In analogy to example 41f, 6-(4-fluorophenyl)-8-methoxy-5-(trifluoromethyl)quinazolin-4(3H)-one (instead of 6-bromo-8-methoxy-5-(trifluoromethyl)quinazolin-4(3H)-one) was reacted with boron tribromide. Evaporation and trituration with aqueous sodium bicarbonate solution afforded the title compound as a light purple solid (30%). MS: m/e=323.0 [M–H]$^-$.

EXAMPLE 44

6-Bromo-8-hydroxy-5-nitro-3H-quinazolin-4-one a) 6-Bromo-8-methoxy-5-nitroquinazolin-4(3H)-one Nitric acid (10 ml of a 65% solution) was cooled in an ice bath and conc. sulfuric acid (10 ml) was added at a rate keeping temperature <10° C. 6-Bromo-8-methoxy-3H-quinazolin-4-one (example 2a) was added in small portions keeping temperature <10° C. The mixture was stirred in an ice bath for 1 hour, allowed to reach 20° C. and poured on ice (50 g). Filtration, washing with water and drying furnished the title compound as a grey solid (3.4 g, 97%). MS: m/e=300.0/298.1 [M–H]$^-$.

b) 6-Bromo-8-hydroxy-5-nitro-3H-quinazolin-4-one

In analogy to example 41f, 6-bromo-8-methoxy-5-nitroquinazolin-4(3H)-one (instead of 6-bromo-8-methoxy-5-(trifluoromethyl)quinazolin-4(3H)-one) was reacted with boron tribromide. Evaporation and trituration with aqueous sodium bicarbonate solution afforded the title compound as a grey solid (43%). MS: m/e=285.7/283.8 [M–H]$^-$.

EXAMPLE 45

8-Hydroxy-6-(1-(2-methoxyethyl)-1H-pyrazol-5-yl) quinazolin-4(3H)-one a) 5-Iodo-1-(2-methoxy-ethyl)-1H-pyrazole 1-(2-methoxyethyl)-1H.pyrazole (CAS Registry No. 304693-68-3) (1.5 g, 12 mmol) was dissolved in THF (30 ml) and cooled in a dry ice/acetone bath. Keeping temperature <–70° C. n-butyllithium (11 ml of a 1.6M solution in hexane) was added dropwise. After 1 hour iodine (4.5 g, 18 mmol) was added. Temperature was allowed to reach 20° C. and stirring was continued for 2 hours. The reaction mixture was adsorbed on silica and chromatographed (silica gel, heptane/ethyl acetate=100:00 to 0:100). The title compound was isolated as a yellow solid (0.35 g, 6%). MS: m/e=253.1 [M+H]$^+$.

b) 8-Hydroxy-6-(1-(2-methoxyethyl)-1H-pyrazol-5-yl)quinazolin-4(3H)-one

In analogy to example 28b/c, 6-(4,4,5,5-tetramethyl-1,3,2-dioxaborolan-2-yl)-8-((2-(trimethylsilyl)ethoxy) methoxy)-3-((2-(trimethylsilyl)ethoxy)methyl)quinazolin-4 (3H)-one (example 28a), 5-iodo-1-(2-methoxy-ethyl)-1H-pyrazole (instead of 1,2,3-trifluoro-5-iodobenzene), bis (diphenylphosphino)ferrocene-palladium(II)dichloride in dioxane was reacted with aqueous 2M potassium carbonate solution. After extractive workup and chromatographic purification the SEM protected title compound was obtained as a light brown oil (27%). Reaction with trifluoroacetic acid, evaporation and extractive workup (ethyl acetate/water) followed by preparative HPLC furnished the title compound as an off-white solid (22%). MS: m/e=285.3 [M–H]$^-$

EXAMPLE 46

8-Hydroxy-6-(4-(methoxymethyl)-2-methylthiazol-5-yl)quinazolin-4(3H)-one a) 5-Iodo-4-methoxymethyl-2-methyl-thiazole A suspension of 4-(methoxymethyl)-2-methylthiazole (CAS Registry No. 478031-96-8) (0.33 g, 2.3 mmol), silver sulfate (0.43 g, 1.4 mmol) and iodine (0.59 g, 2.3 mmol) in methanol (10 ml) was stirred at room temperature for 16 hours. After filtration the organic phase was adsorbed on silica and chromatographed (silica gel, heptane/ethyl acetate=100:00 to 70:30). The title compound was isolated as a white solid (0.16 g, 26%). MS: m/e=237.9 [M-OCH$_3$]$^+$.

b) 8-Hydroxy-6-(4-(methoxymethyl)-2-methylthiazol-5-yl)quinazolin-4(3H)-one

In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), 5-iodo-4-methoxymethyl-2-methyl-thiazole (instead of 1,2,3-trifluoro-5-iodobenzene), bis(diphenylphosphino)ferrocene-palladium(II)dichloride in dioxane was reacted with aqueous 2M potassium carbonate solution. After extractive workup and chromatographic purification the SEM protected title compound was obtained as a light brown oil (35%). Reaction with trifluoroacetic acid, evaporation, coevaporation with methanol and trituration with ethyl acetate furnished the title compound as a light brown solid (88%). MS: m/e=302.1 [M–H]$^-$

EXAMPLE 47

8-Hydroxy-6-(1-(2-methoxyethyl)-1H-pyrazol-4-yl)quinazolin-4(3H)-one a) 4-Iodo-1-(2-methoxyethyl)-1H-pyrazole A suspension of 1-(2-methoxyethyl)-1H.pyrazole (CAS Registry No. 304693-68-3) (2.4 g, 19 mmol), silver sulfate (3.6 g, 11 mmol) and iodine (4.4 g, 19 mmol) in methanol (30 ml) was stirred at room temperature for 4 hours. After filtration the organic phase was evaporated. The title compound was isolated as a yellow solid (6.5 g, 136%) and was used in the next step without further purification. MS: m/e=253.0 [M+H]$^+$.

b) 8-Hydroxy-6-(1-(2-methoxyethyl)-1H-pyrazol-4-yl)quinazolin-4(3H)-one

In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), 4-iodo-1-(2-methoxyethyl)-1H-pyrazole (instead of 1,2,3-trifluoro-5-iodobenzene), bis(diphenylphosphino)ferrocene-palladium(II)dichloride in dioxane was reacted with aqueous 2M potassium carbonate solution. After extractive workup and chromatographic purification the SEM protected title compound was obtained as a light brown oil (42%). Reaction with trifluoroacetic acid, evaporation, trituration first with methanol and then with ethyl acetate furnished the title compound as a light grey solid (88%).
MS: m/e=285.0 [M–H]$^-$

EXAMPLE 48

6-(2-Chloro-5-methanesulfonyl-phenyl)-8-hydroxy-3H-quinazolin-4-one

In analogy to example 28b/c, 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (example 28a), 1-chloro-2-iodo-4-(methylsulfonyl)benzene (instead of 1,2,3-trifluoro-5-iodobenzene), bis(diphenylphosphino)ferrocene-palladium(II)dichloride in dioxane was reacted with aqueous 2M potassium carbonate solution. After extractive workup and chromatographic purification the SEM protected title compound was obtained as a light yellow oil (44%). Reaction with trifluoroacetic acid, evaporation, trituration with methanol and then purification by preparative HPLC furnished the title compound as a white solid (88%). MS: m/e=349.1 [M–H]$^-$

EXAMPLE 49

6-(4-Fluorophenyl)-8-hydroxy-5-phenylquinazolin-4(3H)-one a) 6-Bromo-8-methoxy-3-((2-(trimethylsilyl)ethoxy)methyl)quinazolin-4(3H)-one To a suspension of 6-bromo-8-methoxy-3H-quinazolin-4-one (10 g, 39 mmol) in dimethylformamide (150 ml) was added in 5 portions sodium hydride (2.6 g of a 55% dispersion in mineral oil, 59 mmol). The mixture was stirred at 60° C. for 90 minutes. With ice bath cooling SEM-chloride (7.2 g, 43.1 mmol) was added dropwise. After 1 hours the temperature was allowed to reach 20° C. and stirring was continued for 3 d. All volatiles were evaporated and the residue was partitioned (ethyl acetate/brine). The organic layer was dried (Na$_2$SO$_4$), concentrated and chromatographed (silica gel, heptane/ethyl acetate=100:0 to 0:100) and triturated with hexane to furnish the title compound as a white solid (7.2 g, 48%). MS: m/e=385.0/387.0 [M+H]$^+$.

b) 6-(4-Fluorophenyl)-8-methoxy-3-((2-(trimethylsilyl)ethoxy)methyl)quinazolin-4(3H)-one A mixture of 6-bromo-8-methoxy-3-((2-(trimethylsilyl)ethoxy)methyl)quinazolin-4(3H)-one (3.0 g, 7.8 mmol), bis(diphenylphosphino)ferrocene-palladium(II)dichloride dichloromethane complex (1.9 g, 2.3 mmol), 4-fluorophenylboronic acid (1.4 g, 10 mmol) and potassium carbonate (8 ml of a 2M aqueous solution) in dioxane (80 ml) was stirred at 90° C. for 3 hours. After filtration all volatiles were evaporated and the residue was partitioned (ethyl acetate/water). The organic phase was dried (Na$_2$SO$_4$), adsorbed on silica and chromatographed (silica gel, heptane/ethyl acetate=100:00 to 10:90) to furnish the title compound as an off-white solid (2.9 g, 94%). MS: m/e=401.2 [M+H]$^+$.

c) 5-Bromo-6-(4-fluorophenyl)-8-methoxy-3-((2-(trimethylsilyl)ethoxy)methyl)quinazolin-4(3H)-one A solution of 6-(4-fluorophenyl)-8-methoxy-3-((2-(trimethylsilyl)ethoxy)methyl)quinazolin-4(3H)-one (2.6 g, 6.4 mmol) in acetic acid (30 ml) was cooled in a water bath at room temperature. Bromine (1.2 g, 7.7 mmol) was added dropwise followed by addition of silver sulfate (1.2 g, 3.9 mmol). The mixture was stirred at room temperature for 16 hours. Toluene (100 ml) was added and after filtration all volatiles were evaporated. Residual volatiles were removed by coevaporation with toluene. After adsorption on silica the compound was purified by chromatography (silica gel, heptane/ethyl acetate=100:00 to 0:100) to furnish the title compound as a light brown foam (1.4 g, 45%). MS: m/e=479.0/481.0 [M+H]$^+$.

d) 6-(4-Fluorophenyl)-8-hydroxy-5-phenylquinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, phenylboronic acid (instead of p-tolylboronic acid) and potassium carbonate (2M aqueous solution) in dioxane. After workup and chromatographic purification the (methyl and SEM) bis-protected title compound was isolated as a light yellow oil (92%). Further reaction with boron tribromide followed by workup and preparative HPLC purification furnished the title compound as a light green solid (66%). MS: m/e=333.0 [M+H]$^+$.

EXAMPLE 50/51

6-(4-Fluorophenyl)-8-hydroxy-5-p-tolylquinazolin-4(3H)-one and 7-bromo-6-(4-fluorophenyl)-8-hydroxy-5-p-tolylquinazolin-4(3H)-one a) 6-(4-Fluorophenyl)-8-methoxy-5-p-tolyl-3-(2-trimethylsilanyl-ethoxymethyl)-3H-quinazolin-4-one and 7-bromo-6-(4-fluorophenyl)-8-hydroxy-5-p-tolylquinazolin-4(3H)-one A mixture of 5-bromo-6-(4-fluorophenyl)-8-methoxy-3-((2-(trimethylsilyl)ethoxy)methyl)quinazolin-4(3H)-one (0.20 g, 0.42 mmol)) (example 49c), bis(diphenylphosphino)ferrocene-palladium(II)dichloride dichloromethane complex (0.10 g, 0.13 mmol), p-tolylboronic acid (0.074 g, 0.54 mmol) and potassium carbonate (2 ml of a 2M aqueous solution) in dioxane (10 ml) was stirred at 90° C. for 1 hour. After filtration all volatiles were evaporated and the residue was partitioned (ethyl acetate/brine). The organic phase was adsorbed on silica and chromatographed (silica gel, heptane/ethyl acetate=100:00 to 25:75) to furnish the title compound as a light brown oil (0.18 g, 87%). MS: m/e=491.4 [M+H]$^+$.

b) 6-(4-Fluorophenyl)-8-hydroxy-5-p-tolylquinazolin-4(3H)-one and 7-bromo-6-(4-fluorophenyl)-8-hydroxy-5-p-tolylquinazolin-4(3H)-one To a solution of 6-(4-fluorophenyl)-8-methoxy-5-p-tolyl-3-(2-trimethylsilanyl-ethoxymethyl)-3H-quinazolin-4-one (0.18 g, 0.36 mmol) in dichloromethane (10 ml) was added boron tribromide (2 ml of a 2M solution in dichloromethane). The mixture was stirred at room temperature for 1 hour. After evaporation of all volatiles the residue was purified by preparative HPLC: Gemini Axia 5μ C18A 110A 100×30 mm. Gradient (0.1% formic acid in water)/methanol=10/90 to 40/60. 6-(4-Fluorophenyl)-8-hydroxy-5-p-tolylquinazolin-4(3H)-one was obtained as a white solid (0.022 g, 18%). MS: m/e=347.1 [M+H]$^+$.

Additionally, 7-bromo-6-(4-fluorophenyl)-8-hydroxy-5-p-tolylquinazolin-4(3H)-one was isolated as a white solid (0.037 g, 24%). MS: m/e=422.9/424.9 [M−H]$^-$.

EXAMPLE 52

6-(4-Fluorophenyl)-8-hydroxy-5-(3-(methylsulfonyl)phenyl)quinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 3-(methylsulfonyl)phenylboronic acid (instead of p-tolylboronic acid) and potassium carbonate (2M aqueous solution) in dioxane. After workup and chromatographic purification the (methyl and SEM) bis-protected title compound was isolated as a light yellow oil (82%). Further reaction with boron tribromide followed by workup and trituration with saturated aqueous sodium bicarbonate solution furnished the title compound as a white solid (47%). MS: m/e=409.2 [M−H]$^-$.

EXAMPLE 53

6-(4-Fluorophenyl)-8-hydroxy-5-(3-(trifluoromethyl)phenyl)quinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 3-(trifluoromethyl)phenylboronic acid (instead of p-tolylboronic acid) and potassium carbonate (2M aqueous solution) in dioxane. After workup and chromatographic purification the (methyl and SEM) bis-protected title compound was isolated as a light yellow oil (84%). Further reaction with boron tribromide followed by workup and preparative HPLC purification furnished the title compound as an off-white solid (39%). MS: m/e=401.3 [M+H]$^+$.

EXAMPLE 54

6-(4-Fluorophenyl)-8-hydroxy-4-oxo-3,4-dihydroquinazoline-5-carbonitrile a) 6-(4-Fluorophenyl)-8-methoxy-4-oxo-3-((2-(trimethylsilyl)ethoxy)methyl)-3,4-dihydroquinazoline-5-carbonitrile A mixture of 5-bromo-6-(4-fluorophenyl)-8-methoxy-3-((2-(trimethylsilyl)ethoxy)methyl)quinazolin-4(3H)-one (example 49c) (0.2 g, 0.42 mmol), L-proline (0.048 g, 0.42 mmol) and copper(I)cyanide in dimethylformamide (1 ml) was reacted at 120° C. for 6 hours, stirring was then continued at 100° C. for 16 hours. After evaporation of all volatiles the residue was partitioned (ethyl acetate/water). The organic phase was dried (Na$_2$SO$_4$), adsorbed on silica and chromatographed (silica gel, heptane/ethyl acetate=100:00 to 0:100) to furnish the title compound as a white solid (0.11 g, 61%). MS: m/e=484.3 [M+CH$_3$COO]$^-$.

b) 6-(4-Fluorophenyl)-8-hydroxy-4-oxo-3,4-dihydroquinazoline-5-carbonitrile 6-(4-Fluorophenyl)-8-methoxy-4-oxo-3-((2-(trimethylsilyl)ethoxy)methyl)-3,4-dihydroquinazoline-5-carbonitrile (0.10 g, 0.23 mmol) was dissolved in dichloromethane (5 ml) and boron tribromide (2 ml of a 1M solution in dichloromethane) was added dropwise. After 16 hours stirring at room temperature all volatiles were evaporated and the residue was triturated with saturated aqueous sodium bicarbonate solution. Preparative HPLC purification: Gemini Axia 5μ C18A 110A 100×30 mm. Gradient (0.1% formic acid in water)/methanol=10/90 to 40/60 furnished the title compound as an off-white solid (8%). MS: m/e=282.3 [M+H]$^+$.

EXAMPLE 55

N,N-Diethyl-4-(6-(4-fluorophenyl)-8-hydroxy-4-oxo-3,4-dihydroquinazolin-5-yl)benzamide In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 4-(diethylcarbamoyl)phenylboronic acid (instead of p-tolylboronic acid) and potassium carbonate (2M aqueous solution) in dioxane. After workup and chromatographic purification the (methyl and SEM) bis-protected title compound was isolated as an off-white solid (62%). Further reaction with boron tribromide followed by workup and trituration with saturated aqueous sodium bicarbonate solution furnished the title compound as a light purple solid (65%). MS: m/e=432.3 [M+H]$^+$.

EXAMPLE 56

6-(4-Fluorophenyl)-8-hydroxy-5-(pyridin-4-yl)quinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, pyridine-4-ylboronic acid (instead of p-tolylboronic acid) and potassium carbonate (2M aqueous solution) in dioxane. After workup and chromatographic purification the (methyl and SEM) bis-protected title compound was isolated as a light brown oil (72%). Further reaction with boron tribromide was followed by workup and trituration with saturated aqueous sodium bicarbonate solution. Preparative HPLC purification: Gemini Axia 5μ C18A 110A 100×30 mm. Gradient (0.1% formic acid in water)/methanol=10/90 to 40/60 furnished the title compound as a light brown solid (8%). MS: m/e=334.3 [M+H]$^+$.

EXAMPLE 57

6-(4-Fluorophenyl)-8-hydroxy-5-(4-(methylsulfonyl)phenyl)quinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 4-(methylsulfonyl)phenylboronic acid (instead of p-tolylboronic acid) and potassium carbonate (2M aqueous solution) in dioxane. After workup and chromatographic purification the (methyl and SEM) bis-protected title compound was isolated as a light yellow oil (57%). Further reaction with boron tribromide was followed by workup and trituration with saturated aqueous sodium bicarbonate solution. The title compound was obtained as an off-white solid (65%). MS: m/e=411.1 [M+H]$^+$.

EXAMPLE 58

6-(4-Fluorophenyl)-8-hydroxy-5-(2-methylpyridin-4-yl)quinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 2-methylpyridin-4-ylboronic acid (instead of p-tolylboronic acid) and potassium carbonate (2M aqueous solution) in dioxane. After workup and chromatographic purification the (methyl and SEM) bis-protected title compound was isolated as a light yellow oil (75%). Further reaction with boron tribromide was followed by workup and trituration with saturated aqueous sodium bicarbonate solution. The title compound was obtained as an off-white solid (70%). MS: m/e=346.0 [M−H]$^-$.

EXAMPLE 59

6-(4-Fluorophenyl)-8-hydroxy-5-(2-morpholinopyridin-4-yl)quinazolin-4(3H)-one

In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 2-morpholinopyridin-4-ylboronic acid (instead of p-tolylboronic acid) and potassium carbonate (2M aqueous solution) in dioxane. After workup and chromatographic purification the (methyl and SEM) bis-protected title compound was isolated as a yellow oil (71%). Further reaction with boron tribromide was followed by workup and trituration with saturated aqueous sodium bicarbonate solution. The title compound was obtained as a light green solid (47%). MS: m/e=419.0 [M+H]$^+$.

EXAMPLE 60

6-(6-(Dimethylamino)pyridin-3-yl)-8-hydroxyquinazolin-4(3H)-one 1:1 salt with trifluoroacetate In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis (diphenylphosphino)ferrocene-palladium(II)dichloride, 2-dimethylaminopyridin-5-ylboronic acid (CAS Registry No. 579525-46-5) (instead of 3,4-dihydronaphthalen-2-ylboronic acid), 2.5 equivalents of 2M aqueous potassium carbonate solution and dioxane (instead of dimethylformamide). The mixture was stirred at 90° C. for 2 hours. After extractive workup and chromatographic purification the SEM protected title compound was isolated as an off-white solid (81%). In analogy to example 7c, treatment with trifluoroacetic acid and evaporation of all volatiles afforded the title compound which was purified by repeated trituration with ethyl acetate. The title compound was obtained as a white solid (65%). MS: m/e=283.1 [M+H]$^+$.

EXAMPLE 61

6-(4-Fluorophenyl)-8-hydroxy-5-(1-methyl-1,2,3,6-tetrahydropyridin-4-yl)quinazolin-4(3H)-one In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 1-methyl-4-(4,4,5,5-tetramethyl-1,3,2-dioxaborolan-2yl)-1,2,3,6-tetrahydropyridine (instead of p-tolylboronic acid) and potassium carbonate (2M aqueous solution) in dioxane. After workup and chromatographic purification the (methyl and SEM) bis-protected title compound was isolated as a colorless oil (95%). Further reaction with boron tribromide was followed by workup and trituration with saturated aqueous sodium bicarbonate solution. The title compound was obtained as an off-white solid (17%). MS: m/e=352.1 [M+H]$^+$.

EXAMPLE 62

8-Hydroxy-6-(6-morpholinopyridin-2-yl)quinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 6-morpholinopyridin-2ylboronic acid (CAS Registry No. 1310385-04-6) (instead of 3,4-dihydronaphthalen-2-ylboronic acid), 2.5 equivalents of 2M aqueous potassium carbonate solution and dioxane (instead of dimethylformamide). The mixture was stirred at 90° C. for 2 hours. After extractive workup and chromatographic purification the SEM protected title compound was isolated as an off-white solid (45%). In analogy to example 7c, treatment with trifluoroacetic acid, evaporation of all volatiles, coevaporation with methanol and trituration with saturated aqueous sodium bicarbonate solution afforded the title compound which was purified by repeated trituration with ethyl acetate. The title compound was obtained as an off-white solid (73%). MS: m/e=325.1 [M+H]$^+$.

EXAMPLE 63

8-Hydroxy-6-(6-(pyrrolidin-1-yl)pyridin-2-yl)quinazolin-4(3H)-one

In analogy to example 7b/c, 6-bromo-8-(2-trimethylsilanyl-ethoxymethoxy)-3-(2-trimethylsilanyl-ethoxymethyl)-3H-quinazolin-4-one (example 7a) was reacted with bis(diphenylphosphino)ferrocene-palladium(II)dichloride, 6-(pyrrolidin-1-yl)pyridine-2-boronic acid (CAS Registry No. 1310404-18-2) (instead of 3,4-dihydronaphthalen-2-ylboronic acid), 2.5 equivalents of 2M aqueous potassium carbonate solution and dioxane (instead of dimethylformamide). The mixture was stirred at 90° C. for 2 hours. After extractive workup and chromatographic purification the SEM protected title compound was isolated as a colorless oil (7%). In analogy to example 7c, treatment with trifluoroacetic acid, evaporation of all volatiles, coevaporation with methanol and trituration with saturated aqueous sodium bicarbonate solution afforded the title compound which was purified by trituration with ethyl acetate. The title compound was obtained as an off-white solid (59%). MS: m/e=309.1 [M+H]$^+$.

EXAMPLE 64

4-[6-(4-Fluoro-phenyl)-8-hydroxy-4-oxo-3,4-dihydro-quinazolin-5-yl]-benzonitrile In analogy to example 50a/b, 5-bromo-6-(4-fluorophenyl)-8-methoxy-3-((2-(trimethylsilyl)ethoxy)methyl)quinazolin-4(3H)-one (example 49c) was reacted with bis(diphenylphosphino)ferrocene-palladium(II)dichloride dichloromethane complex, 4-cyanophenylboronic acid (instead of p-tolylboronic acid) and potassium carbonate (2M aqueous solution) in dioxane. After workup and chromatographic purification the (methyl and SEM) bis-protected title compound was isolated as a light yellow oil (69%). Further reaction with boron tribromide was followed by workup and trituration with ethyl acetate. The title compound was obtained as an off-white solid (13%). MS: m/e=356.1 [M−H]$^-$.

EXAMPLE 65

8-Hydroxy-6-(hydroxy(p-tolyl)methyl)quinazolin-4(3H)-one a) Benzyl 2-amino-3-(benzyloxy)-5-iodobenzoate

Benzyl 2-amino-3-(benzyloxy)benzoate (15.0 g, 45.0 mmol, CAS103929-64-2) and sodium acetate (11.2 g, 135 mmol) were combined with acetic acid (270 ml) under argon at room temperature to give a colorless suspension. Iodine chloride (14.6 g, 90.0 mmol) were added slowly at room temperature. The reaction mixture was stirred for 4 hours at room temperature. Extraction with ethyl acetate/water and washing with saturated aqueous sodium thiosulfate solution and chromatography (silica gel, heptane/ethyl acetate=90:10 to 80:20) yielded the title compound as colorless solid (9.2 g, 45%). 1H-NMR (CDCl$_3$): 5.04 (s, 2H), 5.31 (s, 2H), 6.1 (br s, 2H), 7.125 (d, J=3 Hz, 1H), 7.35-7.45 (m, 10H), 7.835 (d, J=3 Hz, 1H).

b) 2-Amino-3-(benzyloxy)-5-iodobenzoic acid

Benzyl 2-amino-3-(benzyloxy)-5-iodobenzoate (9.2 g, 20.0 mmol) was combined with methanol (195 ml) to give a colorless solution. The reaction mixture was diluted with water (0.5 ml) and lithium hydroxide monohydrate (2.14 g, 50.1 mmol) was added. The reaction mixture was heated to 90° C. and stirred for 20 hours. The reaction mixture was concentrated and neutralized at 10° C. with 1N hydrochlorid acid and buffer pH7 and filtered. The residue was dissolved in ethyl acetate, dried over sodium sulfate and the solvent was distilled off to yield the title compound as white solid (7.02 g, 95%). MS: m/e=370.0 [M+H]$^+$.

c) 8-(Benzyloxy)-6-iodoquinazolin-4(3H)-one

2-Amino-3-(benzyloxy)-5-iodobenzoic acid (7.00 g, 19.0 mmol) was combined with formamide (250 ml) to give a colorless solution. The reaction mixture was heated to 155° C. and stirred for 5 hours. The mixture was cooled to 20° C. The precipitated crystals were filtered and washed with ethyl acetate, then with heptane and dried to yield the title compound as light brown solid (6.0 g, 84%). MS: m/e=379.2 [M+H]$^+$.

d) 8-(Benzyloxy)-6-(hydroxy(p-tolyl)methyl)quinazolin-4(3H)-one

To a solution of 8-(benzyloxy)-6-iodoquinazolin-4(3H)-one (0.10 g, 0.26 mmol) and N',N',N',N'-tetramethylethylendiamine (0.03 g, 0.26 mmol) in tetrahydrofuran (30 ml) were added at −78° C. methyllithium (1.6M in THF, 0.17 ml, 0.26 mmol) and after 5 minutes tert-butyllithium (1.6M in hexane, 0.33 ml, 0.53 mmol). After 1 hour 4-methylbenzaldehyde (0.03 g, 0.26 mmol) was added and stirring was continued until the mixture had warmed to room temperature. Extraction with ethyl acetate and chromatography (silica gel, dichloromethane/methanol=99:1 to 95:5) yielded the title compound as colorless oil (0.01 g, 10%). MS: m/e=373.1 [M+H]$^+$.

e) 8-Hydroxy-6-(hydroxy(p-tolyl)methyl)quinazolin-4(3H)-one

To a solution of 8-(benzyloxy)-6-(hydroxy(p-tolyl) methyl)quinazolin-4(3H)-one (0.01 g, 0.03 mmol) in dichloromethane (1.0 ml) was added boron tribromide (1M in dichloromethane, 0.13 ml, 0.13 mmol). Stirring at room temperature overnight, extraction with ethyl acetate and chromatography (silica gel, dichloromethane/methanol=98:2 to 90:10) yielded the title compound as a viscous oil (0.007 g, 97%). MS: m/e=283.3 [M+H]$^+$.

EXAMPLE 66

8-Hydroxy-6-(4-methylbenzoyl)quinazolin-4(3H)-one a) 8-(Benzyloxy)-6-(4-methylbenzoyl)quinazolin-4(3H)-one 8-(Benzyloxy)-6-(hydroxy(p-tolyl)methyl)quinazolin-4(3H)-one (0.07 g, 0.19 mmol) and manganese dioxide (0.40 g, 4.63 mmol) in dichloromethane (50 ml) were stirred at room temperature overnight. Filtration and chromatography (silica gel, dichloromethane/methanol=95:5) yielded the title compound as a white solid (0.02 g, 23%). MS: m/e=371.1 [M+H]$^+$.

b) 8-Hydroxy-6-(4-methylbenzoyl)quinazolin-4(3H)-one

To a solution of 8-(benzyloxy)-6-(4-methylbenzoyl)quinazolin-4(3H)-one (0.02 g, 0.04 mmol) in dichloromethane (2.0 ml) was added a solution of boron tribromide (1 M in dichloromethane, 0.22 ml, 0.22 mmol). The mixture was stirred at room temperature overnight. Extraction with ethyl acetate and chromatography (silica gel, dichloromethane/methanol=95:5) yielded the title compound as light yellow solid (0.004 g, 36%). MS: m/e=278.8 [M−H]$^−$.

EXAMPLE 67

8-Hydroxy-6-(hydroxy(phenyl)methyl)quinazolin-4(3H)-one a) 8-(Benzyloxy)-6-(hydroxy(phenyl)methyl)quinazolin-4(3H)-one

To a solution of 8-(benzyloxy)-6-iodoquinazolin-4(3H)-one (0.50 g, 1.32 mmol) in tetrahydrofuran (75 ml) were added sodium hydride (0.11 g, 2.64 mmol) and N',N',N',N'-tetramethylethylenediamine (0.15 g, 0.20 ml, 1.32 mmol). After stirring for 30 minutes the mixture was cooled to −78° C. and tert-butyllithium (1.6 M in hexane, 1.65 ml, 2.64 mmol) was added. After 1 hour benzaldehyde (0.70 g, 0.67 ml, 6.61 mmol) was added and the mixture was allowed to warm up to room temperature. Extraction with ethyl acetate and chromatography (silica gel, dichloromethane/methanol=100:0 to 95:5) yielded the title compound as white solid (0.22 g, 46%). MS: m/e=359.1 [M+H]$^+$.

b) 8-Hydroxy-6-(hydroxy(phenyl)methyl)quinazolin-4(3H)-one

To a solution of 8-(benzyloxy)-6-(hydroxy(phenyl) methyl)quinazolin-4(3H)-one (0.05 g, 0.14 mmol) in methanol (50 ml) was added palladium on carbon (10%, 0.015 mg, 0.014 mmol). The mixture was hydrogenated overnight, filtered and purified by chromatography (silica gel, ethyl acetate) to yield the title compound as light yellow solid (0.02 g, 35%). MS: m/e=266.9 [M−H]$^−$.

EXAMPLE 68

6-Benzoyl-8-hydroxy-3H-quinazolin-4-one a) 6-Benzoyl-8-(benzyloxy)quinazolin-4(3H)-one

To a solution of 8-(benzyloxy)-6-(hydroxy(phenyl) methyl)quinazolin-4(3H)-one (0.17 g, 0.47 mmol) in dichloromethane (123 ml) was added manganese dioxide (1.03 g, 11.9 mmol). The mixture war stirred overnight at room temperature, filtered and purified by chromatography (silica gel, dichloromethane/methanol=100:0 to 95:5) to yield the title compound as white solid (0.13 g, 78%). MS: m/e=357.1 [M+H]$^+$.

b) 6-Benzoyl-8-hydroxy-3H-quinazolin-4-one

To a solution of 6-benzoyl-8-(benzyloxy)quinazolin-4 (3H)-one (0.05 g, 0.13 mmol) in dichloromethane (5.75 ml) was added boron tribromide (1M in dichloromethane, 0.65 ml, 0.65 mmol) and the mixture was stirred at room temperature overnight. Extraction with ethyl acetate and chromatography (silica gel, dichloromethane/methanol=95:5) yielded the title compound as white solid (0.02 g, 52%). MS: m/e=267.0 [M+H]$^+$.

EXAMPLE 69

8-Hydroxy-6-(tetrahydro-2H-pyran-4-yl)quinazolin-4(3H)-one 2,2,2-trifluoroacetate a) 6-(3,6-Dihydro-2H-pyran-4-yl)-8-((2-(trimethylsilyl)ethoxy)methoxy-3-((2-(trimethylsilyl)ethoxy)methyl)quinazolin-4(3H)-one 6-Bromo-8-((2-(trimethylsilyl)ethoxy)methoxy)-3-((2-(trimethylsilyl)ethoxy)methyl)quinazolin-4(3H)-one (example 7a, 0.45 g, 0.90 mmol), tetrakis(triphenylphosphine) palladium (0.05 g, 0.05 mmol) and 2,6-di-tert-butyl-4-methylphenol (0.02 g, 0.09 mmol) were combined with toluene (17.9 ml) to give a yellow solution. Tributyl(3,6-dihydro-2H-pyran-4-yl)stannane (0.37 g, 0.99 mmol) was added and the reaction mixture was refluxed for 2 hours. Tetrakis(triphenylphosphine)palladium (0.11 g, 0.09 mmol) was added and the reaction mixture was refluxed for 3 hours, then cooled to room temperature. Aqueous potassium fluoride solution (20%, 5 ml) was added and the mixture was stirred for 1 hour at room temperature. Extraction with ethyl acetate and chromatography (silica gel, ethyl acetate/heptane=20:80 to 70:30) yielded the title compound as light yellow solid (0.30 g, 66%). MS: m/e=505.2 [M+H]$^+$.

b) 6-(Tetrahydro-2H-pyran-4-yl)-8-((2-(trimethylsilyl)ethoxy)methoxy)-3-((2-(trimethylsilyl)ethoxy)methyl)-2,3-dihydroquinazolin-4(1H)-one 6-(3,6-Dihydro-2H-pyran-4-yl)-8-((2-(trimethylsilyl)ethoxy)methoxy)-3-((2-(trimethylsilyl)ethoxy)methyl)quinazolin-4(3H)-one (0.06 g, 0.12 mmol) was combined with ethyl acetate (5 ml) and palladium on carbon (10%, 6.0 mg). The reaction was hydrogenated for 15 hours at 25° C. The reaction mixture was filtered and the solvent was distilled off to yield the title compound as colorless oil (0.061 g, 99%). MS: m/e=507.3 [M−H]$^-$.

c) 6-(Tetrahydro-2H-pyran-4-yl)-8-((2-(trimethylsilyl)ethoxy)methoxy)-3-((2-(trimethylsilyl)ethoxy)methyl)quinazolin-4(3H)-one 6-(Tetrahydro-2H-pyran-4-yl)-8-((2-(trimethylsilyl)ethoxy)methoxy)-3-((2-(trimethylsilyl)ethoxy)methyl)-2,3-dihydroquinazolin-4(1H)-one (0.06 g, 0.11 mmol) and 4,5-dichloro-3,6-dioxocyclohexa-1,4-diene-1,2-dicarbonitrile (0.04 g, 0.16 mmol) were combined with ethyl acetate (2 ml) to give a brown solution. The reaction mixture was stirred for 4 hours at 25° C. The crude material was purified by chromatography (silica gel, ethyl acetate/heptane=50:50), to yield the title compound as colorless oil (0.04 g, 99%). MS: m/e=507.4 [M+H]$^+$.

d) 8-Hydroxy-6-(tetrahydro-2H-pyran-4-yl)quinazolin-4(3H)-one 2,2,2-trifluoroacetate 6-(Tetrahydro-2H-pyran-4-yl)-8-((2-(trimethylsilyl)ethoxy)methoxy)-3-((2-(trimethylsilyl)ethoxy)methyl)quinazolin-4(3H)-one (0.04 g, 0.07 mmol) was combined with dichloromethane (1 ml) to give a colorless solution. Trifluoroacetic acid (1.00 ml) was added and the mixture was stirred at 25° C. for 16 hours. The crude reaction mixture was concentrated in vacuo and the residue was triturated with diethyl ether (2 mL) and was filtered to yield the title compound as light grey solid (0.02 g, 75%). MS: m/e=245.0 [M−H]$^-$.

EXAMPLE 70

6-(3,6-Dihydro-2H-pyran-4-yl)-8-hydroxyquinazolin-4(3H)-one

In a sealed glass tube 6-(3,6-dihydro-2H-pyran-4-yl)-8-((2-(trimethylsilyl)ethoxy)methoxy)-3-((2-(trimethylsilyl)ethoxy)methyl)quinazolin-4(3H)-one (example 69a, 0.03 g, 0.05 mmol), formic acid (2.44 g, 2.00 ml, 53.0 mmol) and water (0.20 g, 11.1 mmol) were combined to give a yellow solution. The mixture was heated to 90° C. and stirred for 2 hours. The reaction mixture was filtered and concentrated in vacuo. Toluene was added and distilled off three times to yield the title compound as white solid (0.01 g, 81%). MS: m/e=245.1 [M+H]$^+$.

EXAMPLE 71

8-Hydroxy-6-(3-(methoxymethyl)phenyl)quinazolin-4(3H)-one a) 6-(3-Methoxymethyl)phenyl)-8-((2-(trimethylsilyl)ethoxy)methoxy)-3-((2-(trimethylsilyl)ethoxy)methyl)quinazolin-4(3H)-one A mixture of 6-bromo-8-(2-trimethylsilanyl-ethoxymethoxy)-3-(2-trimethylsilanyl- ethoxymethyl)-3H-quinazolin-4-one (0.10 g, 0.20 mmol), bis(diphenylphosphino)ferrocene-palladium(II)dichloride (0.02 g, 0.03 mmol), 3-(methoxymethyl)phenylboronic acid (0.04 g, 0.26 mmol) and potassium carbonate (0.06 g, 0.4 mmol) in dimethylformamide (5 ml) and water (0.5 ml) was stirred at 100° C. for 4 hours. Extraction with ethyl acetate and chromatography (silica gel, ethyl acetate/heptane=20:80 to 50:50) yielded the title compound as a light yellow solid (0.06 g, 58%). MS: m/e=543.5 [M+H]$^+$.

b) 8-Hydroxy-6-(3-(methoxymethyl)phenyl)quinazolin-4(3H)-one 6-(3-(Methoxymethyl)phenyl)-8-((2-(trimethylsilyl)ethoxy)methoxy)-3-((2-(trimethylsilyl)ethoxy)methyl)quinazolin-4(3H)-one (0.14 g, 0.25 mmol) in formic acid (9 ml) and water (1 mL) was stirred at 100° C. for 2 hours. Volatiles were distilled off. Toluene was added and distilled off two times to yield the title compound as light brown solid (0.07 g, 92%). MS: m/e=283.1 [M+H]$^+$.

EXAMPLE 72

8-Hydroxy-6-(5-methylthiazol-2-yl)quinazolin-4(3H)-one a) 6-(5-Methylthiazol-2-yl)-8-((2-(trimethylsilyl)ethoxy)methoxy)-3-((2-(trimethylsilyl)ethoxy)methyl)quinazolin-4(3H)-one 6-Bromo-8-((2-(trimethylsilyl)ethoxy)methoxy)-3-((2-(trimethylsilyl)ethoxy)methyl)quinazolin-4(3H)-one (0.10 g, 0.20 mmol), tetrakis(triphenylphosphine)palladium (0.01 g, 0.01 mmol) and 2,6-di-tert-butyl-4-methylphenol (0.004 mg, 0.02 mmol) was combined with toluene (2.4 ml). 5-Methyl-2-(tributylstannyl)thiazole (0.08 g, 0.20 mmol) was added and the reaction mixture was refluxed for 2 hours. Tetrakis(triphenylphosphine)palladium (0.02 g, 0.02 mmol) was added and the reaction mixture was refluxed for 24 hours and then stirred at room temperature over the weekend. Aqueous potassium fluoride solution (20%, 10 ml) was added and the mixture was stirred for 30 minutes at room temperature. Extraction with ethyl acetate and chromatography (silica gel, ethyl acetate/heptane=20:80 to 50:50) yielded the title compound as white solid (0.03 g, 24%). MS: m/e=520.3 [M+H]$^+$.

b) 8-Hydroxy-6-(5-methylthiazol-2-yl)quinazolin-4(3H)-one 6-(5-Methylthiazol-2-yl)-8-((2-(trimethylsilyl)ethoxy)methoxy)-3-((2-(trimethylsilyl)ethoxy)methyl)quinazolin-4(3H)-one (0.03 g, 0.05 mmol) in formic acid (11.1 g, 9.22 ml, 240 mmol) and water (1.0 ml) was stirred for 1.5 hours at 90° C. Volatiles were distilled off. Methanol was added and distilled off to yield the title compound as white solid (0.01 g, 88%). MS: m/e=260.0 [M+H]$^+$.

EXAMPLE 73

8-Hydroxy-6-(1-methyl-1H-imidazol-2-yl)quinazolin-4(3H)-one a) 6-(1-Methyl-1H-imidazol-2-yl)-8-(2-trimethylsilanyl-ethoxymethoxy)-3-(2-trimethylsilanyl-ethoxymethyl)-3H-quinazolin-4-one 6-bromo-8-((2-(trimethylsilyl)ethoxy)methoxy)-3-((2-(trimethylsilyl)ethoxy)methyl)quinazolin-4(3H)-one (1.50 g, 2.99 mmol), tetrakis(triphenylphosphine)palladium (0.35 g, 0.30 mmol) and 2,6-di-tert-butyl-4-methylphenol (0.07 g, 0.30 mmol) was combined with toluene (35 ml) to give an orange suspension. 1-Methyl-2-(tributylstannyl)-1H-imidazole (1.11 g, 2.99 mmol) was added and the reaction mixture was refluxed for 20 hours. Aqueous potassium fluoride solution (20%, 150 ml) was added and the mixture stirred for 30 minutes at room temperature. Extraction with ethyl acetate and chromatography (silica gel, ethyl acetate/methanol=100:0 to 90:10 and dichloromethane/methanol=100:0 to 80:20) yielded the title compound as white solid (0.16 g, 10%). MS: m/e=503.2 $[M+H]^+$.

b) 8-Hydroxy-6-(1-methyl-1H-imidazol-2-yl)quinazolin-4(3H)-one 6-(1-Methyl-1H-imidazol-2-yl)-8-((2-(trimethylsilyl) ethoxy)methoxy)-3-((2-(trimethylsilyl)ethoxy)methyl)quinazolin-4(3H)-one (0.03 g, 0.05 mmol) in formic acid (12.4 g, 10.3 ml, 269 mmol) and water (1.1 ml) was stirred for 1.5 hours at 90° C. Volatiles were distilled off. Methanol was added and distilled off to yield the title compound as white solid (0.01 g, 92%). MS: m/e=243.2 $[M+H]^+$.

EXAMPLE 74

8-Hydroxy-6-nicotinoylquinazolin-4(3H)-one a) 8-(Benzyloxy)-6-(hydroxy(pyridin-3-yl)methyl) quinazolin-4(3H)-one To 8-(benzyloxy)-6-iodoquinazolin-4(3H)-one (0.10 g, 0.26 mmol) in tetrahydrofuran (20 ml) was added and N',N',N',N'-tetramethylethylenediamine (0.03 g, 0.04 ml, 0.26 mmol) and sodium hydride (0.02 g, 0.53 mmol) to give a beige suspension. After stirring for 45 minutes the reaction mixture was cooled to 0° C. and isopropylmagnesium chloride-lithium chloride complex (14% in tetrahydrofuran, 0.44 ml, 0.53 mmol) was added to give a beige suspension. After stirring for 30 minutes at 0° C. freshly distilled nicotinaldehyde (0.14 g, 0.12 ml, 1.32 mmol) was added and the reaction mixture was allowed to warm up to RT over night to give a yellow suspension. Addition of methanol (0.5 ml) and chromatography (C, 18 reverse phase HPLC, methanol/water (0.1% formic acid)=20:80 to 98:2) yielded the title compound as white solid (0.07 g, 76%). MS: m/e=358.0 $[M-H]^-$.

b) 8-(Benzyloxy)-6-nicotinoylquinazolin-4(3H)-one

To 8-(benzyloxy)-6-(hydroxy(pyridin-3-yl)methyl)quinazolin-4(3H)-one (0.07 g, 0.20 mmol) suspended in dichloromethane (100 ml) was added manganese(IV) oxide (0.44 g, 5.01 mmol) to give a black suspension. The mixture was stirred at room temperature overnight, filtered and the solvent was distilled off to yield the title compound as white solid (0.04 g, 57%). MS: m/e=358.1 $[M+H]^+$.

c) 8-Hydroxy-6-nicotinoylquinazolin-4(3H)-one

To 8-(benzyloxy)-6-nicotinoylquinazolin-4(3H)-one (0.04 g, 0.11 mmol) in dichloromethane (50 ml) was added boron tribromide (1M in dichloromethane, 0.53 ml, 0.53 mmol) at room temperature to give a yellow suspension. The mixture was stirred overnight. Boron tribromide (1M in dichloromethane, 0.53 ml, 0.53 mmol) was added again and stirring was continued. Filtration delivered the title compound as light brown solid (0.04 g, quant.). MS: m/e=265.7 $[M-H]^-$.

EXAMPLE 75

8-Hydroxy-6-(1-methyl-1H-imidazol-4-yl)quinazolin-4(3H)-one a) 6-(1-Methyl-1H-imidazol-4-yl)-8-((2-(trimethylsilyl)ethoxy)methoxy)-3-((2-(trimethylsilyl)ethoxy) methyl)quinazolin-4(3H)-one A suspension of 4-bromo-1-methyl-1H-imidazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water (0.1% formic acid)=40:60 to 100:0) yielded the title compound as white solid (0.01 g, 20%). MS: m/e=503.7 $[M+H]^+$.

b) 8-Hydroxy-6-(1-methyl-1H-imidazol-4-yl)quinazolin-4(3H)-one 6-(1-Methyl-1H-imidazol-4-yl)-8-((2-(trimethylsilyl) ethoxy)methoxy)-3-((2-(trimethylsilyl)ethoxy)methyl)quinazolin-4(3H)-one (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid. MS: m/e=243.7 $[M+H]^+$.

EXAMPLE 76

8-Hydroxy-6-(5-methyl-3-phenylisoxazol-4-yl)quinazolin-4(3H)-one a) 6-(5-Methyl-3-phenylisoxazol-4-yl)-8-((2-(trimethylsilyl)ethoxy)methoxy)-3-((2-(trimethylsilyl) ethoxy)methyl)quinazolin-4(3H)-one A suspension of 4-bromo-5-methyl-3-phenylisoxazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water (0.1% formic acid)=40:60 to 100:0) yielded the title compound as white solid (0.01 g, 22%). MS: m/e=580.7 $[M+H]^+$.

b) 8-Hydroxy-6-(5-methyl-3-phenylisoxazol-4-yl) quinazolin-4(3H)-one 6-(5-Methyl-3-phenylisoxazol-4-yl)-8-((2-(trimethylsilyl)ethoxy)methoxy)-3-((2- (trimethylsilyl)ethoxy)methyl)

quinazolin-4(3H)-one (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid. MS: m/e=320.5 [M+H]$^+$.

EXAMPLE 77

4-(8-Hydroxy-4-oxo-3,4-dihydroquinazolin-6-yl)-N,N-dimethyl-1H-imidazole-1-sulfonamide a) N,N-Dimethyl-4-(4-oxo-8-((2-(trimethylsilyl)ethoxy)methoxy)-3-((2-(trimethylsilyl)ethoxy)methyl)-3,4-dihydroquinazolin-6-yl)-1H-imidazole-1-sulfonamide A suspension of 4-bromo-imidazole-1-sulfonic acid dimethylamide (0.025 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water=40:60 to 100:0) yielded the title compound as white solid (0.015 g, 24%). MS: m/e=595.8 [M+H]$^+$.

b) 4-(8-Hydroxy-4-oxo-3,4-dihydroquinazolin-6-yl)-N,N-dimethyl-1H-imidazole-1-sulfonamide N,N-dimethyl-4-(4-oxo-8-((2-(trimethylsilyl)ethoxy)methoxy)-3-((2-(trimethylsilyl)ethoxy)methyl)-3,4-dihydroquinazolin-6-yl)-1H-imidazole-1-sulfonamide (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid. MS: m/e=336.6 [M+H]$^+$.

EXAMPLE 78

6-(3,5-Dimethylisoxazol-4-yl)-8-hydroxyquinazolin-4(3H)-one a) 6-(3,5-Dimethylisoxazol-4-yl)-8-((2-(trimethylsilyl)ethoxy)methoxy)-3-((2-(trimethylsilyl)ethoxy)methyl)quinazolin-4(3H)-one A suspension of 4-bromo-3,5-dimethyl-isoxazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water=40:60 to 100:0) yielded the title compound as white solid (0.01 g, 28%). MS: m/e=518.7 [M+H]$^+$.

b) 6-(3,5-Dimethylisoxazol-4-yl)-8-hydroxyquinazolin-4(3H)-one 6-(3,5-Dimethylisoxazol-4-yl)-8-((2-(trimethylsilyl)ethoxy)methoxy)-3-((2-(trimethylsilyl)ethoxy)methyl)quinazolin-4(3H)-one (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.004 g, 17%). MS: m/e=258.6 [M+H]$^+$.

EXAMPLE 79

8-Hydroxy-6-(1-methyl-1H-imidazol-5-yl)quinazolin-4(3H)-one a) 6-(1-Methyl-1H-imidazol-5-yl)-8-((2-(trimethylsilyl)ethoxy)methoxy)-3-((2-(trimethylsilyl)ethoxy)methyl)quinazolin-4(3H)-one A suspension of 5-bromo-1-methyl-1H-imidazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water=40:60 to 100:0) yielded the title compound as white solid (0.005 g, 12%). MS: m/e=503.7 [M+H]$^+$.

b) 8-Hydroxy-6-(1-methyl-1H-imidazol-5-yl)quinazolin-4(3H)-one 6-(1-Methyl-1H-imidazol-5-yl)-8-((2-(trimethylsilyl)ethoxy)methoxy)-3-((2-(trimethylsilyl)ethoxy)methyl)quinazolin-4(3H)-one (0.005 g, 0.01 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid. MS: m/e=243.5 [M+H]$^+$.

EXAMPLE 80

Ethyl 2-(8-hydroxy-4-oxo-3,4-dihydroquinazolin-6-yl)-4-methyl-1H-imidazole-5-carboxylate a) 4-Methyl-2-(4-oxo-8-((2-(trimethylsilyl)ethoxy)methoxy)-3-((2-(trimethylsilyl)ethoxy)methyl)-3,4-dihydroquinazolin-6-yl)-1H-imidazole-5-carboxylate A suspension of 4-bromo-2-methyl-cyclopenta-1,3-dienecarboxylic acid ethyl ester (0.02 g, 0.1 mmol), (6-(4,4,5,5-tetramethyl-1,3,2-dioxaborolan-2-yl)-8-((2-(trimethylsilyl)ethoxy)methoxy)-3-42-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water (0.1% formic acid)=40:60 to 100:0) yielded the title compound as white solid (0.01 g, 21%). MS: m/e=575.7 [M+H]⁺.

b) Ethyl 2-(8-hydroxy-4-oxo-3,4-dihydroquinazolin-6-yl)-4-methyl-1H-imidazole-5-carboxylate 4-Methyl-2-(4-oxo-8-((2-(trimethylsilyl)ethoxy) methoxy)-3-((2-(trimethylsilyl)ethoxy)methyl)-3,4-dihydroquinazolin-6-yl)-1H-imidazole-5-carboxylate (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.002 g, 35%). MS: m/e=315.6 [M+H]⁺.

EXAMPLE 81

Methyl 5-(8-hydroxy-4-oxo-3,4-dihydroquinazolin-6-yl)-4-methylthiophene-2-carboxylate a) Methyl 4-methyl-5-(4-oxo-8-((2-(trimethylsilyl) ethoxy)methoxy)-3-((2-(trimethylsilyl)ethoxy) methyl)-3,4-dihydroquinazolin-6-yl)thiophene-2-carboxylate A suspension of 5-bromo-4-methyl-thiophene-2-carboxylic acid methyl ester (0.02 g, 0.1 mmol), (6-(4,4,5,5-tetramethyl-1,3,2-dioxaborolan-2-yl)-8-((2-(trimethylsilyl) ethoxy)methoxy)-3-((2-(trimethylsilyl)ethoxy)methyl) quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water (0.1% formic acid)=40:60 to 100:0) yielded the title compound as white solid (0.01 g, 23%). MS: m/e=577.7 [M+H]⁺.

b) Methyl 5-(8-hydroxy-4-oxo-3,4-dihydroquinazolin-6-yl)-4-methylthiophene-2-carboxylate Methyl 4-methyl-5-(4-oxo-8-((2-(trimethylsilyl)ethoxy) methoxy)-3-((2-(trimethylsilyl)ethoxy)methyl)-3,4-dihydroquinazolin-6-yl)thiophene-2-carboxylate (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.003 g, 57%). MS: m/e=317.5 [M+H]⁺.

EXAMPLE 82

8-Hydroxy-6-(1-methyl-3-(trifluoromethyl)-1H-pyrazol-4-yl)quinazolin-4(3H)-one a) 6-(1-Methyl-3-(trifluoromethyl)-1H-pyrazol-4-yl)-8-((2-(trimethylsilyl)ethoxy)methoxy)-3-((2-(trimethylsilyl)ethoxy)methyl)quinazolin-4(3H)-one A suspension of 4-bromo-1-methyl-3-trifluoromethyl-1H-pyrazole (0.02 g, 0.10 mmol), (6-(4,4,5,5-tetramethyl-1,3,2-dioxaborolan-2-yl)-8-((2-(trimethylsilyl)ethoxy) methoxy)-3-((2-(trimethylsilyl)ethoxy)methyl)quinazolin-4 (3H)-one (0.05 g, 0.08 mmol, example 28), bis (diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water=40:60 to 100:0) yielded the title compound as white solid (0.005 g, 11%). MS: m/e=571.6 [M+H]⁺.

b) 8-Hydroxy-6-(1-methyl-3-(trifluoromethyl)-1H-pyrazol-4-yl)quinazolin-4(3H)-one 6-(1-Methyl-3-(trifluoromethyl)-1H-pyrazol-4-yl)-8-((2-(trimethylsilyl)ethoxy)methoxy)-3-((2-(trimethylsilyl) ethoxy)methyl)quinazolin-4(3H)-one in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid. MS: m/e=311.5 [M+H]⁺.

EXAMPLE 83

8-Hydroxy-6-(5-methyl-1,3,4-thiadiazol-2-yl)quinazolin-4(3H)-one a) 6-(5-Methyl-1,3,4-thiadiazol-2-yl)-8-((2-(trimethylsilyl)ethoxy)methoxy)-3-((2-(trimethylsilyl) ethoxy)methyl)quinazolin-4(3H)-one A suspension of 2-bromo-5-methyl-[1,3,4]thiadiazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water=40:60 to 100:0) yielded the title compound as white solid (0.02 g, 44%). MS: m/e=521.7 [M+H]⁺.

b) 8-Hydroxy-6-(5-methyl-1,3,4-thiadiazol-2-yl) quinazolin-4(3H)-one 6-(5-Methyl-1,3,4-thiadiazol-2-yl)-8-((2-(trimethylsilyl) ethoxy)methoxy)-3-((2-(trimethylsilyl)ethoxy)methyl)quinazolin-4(3H)-one (0.02 g, 0.03 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.003 g, 33%). MS: m/e=261.4 [M+H]⁺.

EXAMPLE 84

Methyl 2-(8-hydroxy-4-oxo-3,4-dihydroquinazolin-6-yl)thiazole-4-carboxylate a) Methyl 2-(4-oxo-8-((2-(trimethylsilyl)ethoxy) methoxy)-3-((2-(trimethylsilyl)ethoxy)methyl)-3,4-dihydroquinazolin-6-yl)thiazole-4-carboxylate A suspension of 2-bromo-thiazole-4-carboxylic acid methyl ester (0.02 g, 0.1 mmol), (6-(4,4,5,5-tetramethyl-1, 3,2-dioxaborolan-2-yl)-8-((2-(trimethylsilyl)ethoxy)
methoxy)-3-((2-(trimethylsilyl)ethoxy)methyl)quinazolin-4
(3H)-one (0.05 g, 0.08 mmol, example 28), bis
(diphenylphosphino)ferrocene-palladium(II)dichloride
(0.01 g, 0.01 mmol), potassium carbonate (0.03 g, 0.25
mmol) and water (0.2 ml) in dimethylformamide (1 ml) was
stirred in a sealed tube at 100° C. for 2 hours and then at 80°
C. overnight. Filtration and chromatography (C, 18 reverse
phase HPLC, methanol/water=40:60 to 100:0) yielded the
title compound as white solid (0.015 g, 32%). MS:
m/e=563.9 [M+H]$^+$.

b) Methyl 2-(8-hydroxy-4-oxo-3,4-dihydroquinazo-
lin-6-yl)thiazole-4-carboxylate Methyl 2-(4-oxo-8-((2-(trimethylsilyl)ethoxy)methoxy)-
3-((2-(trimethylsilyl)ethoxy)methyl)-3,4-dihydroquinazo-
lin-6-yl)thiazole-4-carboxylate (0.01 g, 0.02 mmol) in water
(0.2 ml) and formic acid (1.8 ml) was stirred for 2 hours at
100° C. and then overnight at 80° C. Removal of the solvent
and chromatography (C18 reverse phase HPLC, methanol/
water (0.1% formic acid)=10:90 to 98:2) yielded the title
compound as white solid (0.002 g, 24%). MS: m/e=303.5
[M+H]$^+$.

EXAMPLE 85

8-Hydroxy-6-(2-methylthiazol-4-yl)quinazolin-4
(3H)-one a) 6-(2-Methylthiazol-4-yl)-8-((2-(trimethylsilyl)
ethoxy)methoxy)-3-((2-(trimethylsilyl)ethoxy)
methyl)quinazolin-4(3H)-one A suspension of 4-bromo-2-methyl-thiazole (0.02 g, 0.1
mmol), (6-(4,4,5,5-tetramethyl-1,3,2-dioxaborolan-2-yl)-8-
((2-(trimethylsilyl)ethoxy)methoxy)-3-((2-(trimethylsilyl)
ethoxy)methyl)quinazolin-4(3H)-one (0.05 g, 0.08 mmol,
example 28), bis(diphenylphosphino)ferrocene-palladium
(II)dichloride (0.01 g, 0.01 mmol), potassium carbonate
(0.03 g, 0.25 mmol) and water (0.2 ml) in dimethylforma-
mide (1 ml) was stirred in a sealed tube at 100° C. for 2 hours
and then at 80° C. overnight. Filtration and chromatography
(C, 18 reverse phase HPLC, methanol/water=40:60 to 100:
0) yielded the title compound as white solid (0.006 g, 14%).
MS: m/e=520.7 [M+H]$^+$.

b) 8-Hydroxy-6-(2-methylthiazol-4-yl)quinazolin-4
(3H)-one 6-(2-Methylthiazol-4-yl)-8-((2-(trimethylsilyl)ethoxy)
methoxy)-3-((2-(trimethylsilyl)ethoxy)methyl)quinazolin-4
(3H)-one (0.01 g, 0.02 mmol) in water (0.2 ml) and formic
acid (1.8 ml) was stirred for 2 hours at 100° C. and then
overnight at 80° C. Removal of the solvent and chromatog-
raphy (C18 reverse phase HPLC, methanol/water (0.1%
formic acid)=10:90 to 98:2) yielded the title compound as
white solid. MS: m/e=260.6 [M+H]$^+$.

EXAMPLE 86

8-Hydroxy-6-(imidazo[1,2-a]pyridin-3-yl)quinazo-
lin-4(3H)-one a) 6-(Imidazo[1,2-a]pyridin-3-yl)-8-((2-(trimethylsi-
lyl)ethoxy)methoxy)-3-((2-(trimethylsilyl)ethoxy)
methyl)quinazolin-4(3H)-one A suspension of 3-bromo-imidazo[1,2-a]pyridine (0.02 g,
0.1 mmol), (6-(4,4,5,5-tetramethyl-1,3,2-dioxaborolan-2-
yl)-8-((2-(trimethylsilyl)ethoxy)methoxy)-3-((2-(trimethyl-
silyl)ethoxy)methyl)quinazolin-4(3H)-one (0.05 g, 0.08
mmol, example 28), bis(diphenylphosphino)ferrocene-pal-
ladium(II)dichloride (0.01 g, 0.01 mmol), potassium car-
bonate (0.03 g, 0.25 mmol) and water (0.2 ml) in dimeth-
ylformamide (1 ml) was stirred in a sealed tube at 100° C.
for 2 hours and then at 80° C. overnight. Filtration and
chromatography (C, 18 reverse phase HPLC, methanol/
water=40:60 to 100:0) yielded the title compound as white
solid (0.008 g, 18%). MS: m/e=539.8 [M+H]$^+$.

b) 8-Hydroxy-6-(imidazo[1,2-a]pyridin-3-yl)qui-
nazolin-4(3H)-one 6-(Imidazo[1,2-a]pyridin-3-yl)-8-((2-(trimethylsilyl)
ethoxy)methoxy)-3-((2-(trimethylsilyl)ethoxy)methyl)qui-
nazolin-4(3H)-one in water (0.2 ml) and formic acid (1.8 ml)
was stirred for 2 hours at 100° C. and then overnight at 80°
C. Removal of the solvent and chromatography (C18 reverse
phase HPLC, methanol/water (0.1% formic acid)=10:90 to
98:2) yielded the title compound as white solid. MS:
m/e=279.6 [M+H]$^+$.

EXAMPLE 87

6-(1,2-Dimethyl-1H-imidazol-5-yl)-8-hydroxyqui-
nazolin-4(3H)-one a) 6-(1,2-Dimethyl-1H-imidazol-5-yl)-8-((2-(trim-
ethylsilyl)ethoxy)methoxy)-3-((2-(trimethylsilyl)
ethoxy)methyl)quinazolin-4(3H)-one A suspension of 5-bromo-1,2-dimethyl-1H-imidazole
(0.02 g, 0.1 mmol), (6-(4,4,5,5-tetramethyl-1,3,2-dioxaboro-
lan-2-yl)-8-((2-(trimethylsilyl)ethoxy)methoxy)-3-((2-
(trimethylsilyl)ethoxy)methyl)quinazolin-4(3H)-one (0.05
g, 0.08 mmol, example 28), bis(diphenylphosphino)ferro-
cene-palladium(II)dichloride (0.01 g, 0.01 mmol), potas-
sium carbonate (0.03 g, 0.25 mmol) and water (0.2 ml) in
dimethylformamide (1 ml) was stirred in a sealed tube at
100° C. for 2 hours and then at 80° C. overnight. Filtration
and chromatography (C, 18 reverse phase HPLC, methanol/
water=40:60 to 100:0) yielded the title compound as white
solid (0.006 g, 14%). MS: m/e=517.8 [M+H]$^+$.

b) 6-(1,2-Dimethyl-1H-imidazol-5-yl)-8-hydroxy-
quinazolin-4(3H)-one 6-(1,2-Dimethyl-1H-imidazol-5-yl)-8-((2-(trimethylsilyl)
ethoxy)methoxy)-3-((2-(trimethylsilyl)ethoxy)methyl)qui-
nazolin-4(3H)-one in water (0.2 ml) and formic acid (1.8 ml)
was stirred for 2 hours at 100° C. and then overnight at 80°
C. Removal of the solvent and chromatography (C18 reverse
phase HPLC, methanol/water (0.1% formic acid)=10:90 to
98:2) yielded the title compound as white solid. MS:
m/e=257.6 [M+H]$^+$.

EXAMPLE 88

Methyl 4-(8-hydroxy-4-oxo-3,4-dihydroquinazolin-
6-yl)-1-methyl-1H-pyrazole-3-carboxylate a) Methyl 1-methyl-4-(4-oxo-8-((2-(trimethylsilyl)
ethoxy)methoxy)-3-((2-(trimethylsilyl)ethoxy)
methyl)-3,4-dihydroquinazolin-6-yl)-1H-pyrazole-3-
carboxylate A suspension of 4-bromo-1-methyl-1H-pyrazole-3-car-
boxylic acid methyl ester (0.02 g, 0.1 mmol), (6-(4,4,5,5- tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water=40:60 to 100:0) yielded the title compound as white solid (0.01 g, 29%). MS: m/e=561.5 [M+H]$^+$.

b) Methyl 4-(8-hydroxy-4-oxo-3,4-dihydroquinazolin-6-yl)-1-methyl-1H-pyrazole-3-carboxylate Methyl 1-methyl-4-(4-oxo-8-((2-(trimethylsilyl)ethoxy)methoxy)-3-((2-(trimethylsilyl)ethoxy)methyl)-3,4-dihydroquinazolin-6-yl)-1H-pyrazole-3-carboxylate (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.003 g, 52%). MS: m/e=301.1 [M+H]$^+$.

EXAMPLE 89

8-Hydroxy-6-(5-(pyridin-2-yl)thiophen-2-yl)quinazolin-4(3H)-one a) 6-(5-(Pyridin-2-yl)thiophen-2-yl)-8-((2-(trimethylsilyl)ethoxy)methoxy)-3-((2-(trimethylsilyl)ethoxy)methyl)quinazolin-4(3H)-one A suspension of 2-(5-bromo-thiophen-2-yl)-pyridine (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water=40:60 to 100:0) yielded the title compound as white solid (0.01 g, 25%). MS: m/e=582.6 [M+H]$^+$.

b) 8-Hydroxy-6-(5-(pyridin-2-yl)thiophen-2-yl)quinazolin-4(3H)-one

Methyl 1-methyl-4-(4-oxo-8-((2-(trimethylsilyl)ethoxy)methoxy)-3-((2-(trimethylsilyl)ethoxy)methyl)-3,4-dihydroquinazolin-6-yl)-1H-pyrazole-3-carboxylate (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.003 g, 54%). MS: m/e=322.6 [M+H]$^+$.

EXAMPLE 90

8-Hydroxy-6-(thiazol-5-yl)quinazolin-4(3H)-one a) 6-(Thiazol-5-yl)-8-((2-(trimethylsilyl)ethoxy)methoxy)-3-((2-(trimethylsilyl)ethoxy)methyl)quinazolin-4(3H)-one A suspension of 5-bromo-thiazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water=40:60 to 100:0) yielded the title compound as white solid (0.01 g, 26%). MS: m/e=506.7 [M+H]$^+$.

b) 8-Hydroxy-6-(thiazol-5-yl)quinazolin-4(3H)-one 6-(Thiazol-5-yl)-8-((2-(trimethylsilyl)ethoxy)methoxy)-3-((2-(trimethylsilyl)ethoxy)methyl)quinazolin-4(3H)-one (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.002 g, 31%). MS: m/e=246.6 [M+H]$^+$.

EXAMPLE 91

8-Hydroxy-6-(thiazol-4-yl)quinazolin-4(3H)-one a) 6-(Thiazol-4-yl)-8-((2-(trimethylsilyl)ethoxy)methoxy)-3-((2-(trimethylsilyl)ethoxy)methyl)quinazolin-4(3H)-one A suspension of 4-bromo-thiazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium(II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C18 reverse phase HPLC, methanol/water (0.1% formic acid)=40:60 to 100:0) yielded the title compound as white solid (0.01 g, 18%). MS: m/e=506.7 [M+H]$^+$.

b) 8-Hydroxy-6-(thiazol-4-yl)quinazolin-4(3H)-one 6-(Thiazol-4-yl)-8-((2-(trimethylsilyl)ethoxy)methoxy)-3-((2-(trimethylsilyl)ethoxy)methyl)quinazolin-4(3H)-one (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water=10:90 to 98:2) yielded the title compound as white solid (0.003 g, 57%). MS: m/e=246.6 [M+H]$^+$.

EXAMPLE 92

8-Hydroxy-6-(isothiazol-4-yl)quinazolin-4(3H)-one a) 6-(Isothiazol-4-yl)-8-((2-(trimethylsilyl)ethoxy)methoxy)-3-((2-(trimethylsilyl)ethoxy)methyl)quinazolin-4(3H)-one A suspension of 4-bromo-isothiazole (0.02 g, 0.1 mmol), (6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.05 g, 0.08 mmol, example 28), bis(diphenylphosphino)ferrocene-palladium (II)dichloride (0.01 g, 0.01 mmol), potassium carbonate (0.03 g, 0.25 mmol) and water (0.2 ml) in dimethylformamide (1 ml) was stirred in a sealed tube at 100° C. for 2 hours and then at 80° C. overnight. Filtration and chromatography (C, 18 reverse phase HPLC, methanol/water (0.1% formic acid)=40:60 to 100:0) yielded the title compound as white solid (0.01 g, 16%). MS: m/e=506.7 [M+H]+.

b) 8-Hydroxy-6-(isothiazol-4-yl)quinazolin-4(3H)-one 6-(Isothiazol-4-yl)-8-((2-(trimethylsilyl)ethoxy) methoxy)-3-((2-(trimethylsilyl)ethoxy)methyl)quinazolin-4 (3H)-one (0.01 g, 0.02 mmol) in water (0.2 ml) and formic acid (1.8 ml) was stirred for 2 hours at 100° C. and then overnight at 80° C. Removal of the solvent and chromatography (C18 reverse phase HPLC, methanol/water (0.1% formic acid)=10:90 to 98:2) yielded the title compound as white solid (0.002 g, 14%). MS: m/e=246.6 [M+H]+.

EXAMPLE 93

8-Hydroxy-6-isonicotinoylquinazolin-4(3H)-one a) 8-(Benzyloxy)-6-(hydroxy(pyridin-4-yl)methyl) quinazolin-4(3H)-one To 8-(benzyloxy)-6-iodoquinazolin-4(3H)-one (0.10 g, 0.26 mmol) in tetrahydrofuran (20.0 ml) was added and N',N',N',N'-tetramethylethylenediamine (0.03 g, 0.04 ml, 0.26 mmol) and sodium hydride (0.02 g, 0.53 mmol) to give a beige suspension. After stirring for 45 minutes the reaction mixture was cooled to 0° C. and isopropylmagnesium chloride-lithium chloride complex (14% in tetrahydrofuran, 0.44 ml, 0.53 mmol) was added to give a beige suspension. After stirring for 30 minutes at 0° C. freshly distilled isonicotinaldehyde (0.14 g, 0.12 ml, 1.32 mmol) was added and the reaction mixture was allowed to warm up to room temperature over night to give a yellow suspension. Addition of methanol (0.5 ml) and chromatography (C18 reverse phase HPLC, methanol/water (0.1% formic acid)=20:80 to 98:2) yielded the title compound as white solid (0.06 g, 67%). MS: m/e=358.0 [M+H]+.

b) 8-(Benzyloxy)-6-isonicotinoylquinazolin-4(3H)-one

To 8-(benzyloxy)-6-(hydroxy(pyridin-4-yl)methyl)quinazolin-4(3H)-one (0.06 g, 0.18 mmol) suspended in dichloromethane (100 ml) was added manganese(IV) oxide (0.39 g, 5.01 mmol) to give a black suspension. The mixture was stirred at room temperature overnight, filtered and the solvent was distilled off to yield the title compound as white solid (0.04 g, 58%). MS: m/e=358.1 [M+H]+.

c) 8-Hydroxy-6-isonicotinoylquinazolin-4(3H)-one

To 8-(benzyloxy)-6-isonicotinoylquinazolin-4(3H)-one (0.04 g, 0.10 mmol) in dichloromethane (70 ml) was added boron tribromide (1M in dichloromethane, 0.52 ml, 0.52 mmol) at room temperature to give a yellow suspension. The mixture was stirred overnight. Boron tribromide (1M in dichloromethane, 0.52 ml, 0.52 mmol) was added again and stirring was continued. Filtration delivered the title compound as light brown solid (0.01 g, 29%.). MS: m/e=268.3 [M+H]+.

EXAMPLE 94

8-Hydroxy-6-(5-methylthiophene-2-carbonyl)quinazolin-4(3H)-one a) 8-(Benzyloxy)-6-(hydroxy(5-methylthiophen-2-yl)methyl)quinazolin-4(3H)-one To 8-(benzyloxy)-6-iodoquinazolin-4(3H)-one (0.10 g, 0.26 mmol) in tetrahydrofuran (20.0 ml) was added and N',N',N',N'-tetramethylethylenediamine (0.03 g, 0.04 ml, 0.26 mmol) and sodium hydride (0.02 g, 0.53 mmol) to give a beige suspension. After stirring for 1.5 hours the reaction mixture was cooled to 0° C. and isopropylmagnesium chloride-lithium chloride complex (14% in tetrahydrofuran, 0.44 ml, 0.53 mmol) was added to give a beige suspension. After stirring for 45 minutes at 0° C. 5-methylthiophene-2-carbaldehyde (0.17 g, 0.14 ml, 1.32 mmol) was added and the reaction mixture was allowed to warm up to room temperature to give a yellow suspension. Addition of methanol (0.5 ml) and chromatography (silica gel, dichloromethane/methanol=98:2 to 90:10) yielded the title compound as white solid (0.05 g, 54%). MS: m/e=379.2 [M+H]+.

b) 8-(Benzyloxy)-6-(5-methylthiophene-2-carbonyl) quinazolin-4(3H)-one

To 8-(benzyloxy)-6-(hydroxy(5-methylthiophen-2-yl) methyl)quinazolin-4(3H)-one (0.05 g, 0.14 mmol) suspended in dichloromethane (100 ml) was added manganese (IV) oxide (0.31 g, 3.57 mmol) to give a black suspension. The mixture was stirred at room temperature overnight. Filtration and chromatography (silica gel, dichloromethane/methanol 100:0 to 95:5 yielded the title compound as white solid (0.05 g, 93%). MS: m/e=374.9 [M+H]+.

c) 8-Hydroxy-6-(5-methylthiophene-2-carbonyl) quinazolin-4(3H)-one

To 8-(benzyloxy)-6-(5-methylthiophene-2-carbonyl)quinazolin-4(3H)-one (0.05 g, 0.13 mmol) in dichloromethane (70 ml) was added boron tribromide (1M in dichloromethane, 0.66 ml, 0.66 mmol) at room temperature to give a yellow suspension. The mixture was stirred for 3 hours and then quenched with methanol. Chromatography (C, 18 reverse phase HPLC, methanol/water (0.1% formic acid)=20:80 to 66:40) delivered the title compound as light brown solid (0.01 g, 39%.). MS: m/e=287.0 [M+H]+.

EXAMPLE 95

6-(1,5-Dimethyl-3-(trifluoromethyl)-1H-pyrazol-4-yl)-8-hydroxyquinazolin-4(3H)-one a) 6-1,5-Dimethyl-3-trifluoromethyl)-1H-pyrazol-4-yl)-8-((2-trimethylsilyl)ethoxy)methoxy)-3-((2-(trimethylsilyl)ethoxy)methyl)quinazolin-4(3H)-one A solution of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.15 g, 0.27 mmol) and 4-bromo-1,5-dimethyl-3-(trifluoromethyl)-1H-pyrazole (0.07 g, 0.27 mmol) and potassium carbonate (0.11 g, 0.82 mmol) in dimethylformamide (6 ml) and water (0.6 ml) was treated with bis(diphenylphosphino)ferrocene-palladium(II)dichloride (0.02 g, 0.03 mmol). The reaction mixture was stirred at 100° C. for 2 hours. Extraction with ethyl acetate and chromatography (silica gel, ethyl acetate/heptane=40:60 to 60:40) yielded the title compound as colorless oil (0.05 g, 31%). MS: m/e=585.3 [M+H]+.

b) 6-(1,5-Dimethyl-3-(trifluoromethyl)-1H-pyrazol-4-yl)-8-hydroxyquinazolin-4(3H)-one To 6-(1,5-dimethyl-3-(trifluoromethyl)-1H-pyrazol-4-yl)-8-((2-(trimethylsilyl)ethoxy)methoxy)-3-42-(trimethylsilyl)ethoxy)methyl)quinazolin-4(3H)-one (0.05 g, 0.09 mmol) was added water and formic acid. The reaction mixture was stirred at 100° C. for 2 hours. The solvent was distilled off to yield the title compound as off-white solid (0.03 g, 90%). MS: m/e=325.2 [M+H]+.

EXAMPLE 96

8-Hydroxy-6-(1-methyl-1H-indazol-5-yl)quinazolin-4(3H)-one a) 6-(1-Methyl-1H-indazol-5-yl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.15 g, 0.27 mmol) and 5-bromo-1-methyl-1H-indazole (0.06 g, 0.27 mmol) and potassium carbonate (0.04 g, 0.03 mmol) in dimethylformamide (6 ml) and water (0.6 ml) was treated with bis(diphenylphosphino)ferrocene-palladium(II)dichloride (0.02 g, 0.03 mmol). The reaction mixture was stirred at 100° C. for 2 hours. Filtration and chromatography (C18 reverse phase HPLC, methanol/water (0.1% formic acid)=20:80 to 80:20) yielded the title compound as light brown solid (0.04 g, 27%). MS: m/e=553.5 [M+H]+.

b) 8-Hydroxy-6-(1-methyl-1H-indazol-5-yl)quinazolin-4(3H)-one

To 6-(1-methyl-1H-indazol-5-yl)-8-((2-(trimethylsilyl)ethoxy)methoxy)-3-((2-(trimethylsilyl)ethoxy)methyl)quinazolin-4(3H)-one (0.04 g, 0.07 mmol) was added water (0.3 ml) and formic acid (3.0 ml). The reaction mixture was stirred at 90° C. for 2 h. The solvent was distilled off to yield the title compound as white solid (0.02 g, 99%). MS: m/e=290.9 [M–H]−.

EXAMPLE 97

8-Hydroxy-6-(3-methyl-5-(piperidine-1-carbonyl)thiophen-2-yl)quinazolin-4(3H)-one a) 4-M ethyl-5-(4-oxo-8-((2-(trimethylsilyl)ethoxy)methoxy)-3-((2-(trimethylsilyl)ethoxy)methyl)-3,4-dihydroquinazolin-6-yl)thiophene-2-carboxylic acid To methyl 4-methyl-5-(4-oxo-8-((2-(trimethylsilyl)ethoxy)methoxy)-3-((2-(trimethylsilyl)ethoxy)methyl)-3,4-dihydroquinazolin-6-yl)thiophene-2-carboxylate (0.50 g, 0.87 mmol) was added methanol (1.0 ml), water (3.0 ml), tetrahydrofuran (3.0 ml) and lithium hydroxide (0.04 g, 1.73 mmol). The reaction mixture was stirred for 2 hours at 60° C. and extracted with ethyl acetate/aqueous buffer (pH 7) to yield the title compound as white solid (0.22 g, 45%). MS: m/e=563.2 [M+H]+.

b) 6-(3-Methyl-5-(piperidine-1-carbonyl)thiophen-2-yl)-8-((2-trimethylsilyl)ethoxy)methoxy)-3-((2-(trimethylsilyl)ethoxy)methyl)quinazolin-4(3H)-one A mixture of 4-methyl-5-(4-oxo-8-((2-(trimethylsilyl)ethoxy)methoxy)-3-((2-(trimethylsilyl)ethoxy)methyl)-3,4-dihydroquinazolin-6-yl)thiophene-2-carboxylic acid (0.10 g, 0.18 mmol), piperidine (0.02 g, 0.02 ml, 0.21 mmol), N,N-diisopropylethylamine (0.05 g, 0.06 ml, 0.04 mmol), and O-(7-azabenzotriazol-1-yl)-N,N,N',N'-tetramethyluronium hexafluorophosphate (HATU, 0.07 g, 0.18 mmol) in dimethylformamide (5.0 ml) was stirred at room temperature overnight. Extraction with ethyl acetate and chromatography (silica gel, ethyl acetate/heptane=20:80 to 50:50) yielded the title compound as colorless oil (0.11 g, 97%). MS: m/e=630.5 [M+H]+.

c) 8-Hydroxy-6-(3-methyl-5-(piperidine-1-carbonyl)thiophen-2-yl)quinazolin-4(3H)-one To 6-(3-methyl-5-(piperidine-1-carbonyl)thiophen-2-yl)-8-((2-(trimethylsilyl)ethoxy)methoxy)-3-((2-(trimethylsilyl)ethoxy)methyl)quinazolin-4(3H)-one (0.11 g, 0.17 mmol) was added water (1.0 ml) and formic acid (9.0 ml). The reaction mixture was stirred at 100° C. for 1.5 hours. The solvent was distilled off to yield the title compound as light grey solid (0.05 g, 90%). MS: m/e=370.0 [M+H]+.

EXAMPLE 98

6-(2-Benzylphenyl)-8-hydroxyquinazolin-4(3H)-one a) 6-((2-Benzylphenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.17 g, 0.30 mmol) and 1-benzyl-2-bromobenzene (0.05 g, 0.20 mmol) and potassium carbonate (0.06 g, 0.04 mmol) in dioxane (6 ml) and water (0.3 ml) was treated with bis(diphenylphosphino)ferrocene-palladium(II)dichloride (0.02 g, 0.03 mmol). The reaction mixture was stirred at 90° C. for 6 hours. Extraction with ethyl acetate and chromatography (silica gel, ethyl acetate/heptane=1:3 to 1:21 yielded the title compound as light yellow oil (0.08 g, 68%). MS: m/e=589.3 [M+H]+.

b) 6-(2-Benzylphenyl)-8-hydroxyquinazolin-4(3H)-one

To 6-(2-Benzylphenyl)-8-((2-(trimethylsilyl)ethoxy)methoxy)-3-((2-(trimethylsilyl)ethoxy)methyl)quinazolin-4(3H)-one (0.08 g, 0.14 mmol) was added water (1.0 ml) and formic acid (9.0 ml). The reaction mixture was stirred at 100° C. for 2 hours. The solvent was distilled off to yield the title compound as white solid (0.04 g, 95%). MS: m/e=327.1 [M–H]−.

EXAMPLE 99

6-(2-Benzoylphenyl)-8-hydroxyquinazolin-4(3H)-one a) 6-((2-Benzylphenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.16 g, 0.29 mmol) and (2-bromophenyl)(phenyl)methanone (0.05 g, 0.19 mmol) and potassium carbonate (0.05 g, 0.04 mmol) in dioxane (5 ml) and water (0.3 ml) was treated with bis(diphenylphosphino)ferrocene-palladium(II)dichloride (0.02 g, 0.03 mmol). The reaction mixture was stirred at 100° C. for 2 hours. Extraction with ethyl acetate and chromatography (silica gel, ethyl acetate/heptane=1:3 to 1:1) yielded the title compound as light yellow oil (0.11 g, 99%). MS: m/e=603.2 [M+H]$^+$.

b) 6-(2-Benzoylphenyl)-8-hydroxyquinazolin-4(3H)-one

To 6-(2-benzoylphenyl)-8-((2-(trimethylsilyl)ethoxy)methoxy)-3-((2-(trimethylsilyl)ethoxy)methyl)quinazolin-4(3H)-one (0.07 g, 0.11 mmol) was added water (0.5 ml) and formic acid (4.5 ml). The reaction mixture was stirred at 100° C. for 0.5 hours. The solvent was distilled off to yield the title compound as white solid (0.02 g, 45%). MS: m/e=341.1 [M−H]$^−$.

EXAMPLE 100

6-(4-Pentafluorosulfanylphenyl)-8-hydroxyquinazolin-4(3H)-one a) 6-(4-Pentafluorosulfanylphenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.15 g, 0.27 mmol) and 1-bromo-4-(pentafluorsulfanyl)benzene (0.05 g, 0.18 mmol) and potassium carbonate (0.06 g, 0.04 mmol) in dioxane (5 ml) and water (0.5 ml) was treated with bis(diphenylphosphino)ferrocene-palladium(II)dichloride (0.02 g, 0.03 mmol). The reaction mixture was stirred at 100° C. for 8.5 hours. Extraction with ethyl acetate and chromatography (silica gel, dichloromethane/methanol=99:1 to 98:2) yielded the title compound as colorless oil (0.10 g, 88%). MS: m/e=625.4 [M+H]$^+$.

b) 6-(4-Pentafluorosulfanylphenyl)-8-hydroxyquinazolin-4(3H)-one

To 6-(4-pentafluorosulfanylphenyl)-8-((2-(trimethylsilyl)ethoxy)methoxy)-3-((2-(trimethylsilyl)ethoxy)methyl)quinazolin-4(3H)-one (0.10 g, 0.16 mmol) was added water (1.0 ml) and formic acid (9.0 ml). The reaction mixture was stirred at 100° C. for 1.5 hours. The solvent was distilled off to yield the title compound as white solid (0.04 g, 62%). MS: m/e=362.8 [M−H]$^−$.

EXAMPLE 101

5-Chloro-6-(4-fluorophenyl)-8-hydroxyquinazolin-4(3H)-one a) 5-Bromo-4-chloro-7-methoxyinoline-2,3-dione To a solution of 4-chloro-7-methoxyindoline-2,3-dione (CAS60706-07-2, 0.43 g, 2.01 mmol) in ethanol (4.0 ml) at 80° C. was added a solution of bromine (0.64 g, 4.02 mmol) in ethanol (4.0 ml) during 45 minutes. The reaction mixture was stirred at 70° C. for 18 h. Removal of the solvent by distillation and chromatography (silica gel, ethyl acetate/heptane=10:90 to 60:40) yielded the title compound as dark red solid (0.3 g, 48%). MS: m/e=308.9, 310.9 [M+NH$_4$]$^+$.

b) 4-Chloro-5-(4-fluorophenyl)-7-methoxyindoline-2,3-dione

In a 20 ml tube, 5-bromo-4-chloro-7-methoxyindoline-2,3-dione (0.17 g, 0.50 mmol), 4-fluorophenylboronic acid (0.11 g, 0.75 mmol) and potassium carbonate (0.07 g, 0.50 mmol) were combined under argon with dioxane (8 ml) and water (0.8 ml) to give a brown suspension. Bis(diphenylphosphino)ferrocene-palladium(II)dichloride (0.04 g, 0.05 mmol) was added, evacuating and flushing with Argon repeated and the mixture heated to 100° C. for 18 hours. The crude material was purified by chromatography (C18 reverse phase HPLC, methanol/water (0.1% formic acid)=20:80 to 95:5) to yield the title compound as red solid (0.06 g, 38%). MS: m/e=303.8 [M−H]$^−$.

c) 4-Amino-2-chloro-4'-fluoro-5-methoxybiphenyl-3-carboxylic acid

4-Chloro-5-(4-fluorophenyl)-7-methoxyindoline-2,3-dione (0.03 g, 0.1 mmol) was suspended in 1N aqueous sodium hydroxide (0.97 ml, 0.97 mmol). A solution of hydrogen peroxide (0.04 ml, 0.04 mmol) was added and the reaction mixture was stirred for 20 minutes at room temperature. Then it was cooled to 0° C. and acetic acid (0.06 g, 0.06 ml, 0.97 mmol) and 3N hydrochloric acid (0.32 ml, 0.97 mmol) was added. The precipitate was collected and dried to yield the title compound as white solid (0.02 g, 65%). MS: m/e=293.8 [M−H]$^−$.

d) 5-Chloro-6-(4-fluorophenyl)-8-methoxyquinazolin-4(3H)-one

4-Amino-2-chloro-4'-fluoro-5-methoxybiphenyl-3-carboxylic acid (0.02 g, 0.06 mmol) was combined with formamide (2.6 g, 2.3 ml, 58 mmol) to give a colorless solution. The mixture was heated at 155° C. for 5 hours. Removal of the formamide by distillation and chromatography (C18 reverse phase HPLC, methanol/water (0.1% formic acid)=20:80 to 95:5) yielded the title compound as white solid (0.002 g, 10%). MS: m/e=303.0 [M−H]$^−$.

e) 5-Chloro-6-(4-fluorophenyl)-8-hydroxyquinazolin-4(3H)-one

In a 10 mL round-bottomed flask, 5-chloro-6-(4-fluorophenyl)-8-methoxyquinazolin-4(3H)-one (0.07 g, 0.23 mmol) and boron tribromide (1 M in dichloromethane, 1.61 ml, 1.61 mmol) in dichloromethane (2.0 ml) was stirred for 18 hours at room temperature. Addition of methanol, removal of the solvents by distillation and (C18 reverse phase HPLC, methanol/water (0.1% formic acid)=20:80 to 95:5) yielded the title compound as white solid (0.03 g, 49%). MS: m/e=288.5 [M−H]$^−$.

EXAMPLE 102

5,6-Bis(4-fluorophenyl)-8-hydroxyquinazolin-4(3H)-one a) 4,5-Bis(4-fluorophenyl)-7-methoxyindoline-2,3-dione In a 20 ml tube, 5-bromo-4-chloro-7-methoxyindoline-2,3-dione (0.17 g, 0.50 mmol), 4-fluorophenylboronic acid (0.11 g, 0.75 mmol) and potassium carbonate (69.1 mg, 0.50 mmol) were combined with dioxane (8 ml) and water (0.8 ml) to give a brown suspension. Bis(diphenylphosphino) ferrocene-palladium(II)dichloride (0.04 g, 0.05 mmol) was added, and the mixture was heated at 100° C. for 18 hours. Chromatography (C18 reverse phase HPLC, methanol/water (0.1% formic acid)=20:80 to 95:5) yielded the title compound as red solid (0.05 g, 28%), MS: m/e=364.1 [M−H]⁻, and a fraction of 4-chloro-5-(4-fluorophenyl)-7-methoxyindoline-2,3-dione (0.06 g, 38%), MS: m/e=303.8 [M−H]⁻.

b) 4'-Amino-4,4''-difluoro-5'-methoxy-[1,1';2',1'']terphenyl-3'-carboxylic acid 4,5-Bis(4-fluorophenyl)-7-methoxyindoline-2,3-dione (0.20 g, 0.55 mmol) was suspended in 1N aqueous sodium hydroxide (5.47 ml, 5.47 mmol). A solution of hydrogen peroxide (0.23 ml, 2.19 mmol) was added and the reaction mixture was stirred for 20 minutes at room temperature. Then it was cooled to 0° C. and acetic acid (0.33 g, 0.32 ml, 5.47 mmol) and 3N hydrochloric acid (1.82 ml, 5.5 mmol) was added. The precipitate was collected and purified by chromatography (C18 reverse phase HPLC, methanol/water (0.1% formic acid)=20:80 to 95:5) to yield the title compound as white solid (0.08 g, 39%). MS: m/e=354.0 [M−H]⁻.

c) 5,6-Bis(4-fluorophenyl)-8-methoxyquinazolin-4(3H)-one

4'-Amino-4,4''-difluoro-5'-methoxy-[1,1';2',1'']terphenyl-3'-carboxylic acid (0.07 g, 0.20 mmol) was combined with formamide (1.83 g, 1.61 ml, 40.5 mmol) to give a colorless solution. The reaction mixture was heated at 155° C. for 5 hours. Removal of the formamide by distillation and chromatography (silica gel, methanol/dichloromethane=0:100 to 5:95) yielded the title compound as white solid (0.03 g, 45%). MS: m/e=362.9 [M−H]⁻.

d) 5,6-Bis(4-fluorophenyl)-8-hydroxyquinazolin-4(3H)-one 5,6-Bis(4-fluorophenyl)-8-methoxyquinazolin-4(3H)-one (0.05 g, 0.12 mmol) and boron tribromide (1 M in dichloromethane, 0.87 ml, 0.87 mmol) in dichloromethane (5.0 ml) were stirred for 3 h at room temperature. Addition of methanol, removal of the solvents by distillation and chromatography (C18 reverse phase HPLC, methanol/water (0.1% formic acid)=20:80 to 95:5) yielded the title compound as white solid (0.03 g, 63%). MS: m/e=349.1 [M−H]⁻.

EXAMPLE 103

8-Hydroxy-6-[3-methyl-5-(4-methyl-piperazine-1-carbonyl)-thiophen-2-yl]-3H-quinazolin-4-one a) 6-(3-Methyl-5-(4-methylpiperazine-1-carbonyl)thiophen-2-yl)-8-((2-(trimethylsilyl)ethoxy)methoxy)-3-((2-(trimethylsilyl)ethoxy)methyl)quinazolin-4(3H)-one A mixture of 4-methyl-5-(4-oxo-8-((2-(trimethylsilyl)ethoxy)methoxy)-3-((2-(trimethylsilyl)ethoxy)methyl)-3,4-dihydroquinazolin-6-yl)thiophene-2-carboxylic acid (0.08 g, 0.14 mmol), 1-methylpiperazine (0.02 g, 0.02 ml, 0.17 mmol), N, N-diisopropylethylamine (0.04 g, 0.05 ml, 0.03 mmol), and O-(7-azabenzotriazol-1-yl)-N,N,N',N'-tetramethyluronium hexafluorophosphate (HATU, 0.05 g, 0.14 mmol) in dimethylformamide (5.5 ml) was stirred at room temperature overnight. Extraction with ethyl acetate and chromatography (silica gel, dichloromethane/methanol=98:2 to 95:5) yielded the title compound as colorless oil (0.06 g, 63%). MS: m/e=645.2 [M+H]⁺.

b) 8-Hydroxy-6-[3-methyl-5-(4-methyl-piperazine-1-carbonyl)-thiophen-2-yl]-3H-quinazolin-4-one To 6-(3-methyl-5-(4-methylpiperazine-1-carbonyl)thiophen-2-yl)-8-((2-(trimethylsilyl)ethoxy)methoxy)-3-((2-(trimethylsilyl)ethoxy)methyl)quinazolin-4(3H)-one (0.06 g, 0.09 mmol) was added water (3.0 ml) and formic acid (27 ml). The reaction mixture was stirred at 90° C. for 2 hours and then saturated aqueous sodium hydrogencarbonate was added. Extraction with ethyl acetate yielded the title compound as white solid (0.01 g, 20%). MS: m/e=385.2 [M+H]⁺.

EXAMPLE 104

N-(5-(8-Hydroxy-4-oxo-3,4-dihydroquinazolin-6-yl)-6-(methoxymethyl)pyridin-2-yl)pivalamide a) N-(6-(Methoxymethyl)-5-(4-oxo-8-((2-(trimethylsilyl)ethoxy)methoxy)-3-((2-(trimethylsilyl)ethoxy)methyl)-3,4-dihydroquinazolin-6-yl)pyridin-2-yl)pivalamide A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.18 g, 0.33 mmol) and N-(5-bromo-6-(methoxymethyl)pyridin-2-yl)pivalamide (0.10 g, 0.33 mmol) and potassium carbonate (0.14 g, 0.10 mmol) in dimethylformamide (4 ml) and water (0.4 ml) was treated with bis(diphenylphosphino)ferrocene-palladium(II)dichloride (0.02 g, 0.03 mmol). The reaction mixture was stirred at 100° C. overnight. Extraction with ethyl acetate and chromatography (silica gel, ethyl acetate/heptane=50:50 to 100:0) yielded the title compound as brown oil (0.11 g, 50%). MS: m/e=643.3 [M+H]⁺.

b) N-(5-(8-Hydroxy-4-oxo-3,4-dihydroquinazolin-6-yl)-6-(methoxymethyl)pyridin-2-yl)pivalamide N-(6-(Methoxymethyl)-5-(4-oxo-8-((2-(trimethylsilyl)ethoxy)methoxy)-3-((2-(trimethylsilyl)ethoxy)methyl)-3,4-dihydroquinazolin-6-yl)pyridin-2-yl)pivalamide (0.11 g, 0.16 mmol) was combined with formic acid (9 ml) and Water (1 ml) and heated at 100° C. for 2 hours. Addition of methanol, removal of the solvents by distillation and trituration with diethyl ether (1 ml) yielded the title compound as grey solid (0.05 g, 72%). MS: m/e=383.0 [M+H]⁺.

EXAMPLE 105

6-Bromo-8-hydroxy-5-(2-methylpyridin-4-yl)quinazolin-4(3H)-one a) 7-Methoxy-4-(2-methylpyridin-4-yl)indoline-2,3-dione 4-Bromo-7-methoxyindoline-2,3-dione (CAS67303-38-2, 1.28 g, 5.00 mmol), 2-methylpyridin-4-ylboronic acid (0.69 g, 5.00 mmol) and potassium carbonate (0.69 g, 5.00 mmol) were combined with dioxane (70 ml) and water (7.0 ml) to give a brown suspension. Bis(diphenylphosphino)ferrocene-palladium(II)dichloride (0.37 g, 0.50 mmol) were added and the reaction mixture was stirred at 95° C. for 18 hours. Chromatography (silica gel, methanol/dichloromethane=0:100 to 10:90) yielded the title compound as red solid (0.95 g, 71%). MS: m/e=266.8 [M−H]−.

b) 5-Bromo-7-methoxy-4-(2-methylpyridin-4-yl)indoline-2,3-dione

To a solution of 7-methoxy-4-(2-methylpyridin-4-yl)indoline-2,3-dione (0.81 g, 3.02 mmol) in acetic acid (16 ml) was slowly added bromine (0.97 g, 6.04 mmol). The reaction mixture was stirred at 25° C. for 3 hours and was then heated to 80° C. 20 hours. Filtration and trituration with diethyl ether yielded the title compound as brown solid (1.0 g, 96%). MS: m/e=348.9, 346.9 [M+H]+.

c) 2-Amino-5-bromo-3-methoxy-6-(2-methylpyridin-4-yl)benzoic acid

5-Bromo-7-methoxy-4-(2-methylpyridin-4-yl)indoline-2,3-dione (0.15 g, 0.43 mmol) was suspended in 1N aqueous sodium hydroxide (4.32 ml, 4.32 mmol). A solution of hydrogen peroxide (0.18 ml, 1.73 mmol) was added at 0° C. and the reaction mixture was then stirred for 20 minutes at room temperature. At 0° C. acetic acid (0.26 g, 0.25 ml, 4.32 mmol) and 3N hydrochloric acid (1.44 ml, 4.32 mmol) were added. The precipitate was filtered to yield the title compound as brown solid (0.10 g, 69%). MS: m/e=337.0, 339.0 [M+H]+.

d) 6-Bromo-8-hydroxy-5-(2-methylpyridin-4-yl)quinazolin-4(3H)-one

2-Amino-5-bromo-3-methoxy-6-(2-methylpyridin-4-yl)benzoic acid (0.32 g, 0.95 mmol) and formamide (1.71 g, 1.51 ml, 38.0 mmol) were heated in a microwave at 160° C. for 45 minutes. The mixture was concentrated in vacuo and purified by chromatography (silica gel, methanol/dichloromethane=0:100 to 20:80 and silica gel, methanol/ethyl acetate=0:100 to 100:0 and HPLC, C18 reverse phase, methanol/water (0.1% triethylamine)=20:80 to 95:5) to yield the title compound as brown oil (0.01 g, 4%). MS: m/e=332.0, 334.1 [M+H]+.

EXAMPLE 106

N-(2-(Diisopropylamino)ethyl)-4-(8-hydroxy-4-oxo-3,4-dihydroquinazolin-6-yl)-N-isopropyl-3-(methoxymethyl)benzamide 2,2,2-trifluoroacetate a) 3-(Methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzoic acid Methyl 3-(methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzoate (0.80 g, 1.33 mmol) and 1 N aqueous lithium hydroxide (50.0 ml, 50.0 mmol) in tetrahydrofuran (40 ml) and MeOH (2.5 ml) were stirred for 2 hours. Acidification with saturated aqueous ammonium chloride/water=1:3 (450 mL) and extraction with ethyl acetate yielded the title compound as colorless solid (0.65 g, 83%). MS: m/e=587.1 [M+H]+.

b) N-(2-(Diisopropylamino)ethyl)-N-isopropyl-3-(methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzamide A mixture of 3-(methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzoic acid (0.15 g, 0.26 mmol), N1,N1,N2-triisopropylethane-1,2-diamine (0.05 g, 0.26 mmol), N, N-diisopropylethylamine (0.17 g, 0.22 ml, 1.28 mmol), and O-(7-azabenzotriazol-1-yl)-N,N,N′,N′-tetramethyluronium hexafluorophosphate (HATU, 0.19 g, 0.51 mmol) in dimethylformamide (6 ml) was stirred at room temperature for 20 hours. Extraction with ethyl acetate and chromatography (silica gel, dichloromethane/methanol=95:5) yielded the title compound as colorless oil (0.08 g, 41%). MS: m/e=755.5 [M+H]+.

c) N-(2-(Diisopropylamino)ethyl)-4-(8-hydroxy-4-oxo-3,4-dihydro quinazolin-6-yl)-N-isopropyl-3-(methoxymethyl)benzamide 2,2,2-trifluoroacetate To N-(2-(diisopropylamino)ethyl)-N-isopropyl-3-(methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzamide (0.08 g, 0.10 mmol) in dichloromethane (2 ml) was added slowly trifluoroacetic acid (2.96 g, 2 ml, 26.0 mmol) and the mixture was stirred at room temperature for 1 hour. The solvents were distilled off and the residue was treated with methanol (3×5 ml). Trituration with diethyl ether (1 ml) yielded the title compound as light brown solid (0.05 g, 76%). MS: m/e=495.1 [M+H]+.

EXAMPLE 107

8-Hydroxy-6-(4-((4-isopropylpiperazin-1-yl)methyl)-2-(methoxymethyl)phenyl)quinazolin-4(3H)-one tetrakis(2,2,2-trifluoroacetate)

a) 6-(4-(Hydroxymethyl)-2-(methoxymethyl)phenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (1.80 g, 3.29 mmol) and (4-bromo-3-(methoxymethyl)phenyl)methanol (0.76 g, 3.29 mmol) and potassium carbonate (1.36 g, 9.87 mmol) in dioxane (25 ml) and water (0.2 ml) was treated with bis(diphenylphosphino)ferrocene-palladium(II)dichloride (0.24 g, 0.33 mmol). The reaction mixture was stirred at 100° C. for 15 hours. Extraction with ethyl acetate and chromatography (silica gel, ethyl acetate/heptane=50:50 to 100:0) yielded the title compound as brown oil (1.18 g, 63%). MS: m/e=573.3 [M+H]+.

b) 3-(Methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzyl methanesulfonate To 6-(4-(hydroxymethyl)-2-(methoxymethyl)phenyl)-8-((2-(trimethylsilyl)ethoxy)methoxy)-3-((2-(trimethylsilyl)ethoxy)methyl)quinazolin-4(3H)-one (0.33 g, 0.52 mol) and triethylamine (0.11 g, 0.15 ml, 0.68 mmol) was slowly added at 0° C. methanesulfonyl chloride (0.08 g, 0.05 ml, 0.68 mmol). The mixture was stirred at 0° C. for 3 hours and was then poured into saturated aqueous sodium bicarbonate (10 ml). Extraction with dichloromethane yielded the title compound as brown oil (0.35 g, 93%). MS: m/e=651.3 [M+H]$^+$.

c) 6-(4-((4-Isopropylpiperazin-1-yl)-2-(methoxymethyl)phenyl)-8-((2-(trimethylsilyl)ethoxy)methoxy)-3-((2-(trimethylsilyl)ethoxy)methyl)quinazolin-4(3H)-one 1-Isopropylpiperazine (0.07 g, 0.54 mmol), cesium carbonate (0.53 g, 1.61 mmol), 3-(methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzyl methanesulfonate (0.35 g, 0.54 mmol) in dimethylformamide (10 ml) were stirred at room temperature overnight. Extraction with ethyl acetate and chromatography (silica gel, dichloromethane/methanol=100:0 to 70:30) yielded the title compound as light yellow oil (0.12 g, 32%), MS: m/e=682.3 [M−H]$^-$. A second fraction was isolated and identified as 3-(methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzyl 4-isopropylpiperazine-1-carboxylate (0.06 g, 14%, light yellow oil), MS: m/e=726.3 [M−H]$^-$.

d) 8-Hydroxy-6-((4-((4-isopropylpiperazin-1-yl)methyl)-2-(methoxymethyl)phenyl)quinazolin-4(3H)-one tetrakis(2,2,2-trifluoroacetate)

6-(4-((4-Isopropylpiperazin-1-yl)methyl)-2-(methoxymethyl)phenyl)-8-((2-(trimethylsilyl)ethoxy)methoxy)-3-((2-(trimethylsilyl)ethoxy)methyl)quinazolin-4(3H)-one (0.11 g, 0.16 mmol) and trifluoroacetic acid (2.22 g, 1.5 ml, 19.5 mmol) in dichloromethane (3 ml) were stirred at room temperature for 1 hour. The solvents were removed by distillation and the residue treated with methanol (3×5 ml). Trituration with diethyl ether/pentane (2 ml) yielded the title compound as off-white solid (0.09 g, 61%). MS: m/e=423.3 [M+H]$^+$.

EXAMPLE 108

8-Hydroxy-6-(2-isopropyl-1,2,3,4-tetrahydroisoquinolin-5-yl)quinazolin-4(3H)-one 2,2,2-trifluoroacetate a) 6-(2-Isopropyl-1,2,3,4-tetrahydro-isoquinolin-5-yl)-8-(2-trimethylsilanyl-ethoxymethoxy)-3-(2-trimethylsilanyl-ethoxymethyl)-3#H!-quinazolin-4-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.39 g, 0.71 mmol) and 5-bromo-2-isopropyl-1,2,3,4-tetrahydroisoquinoline (0.18 g, 0.71 mmol) and potassium carbonate (0.29 g, 2.12 mmol) in dioxane (20 ml) and water (2 ml) was treated with bis(diphenylphosphino)ferrocene-palladium(II)dichloride (0.05 g, 0.07 mmol). The reaction mixture was stirred at 100° C. for 10 hours. Extraction with ethyl acetate and chromatography (silica gel, ethyl acetate/heptane=0:100 to 30:70, followed by methanol) yielded the title compound as brown oil (0.27 g, 63%). MS: m/e=596.5 [M+H]$^+$.

b) 8-Hydroxy-6-(2-isopropyl-1,2,3,4-tetrahydroisoquinolin-5-yl)quinazolin-4(3H)-one 2,2,2-trifluoroacetate In a 10 mL round-bottomed flask, 6-(2-isopropyl-1,2,3,4-tetrahydroisoquinolin-5-yl)-8-((2-(trimethylsilyl)ethoxy)methoxy)-3-((2-(trimethylsilyl)ethoxy)methyl)quinazolin-4(3H)-one (0.26 g, 0.44 mmol) and trifluoroacetic acid (2.98 g, 2.02 ml, 26.2 mmol) in dichloromethane (5 ml) were stirred at room temperature for 1 hour. The solvent was removed by distillation and the residue was triturated with diethyl ether (2 ml) to yield the title compound as grey solid (0.20 g, 99%). MS: m/e=336.2 [M+H]$^+$.

EXAMPLE 109

4-(8-Hydroxy-4-oxo-3,4-dihydroquinazolin-6-yl)-3-(methoxymethyl)benzyl 4-isopropylpiperazine-1-carboxylate bis(2,2,2-trifluoroacetate)

3-(Methoxymethyl)-4-(4-oxo-8-((2-(trimethylsilyl)ethoxy)methoxy)-3-((2-(trimethylsilyl)ethoxy)methyl)-3,4-dihydroquinazolin-6-yl)benzyl 4-isopropylpiperazine-1-carboxylate (0.06 g, 0.08 mmol) and trifluoroacetic acid (1.48 g, 1 ml, 13.0 mmol) in dichloromethane (3 ml) was stirred at room temperature for 1 hour. The solvent was removed by distillation and the residue was triturated with diethyl ether (1 ml) to yield the title compound as off-white solid (0.05 g, 97%). MS: m/e=467.1 [M+H]$^+$.

EXAMPLE 110

8-Hydroxy-6-(2-(methoxymethyl)pyridin-3-yl)quinazolin-4(3H)-one bis(2,2,2-trifluoroacetate)

a) 6-((2-(Methoxymethyl)pyridin-3-yl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethyl silyl)ethoxy)methoxy)-3-((2-(trimethylsilyl)ethoxy)methyl)quinazolin-4(3H)-one (0.90 g, 1.64 mmol) and 3-bromo-2-(methoxymethyl)pyridine (0.33 g, 1.64 mmol) and cesium carbonate (0.54 g, 1.64 mmol) in dioxane (30 ml) and water (3 ml) was treated with bis(diphenylphosphino)ferrocene-palladium(II)dichloride (0.27 g, 0.33 mmol). The reaction mixture was stirred at 130° C. for 1.5 hours. Chromatography (silica gel, methanol/dichloromethane=0:100 to 5:95 followed by silica gel, ethyl acetate/heptane=15:85 to 100:0) yielded the title compound as off-white solid (0.65 g, 73%). MS: m/e=602.4 [M+Ac]$^-$.

b) 8-Hydroxy-6-(2-(methoxymethyl)pyridin-3-yl)quinazolin-4(3H)-one bis(2,2,2-trifluoroacetate)

6-(2-(Methoxymethyl)pyridin-3-yl)-8-((2-(trimethylsilyl)ethoxy)methoxy)-3-((2-(trimethylsilyl)ethoxy)methyl)quinazolin-4(3H)-one (0.64 g, 1.18 mmol) and trifluoroacetic acid (4.03 g, 2.72 ml, 35.3 mmol) in dichloromethane (10 ml) was stirred at room temperature for 1 hour. The solvent was removed by distillation and the residue was triturated with diethyl ether (1 ml) to yield the title compound as light brown solid (0.49 g, 81%). MS: m/e=284.1 [M+H]$^+$.

EXAMPLE 111

8-Hydroxy-6-[3-(4-methyl-piperazine-1-sulfonyl)-phenyl]-3#H!-quinazolin-4-one; compound with trifluoro-acetic acid a) 6-(3-(4-Methylpiperazin-1-ylsulfonyl)phenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.10 g, 0.18 mmol) and 1-(3-bromophenylsulfonyl)-4-methylpiperazine (0.06 g, 0.18 mmol) and cesium carbonate (0.08 g, 0.05 mmol) in dioxane (8 ml) and water (0.8 ml) was treated with bis(diphenylphosphino)ferrocene-palladium(II)dichloride (0.01 g, 0.02 mmol). The reaction mixture was stirred at 90° C. for 3 hours. Extraction with ethyl acetate and chromatography (silica gel, methanol/dichloromethane=0:100 to 10:90) yielded the title compound as brown solid (0.07 g, 55%). MS: m/e=661.3 [M+H]$^+$.

b) 8-Hydroxy-6-[3-(4-methyl-piperazine-1-sulfonyl)-phenyl]-3#H!-quinazolin-4-one; compound with trifluoro-acetic acid 6-(3-(4-Methylpiperazin-1-yl sulfonyl)phenyl)-8-((2-(trimethylsilyl)ethoxy)methoxy)-3-((2-(trimethylsilyl)ethoxy)methyl)quinazolin-4(3H)-one (0.06 g, 0.09 mmol) and trifluoroacetic acid (1.48 g, 1.0 ml, 0.01 mmol) in dichloromethane (1.6 ml) was stirred at room temperature for 1 hour. The solvent was removed by distillation and the residue was triturated with diethyl ether/pentane (1 ml) to yield the title compound as light brown solid (0.02 g, 49%). MS: m/e=398.9 [M−H]$^-$.

EXAMPLE 112

6-(2-Acetylphenyl)-8-hydroxyquinazolin-4(3H)-one a) 6-((2-Acetylphenyl)-8-((2-(trimethylsilyl)ethoxy)methoxy)-3-((2-(trimethylsilyl)ethoxy)methyl)quinazolin-4(3H)-one A mixture of 6-Bromo-8-((2-(trimethylsilyl)ethoxy)methoxy)-3-((2-(trimethylsilyl)ethoxy)methyl)quinazolin-4(3H)-one (0.60 g, 1.20 mmol) and 2-acetylphenylboronic acid (0.29 g, 1.79 mmol) and potassium carbonate (0.17 g, 1.2 mmol) in dioxane (60 ml) and water (6 ml) was treated with bis(diphenylphosphino)ferrocene-palladium(II)dichloride (0.09 g, 0.12 mmol). The reaction mixture was stirred at 95° C. for 3 hours. Chromatography (silica gel, ethyl acetate/heptane=0:100 to 60:40) yielded the title compound as yellow oil (0.51 g, 79%). MS: m/e=599.5 [M+Ac]$^-$.

b) 6-(2-Acetylphenyl)-8-hydroxyquinazolin-4(3H)-one 6-(2-Acetylphenyl)-8-((2-(trimethylsilyl)ethoxy)methoxy)-3-((2-(trimethylsilyl)ethoxy)methyl)quinazolin-4(3H)-one (0.50 g, 0.92 mmol) and trifluoroacetic acid (3.15 g, 2.13 ml, 27.6 mmol) in dichloromethane (10 ml) was stirred at room temperature for 1 hour. The solvent was removed by distillation and the residue was triturated with diethyl ether to yield the title compound as off-white solid (0.18 g, 68%). MS: m/e=281.0 [M+H]$^+$.

EXAMPLE 113

8-Hydroxy-6-(2-(2-hydroxypropan-2-yl)phenyl)quinazolin-4(3H)-one

To 6-(2-acetylphenyl)-8-hydroxyquinazolin-4(3H)-one (0.11 g, 0.39 mmol) in tetrahydrofuran (10 ml) at −74° C. was added methyl magnesium chloride (solution in tetrahydrofuran, 0.19 ml, 0.47 mmol) and the mixture was allowed to warm to room temperature. Additional methyl magnesium chloride (0.19 ml, 0.47 mmol) was added and the mixture was refluxed for 20 hours. After quenching with methanol the mixture was added to saturated aqueous ammonium chloride solution (10 ml) and extracted with ethyl acetate. Chromatography (C18 reverse phase HPLC, methanol/water (0.1% formic acid)=20:80 to 95:5) yielded the title compound as white solid (0.02 g, 17%). MS: m/e=297.2 [M+H]$^+$.

EXAMPLE 114

8-Hydroxy-6-(2-(methylsulfanylmethyl-phenyl)-3H-quinazolin-4-one 2,2,2-trifluoroacetate a) 6-(2-Methylsulfanylmethyl-phenyl)-8-(2-trimethylsilanyl-ethoxymethoxy)-3-(2-trimethylsilanyl-ethoxymethyl)-3H-quinazolin-4-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (1.00 g, 1.82 mmol) and 2-bromobenzyl)(methyl)sulfane (0.39 g, 1.82 mmol) and potassium carbonate (0.76 g, 5.47 mmol) in dioxane (20 ml) and water (2 ml) was treated with bis(diphenylphosphino)ferrocene-palladium(II)dichloride (0.13 g, 0.18 mmol). The reaction mixture was stirred at 90° C. for 15 hours. Extraction with ethyl acetate and chromatography (silica gel, ethyl acetate/heptane=0:100 to 100:0) yielded the title compound as yellow oil (0.55 g, 54%). MS: m/e=559.2 [M+H]$^+$.

b) 8-Hydroxy-6-(2-(methylsulfanylmethyl-phenyl)-3H-quinazolin-4-one 2,2,2-trifluoroacetate 6-(2-Methylsulfanylmethyl-phenyl)-8-(2-trimethylsilanyl-ethoxymethoxy)-3-(2-trimethylsilanyl-ethoxymethyl)-3H-quinazolin-4-one (0.04 g, 0.06 mmol) and trifluoroacetic acid (1.48 g, 1.0 ml, 13.0 mmol) in dichloromethane (3 ml) was stirred at room temperature for 2 hours. The solvent was removed by distillation and methanol was added. Removal of the solvent by distillation yielded the title compound as light brown solid (0.03 g, 97%). MS: m/e=299.4 [M+H]$^+$.

EXAMPLE 115

8-Hydroxy-6-(2-(methylsulfonylmethyl)phenyl)quinazolin-4(3H)-one 2,2,2-trifluoroacetate a) 6-((2-Methylsulfonylmethyl)phenyl)-8-((2-(trimethylsilyl)ethoxy)methoxy)-3-((2-(trimethylsilyl)ethoxy)methyl)quinazolin-4(3H)-one To 6-(2-methylsulfanylmethyl-phenyl)-8-(2-trimethylsilanyl-ethoxymethoxy)-3-(2-trimethylsilanyl-ethoxymethyl)-3H-quinazolin-4-one (0.13 g, 0.23 mmol) in dichloromethane (10 ml) was added at 0° C. m-chloroperbenzoic acid (0.09 g, 0.51 mmol). After 30 minutes the mixture was warmed to 25° C. and stirred for 1 h. Extraction with saturated aqueous bicarbonate and ethyl acetate and chromatography (silica gel, ethyl acetate/heptane=50:50 to 100:0) yielded the title compound as yellow oil (0.04 g, 29%). MS: m/e=591.2 [M+H]$^+$.

b) 8-Hydroxy-6-(2-(methylsulfonylmethyl)phenyl)quinazolin-4(3H)-one 2,2,2-trifluoroacetate 6-(2-(M ethylsulfonylmethyl)phenyl)-8-((2-(trimethylsilyl)ethoxy)methoxy)-3-((2-(trimethylsilyl)ethoxy)methyl)quinazolin-4(3H)-one (0.04 mg, 0.06 mmol) and trifluoroacetic acid (0.74 g, 0.5 ml, 6.49 mmol) in dichloromethane (2 ml) was stirred at room temperature for 2 hours. The solvent was removed by distillation and methanol was added. Removal of the solvent by distillation yielded the title compound as light brown solid (0.3 g, 94%). MS: m/e=331.3 [M+H]$^+$.

EXAMPLE 116

8-Hydroxy-6-(2-(2-(methylsulfonyl)ethyl)phenyl)quinazolin-4(3H)-one 2,2,2-trifluoroacetate a) 6-(2-(2-Methylthio)ethyl)phenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.50 g, 0.91 mmol) and 2-bromophenethyl)(methyl)sulfane (0.21 g, 0.91 mmol) and potassium carbonate (0.38 g, 2.73 mmol) in dioxane (10 ml) and water (1 ml) was treated with bis(diphenylphosphino)ferrocene-palladium(II)dichloride (0.07 g, 0.09 mmol). The reaction mixture was stirred at 90° C. for 15 hours. Extraction with ethyl acetate and chromatography (silica gel, ethyl acetate/heptane=20:80 to 100:0) yielded the title compound as yellow oil (0.45 g, 86%). MS: m/e=573.3 [M+H]$^+$.

b) 6-(2-(2-Methylsulfonyl)ethyl)phenyl)-8-((2-(trimethylsilyl)ethoxy)methoxy)-3-((2-(trimethylsilyl)ethoxy)methyl)quinazolin-4(3H)-one To 6-(2-(2-(methylthio)ethyl)phenyl)-8-((2-(trimethylsilyl)ethoxy)methoxy)-3-((2-(trimethylsilyl)ethoxy)methyl)quinazolin-4(3H)-one (0.44 g, 0.77 mmol) in dichloromethane (10 ml) was added at 0° C. m-chloroperbenzoic acid (0.29 g, 1.69 mmol). After 30 minutes the mixture was warmed to 25° C. and stirred for 1 hour. Removal of the solvent by distillation and chromatography (silica gel, ethyl acetate/heptane=10:90 to 100:0) yielded the title compound as yellow oil (0.39 g, 84%). MS: m/e=606.2 [M+H]$^+$.

c) 8-Hydroxy-6-(2-(2-(methylsulfonyl)ethyl)phenyl)quinazolin-4(3H)-one 2,2,2-trifluoroacetate 6-(2-(2-(Methylsulfonyl)ethyl)phenyl)-8-((2-(trimethylsilyl)ethoxy)methoxy)-3-((2-(trimethylsilyl)ethoxy)methyl)quinazolin-4(3H)-one (0.04 g, 0.06 mmol) and trifluoroacetic acid (2.96 g, 2.0 ml, 26 mmol) in dichloromethane (10 ml) was stirred at room temperature for 1 hour. The solvent was removed by distillation and methanol was added. Removal of the solvent by distillation yielded the title compound as off-white solid (0.22 g, 74%). MS: m/e=345.0 [M+H]$^+$.

EXAMPLE 117

6-Bromo-5-chloro-8-hydroxyquinazolin-4(3H)-one a) 6-Bromo-5-chloro-8-methoxyquinazolin-4(3H)-one 6-Bromo-8-methoxyquinazolin-4(3H)-one (1.50 g, 5.88 mmol) was combined with sulfuric acid (66.2 g, 36 ml, 675 mmol) to give a brown suspension. At room temperature was added 1-chloropyrrolidine-2,5-dione (1.18 g, 8.82 mmol) in portions during a period of 10 minutes. After stirring for 15 minutes the two educts were completely dissolved. The mixture was stirred at room temperature for 23 hours. Part of the solution (12 ml) was removed for reaction control. Additional 1-chloropyrrolidine-2,5-dione (0.79 g, 5.88 mmol) were added and the mixture was heated at 50° C. for 80 hours and then at 60° C. for 1.5 hours. After cooling to room temperature the mixture was added to ice/water and aqueous ammonium hydroxide (25%, 100 ml) was added keeping the temperature below 10° C. The precipitate was filtered off and dried to yield the title compound as off-white solid (1.14 g, 67%). MS: m/e=288.6 [M−H]$^-$.

b) 6-Bromo-5-chloro-8-hydroxyquinazolin-4(3H)-one

6-Bromo-5-chloro-8-methoxyquinazolin-4(3H)-one (0.07 g, 0.22 mmol) was combined with aqueous hydrobromic acid (10.4 g, 7 ml, 79.9 mmol) and heated to 140° C. to give an orange solution. The mixture was stirred for 23 hours at 140° C. A precipitate formed after cooling to room temperature. Filtration and drying (desiccator) yielded the title compound as grey solid (0.04 g, 57%). MS: m/e=274.7 [M−H]$^-$.

EXAMPLE 118

8-Hydroxy-6-(2-((2-(1-(2,2,2-trifluoroethyl)piperidin-4-yl)ethoxy)methyl)phenyl)quinazolin-4(3H)-one 2,2,2-trifluoroacetate a) 2,2,2-Trifluoro-1-(4-(2-hydroxyethyl)piperidin-1-yl)ethanone 2-(Piperidin-4-yl)ethanol (2.00 g, 15.5 mmol) and Et3N (2.35 g, 3.24 ml, 23.2 mmol) were combined with dichloromethane (50 ml) to give a colorless solution. 2,2,2-Trifluoroacetic anhydride (3.25 g, 2.15 ml, 15.5 mmol) was added slowly at 0° C. The reaction mixture was stirred for 15 h at 25° C. and washed with 1 M aqueous hydrochloric acid, saturated aqueous bicarbonate and brine. Chromatography (silica gel, ethyl acetate/heptane=20:80 to 50:50) yielded the title compound as light yellow oil (1.55 g, 55%). MS: m/e=226.1 [M+H]$^+$.

b) 2-(1-(2,2,2-Trifluoroethyl)piperidin-4-yl)ethanol

To borane tetrahydrofuran complex (1.6 ml, 1.6 mmol) was slowly added at 0° C. 2,2,2-trifluoro-1-(4-(2-hydroxyethyl)piperidin-1-yl)ethanone (0.20 g, 0.89 mmol) in tetrahydrofuran (3 ml). The reaction mixture was then stirred at 80° C. for 3 hours, cooled to room temperature and quenched with 6N aqueous hydrochloric acid. The solvent was removed by distillation and water (10 ml) was added. Extraction with ethyl acetate and chromatography yielded the title compound as light yellow oil (0.17 g, 92%). MS: m/e=212.2 [M+H]$^+$.

c) 4-(2-(2-Bromobenzyloxy)ethyl)-1-(2,2,2-trifluoroethyl)piperidine

To 2-(1-(2,2,2-trifluoroethyl)piperidin-4-yl)ethanol (0.14 g, 0.64 mmol) in tetrahydrofuran (10 ml) was added sodium hydride (0.04 g, 0.83 µmol) and the mixture was stirred at 50° C. for 30 minutes. Then 1-bromo-2-(bromomethyl) benzene (0.18 g, 0.70 mmol) in tetrahydrofuran (2 ml) was added. The reaction mixture was stirred at 80° C. for 15 hours. The reaction mixture was poured into water (10 ml) and extracted with ethyl acetate. Chromatography (silica gel, ethyl acetate/heptane=0:100 to 100:0) yielded the title compound as light yellow oil (0.15 g, 63%). MS: m/e=380.2, 382.1 [M+H]$^+$.

d) 6-(2-((2-(1-(2,2,2-Trifluoroethyl)piperidin-4-yl)ethoxy)methyl)phenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.07 g, 0.13 mmol) and 4-(2-(2-bromobenzyloxy)ethyl)-1-(2,2,2-trifluoroethyl)piperidine (0.05 g, 0.13 mmol) and potassium carbonate (0.05 g, 0.39 mmol) in dioxane (5 ml) and water (0.5 ml) was treated with bis(diphenylphosphino)ferrocene-palladium(II)dichloride (0.01 g, 0.01 mmol). The reaction mixture was stirred at 100° C. for 15 hours. Chromatography (silica gel, ethyl acetate/heptane=20:80 to 50:50) yielded the title compound as light yellow oil (0.04 g, 43%). MS: m/e=722.9 [M+H]$^+$.

e) 8-Hydroxy-6-(2-((2-(1-(2,2,2-trifluoroethyl)piperidin-4-yl)ethoxy)methyl)phenyl)quinazolin-4(3H)-one 2,2,2-trifluoroacetate 6-(2-((2-(1-(2,2,2-Trifluoroethyl)piperidin-4-yl)ethoxy)methyl)phenyl)-8-((2-(trimethylsilyl)ethoxy)methoxy)-3-((2-(trimethylsilyl)ethoxy)methyl)quinazolin-4(3H)-one (0.04 g, 0.06 mmol) and trifluoroacetic acid (0.74 g, 0.5 ml, 0.01 mmol) in dichloromethane (3 ml) was stirred at room temperature for 1 hour. The solvent was removed by distillation and methanol was added. Removal of the solvent by distillation yielded the title compound as light grey solid (0.03 g, 91%). MS: m/e=462.1 [M+H]$^+$.

EXAMPLE 119

5-Chloro-8-hydroxy-6-(2-(methylsulfonylmethyl) phenyl)quinazolin-4(3H)-one a) 6-Bromo-5-chloro-8-((2-methoxyethoxy) methoxy)-3-((2-methoxyethoxy)methyl)quinazolin-4 (3H)-one To 6-bromo-5-chloro-8-hydroxyquinazolin-4(3H)-one hydrobromide (1.80 g, 5.05 mmol) in dichloromethane (54 ml) was added at room temperature N,N-diisopropylethylamine (4.57 g, 6.05 ml, 35.4 mmol). The mixture was stirred for 15 minutes and 1-chloromethoxy-2-methoxy-ethane (1.89 g, 1.72 ml, 15.2 mmol) was added. After stirring overnight at room temperature again N,N-diisopropylethylamine (1.31 g, 1.73 ml, 10.0 mmol) and 1-chloromethoxy-2-methoxy-ethane (0.63 g, 0.57 ml, 5.10 mmol) were added and stirring was continued for 3 hours. The mixture was added to water (75 ml). Extraction with dichloromethane and trituration with diethyl ether yielded the title compound as off-white solid (0.98 g, 43%). MS: m/e=452.1, 453.0 [M+H]$^+$.

b) 5-Chloro-8-((2-methoxyethoxy)methoxy)-3-((2-methoxyethoxy)methyl)-6-(2-(methylthiomethyl) phenyl)quinazolin-4(3H)-one To 6-bromo-5-chloro-8-((2-methoxyethoxy)methoxy)-3-((2-methoxyethoxy)methyl)quinazolin-4(3H)-one (0.30 g, 0.66 mmol) and 4,4,5,5-tetramethyl-2-(2-(methylthiomethyl)phenyl)-1,3,2-dioxaborolane (0.18 g, 0.66 mmol) and potassium carbonate (0.28 g, 1.99 mmol) in dioxane (10 ml) and water (1 ml) was added bis(diphenylphosphino)ferrocene-palladium(II)dichloride (0.05 g, 0.07 mmol) and the reaction mixture was heated at 100° C. for 15 hours. Chromatography (silica gel, methanol/dichloromethane=0: 100 to 20:100) yielded the title compound as brown oil (0.33 g, 98%). MS: m/e=509.2 [M+H]$^+$.

c) 5-Chloro-8-((2-methoxyethoxy)methoxy)-3-((2-methoxyethoxy)methyl)-6-(2-(methylsulfonylmethyl)phenyl)quinazolin-4(3H)-one To 5-chloro-8-((2-methoxyethoxy)methoxy)-3-((2-methoxyethoxy)methyl)-6-(2-(methylthiomethyl)phenyl) quinazolin-4(3H)-one (0.20 g, 0.39 mmol) in dichloromethane (15 ml) was added at 0° C. m-chloroperbenzoic acid (0.15 g, 0.86 mmol). After 30 minutes the mixture was warmed to 25° C. and stirred for 1 hour. Extraction with saturated aqueous bicarbonate and ethyl acetate and chromatography (silica gel, methanol/dichloromethane=0:100 to 20:80) yielded the title compound as brown solid (0.11 g, 53%). MS: m/e=541.3 [M+H]$^+$.

d) 5-Chloro-8-hydroxy-6-(2-(methylsulfonylmethyl) phenyl)quinazolin-4(3H)-one 5-Chloro-8-((2-methoxyethoxy)methoxy)-3-((2-methoxyethoxy)methyl)-6-(2-(methylsulfonylmethyl)phenyl)quinazolin-4(3H)-one (0.11 g, 0.21 mmol) and trifluoroacetic acid (5.0 ml) and water (2 ml) was stirred at 100° C. for 15 hours. The solvent was removed by distillation. Trituration with diethyl ether yielded the title compound as brown solid (0.06 g, 84%). MS: m/e=262.9 [M−H]$^−$.

EXAMPLE 120

5-Chloro-8-hydroxy-6-(2-((2-(1-(2,2,2-trifluoroethyl)piperidin-4-yl)ethoxy)methyl)phenyl)quinazolin-4(3H)-one 2,2,2-trifluoroacetate a) 4-(2-(2-(4,4,5,5-Tetramethyl-1,3,2-dioxaborolan-2-yl)benzyloxy)ethyl)-1-(2,2,2-trifluoroethyl)piperidine To 4-(2-(2-bromobenzyloxy)ethyl)-1-(2,2,2-trifluoroethyl)piperidine (0.10 g, 0.26 mmol) and 4,4,4',4',5,5,5',5'-octamethyl-2,2'-bi(1,3,2-dioxaborolane) (0.17 g, 0.66 mmol) and potassium carbonate (0.13 g, 1.31 mmol) in dioxane (10 ml) was added bis(diphenylphosphino)ferrocene-palladium(II)dichloride (0.02 g, 0.03 mmol) and the reaction mixture was heated at 80° C. for 15 hours. Chromatography (silica gel, ethyl acetate/heptane=10:90 to 100:0) yielded the title compound as light yellow oil (0.11 g, 98%). MS: m/e=428.1 [M+H]$^+$.

b) 5-Chloro-8-((2-methoxyethoxy)methoxy)-3-((2-methoxyethoxy)methyl)-6-(2-((2-(1-(2,2,2-trifluoroethyl)piperidin-4-yl)ethoxy)methyl)phenyl)quinazolin-4(3H)-one To 6-bromo-5-chloro-8-((2-methoxyethoxy)methoxy)-3-((2-methoxyethoxy)methyl)quinazolin-4(3H)-one (0.25 g, 0.55 mmol) and 4-(2-(2-(4,4,5,5-tetramethyl-1,3,2-dioxaborolan-2-yl)benzyloxy)ethyl)-1-(2,2,2-trifluoroethyl)piperidine (0.24 g, 0.55 mmol) and potassium carbonate (0.23 g, 1.66 mmol) in dioxane (10 ml) and water (1 ml) was added bis(diphenylphosphino)ferrocene-palladium(II)dichloride (0.04 g, 0.06 mmol) and the reaction mixture was heated at 100° C. for 15 hours. Chromatography (silica gel, methanol/dichloromethane=0:100 to 20:100) yielded the title compound as brown oil (0.04 g, 11%). MS: m/e=672.2 [M+H]$^+$.

c) 5-Chloro-8-hydroxy-6-(2-((2-(1-(2,2,2-trifluoroethyl)piperidin-4-yl)ethoxy)methyl)phenyl)quinazolin-4(3H)-one 2,2,2-trifluoroacetate 5-Chloro-8-((2-methoxyethoxy)methoxy)-3-((2-methoxyethoxy)methyl)-6-(2-((2-(1-(2,2,2-trifluoroethyl)piperidin-4-yl)ethoxy)methyl)phenyl)quinazolin-4(3H)-one (0.04 g, 0.06 mmol) in trifluoroacetic acid (5 ml) and water (2 ml) was stirred at 100° C. for 15 hours. The solvent was removed by distillation and methanol was added. Removal of the solvent by distillation yielded the title compound as brown solid (0.02 g, 58%). MS: m/e=496.0 [M+H]$^+$.

EXAMPLE 121

8-Hydroxy-6-(2-((2-(4-(2,2,2-trifluoroethyl)piperazin-1-yl)ethoxy)methyl)phenyl)quinazolin-4(3H)-one 2,2,2-trifluoroacetate a) 1-(2-(2-Bromobenzyloxy)ethyl)-4-(2,2,2-trifluoroethyl)piperazine A mixture of 1-bromo-2-((2-bromoethoxy)methyl)benzene (CAS 18800-28-7, 0.20 g, 0.68 mmol), 1-(2,2,2-trifluoroethyl)piperazine dihydrochloride (0.16 g, 0.68 mmol) and sodium carbonate (0.36 g, 3.4 mmol) in tetrahydrofuran (5 ml) was heated at 85° C. for 15 hours. Extraction with ethyl acetate and chromatography (silica gel, ethyl acetate/heptane=10:90 to 100:0) yielded the title compound as yellow oil (0.12 g, 45%). MS: m/e=383.0, 381.2 [M+H]$^+$.

b) 6-(2-((2-(4-(2,2,2-Trifluoroethyl)piperazin-1-yl)ethoxy)methyl)phenyl)-8-((2-(trimethylsilyl)ethoxy)methoxy)-3-((2-(trimethylsilyl)ethoxy)methyl)quinazolin-4(3H)-one A mixture of 6-(4,4,5,5-tetramethyl-1,3,2-dioxaborolan-2-yl)-8-((2-(trimethylsilyl)ethoxy)methoxy)-3-((2-(trimethylsilyl)ethoxy)methyl)quinazolin-4(3H)-one (0.16 g, 0.29 mmol) and 1-(2-(2-bromobenzyloxy)ethyl)-4-(2,2,2-trifluoroethyl)piperazine (0.11 g, 0.29 mmol) and potassium carbonate (0.12 g, 0.87 mmol) in dioxane (11 ml) and water (0.5 ml) was treated with bis(diphenylphosphino)ferrocene-palladium(II)dichloride (0.02 g, 0.03 mmol). The reaction mixture was stirred at 100° C. for 15 hours. Chromatography (silica gel, ethyl acetate/heptane=20:80 to 100:0) yielded the title compound as brown oil (0.04 g, 43%). MS: m/e=723.4 [M+H]$^+$.

c) 8-Hydroxy-6-(2-((2-(4-(2,2,2-trifluoroethyl)piperazin-1-yl)ethoxy)methyl)phenyl)quinazolin-4(3H)-one 2,2,2-trifluoroacetate 6-(2-((2-(4-(2,2,2-Trifluoroethyl)piperazin-1-yl)ethoxy)methyl)phenyl)-8-((2-(trimethylsilyl)ethoxy)methoxy)-3-((2-(trimethylsilyl)ethoxy)methyl)quinazolin-4(3H)-one (0.06 g, 0.09 mmol) and trifluoroacetic acid (1.01 g, 0.7 ml, 0.01 mmol) in dichloromethane (5 ml) was stirred at room temperature for 1 hour. The solvent was removed by distillation and methanol was added. Removal of the solvent by distillation yielded the title compound as light brown solid (0.03 g, 63%). MS: m/e=461.3 [M−H]$^-$.

EXAMPLE 122

5-Bromo-6-(4-fluorophenyl)-8-hydroxyquinazolin-4(3H)-one

To 5-bromo-6-(4-fluorophenyl)-8-methoxy-3-((2-(trimethylsilyl)ethoxy)methyl)quinazolin-4(3H)-one (0.15 g, 0.3 mmol) in dichloromethane (10 ml) was added boron tribromide (1 M in dichloromethane, 1.5 ml, 15.9 mmol) and the mixture was stirred overnight at room temperature. Removal of the solvent by distillation and chromatography (C18 reverse phase, methanol/water (0.1% formic acid)=20:80 to 95:5) yielded the title compound as light brown solid (0.01 g, 12%). MS: m/e=332.8, 335.0 [M−H]$^-$.

EXAMPLE 123

7-Fluoro-5,6-bis(4-fluorophenyl)-8-hydroxyquinazolin-4(3H)-one a) N-(5-Bromo-3-fluoro-2-methoxy-phenyl)-2-[(E)-hydroxyimino]-acetamide In a 500 ml three-necked flask, 2,2,2-trichloroethane-1,1-diol (8.68 g, 52.5 mmol) and sodium sulfate (47.4 g, 334 mmol) were combined with water (122 ml) to give a colorless solution. The reaction mixture was heated to 50° C. and a mixture of 5-bromo-3-fluoro-2-methoxyaniline (CAS 239122-51-1, 10.50 g, 47.7 mmol) in water (60 ml), dioxane (60 ml) and aqueous hydrochloric acid (7.84 ml, 95.4 mmol) were added. Then hydroxylamine hydrochloride (9.95 g, 143 mmol) in water (60 ml) was added. The reaction mixture was heated to 70° C. and stirred for 15 hours and then cooled to room temperature. The precipitate was filtered off and washed with water (50 ml) and dried in vacuo to yield the title compound as brown solid (13.4 g, 96%). MS: m/e=289.1, 291.3 [M−H]$^-$.

b) 4-Bromo-6-fluoro-7-methoxy-1H-indole-2,3-dione

N-(5-Bromo-3-fluoro-2-methoxyphenyl)-2-(hydroxyimino)acetamide (10.1 g, 34.7 mmol) and sulfuric acid (15 ml, 281 mmol) were combined under cooling in an ice bath. The reaction mixture was stirred at 50° C. for 3 hours and then during the weekend. The mixture was added to water (200 ml) and stirred for 30 minutes. The precipitate was filtrated off and dried in vacuo to yield the title compound as dark red solid (9.41 g, 99%). MS: m/e=274.3, 276.2 [M+H]⁺.

c) 6-Fluoro-4-(4-fluorophenyl)-7-methoxyindoline-2,3-dione

To 4-bromo-6-fluoro-7-methoxyindoline-2,3-dione (10.2 g, 37.1 mmol), 4-fluorophenylboronic acid (5.71 g, 40.8 mmol) and cesium carbonate (12.1 g, 37.1 mmol) in dioxane (110 ml) and water (11 ml) was added bis(diphenylphosphino)ferrocene-palladium(II)dichloride (1.36 g, 1.86 mmol). The mixture was heated to 80° C. and stirred for 15 hours. Removal of the solvent by distillation and chromatography (silica gel, ethyl acetate/heptane=20:80 to 100:0) yielded the title compound as dark brown solid (5.75 g, 54%). MS: m/e=290.3 [M+H]⁺.

d) 3-Amino-5,4'-difluoro-4-methoxy-biphenyl-2-carboxylic acid

6-Fluoro-4-(4-fluorophenyl)-7-methoxyindoline-2,3-dione (2.63 g, 9.09 mmol) was combined with aqueous 2N sodium hydroxide (96.0 ml, 192 mmol) to give a dark brown suspension. At −10° C. hydrogen peroxide (5.25 ml, 60.0 mmol) was added slowly and the mixture was stirred at room temperature for 30 minutes. Again hydrogen peroxide (5.25 ml, 60.0 mmol) was added and the mixture was stirred at 50° C. for 15 hours. The mixture was cooled to room temperature and acidified with aqueous hydrochloric acid (pH=1). Extraction with ethyl acetate and removal of the solvent by distillation yielded the title compound as a brown solid (2.51 g, 99%). MS: m/e=278.5 [M−H]⁻.

e) 6-Bromo-7-fluoro-5-(4-fluorophenyl)-8-methoxy-quinazolin-4(3H)-one

3-Amino-4',5-difluoro-4-methoxybiphenyl-2-carboxylic acid (10.1 g, 3.63 mmol) in methanol (50 ml) was kept between −10 to −15° C. while N-bromosuccinimide (0.68 g, 3.81 mmol) was added. The mixture was stirred for 25 minutes at −15° C. The solvent was distilled off and to the crude material (3-amino-6-bromo-4',5-difluoro-4-methoxy-biphenyl-2-carboxylic acid) was added formamide (11.3 g, 10 ml, 251 mmol). The orange solution was stirred at 150° C. overnight and then the formamide was distilled off. Chromatography (silica gel, ethyl acetate/heptane=40:60 to 100:0) yielded the title compound as brown solid (0.36 g, 27%, contains about 10% of the side product 7-fluoro-5-(4-fluoro-phenyl)-8-methoxy-3H-quinazolin-4-one), MS: m/e=367, 369.2 [M+H]⁺.

f) 7-Fluoro-5,6-bis(4-fluorophenyl)-8-methoxyquinazolin-4(3H)-one

To 6-bromo-7-fluoro-5-(4-fluorophenyl)-8-methoxyquinazolin-4(3H)-one (0.36 g, 0.97 mmol), 4-fluorophenylboronic acid (0.14 g, 0.97 mmol) and cesium carbonate (0.32 g, 0.97 mmol) in dioxane (30 ml) and water (3 ml) was added bis(diphenylphosphino)ferrocene-palladium(II)dichloride (0.04 g, 0.05 mmol). The reaction mixture was stirred at 80° C. for 20 hours. Again bis(diphenylphosphino)ferrocene-palladium(II)dichloride (0.04 g, 0.05 mmol) was added. After stirring for further 7.5 hours 4-fluorophenylboronic acid (0.14 g, 0.97 mmol) and bis(diphenylphosphino)ferrocene-palladium(II)dichloride (0.04 g, 0.05 mmol) were added and stirring was continued overnight at 80° C. Chromatography (silica gel, methanol/dichloromethane=2:98 to 5:95) yielded a mixture of educt, product and educt without bromine (200 mg). To this mixture were added 4-fluorophenylboronic acid (0.07 g, 0.53 mmol) and cesium carbonate (0.52 g, 1.59 mmol) in dioxane (16.5 ml) and water (1.65 ml) and bis(diphenylphosphino)ferrocene-palladium(II)dichloride (0.02 g, 0.03 mmol). The reaction mixture was stirred at 80° C. for 6 hours. Chromatography (silica gel, methanol/dichloromethane=0:100 to 5:95) yielded the title compound as off-white solid (0.10 g, 38%, contains about 10% of 7-fluoro-5-(4-fluoro-phenyl)-8-methoxy-3H-quinazolin-4-one). MS: m/e=383.3 [M+H]⁺.

g) 7-Fluoro-5,6-bis(4-fluorophenyl)-8-hydroxyquinazolin-4(3H)-one

To (7-fluoro-5,6-bis(4-fluorophenyl)-8-methoxyquinazolin-4(3H)-one (0.10 g, 0.25 mmol) in dichloromethane (12 ml) was added boron tribromide (1 M in dichloromethane, 0.76 ml, 0.76 mmol). After stirring for 1 hour at room temperature boron tribromide (1 M in dichloromethane, 0.76 ml, 0.76 mmol) was added again and stirring was continued overnight. Methanol was added and the solvents were removed by distillation. Chromatography (C18 reverse phase, methanol/water (0.1% formic acid)=20:80 to 95:5) yielded the title compound as grey solid (0.05 g, 56%), MS: m/e=369.4 [M+H]⁺, and a second product.

EXAMPLE 124

7-Fluoro-5-(4-fluorophenyl)-8-hydroxyquinazolin-4(3H)-one

The second product in Example 123 g was identified as the title compound, a grey solid (21 mg). MS: m/e=275.2 [M+H]⁺.

EXAMPLE 125

6-(4-Fluorophenyl)-8-hydroxyquinazolin-4(3H)-one a) 6-(4-Fluorophenyl)-8-methoxyquinazolin-4(3H)-one

Dichloro-1,1'-bis(diphenylphosphino)ferrocene palladium(II) (144 mg, 0.176 mmol) was added to a mixture of 6-bromo-8-methoxyquinazolin-4(3H)-one (example 2a, 700 mg, 2.74 mmol), 4-fluorophenylboronic acid (576 mg, 4.12 mmol) and cesium carbonate (1.79 g, 5.49 mmol) in dioxane (6 ml)/water (0.3 ml). The mixture was heated in a sealed tube under microwave irradiation at 120° C. for 30 minutes. Water (100 ml) was added. Extraction with dichloromethane/methanol (9:1) and chromatography (silica gel, methanol/dichloromethane=0:100 to 10:90) yielded the title compound (0.31 g). MS: m/e=271.1 [M+H]⁺.

b) 6-(4-Fluorophenyl)-8-hydroxyquinazolin-4(3H)-one

1M Boron tribromide in dichloromethane (3.9 ml, 3.9 mmol) was added to 6-(4-fluorophenyl)-8-methoxyquinazolin-4(3H)-one (130 mg, 0.481 mmol) in dichloromethane (15 ml) slowly keeping the reaction temperature below −20° C. The mixture was allowed to warm to room temperature and was stirred for 18 h. Methanol (7 ml) was added and the mixture was stirred for 2 h. The mixture was concentrated. Chromatography (silica gel, methanol/dichloromethane=0:

100 to 50:50) followed by C18 reverse phase HPLC (methanol/water (0.1% formic acid)=40:60 to 100:0) gave the title product as a grey solid (0.04 g). MS: m/e=254.9 [M−H]⁻.

EXAMPLE 126

6-Bromo-8-hydroxyquinazolin-4(3H)-one

The title compound (10 mg) was obtained as a light brown solid in analogy to example 125b from 6-bromo-8-methoxy-quinazolin-4(3H)-one (example 2a, 0.05 g). MS: m/e=241.1/243.1 [M+H]⁺.

EXAMPLE 127

6-(4-Fluoro-2-methylphenyl)-8-hydroxyquinazolin-4(3H)-one

The title compound (0.01 g) was obtained analogy to example 125 using 4-fluoro-2-methylphenylboronic acid. MS: m/e=269.4 [M−H]⁻.

EXAMPLE 128

8-Hydroxy-6-phenylquinazolin-4(3H)-one

The title compound (0.02 g) was obtained analogy to example 125 using phenylboronic acid. MS: m/e=237.1 [M−H]⁻.

EXAMPLE 129

8-Hydroxy-6-(4-hydroxyphenyl)quinazolin-4(3H)-one

The title compound (0.001 g) was obtained analogy to example 125 using 4-methoxyphenylboronic acid. MS: m/e=253.1 [M−H]⁻.

EXAMPLE 130

8-Hydroxy-6-p-tolylquinazolin-4(3H)-one

The title compound (0.005 g) was obtained analogy to example 125 using p-tolylboronic acid. MS: m/e=251.4 [M−H]⁻.

EXAMPLE 131

6-(4-Chlorophenyl)-8-hydroxyquinazolin-4(3H)-one

The title compound (0.008 g) was obtained analogy to example 125 using 4-chlorophenylboronic acid. MS: m/e=271.3 [M−H]⁻.

EXAMPLE 132

6-(2-Chlorophenyl)-8-hydroxyquinazolin-4(3H)-one

The title compound (0.008 g) was obtained analogy to example 125 using 2-chlorophenylboronic acid. MS: m/e=271.3 [M−H]⁻.

EXAMPLE 133

6-(2,4-Difluorophenyl)-8-hydroxyquinazolin-4(3H)-one

The title compound (0.008 g) was obtained analogy to example 125 using 2,4-difluorophenylboronic acid. MS: m/e=273.2 [M−H]⁻.

EXAMPLE 134

8-Hydroxy-6-(2-methylpyridin-4-yl)quinazolin-4(3H)-one a) 6-Bromo-4-oxo-3,4-dihydroquinazolin-8-yl tert-butyl carbonate 1M Boron tribromide in dichloromethane (27.4 ml, 27.4 mmol) was added to a suspension of 6-bromo-8-methoxy-quinazolin-4(3H)-one (1.0 g, 3.9 mmol) in dichloromethane (30 ml). The mixture was heated under reflux for 5 h. Methanol (10 ml) was added and the mixture was concentrated to a solid, addition of methanol and evaporation was repeated 2 times. Dichloromethane (100 ml) was added, followed by Hunig's base (3.55 g, 4.79 ml, 27.4 mmol). Di-tert-butyl dicarbonate (1.28 g, 1.37 ml, 5.88 mmol) was added and the mixture was stirred for 1 h at room temperature. The mixture was washed with saturated aqueous ammonium chloride and purified by chromatography (silica gel, ethyl acetate/heptane=0:100 to 100:0) to give the title compound (0.45 g) as a white solid. MS: m/e=340.9/343.1 [M+H]⁺.

b) 8-Hydroxy-6-(2-methylpyridin-4-yl)quinazolin-4(3H)-one

Reaction conditions in analogy to example 125a using 6-bromo-4-oxo-3,4-dihydroquinazolin-8-yl tert-butyl carbonate and 2-methylpyridin-4-ylboronic acid yielded the title compound (0.002 g) as an off-white gum with the tert-butyloxycarbonyl group removed. MS: m/e=254.1 [M+H]⁺.

EXAMPLE 135

8-Hydroxy-6-(4-methoxy-phenyl)-3H-quinazolin-4-one

Reaction conditions in analogy to example 125a using 6-bromo-4-oxo-3,4-dihydroquinazolin-8-yl tert-butyl carbonate and 4-methoxyphenylboronic acid yielded the title compound (0.013 g) as a dark red solid with the tert-butyloxycarbonyl group removed. MS: m/e=269.2 [M+H]⁺.

EXAMPLE 136

6-Bromo-8-hydroxy-7-methylquinazolin-4(3H)-one a) 2-Amino-5-bromo-3-hydroxy-4-methylbenzoic acid Bromine (0.32 g, 103 μl, 2.00 mmol) was added to 2-amino-3-hydroxy-4-methylbenzoic acid (0.17 g, 1 mmol) in acetic acid (10 ml). The mixture was stirred for 30 min and then concentrated to a brown solid. The residue was dissolved in 5 ml methanol and precipitated with water (50 ml). The residue was washed with water (2×20 ml) to give the title compound (0.20 g) as a brown solid. MS: m/e=244.0/246.0 [M–H]⁻.

b)
6-Bromo-8-hydroxy-7-methylquinazolin-4(3H)-one

A mixture of 2-amino-5-bromo-3-hydroxy-4-methylbenzoic acid (0.02 g, 81 µmol) in formamide (2 ml) was stirred for 48 h at 120° C. The crude material was purified by chromatography (C18 reverse phase HPLC, acetonitrile/water (0.1% formic acid)=20:90 to 98:2) to give the title compound (0.026 g) as a brown solid. MS: m/e=253.1/245.1 [M–H]⁻.

EXAMPLE 137

8-Hydroxy-6-iodo-3H-quinazolin-4-one a) 2-Amino-5-iodo-3-methoxybenzoic acid

2-Amino-3-methoxybenzoic acid (0.33 g, 2 mmol) and iodine monochloride (0.65 g, 200 µl, 4.00 mmol) were combined with acetic acid (10 ml) to give a red solution. This solution was stirred overnight. The organic solvent was evaporated. Aqueous sodium hydroxide (1N) solution was added to the residue. The aqueous layer was washed with ethyl acetate, acidified by addition of aqueous hydrochloric acid (1N) and then extracted with ethyl acetate. The organic layers were dried and concentrated to give the title compound (0.43 g) as a dark red solid. MS: m/e=294.0 [M+H]⁺.

b) 6-Iodo-8-methoxyquinazolin-4(3H)-one

2-Amino-5-iodo-3-methoxybenzoic acid (0.43 g, 1.47 mmol) was combined with formamide (3.9 ml) to give a dark red solution. The solution was stirred for 4 h. Water was added and extracted with ethyl acetate. The combined layers were dried and concentrated to give the desired product (0.30 g) as a red solid. MS: m/e=303.0 [M+H]⁺.

c) 8-Hydroxy-6-iodo-3H-quinazolin-4-one

A solution of boron tribromide in dichloromethane (1M, 7 ml, 7 mmol), was added at −78° C. to a suspension of 6-iodo-8-methoxyquinazolin-4(3H)-one (0.30 g, 993 µmol) in dichloromethane (15 ml). The mixture was allowed to warm to room temperature and stirred overnight. The reaction mixture was concentrated. Methanol was added, and then the mixture was concentrated again. Saturated aqueous sodium bicarbonate solution was added and extracted with ethyl acetate. The crude product was purified by preparative C18 reverse phase HPLC (methanol/water (0.1% formic acid)=40:60 to 100:0) to give the title compound (0.01 g) as a white solid. 1H-NMR (DMSO-d6): 5.4 (br s, 1H), 10.2 (br s, 1H), 8.02 (d, J=3.6 Hz, 1H), 7.80 (d, J=1.8 Hz, 1H), 7.47 (d, J=1.8).

EXAMPLE 138

8-hydroxy-6-(2-methylpyridin-3-yl)quinazolin-4(3H)-one a) 8-Methoxy-6-(2-methylpyridin-3-yl)quinazolin-4(3H)-one A mixture of 6-bromo-8-methoxyquinazolin-4(3H)-one (0.15 g, 0.588 mmol), 2-methylpyridin-3-ylboronic acid (0.12 g, 0.882 mmol), dichloro-1,1'-bis(diphenylphosphino)ferrocene palladium(II) (0.01 g, 0.12 mmol) and cesium carbonate (0.38 g, 1.18 mmol) in dioxane (2 ml)/water (0.2 ml) was heated in a microwave oven for 30 min at 130° C. The reaction mixture was poured on water and extracted with dichloromethane. The crude product was purified by chromatography (silica gel, ethyl acetate/methanol=100:0 to 70:30) to give the title compound (0.10 g) as a light brown solid. MS: m/e=268.2 [M+H]⁺.

b) 8-Hydroxy-6-(2-methylpyridin-3-yl)quinazolin-4(3H)-one

The title compound (0.02 g) was obtained as a grey solid from 6-bromo-8-methoxyquinazolin-4(3H)-one in analogy to example 137c. MS: m/e=254.09 [M+H]⁺.

EXAMPLE 139

6-Chloro-8-hydroxyquinazolin-4(3H)-one

The title compound (0.007 g) was obtained as a grey solid in analogy to example 137b,c from 2-amino-5-chloro-3-methoxybenzoic acid. MS: m/e=197.5 [M+H]⁺.

EXAMPLE 140

8-Hydroxy-5-methylquinazolin-4(3H)-one

The title compound (0.007 g) was obtained as a white solid in analogy to example 137b,c from 2-amino-3-methoxy-6-methylbenzoic acid. MS: m/e=177.5 [M+H]⁺.

EXAMPLE 141

8-Hydroxy-6-(4-pyrazol-1-yl-phenyl)-3H-quinazolin-4-one

A solution of cesium carbonate (0.10 g, 0.3 mmol) in water (0.25 ml) was added to a mixture of bis(diphenylphosphino)ferrocene palladium(II) (0.012 g, 15 µmol), 6-bromo-8-methoxyquinazolin-4(3H)-one (0.04 g, 0.15 mmol), and 4-(1H-pyrazol-1-yl)phenylboronic acid (0.04 g, 0.23 mmol) in dioxane (2.5 ml). The mixture was shaken in a sealed tube for 72 h at 100° C. and then concentrated. Acetic acid (0.4 ml), aqueous hydrobromic acid (48%, 0.24 ml) and a solution of hydrobromic acid in acetic acid (33%, 0.35 ml) were added to the residue. The mixture was shaken in a sealed tube at 150° C. for 48 h. The mixture was concentrated and purified by chromatography (C18 reverse phase HPLC, acetonitrile/water (0.1% formic acid)=10:90 to 98:2) gave the title product (0.003 g). MS: m/e=305.1 [M+H]⁺.

EXAMPLE 142

8-Hydroxy-6-(4-morpholin-4-yl-phenyl)-3H-quinazolin-4-one

The title compound (0.002 g) was prepared in analogy to example 141 from 4-morpholinophenylboronic acid. MS: m/e=324.2 [M+H]⁺.

EXAMPLE 143

5-Chloro-8-hydroxyquinazolin-4(3H)-one

Hydrogen peroxide in water (35%, 175 µl, 2.00 mmol) was added to a suspension of 4-chloro-7-methoxyindoline- 2,3-dione (0.22 g, 1 mmol) in 1 N aqueous sodium hydroxide (3 ml). A heavy foaming and gas evolution was observed. The mixture was stirred for 1 h, then acetic acid (229 µl, 4.00 mmol) was added and the mixture was extracted with ethyl acetate. The combined organic layers were dried over sodium sulfate and concentrated to an oil. Formamide (10 ml) was added to the residue and the mixture was heated to 150° C. overnight. The mixture was concentrated to an oil. Boron tribromide in dichloromethane (1M, 10 ml, 10 mmol) was added, followed by dichloromethane (10 ml). The mixture was heated under reflux for 5 h. Methanol (10 ml) was added and evaporated, this was repeated three times. The crude material was purified by preparative HPLC (reversed phase C18, 20 to 98% acetonitrile/water (0.1% formic acid)) to give the desired product (0.07 g) as a brown solid. MS: m/e=197.1 [M+H]+.

EXAMPLE 144

6-(6-Bromo-pyridin-3-yl)-8-hydroxy-3H-quinazolin-4-one

The title compound (0.008 g) was prepared in analogy to example 141 from 6-chloropyridin-3-ylboronic acid (chlorine-bromine exchange was observed in the deprotection step with HBr). MS: m/e=320.1/322.1 [M+H]+.

EXAMPLE 145

8-Hydroxy-6-(2-trifluoromethoxy-phenyl)-3H-quinazolin-4-one

The title compound (0.03 g) was prepared in analogy to example 141 from 2-(trifluoromethoxy)phenylboronic acid. MS: m/e=323.1 [M+H]+.

EXAMPLE 146

8-Hydroxy-6-(3-morpholinophenyl)quinazolin-4(3H)-one a) (6-Bromo-4-oxo-3-(pivaloyloxymethyl)-3,4-dihydroquinazolin-8-yloxy)methyl pivalate Boron tribromide in dichloromethane (1M, 10.0 ml, 10.0 mmol) was added to 6-bromo-8-methoxyquinazolin-4(3H)-one (0.26 g, 1.00 mmol) in dichloromethane (10 ml). The mixture was stirred under reflux for 4 h. Methanol (10 ml) was added and the mixture concentrated to dryness. Addition of methanol and evaporation was repeated three times, and the residue was then dried under high vacuum. Potassium carbonate (0.69 g, 5.00 mmol) was added, followed by dimethylformamide (10.0 ml) and chloromethyl pivalate (0.45 g, 435 µl, 3.00 mmol). The mixture was stirred at 100° C. for 1 h, and then filtered, and concentrated to an oil. The crude material was purified by flash chromatography (silica gel, 0 to 100% ethyl acetate/heptane) to give the desired product (0.32 g) as a white solid. MS: m/e=496.2 [M+H]+.

b) 8-Hydroxy-6-(3-morpholinophenyl)quinazolin-4(3H)-one

A mixture of (6-bromo-4-oxo-3-(pivaloyloxymethyl)-3,4-dihydroquinazolin-8-yloxy)methyl pivalate (0.05 g, 0.1 mmol), potassium carbonate (0.03 g, 200 µmol), 3-morpholinophenylboronic acid (0.03 g, 0.15 mmol) and 3-morpholinophenylboronic acid (0.03 g, 0.15 mmol) in dimethylformamide (1 ml) was heated to 100° C. for 3 h. The mixture was allowed to cool, and ammonia in methanol (7M, 2 ml, 14 mmol) was added. The solution was stirred at room temperature overnight. The crude material was filtered and then purified by preparative HPLC (20 to 98% acetonitrile/water (0.1% formic acid)) to give the desired product (28 mg) as a light brown solid. MS: m/e=324.2 [M+H]+.

EXAMPLE 147

6-(4-Dimethylamino-phenyl)-8-hydroxy-3H-quinazolin-4-one

The title compound (0.001 g) was prepared in analogy to example 141 from 4-(dimethylamino)phenylboronic acid. MS: m/e=282.2 [M+H]+.

EXAMPLE 148

6-(3-Dimethylamino-phenyl)-8-hydroxy-3H-quinazolin-4-one

The title compound (0.06 g) was prepared in analogy to example 141 from 3-(dimethylamino)phenylboronic acid. MS: m/e=282.2 [M+H]+.

EXAMPLE 149

6-(3-Chloro-phenyl)-8-hydroxy-3H-quinazolin-4-one

The title compound (0.005 g) was prepared in analogy to example 141 from 3-chlorophenylboronic acid. MS: m/e=273.2 [M+H]+.

EXAMPLE 150

6-(2,5-Dimethyl-2H-pyrazol-3-yl)-8-hydroxy-3H-quinazolin-4-one

The title compound (0.002 g) was prepared in analogy to example 141 from 1,3-dimethyl-5-(4,4,5,5-tetramethyl-1,3,2-dioxaborolan-2-yl)-1H-pyrazole. MS: m/e=257.4 [M+H]+.

EXAMPLE 151

5-(4-Fluorophenyl)-8-hydroxyquinazolin-4(3H)-one

The title compound (0.02 g) was obtained as a brown solid in analogy to example 125 from 5-bromo-8-methoxyquinazolin-4(3H)-one (example 1a). MS: m/e=255.2 [M−H]−.

EXAMPLE 152

6-[1-(4-Fluoro-phenyl)-1H-pyrazol-4-yl]-8-hydroxy-3H-quinazolin-4-one

The title compound (0.03 g) was obtained as a light brown solid in analogy to example 146b from 1-(4-fluorophenyl)-1H-pyrazol-4-ylboronic acid. MS: m/e=323.2 [M+H]+.

EXAMPLE 153

8-Hydroxy-6-(pyrimidin-5-yl)quinazolin-4(3H)-one 2,2,2-trifluoroacetate

The title compound (0.02 g) was obtained as a white solid in analogy to example 7b/c from pyrimidin-5-ylboronic acid. MS: m/e=241.0 [M+H]$^+$.

EXAMPLE 154

8-Hydroxy-6-(2-methyl-5-trifluoromethyl-2H-pyrazol-3-yl)-3H-quinazolin-4-one

The title compound (0.11 g) was obtained as a white solid in analogy to example 75 from 1-methyl-3-(trifluoromethyl)-1H-pyrazol-5-ylboronic acid. MS: m/e=308.9 [M−H]$^-$.

EXAMPLE 155

6-(2-((Dimethylamino)methyl)phenyl)-8-hydroxyquinazolin-4(3H)-one

The title compound (0.002 g) was obtained in analogy to example 75 from 2-((dimethylamino)methyl)phenylboronic acid. MS: m/e=296.0 [M+H]$^+$.

EXAMPLE 156

8-Hydroxy-6-(1-methyl-1H-indazol-4-yl)quinazolin-4(3H)-one

The title compound (0.004 g) was obtained in analogy to example 75 from 1-methyl-1H-indazol-4-ylboronic acid. MS: m/e=291.4 [M−H]$^-$.

EXAMPLE 157

8-Hydroxy-6-(3-(methylsulfonyl)phenyl)quinazolin-4(3H)-one

The title compound (0.005 g) was obtained in analogy to example 75 from 3-(methylsulfonyl)phenylboronic acid. MS: m/e=316.9 [M+H]$^+$.

EXAMPLE 158

6-(2-Fluoro-4-(methylsulfonyl)phenyl)-8-hydroxyquinazolin-4(3H)-one

The title compound (0.005 g) was obtained in analogy to example 75 from 2-fluoro-4-(methylsulfonyl)phenylboronic acid. MS: m/e=334.9 [M+H]$^+$.

EXAMPLE 159

N-(2-(8-Hydroxy-4-oxo-3,4-dihydroquinazolin-6-yl)phenyl)acetamide

The title compound (0.003 g) was obtained in analogy to example 75 from 2-acetamidophenylboronic acid. MS: m/e=295.6 [M+H]$^+$.

EXAMPLE 160

6-(2,4-Dimethoxypyrimidin-5-yl)-8-hydroxyquinazolin-4(3H)-one

The title compound (0.004 g) was obtained in analogy to example 75 from 2,4-dimethoxypyrimidin-5-ylboronic acid. MS: m/e=300.8 [M+H]$^+$.

EXAMPLE 161

8-Hydroxy-6-(2-methoxyphenyl)quinazolin-4(3H)-one

The title compound (0.005 g) was obtained in analogy to example 75 from 2-methoxyphenylboronic acid. MS: m/e=269.1 [M+H]$^+$.

EXAMPLE 162

8-Hydroxy-6-(2-methoxypyridin-3-yl)quinazolin-4(3H)-one

The title compound (0.007 g) was obtained in analogy to example 75 from 2-methoxypyridin-3-ylboronic acid. MS: m/e=270.1 [M+H]$^+$.

EXAMPLE 163

8-Hydroxy-6-(6-methoxypyridin-3-yl)quinazolin-4(3H)-one

The title compound (0.006 g) was obtained in analogy to example 75 from 6-methoxypyridin-3-ylboronic acid. MS: m/e=270.0 [M+H]$^+$.

EXAMPLE 164

8-Hydroxy-6-(4-methylthiophen-3-yl)quinazolin-4(3H)-one

The title compound (0.005 g) was obtained in analogy to example 75 from 4-methylthiophen-3-ylboronic acid. MS: m/e=259.0 [M+H]$^+$.

EXAMPLE 165

6-(2,5-Dimethylthiophen-3-yl)-8-hydroxyquinazolin-4(3H)-one

The title compound (0.005 g) was obtained in analogy to example 75 from 2,5-dimethylthiophen-3-ylboronic acid. MS: m/e=273.1 [M+H]$^+$.

EXAMPLE 166

8-Hydroxy-6-(6-methylpyridin-3-yl)quinazolin-4(3H)-one

The title compound (0.006 g) was obtained in analogy to example 75 from 6-methylpyridin-3-ylboronic acid. MS: m/e=254.1 [M+H]$^+$.

EXAMPLE 167

8-Hydroxy-6-(quinolin-8-yl)quinazolin-4(3H)-one

The title compound (0.001 g) was obtained in analogy to example 75 from quinolin-8-ylboronic acid. MS: m/e=289.8 [M+H]$^+$.

EXAMPLE 168

8-Hydroxy-6-(isoquinolin-4-yl)quinazolin-4(3H)-one

The title compound (0.002 g) was obtained in analogy to example 75 from isoquinolin-4-ylboronic acid. MS: m/e=290.2 [M+H]$^+$.

EXAMPLE 169

8-Hydroxy-6-(naphthalen-2-yl)quinazolin-4(3H)-one

The title compound (0.005 g) was obtained in analogy to example 75 from naphthalen-2-ylboronic acid. MS: m/e=289.0 [M+H]$^+$.

EXAMPLE 170

8-Hydroxy-6-(naphthalen-1-yl)quinazolin-4(3H)-one

The title compound (0.006 g) was obtained in analogy to example 75 from naphthalen-1-ylboronic acid. MS: m/e=289.0 [M+H]$^+$.

EXAMPLE 171

8-Hydroxy-6-(1,2,3,4-tetrahydroisoquinolin-6-yl)quinazolin-4(3H)-one

The title compound (0.004 g) was obtained in analogy to example 75 from 2-(tert-butoxycarbonyl)-1,2,3,4-tetrahydroisoquinolin-6-ylboronic acid. MS: m/e=294.2 [M+H]$^+$.

EXAMPLE 172

4-(8-Hydroxy-4-oxo-3,4-dihydroquinazolin-6-yl)-N-(2-morpholinoethyl)benzamide

The title compound (0.01 g) was obtained in analogy to example 75 from 2-(tert-butoxycarbonyl)-1,2,3,4-tetrahydroisoquinolin-6-ylboronic acid. MS: m/e=395.5 [M+H]$^+$.

EXAMPLE 173

N-(2-(Dimethylamino)ethyl)-4-(8-hydroxy-4-oxo-3,4-dihydroquinazolin-6-yl)benzamide The title compound (0.005 g) was obtained in analogy to example 75 from 4-(2-(dimethylamino)ethylcarbamoyl)phenylboronic acid hydrochloride. MS: m/e=395.3 [M+H+acetonitrile]$^+$.

EXAMPLE 174

8-Hydroxy-6-(1,2,3,4-tetrahydroisoquinolin-7-yl)quinazolin-4(3H)-one

The title compound (3.6 mg) was obtained in analogy to example 75 from 2-(tert-butoxycarbonyl)-1,2,3,4-tetrahydroisoquinolin-7-ylboronic acid. MS: m/e=294.1 [M+H]$^+$.

EXAMPLE 175

8-Hydroxy-6-(3-(morpholine-4-carbonyl)phenyl)quinazolin-4(3H)-one

The title compound (0.01 g) was obtained in analogy to example 75 from 3-(morpholine-4-carbonyl)phenylboronic acid. MS: m/e=352.0 [M+H]$^+$.

EXAMPLE 176

6-(2,3-Dihydrobenzo[b][1,4]dioxin-6-yl)-8-hydroxyquinazolin-4(3H)-one

The title compound (0.007 g) was obtained in analogy to example 75 from 2,3-dihydrobenzo[b][1,4]dioxin-6-ylboronic acid. MS: m/e=296.9 [M+H]$^+$.

EXAMPLE 177

6-(Benzo[d][1,3]dioxol-5-yl)-8-hydroxyquinazolin-4(3H)-one

The title compound (0.004 g) was obtained in analogy to example 75 from benzo[d][1,3]dioxol-5-ylboronic acid. MS: m/e=282.9 [M+H]$^+$.

EXAMPLE 178

6-(2,4-Dimethylthiazol-5-yl)-8-hydroxyquinazolin-4(3H)-one

The title compound (0.002 g) was obtained in analogy to example 75 from 2,4-dimethyl-5-(4,4,5,5-tetramethyl-1,3,2-dioxaborolan-2-yl)thiazole. MS: m/e=274.1 [M+H]$^+$.

EXAMPLE 179

8-Hydroxy-6-(1-methyl-1H-pyrazol-4-yl)quinazolin-4(3H)-one

The title compound (0.008 g) was obtained in analogy to example 75 from -methyl-4-(4,4,5,5-tetramethyl-1,3,2-dioxaborolan-2-yl)-1H-pyrazole. MS: m/e=243.1 [M+H]$^+$.

EXAMPLE 180

8-Hydroxy-6-(2-hydroxypyridin-3-yl)quinazolin-4(3H)-one

The title compound (0.006 g) was obtained in analogy to example 75 from 2-(cyclopropylmethoxy)-3-(4,4,5,5-tetramethyl-1,3,2-dioxaborolan-2-yl)pyridine. MS: m/e=256.0 [M+H]$^+$.

EXAMPLE 181

8-Hydroxy-6-(1-methyl-1H-pyrazol-5-yl)quinazolin-4(3H)-one

The title compound (0.004 g) was obtained in analogy to example 75 from 1-methyl-5-(4,4,5,5-tetramethyl-1,3,2-dioxaborolan-2-yl)-1H-pyrazole. MS: m/e=243.1 [M+H]$^+$.

EXAMPLE 182

8-Hydroxy-6-(6-morpholinopyridin-3-yl)quinazolin-4(3H)-one

The title compound (0.006 g) was obtained in analogy to example 75 from 4-(5-(4,4,5,5-tetramethyl-1,3,2-dioxaborolan-2-yl)pyridin-2-yl)morpholine. MS: m/e=325.2 [M+H]$^+$.

EXAMPLE 183

6-(6-(Dimethylamino)pyridin-2-yl)-8-hydroxyquinazolin-4(3H)-one

The title compound (0.003 g) was obtained in analogy to example 75 from N,N-dimethyl-6-(4,4,5,5-tetramethyl-1,3,2-dioxaborolan-2-yl)pyridin-2-amine. MS: m/e=283.0 [M+H]$^+$.

EXAMPLE 184

8-Hydroxy-6-(6-(piperazin-1-yl)pyridin-3-yl)quinazolin-4(3H)-one

The title compound (0.002 g) was obtained in analogy to example 75 from N,N-dimethyl-6-(4,4,5,5-tetramethyl-1,3,2-dioxaborolan-2-yl)pyridin-2-amine. MS: m/e=324.3 [M+H]$^+$.

EXAMPLE 185

8-Hydroxy-6-(2-(piperazin-1-yl)pyridin-4-yl)quinazolin-4(3H)-one

The title compound (0.004 g) was obtained in analogy to example 75 from 1-(4-(4,4,5,5-tetramethyl-1,3,2-dioxaborolan-2-yl)pyridin-2-yl)piperazine. MS: m/e=324.3 [M+H]$^+$.

EXAMPLE 186

6-Cyclohexenyl-8-hydroxyquinazolin-4(3H)-one

The title compound (0.004 g) was obtained in analogy to example 75 from 2-cyclohexenyl-4,4,5,5-tetramethyl-1,3,2-dioxaborolane. MS: m/e=243.1 [M+H]$^+$.

EXAMPLE 187

8-Hydroxy-6-morpholinoquinazolin-4(3H)-one a) 6-Morpholino-8-((2-(trimethylsilyl)ethoxy)methoxy)-3-((2-(trimethylsilyl)ethoxy)methyl)quinazolin-4(3H)-one A mixture of morpholine (0.02 g, 230 μmol), 6-bromo-8-((2-(trimethylsilyl)ethoxy)methoxy)-3-((2-(trimethylsilyl)ethoxy)methyl)quinazolin-4(3H)-one (0.03 g, 49.8 μmol), palladium (II) acetate (0.001 g, 4.98 μmol), sodium tert-butoxide (0.01 g, 99.7 μmol) and 2-dicyclohexylphosphino-2',4',6'-triisopropylbiphenyl (x-phos) (0.002 g, 4.98 μmol) in m-xylene (2 ml) was heated to 140° C. for 2 h in a sealed tube. The mixture was filtered. The crude material was purified by preparative HPLC (20 to 98% acetonitrile/water (0.1% formic acid)) to give the title compound (0.01 g) as a white solid. MS: m/e=508.4 [M+H]$^+$.

b) 8-Hydroxy-6-morpholinoquinazolin-4(3H)-one

The title compound (0.007 g) was obtained as a white solid in analogy to example 75b from 6-morpholino-8-((2-(trimethylsilyl)ethoxy)methoxy)-3-((2-(trimethylsilyl)ethoxy)methyl)quinazolin-4(3H)-one. MS: m/e=248.2 [M+H]$^+$.

EXAMPLE 188

6-(1,4-Dimethyl-1H-imidazol-2-yl)-8-hydroxyquinazolin-4(3H)-one

The title compound (0.005 g) was obtained in analogy to example 28b/c from 2-bromo-1,4-dimethyl-1H-imidazole as a light brown solid. MS: m/e=257.1 [M+H]$^+$.

EXAMPLE 189

6-(4-Fluorophenoxy)-8-hydroxyquinazolin-4(3H)-one

A mixture of 6-bromo-8-((2-(trimethylsilyl)ethoxy)methoxy)-3-((2-(trimethylsilyl)ethoxy)methyl)quinazolin-4(3H)-one (0.03 g, 49.8 μmol), 4-fluorophenol (0.02 g, 150 μmol), cesium carbonate (0.07 g, 199 μmol), 2,2,6,6-tetramethylheptane-3,5-dione (0.002 g, 9.97 μmol), and copper (I) chloride (0.01 g, 49.8 μmol) in N-methylpyrrolidone (1 ml) was heated to 150° C. for 3 h. Formic acid (1.00 ml) and water (0.2 ml) were added and the mixture was heated to 120° C. in a sealed tube for 2 h. Concentrated aqueous hydrochloric acid (0.1 ml) was added and the mixture was heated for 30 minutes. The crude material was purified by preparative HPLC (C18, 20 to 98% acetonitrile/water (0.1% formic acid)) to give the title compound (0.003 g) as a light brown oil. MS: m/e=273.2 [M+H]$^+$.

EXAMPLE 190

8-Hydroxy-6-(4-methyl-piperazin-1-yl)-3H-quinazolin-4-one

The title compound (0.01 g) was obtained as a light brown foam in analogy to example 187 from 1-methylpiperazine. MS: m/e=261.1 [M+H]$^+$.

EXAMPLE 191

8-Hydroxy-6-[3-(4-methyl-piperazine-1-carbonyl)-phenyl]-3H-quinazolin-4-one a) 3-[4-Oxo-8-(2-trimethylsilanyl-ethoxymethoxy)-3-(2-trimethylsilanyl-ethoxymethyl)-3,4-dihydro-quinazolin-6-yl]-benzoic acid The title compound (0.10 g) was obtained as a light brown solid in analogy to example 7b from 3-(4,4,5,5-tetramethyl-1,3,2-dioxaborolan-2-yl)benzoic acid using dioxane instead of dimethylformamide. MS: m/e=541.21 [M−H]$^−$.

b) 8-Hydroxy-6-[3-(4-methyl-piperazine-1-carbonyl)-phenyl]-3H-quinazolin-4-one

The title compound (0.02 g) was obtained as a light brown solid in analogy to example 97b/c from 3-[4-oxo-8-(2-trimethylsilanyl-ethoxymethoxy)-3-(2-trimethylsilanyl-ethoxymethyl)-3,4-dihydro-quinazolin-6-yl]-benzoic acid and 1-methylpiperazine. MS: m/e=365.16 [M+H]$^+$.

EXAMPLE 192

6-[3-(1,1-Dioxo-1$\lambda^6$-thiomorpholine-4-carbonyl)-phenyl]-8-hydroxy-3H-quinazolin-4-one The title compound (0.01 g) was obtained as a light brown solid in analogy to example 191b using thiomorpholine1,1-dioxide instead of 1-methylpiperazine. MS: m/e=400.10 [M+H]$^+$.

EXAMPLE 193

8-Hydroxy-6-[2-(4-methyl-piperazine-1-carbonyl)-phenyl]-3H-quinazolin-4-one a) 2-[4-Oxo-8-(2-trimethylsilanyl-ethoxymethoxy)-3-(2-trimethylsilanyl-ethoxymethyl)-3,4-dihydro-quinazolin-6-yl]-benzoic acid ethyl ester The title compound (0.51 g) was obtained as a light brown oil in analogy to example 7b from ethyl 2-(4,4,5,5-tetramethyl-1,3,2-5 dioxaborolan-2-yl)benzoate using dioxane instead of dimethylformamide. MS: m/e=571.3 [M+H]$^+$.

b) 2-[4-Oxo-8-(2-trimethylsilanyl-ethoxymethoxy)-3-(2-trimethylsilanyl-ethoxymethyl)-3,4-dihydro-quinazolin-6-yl]-benzoic acid 2M Aqueous lithium hydroxide (1.75 ml, 3.5 mmol) was added to a solution of 2-[4-oxo-8-(2-trimethylsilanyl-ethoxymethoxy)-3-(2-trimethylsilanyl-ethoxymethyl)-3,4-dihydro-quinazolin-6-yl]-benzoic acid ethyl ester (0.20 g) in ethanol (10 ml). The mixture was stirred for 72 h and then concentrated to an oil. Ethyl acetate (20 ml) was added and washed with water. The organic layer was dried and concentrated to give the title compound (0.10 g) as a light brown solid. MS: m/e=541.3 [M−H]$^-$.

c) 8-Hydroxy-6-[2-(4-methyl-piperazine-1-carbonyl)-phenyl]-3H-quinazolin-4-one

The title compound (0.005 g) was obtained as a light brown solid in analogy to example 97b/c from 2-[4-oxo-8-(2-trimethylsilanyl-ethoxymethoxy)-3-(2-trimethylsilanyl-ethoxymethyl)-3,4-dihydro-quinazolin-6-yl]-benzoic acid ethyl ester and 1-methylpiperazine. MS: m/e=365.2 [M+H]$^+$.

EXAMPLE 194

6-[2-(1,1-Dioxo-1$\lambda^6$-thiomorpholine-4-carbonyl)-phenyl]-8-hydroxy-3H-quinazolin-4-one The title compound (0.004 g) was obtained as a light brown solid in analogy to example 97b/c from 2-[4-oxo-8-(2-trimethylsilanyl-ethoxymethoxy)-3-(2-trimethylsilanyl-ethoxymethyl)-3,4-dihydro-quinazolin-6-yl]-benzoic acid ethyl ester and thiomorpholine-1,1-dioxide. MS: m/e=400.1 [M+H]$^+$.

EXAMPLE 195

5-Fluoro-6-(4-fluorophenyl)-8-hydroxyquinazolin-4(3H)-one a) 6-Bromo-5-fluoro-8-((2-methoxyethoxy)methoxy)-3-((2-methoxyethoxy)methyl)quinazolin-4(3H)-one 1-(Chloromethoxy)-2-methoxyethane (0.17 g, 155 µl, 1.23 mmol) was added to a solution of 6-bromo-5-fluoro-8-hydroxyquinazolin-4(3H)-one (example 196, 0.11 g, 409 µmol) and ethyl diisopropyl amine (0.37 g, 500 µl, 2.86 mmol) in dichloromethane (10 ml). The mixture was stirred for 30 min at room temperature. Saturated aqueous ammonium chloride solution was added (20 ml) and extracted with dichloromethane. The combined organic layers were dried over sodium sulfate and then concentrated to an oil. The product was crystallized with diethyl ether (3 ml) and washed with diethyl ether. The crude material was purified by chromatography (silica gel, 0 to 10% methanol/dichloromethane) to give the title compound (0.08 g) as a white powder. MS: m/e=437.0/439.0 [M+H]$^+$.

b) 5-Fluoro-6-(4-fluorophenyl)-8-hydroxyquinazolin-4(3H)-one

The title compound (0.01 g) was obtained as a white solid from 4-fluorophenylboronic acid and 6-bromo-5-fluoro-8-((2-methoxyethoxy)methoxy)-3-((2-methoxyethoxy)methyl)quinazolin-4(3H)-one in analogy to example 7b/c. MS: m/e=275.1 [M+H]$^+$

EXAMPLE 196

6-Bromo-5-fluoro-8-hydroxyquinazolin-4(3H)-one a)
2-Amino-5-bromo-6-fluoro-3-methoxybenzonitrile A solution of 6-fluoro-3-methoxy-2-nitrobenzonitrile (0.17 g, 872 µmol) with Pd/C 10% (0.04 g) in ethyl acetate (5 ml) was stirred overnight under a hydrogen atmosphere. The mixture was filtered over Celite and concentrated to an oil. The residue was dissolved in acetic acid (5 ml) and bromine (0.14 g, 44.9 µl, 872 µmol) was added. After 15 min, the mixture was concentrated to a brown solid. The crude material was purified by chromatography (silica gel, 0 to 100% ethyl acetate/heptane) to give the title compound (0.16 g) as a light brown solid. m/e=243.9/245.9 [M]$^+$.

b)
6-Bromo-5-fluoro-8-methoxyquinazolin-4(3H)-one

A solution of 2-amino-5-bromo-6-fluoro-3-methoxybenzonitrile (0.13 g, 543 µmol) in formic acid (10 ml) was heated under reflux for 4 h. The mixture was concentrated to give the title compound (0.15 g) as a white solid. MS: m/e=273.1/275.1[M+H]$^+$.

c)
6-Bromo-5-fluoro-8-hydroxyquinazolin-4(3H)-one

1M Boron tribromide in dichloromethane (5 ml, 5.00 mmol) was added to a solution of 6-bromo-5-fluoro-8- methoxyquinazolin-4(3H)-one (0.15 g, 538 µmol) in dichloromethane (5 ml). The mixture was heated to 50° C. overnight. Methanol (5 ml) was added and the mixture concentrated. Addition of methanol and concentration was repeated two times. Diethyl ether (5 ml) was added, the residue was filtered and washed with diethyl ether to give the title compound (0.11 g) as a grey powder. MS: m/e=258.9/260.9 [M+H]$^+$.

EXAMPLE 197

5-Fluoro-8-hydroxyquinazolin-4(3H)-one

The title compound (0.02 g) was obtained as a white solid in analogy to example 196 omitting the bromination in step a. MS: m/e=181.0 [M+H]$^+$.

EXAMPLE 198

5-Fluoro-8-hydroxy-6-(2-methylpyridin-3-yl)quinazolin-4(3H)-one

The title compound (0.004 g) was obtained as a light yellow oil from 2-methylpyridin-3-ylboronic acid and 6-bromo-5-fluoro-8-((2-methoxyethoxy)methoxy)-3-((2-methoxyethoxy)methyl)quinazolin-4(3H)-one in analogy to example 7b/c. MS: m/e=272.1 [M+H]$^+$

EXAMPLE 199

6-[3-(4,4-Difluoro-piperidine-1-carbonyl)-phenyl]-8-hydroxy-3H-quinazolin-4-one

The title compound (0.02 g) was obtained as a light grey solid in analogy to example 191b using 4,4-difluoropiperidine instead of 1-methylpiperazine. MS: m/e=386.13 [M+H]$^+$.

EXAMPLE 200

6-[4-(4,4-Difluoro-piperidine-1-carbonyl)-phenyl]-8-hydroxy-3H-quinazolin-4-one a) 4-[4-Oxo-8-(2-trimethylsilanyl-ethoxymethoxy)-3-(2-trimethylsilanyl-ethoxymethyl)-3,4-dihydroquinazolin-6-yl]-benzoic acid The title compound (0.10 g) was obtained as a light yellow solid in analogy to example 7b from 4-carboxyphenylboronic acid using dioxane instead of dimethylformamide. MS: m/e=543.5 [M+H]$^+$.

b) 6-[4-(4,4-Difluoro-piperidine-1-carbonyl)-phenyl]-8-hydroxy-3H-quinazolin-4-one The title compound (0.02 g) was obtained as a light grey solid in analogy to example 97b/c from 4-[4-oxo-8-(2-trimethylsilanyl-ethoxymethoxy)-3-(2-trimethylsilanyl-ethoxymethyl)-3,4-dihydro-quinazolin-6-yl]-benzoic acid and 4,4-difluoropiperidine. MS: m/e=386.12 [M+H]+.

EXAMPLE 201

7-Fluoro-6-(4-fluorophenyl)-8-hydroxyquinazolin-4(3H)-one a)
6-Bromo-7-fluoro-8-methoxyquinazolin-4(3H)-one Bromine (1.18 g, 380 µl, 7.37 mmol) was added to a solution of 2-amino-4-fluoro-3-methoxybenzoic acid (0.46 g, 2.46 mmol) in acetic acid (10 ml). The mixture was stirred for 20 min at room temperature, concentrated, re-dissolved in methanol (10 ml) and concentrated again to give the intermediate bromide as a brown solid. The residue was suspended in formamide (20.0 ml) and heated to 150° C. overnight. The mixture was concentrated to a brown solid, suspended in methanol (2 ml) and precipitated by addition of diethyl ether (80 ml) to give the title compound (0.67 g) as a light brown solid. MS: m/e=273.0/274.9 [M+H]$^+$.

b) 7-Fluoro-6-(4-fluorophenyl)-8-hydroxyquinazolin-4(3H)-one

The title compound (0.01 g) was obtained as a white solid in analogy to example 125 from 6-bromo-7-fluoro-8-methoxyquinazolin-4(3H)-one. MS: m/e=275.9 [M+H]$^+$.

EXAMPLE 202

6-(2,6-Dimethyl-pyridin-3-yl)-8-hydroxy-3H-quinazolin-4-one

The title compound (0.10 g) was obtained as a dark brown solid in analogy to example 75 from 2,6-dimethyl-3-(4,4,5,5-tetramethyl-1,3,2-dioxaborolan-2-yl)pyridine. MS: m/e=268.2 [M+H]$^+$.

EXAMPLE 203

8-Hydroxy-6-(4-methyl-2-phenylthiazol-5-yl)quinazolin-4(3H)-one

The title compound (0.008 g) was obtained in analogy to example 75 from 4-methyl-2-phenyl-5-(4,4,5,5-tetramethyl-1,3,2-dioxaborolan-2-yl)thiazole. MS: m/e=336.1 [M+H]$^+$.

EXAMPLE 204

8-Hydroxy-6-(5-methyl-1-phenyl-1H-pyrazol-4-yl)quinazolin-4(3H)-one

The title compound (0.01 g) was obtained in analogy to example 75 from 5-methyl-1-phenyl-4-(4,4,5,5-tetramethyl-1,3,2-dioxaborolan-2-yl)-1H-pyrazole. MS: m/e=319.1 [M+H]$^+$.

EXAMPLE 205

8-Hydroxy-6-(3-methyl-1H-pyrazol-4-yl)quinazolin-4(3H)-one

The title compound (0.008 mg) was obtained in analogy to example 75 from 3-methyl-4-(4,4,5,5-tetramethyl-1,3,2-dioxaborolan-2-yl)-1H-pyrazole. MS: m/e=242.8 [M+H]$^+$.

EXAMPLE 206

6-(1,5-Dimethyl-1H-pyrazol-4-yl)-8-hydroxyquinazolin-4(3H)-one

The title compound (0.01 g) was obtained in analogy to example 75 from 1,5-dimethyl-4-(4,4,5,5-tetramethyl-1,3,2-dioxaborolan-2-yl)-1H-pyrazole. MS: m/e=257.1 [M+H]$^+$.

EXAMPLE 207

2-(8-Hydroxy-4-oxo-3,4-dihydroquinazolin-6-yl)benzonitrile

The title compound (0.01 g) was obtained in analogy to example 75 from 2-(4,4,5,5-tetramethyl-1,3,2-dioxaborolan-2-yl)benzonitrile. MS: m/e=264.1 [M+H]$^+$.

EXAMPLE 208

2-(2-(8-Hydroxy-4-oxo-3,4-dihydroquinazolin-6-yl)phenyl)acetonitrile

The title compound (0.02 g) was obtained in analogy to example 75 from 2-(2-(4,4,5,5-tetramethyl-1,3,2-dioxaborolan-2-yl)phenyl)acetonitrile. MS: m/e=278.1 [M+H]$^+$.

EXAMPLE 209

6-(2-(Dimethylamino)phenyl)-8-hydroxyquinazolin-4(3H)-one

The title compound (0.02 g) was obtained in analogy to example 75 from N,N-dimethyl-2-(4,4,5,5-tetramethyl-1,3,2-dioxaborolan-2-yl)aniline. MS: m/e=282.1 [M+H]$^+$.

EXAMPLE 210

8-Hydroxy-6-o-tolylquinazolin-4(3H)-one

The title compound (0.01 g) was obtained in analogy to example 75 from o-tolylboronic acid. MS: m/e=253.0 [M+H]$^+$.

EXAMPLE 211

6-(2-Ethoxy-4-fluorophenyl)-8-hydroxyquinazolin-4(3H)-one

The title compound (0.02 g) was obtained in analogy to example 75 from 2-ethoxy-4-fluorophenylboronic acid. MS: m/e=301.1 [M+H]$^+$.

EXAMPLE 212

8-Hydroxy-6-(2-(methylsulfonyl)phenyl)quinazolin-4(3H)-one

The title compound (0.02 g) was obtained in analogy to example 75 from 2-(methylsulfonyl)phenylboronic acid. MS: m/e=317.0 [M+H]$^+$.

EXAMPLE 213

6-(5-Fluoro-2-methylphenyl)-8-hydroxyquinazolin-4(3H)-one

The title compound (0.02 g) was obtained in analogy to example 75 from 5-fluoro-2-methylphenylboronic acid. MS: m/e=271.1 [M+H]$^+$.

EXAMPLE 214

6-(Biphenyl-2-yl)-8-hydroxyquinazolin-4(3H)-one

The title compound (0.02 g) was obtained in analogy to example 75 from biphenyl-2-ylboronic acid. MS: m/e=315.1 [M+H]$^+$.

EXAMPLE 215

6-(4-Chloro-2-ethoxyphenyl)-8-hydroxyquinazolin-4(3H)-one

The title compound (0.02 g) was obtained in analogy to example 75 from 4-chloro-2-ethoxyphenylboronic acid. MS: m/e=317.1 [M+H]$^+$.

EXAMPLE 216

8-Hydroxy-6-(2-(2,2,2-trifluoroethoxy)pyridin-3-yl)quinazolin-4(3H)-one

The title compound (0.02 g) was obtained in analogy to example 75 from 2-(2,2,2-trifluoroethoxy)pyridin-3-ylboronic acid. MS: m/e=338.1 [M+H]$^+$.

EXAMPLE 217

6-(2-Ethylphenyl)-8-hydroxyquinazolin-4(3H)-one

The title compound (0.02 g) was obtained in analogy to example 75 from 2-ethylphenylboronic acid. MS: m/e=267.1 [M+H]$^+$.

EXAMPLE 218

6-(2-((Diisopropylamino)methyl)phenyl)-8-hydroxyquinazolin-4(3H)-one

The title compound (0.02 g) was obtained in analogy to example 75 from 2-((diisopropylamino)methyl)phenylboronic acid. MS: m/e=352.2 [M+H]$^+$.

EXAMPLE 219

8-Hydroxy-6-(3-methylpyridin-4-yl)quinazolin-4(3H)-one

The title compound (0.02 g) was obtained in analogy to example 75 from 3-methylpyridin-4-ylboronic acid. MS: m/e=254.0 [M+H]$^+$.

EXAMPLE 220

8-Hydroxy-6-(2-(methoxymethyl)phenyl)quinazolin-4(3H)-one

The title compound (0.02 g) was obtained in analogy to example 75 from 2-(methoxymethyl)phenylboronic acid. MS: m/e=283.0 [M+H]$^+$.

EXAMPLE 221

8-Hydroxy-6-(2-(trifluoromethyl)phenyl)quinazolin-4(3H)-one

The title compound (0.004 g) was obtained in analogy to example 75 from 2-(trifluoromethyl)phenylboronic acid. MS: m/e=307.2 [M+H]$^+$.

EXAMPLE 222

8-Hydroxy-6-(2-phenoxyphenyl)quinazolin-4(3H)-one

The title compound (0.014 g) was obtained in analogy to example 75 from 2-phenoxyphenylboronic acid. MS: m/e=330.8 [M+H]$^+$.

EXAMPLE 223

8-Hydroxy-6-(2-(methylthio)phenyl)quinazolin-4(3H)-one

The title compound (0.003 g) was obtained in analogy to example 75 from 2-(methylthio)phenylboronic acid. MS: m/e=284.9 [M+H]$^+$.

EXAMPLE 224

8-Hydroxy-6-(2-morpholinophenyl)quinazolin-4(3H)-one

The title compound (0.006 g) was obtained in analogy to example 75 from 2-morpholinophenylboronic acid. MS: m/e=324.3 [M+H]$^+$.

EXAMPLE 225

6-(2-Ethoxyphenyl)-8-hydroxyquinazolin-4(3H)-one

The title compound (0.005 g) was obtained in analogy to example 75 from 2-ethoxyphenylboronic acid. MS: m/e=283.0 [M+H]$^+$.

EXAMPLE 226

2-(8-Hydroxy-4-oxo-3,4-dihydroquinazolin-6-yl)-N,N-diisopropylbenzamide

The title compound (0.014 g) was obtained in analogy to example 75 from 2-(diisopropylcarbamoyl)phenylboronic acid. MS: m/e=366.1 [M+H]$^+$.

EXAMPLE 227

6-(2-(Benzyloxy)phenyl)-8-hydroxyquinazolin-4(3H)-one

The title compound (0.003 g) was obtained in analogy to example 75 from 2-(benzyloxy)phenylboronic acid. MS: m/e=344.9 [M+H]$^+$.

EXAMPLE 228

6-(2-Butoxyphenyl)-8-hydroxyquinazolin-4(3H)-one

The title compound (0.004 g) was obtained in analogy to example 75 from 2-butoxyphenylboronic acid. MS: m/e=311.3 [M+H]$^+$.

EXAMPLE 229

6-(3-Dimethylaminomethyl-phenyl)-8-hydroxy-3H-quinazolin-4-one

The title compound (0.025 g) was obtained as a purple solid in analogy to example 75 from N,N-dimethyl-1-(3-(4,4,5,5-tetramethyl-1,3,2-dioxaborolan-2-yl)phenyl)methanamine hydrochloride. MS: m/e=296.7 [M+H]$^+$.

EXAMPLE 230

8-Hydroxy-6-(1-methyl-3-(4-methylpiperazine-1-carbonyl)-1H-pyrazol-5-yl)quinazolin-4(3H)-one formate a) Methyl 1-methyl-5-(4-oxo-8-((2-(trimethylsilyl)ethoxy)methoxy)-3-((2-(trimethylsilyl)ethoxy)methyl)-3,4-dihydroquinazolin-6-yl)-1H-pyrazole-3-carboxylate The title compound (0.08 g) was obtained as a light brown solid in analogy to example 80a from methyl 5-bromo-1-methyl-1H-pyrazole-3-carboxylate. MS: m/e=561.2 [M+H]$^+$.

b) 8-Hydroxy-6-(1-methyl-3-(4-methylpiperazine-1-carbonyl)-1H-pyrazol-5-yl)quinazolin-4(3H)-one formate The title compound (0.045 g) was obtained as a light brown solid in analogy to example 193b/c from methyl 1-methyl-5-(4-oxo-8-((2-(trimethylsilyl)ethoxy)methoxy)-3-((2-(trimethylsilyl)ethoxy)methyl)-3,4-dihydroquinazolin-6-yl)-1H-pyrazole-3-carboxylate. MS: m/e=396.2 [M+H]$^+$.

EXAMPLE 231

8-Hydroxy-6-[2-methoxymethyl-4-(4-methyl-piperazine-1-carbonyl)-phenyl]-3H-quinazolin-4-one; compound with formic acid The title compound (0.02 g) was obtained as a light brown powder in analogy to example 230 from methyl 4-bromo-3-(methoxymethyl)benzoate. MS: m/e=409.4 [M+H]$^+$.

EXAMPLE 232

8-Hydroxy-6-(2-(2-(methylamino)ethyl)phenyl)quinazolin-4(3H)-one

The title compound (0.008 g) was obtained as a colorless oil in analogy to example 80 from 2-(2-bromophenyl)-N-methylethanamine using dioxane instead of dimethylformamide in the first step. MS: m/e=296.1 [M+H]$^+$.

EXAMPLE 233

8-Hydroxy-6-[2-methoxymethyl-5-(4-methyl-piperazine-1-carbonyl)-phenyl]-3H-quinazolin-4-one; compound with formic acid The title compound (0.03 g) was obtained as a brown powder in analogy to example 230 from methyl 3-iodo-4-(methoxymethyl)benzoate. MS: m/e=409.0 [M+H]$^+$.

EXAMPLE 234

6-(2-(2-(Dimethylamino)ethyl)phenyl)-8-hydroxy-quinazolin-4(3H)-one

The title compound (0.01 g) was obtained as a light brown oil in analogy to example 80 from 2-(2-bromophenyl)-N,N-dimethylethanamine using dioxane instead of dimethylformamide in the first step. MS: m/e=310.1 [M+H]+.

EXAMPLE 235

8-Hydroxy-6-[2-methoxymethyl-3-(4-methyl-piperazine-1-carbonyl)-phenyl]-3H-quinazolin-4-one The title compound (0.09 g) was obtained as a brown powder in analogy to example 230 from methyl 3-iodo-2-(methoxymethyl)benzoate. MS: m/e=409.2 [M+H]+.

EXAMPLE 236

8-Hydroxy-6-[2-(2-morpholin-4-yl-ethoxymethyl)-phenyl]-3H-quinazolin-4-one

The title compound (0.004 g) was obtained as a colorless oil in analogy to example 80 from 4-(2-(2-bromophenoxy)ethyl)morpholine using dioxane instead of dimethylformamide in the first step. MS: m/e=382.2 [M+H]$^+$.

EXAMPLE 237

8-Hydroxy-6-[2-(2-morpholin-4-yl-ethoxymethyl)-phenyl]-3H-quinazolin-4-one; compound with trifluoro-acetic acid The title compound (0.10 g) was obtained as a grey powder in analogy to example 236 but using TFA/dichloromethane instead of formic acid/water in the deprotection step. The product was purified by precipitation with diethyl ether. MS: m/e=382.2 [M+H]$^+$.

EXAMPLE 238

8-Hydroxy-6-(2-((2-(pyrrolidin-1-yl)ethoxy)methyl)phenyl)quinazolin-4(3H)-one

The title compound (0.009 g) was obtained as a colorless viscous oil in analogy to example 80 from 1-(2-(2-bromophenoxy)ethyl)pyrrolidine using dioxane instead of dimethylformamide in the first step. MS: m/e=366.0 [M+H]$^+$.

EXAMPLE 239

8-Hydroxy-6-[2-(2-pyrrolidin-1-yl-ethoxymethyl)-phenyl]-3H-quinazolin-4-one; compound with trifluoro-acetic acid The title compound (0.11 g) was obtained as a light brown powder in analogy to example 238 but using trifluoroacetic acid/dichloromethane instead of formic acid/water in the deprotection step. The product was purified by precipitation with diethyl ether. MS: m/e=367.3 [M+H]+.

EXAMPLE 240

8-Hydroxy-6-(2-((2-(4-methylpiperazin-1-yl)ethoxy)methyl)phenyl)quinazolin-4(3H)-one The title compound (0.004 g) was obtained as a colorless oil in analogy to example 80 from 1-(2-(2-bromobenzyloxy)ethyl)-4-methylpiperazine using dioxane instead of dimethylformamide in the first step. MS: m/e=395.1 [M+H]$^+$.

EXAMPLE 241

6-(2-((2-(Dimethylamino)ethoxy)methyl)phenyl)-8-hydroxyquinazolin-4(3H)-one

The title compound (0.015 g) was obtained as a colorless oil in analogy to example 80 from 2-(2-bromobenzyloxy)-N,N-dimethylethanamine using dioxane instead of dimethylformamide in the first step. MS: m/e=340.1 [M+H]$^+$.

EXAMPLE 242

8-Hydroxy-6-(2-(3-(pyrrolidin-1-yl)propyl)phenyl) quinazolin-4(3H)-one a) 6-(2-(3-Hydroxypropyl)phenyl)-8-((2-(trimethylsilyl)ethoxy)methoxy)-3-((2-(trimethylsilyl)ethoxy) methyl)quinazolin-4(3H)-one The title compound (0.17 g) was obtained as a light brown oil in analogy to example 80a from 3-(2-bromophenyl) propan-1-ol. MS: m/e=557.5 [M+H]$^+$.

b) 6-(2-(3-Bromopropyl)phenyl)-8-((2-(trimethylsilyl)ethoxy)methoxy)-3-((2-(trimethylsilyl)ethoxy) methyl)quinazolin-4(3H)-one 6-(2-(3-Hydroxypropyl)phenyl)-8-((2-(trimethylsilyl) ethoxy)methoxy)-3-((2-(trimethylsilyl)ethoxy)methyl)quinazolin-4(3H)-one (0.17 g, 296 µmol) and triphenylphosphine (0.16 g, 622 µmol) were combined with dichloromethane (2 ml) and a solution of perbromomethane (0.21 g) in 2 ml dichloromethane was added at 0° C. The mixture was allowed to warm to room temperature and stirred for 2 h. The mixture was concentrated. The product was purified by chromatography (silica gel, 0 to 20% ethyl acetate in dichloromethane) to give the title compound (0.10 g) as a light yellow viscous oil. MS: m/e=619.5/621.5 [M+H]$^+$.

c) 8-Hydroxy-6-(2-(3-(pyrrolidin-1-yl)propyl)phenyl)quinazolin-4(3H)-one 6-(2-(3-Bromopropyl)phenyl)-8-((2-(trimethylsilyl) ethoxy)methoxy)-3-((2-(trimethylsilyl)ethoxy)methyl)quinazolin-4(3H)-one (0.02 g, 32.3 µmol) and pyrrolidine (0.46 g, 6.45 mmol) were combined and stirred at 50° C. for 20 minutes. The reaction mixture was concentrated. Trifluoroacetic acid (1 ml) and dichloromethane (1 ml) were added to the residue. The mixture was stirred for 2 h at room temperature and then concentrated to an oil. The product was purified by preparative HPLC (Gemini Axia 5 um reversed phase C18, 20 to 98% acetonitrile/water (0.1% formic acid) to give the title compound (0.014 g) as a light yellow oil. MS: m/e=350.3 [M+H]$^+$.

EXAMPLE 243

6-(2-(3-(Dimethylamino)propyl)phenyl)-8-hydroxy-quinazolin-4(3H)-one

The title compound (0.01 g) was obtained as a colorless oil in analogy to example 242c using dimethylamine instead of pyrrolidine. MS: m/e=324.3 [M+H]$^+$.

EXAMPLE 244

6-Bromo-7-fluoro-5-(4-fluoro-phenyl)-8-hydroxy-3H-quinazolin-4-one

The title compound (0.007 g) was obtained as a light brown powder in analogy to 137c from 6-Bromo-7-fluoro-5-(4-fluorophenyl)-8-methoxyquinazolin-4(3H)-one (example 123e). MS: m/e=351.1/353.1 [M+H]$^+$.

EXAMPLE 245

7-Chloro-6-(4-fluorophenyl)-8-hydroxyquinazolin-4(3H)-one a) 2-Amino-5-bromo-4-chloro-3-methoxybenzoic acid Hydrogen peroxide in water (1.01 g, 1.01 ml, 10.4 mmol) in 1N aqueous sodium hydroxide (14.7 ml, 14.7 mmol) was added to 6-chloro-7-methoxyindoline-2,3-dione (1.00 g, 4.73 mmol) at 0° C. The mixture was allowed to warm to room temperature and stirred for 1.5 h. The mixture was acidified with 1N aqueous hydrochloric acid and then extracted with ethyl acetate. The organic layer was dried over sodium sulfate and then concentrated to an oil. Bromine (0.76 g, 243 µl, 4.73 mmol) was added to the residue in acetic acid (20 ml). The mixture was stirred for 15 min at room temperature and then concentrated to give the title compound (1.5 g) as a brown solid, which was used without further purification. MS: m/e=282.1/284.1 [M+H]$^+$.

b) 7-Chloro-6-(4-fluorophenyl)-8-hydroxyquinazolin-4(3H)-one

A solution of 2-amino-5-bromo-4-chloro-3-methoxybenzoic acid (0.20 g) in formamide (1 ml) was stirred overnight at 150° C. and then concentrated to an oil.
4-Fluorophenylboronic acid (0.15 g, 1.04 mmol), bis(diphenylphosphino)ferrocene-palladium(II)dichloride dichloromethane complex (0.03 g, 51.8 µmol), potassium carbonate (0.22 g, 1.55 mmol), dioxane (10 ml) and water (1 ml) were added to the residue. The mixture was heated to 100° C. for 2 h and then concentrated to an oil.
The residue was suspended in dichloromethane (10 ml), and 1M boron tribromide in dichloromethane (3.63 ml, 3.63 mmol) was added. The mixture was stirred overnight. Methanol (5 ml) was added, the mixture was concentrated. Addition of methanol and concentration was repeated three times. The crude material was purified by preparative HPLC (Gemini Axia 5 um reversed phase C18, 20 to 98% acetonitrile/water (0.1% formic acid) to give the title compound (0.005 g) as a colorless solid. MS: m/e=291.2 [M+H]$^+$.

EXAMPLE 246

6-Bromo-7-chloro-8-hydroxyquinazolin-4(3H)-one 1,1'-Carbonyldiimidazole (0.04 g, 0.235 mmol) was added to a solution of 2-amino-5-bromo-4-chloro-3-methoxybenzoic acid (0.04 g, 157 µmol) in acetonitrile (5 ml). The mixture was stirred for 1 h at room temperature. Ammonia in water (25%, 10 ml) was added. The mixture was stirred for 15 min and then partitioned between saturated aqueous sodium bicarbonate (50 ml) and ethyl acetate (50 ml). The combined organic layers were dried over sodium sulfate and concentrated to an oil. The residue was suspended in triethyl orthoformate (1.78 g, 2 ml, 12.0 mmol) and heated at 100° C. for 4 h. The mixture was concentrated to an oil. 1M Boron tribromide in dichloromethane (2.65 g, 1 ml, 1.00 mmol) was added to the residue in dichloromethane (5 ml). The mixture was stirred for 2 h at room temperature. Methanol (15 ml) was added and the mixture was concentrated to an oil. Addition of methanol and concentration was repeated two times. The product was purified by preparative HPLC (Gemini Axia 5 um reversed phase C18, 20 to 98% acetonitrile/water (0.1% formic acid)) to give the title compound (0.006 g) as a white solid. MS: m/e=272.8/276.6 [M−H]$^-$.

EXAMPLE 247

6-(3-(2-(Dimethylamino)ethyl)phenyl)-8-hydroxy-quinazolin-4(3H)-one

The title compound (0.01 g) was obtained as a light yellow foam in analogy to example 242 from 2-(3-bromophenyl)ethanol. MS: m/e=310.2 [M+H]$^+$.

EXAMPLE 248

8-Hydroxy-6-(2-(4-(pyrrolidin-1-yl)butyl)phenyl)quinazolin-4(3H)-one

The title compound (0.01 g) was obtained as a light yellow oil in analogy to example 242 from 4-(2-bromophenyl)butan-1-ol. MS: m/e=364.3 [M+H]$^+$.

EXAMPLE 249

8-Hydroxy-6-(2-(propylsulfonyl)phenyl)quinazolin-4(3H)-one

The title compound (0.02 g) was obtained as a white solid in analogy to example 80 from 1-bromo-2-(propylsulfonyl)benzene using dioxane instead of dimethylformamide in the first step. MS: m/e=345.2 [M+H]$^+$.

EXAMPLE 250

2-(8-Hydroxy-4-oxo-3,4-dihydro-quinazolin-6-yl)-N,N-dimethyl-benzenesulfonamide

The title compound (0.03 g) was obtained as a light grey powder in analogy to example 75 from 2-(N,N-dimethylsulfamoyl)phenylboronic acid. MS: m/e=346.3 [M+H]$^+$.

EXAMPLE 251

8-Hydroxy-6-[2-(piperidine-1-sulfonyl)-phenyl]-3H-quinazolin-4-one

The title compound (0.04 g) was obtained as a light grey powder in analogy to example 75 from 2-(piperidin-1-ylsulfonyl)phenylboronic acid. MS: m/e=384.3 [M+H]$^+$.

EXAMPLE 252

6-(4-Fluoro-phenyl)-8-hydroxy-5-nitro-3H-quinazolin-4-one

The title compound (0.006 g) was obtained as a light yellow solid in analogy to example 125 from 6-bromo-8-methoxy-5-nitroquinazolin-4(3H)-one (example 44a). MS: m/e=302.0 [M+H]$^+$.

EXAMPLE 253

5-Amino-6-(4-fluorophenyl)-8-hydroxyquinazolin-4(3H)-one hydrobromide a) 6-Bromo-8-methoxy-5-nitro-3-((2-(trimethylsilyl)ethoxy)methyl)quinazolin-4(3H)-one A suspension of 6-bromo-8-methoxy-5-nitroquinazolin-4(3H)-one (1.42 g, 4.73 mmol) in dimethylformamide (10 ml) was treated with sodium hydride (0.28 g, 7.1 mmol) and stirred at 60° C. for 15 minutes. The homogeneous solution was cooled in an ice bath and 2-(trimethylsilyl) ethoxymethyl chloride (1.18 g, 1.26 ml, 7.1 mmol) was added. Stirring was continued for 1 h at 0° C., then 1 h at room temperature. The solvent was evaporated and the residue was partitioned between water and ethyl acetate. The organic phase was adsorbed on silica. The product was purified by column chromatography (silica gel, 0 to 98% methanol in dichloromethane) to give the title compound (1.45 g) as a white solid. MS: m/e=430.1 [M+H]$^+$.

b) 6-(4-Fluorophenyl)-8-methoxy-5-nitro-3-((2-(trimethylsilyl)ethoxy)methyl)quinazolin-4(3H)-one The title compound (1.09 g) was obtained as a light brown foam in analogy to example 125a from 6-bromo-8-methoxy-5-nitro-3-((2-(trimethylsilyl)ethoxy)methyl)quinazolin-4(3H)-one. MS: m/e=446.1 [M+H]$^+$.

c) 5-Amino-6-(4-fluoro-phenyl)-8-methoxy-3-(2-trimethylsilanyl-ethoxymethyl)-3H-quinazolin-4-one A slurry of 6-(4-fluorophenyl)-8-methoxy-5-nitro-3-((2-(trimethylsilyl)ethoxy)methyl)quinazolin-4(3H)-one (0.30 g, 673 µmol) and Raney nickel (50% in water, 0.2 ml) was stirred at room temperature for 3 h. After filtration the residue was adsorbed on silica. The product was purified by column chromatography (silica gel, 0 to 100% ethyl acetate/heptane) to afford the title compound (0.05 g) as a yellow oil. MS: m/e=416.1 [M+H]$^+$.

d) 5-Amino-6-(4-fluorophenyl)-8-hydroxyquinazolin-4(3H)-one hydrobromide

5-Amino-6-(4-fluorophenyl)-8-methoxy-3-((2-(trimethylsilyl)ethoxy)methyl)quinazolin-4(3H)-one (0.03 g, 67.4 µmol) in hydrobromic acid 48% in water (10 ml) was heated under reflux overnight. The mixture was concentrated, the precipitate washed with diethyl ether and dried under high vacuum to give the title compound (0.02 g) as a white solid. MS: m/e=270.3 [M+H]$^+$.

EXAMPLE 254

N-(6-(4-Fluorophenyl)-8-hydroxy-4-oxo-3,4-dihydroquinazolin-5-yl)benzamide

5-Amino-6-(4-fluorophenyl)-8-hydroxyquinazolin-4(3H)-one hydrobromide (0.03 g, 85.2 µmol) was combined with dimethylformamide (4 ml) to give a brown solution. Hunig's base (0.11 g, 149 µl, 852 µmol) was added to give a dark green solution. Benzoyl chloride (0.02 g, 153 µmol) was added, and the reaction mixture was stirred at room temperature overnight. The product was purified by preparative HPLC (Gemini Axia 5 um reversed phase C18, 20 to 98% acetonitrile/water (0.1% formic acid)) to give the title compound (0.009 g) as a yellow solid. MS: m/e=376.1 [M+H]$^+$.

EXAMPLE 255

5-Chloro-8-hydroxy-6-(2-hydroxymethyl-phenyl)-3H-quinazolin-4-one

The title compound (0.03 g) was obtained as a white solid in analogy to example 75 from 2-(hydroxymethyl)phenylboronic acid and 6-bromo-5-chloro-8-((2-methoxyethoxy)methoxy)-3-((2-methoxyethoxy)methyl)quinazolin-4(3H)-one (example 119a). MS: m/e=303.1 [M+H]$^+$.

EXAMPLE 256

8-Hydroxy-6-(2-((2-(1-methylpiperidin-4-yl)ethoxy)methyl)phenyl)quinazolin-4(3H)-one a) tert-Butyl 4-(2-(2-bromobenzyloxy)ethyl)piperidine-1-carboxylate 1M Sodium bis(trimethylsilyl)amide in tetrahydrofuran (7.85 ml, 7.85 mmol) and 1-bromo-2-(bromomethyl)benzene (1.42 g, 5.67 mmol) were added to tert-butyl 4-(2-hydroxyethyl)piperidine-1-carboxylate (1.0 g, 4.36 mmol) in tetrahydrofuran (15 ml) keeping the reaction temperature below 15° C. The mixture was stirred at 50° C. for 2 h. Water (50 ml) was added and the mixture extracted with dichloromethane. The organic layer was dried and concentrated to give the title compound (1.8 g) as a light yellow oil. MS: m/e=398.4 [M+H]$^+$.

b) 4-(2-(2-Bromobenzyloxy)ethyl)piperidine 6N hydrochloric acid in ethanol (40 ml) was added to tert-butyl 4-((2-(2-bromobenzyloxy)ethyl)piperidine-1-carboxylate (1.8 g, 4.52 mmol). After $CO_2$ evolving had stopped, the mixture was stirred for 30 min at room temperature. Water was added and the mixture was alkalized with addition of saturated aqueous sodium carbonate. The mixture was extracted with dichloromethane, the organic layer was dried and concentrated to give the title compound (1.8 g) as a light yellow oil, which was used without further purification in the next step. MS: m/e=300.1 [M+H]$^+$.

c) 4-(2-(2-Bromobenzyloxy)ethyl)-1-methylpiperidine

Formaldehyde (2.2 g, 2.02 ml, 27.2 mmol) was added to 4-(2-(2-bromobenzyloxy)ethyl)piperidine (1.8 g, 6.04 mmol) in methanol (20 ml). The mixture was stirred at room temperature for 1 h. Sodium triacetoxyborohydride (3.3 g, 15.1 mmol) was added at 0° C. The mixture was stirred for 1 h at room temperature. Methanol was partially evaporated, water (30 ml) was added and the solution was alkalized by addition of saturated aqueous sodium carbonate. The mixture was extracted with dichloromethane. The combined organic layers were dried and concentrated to an oil. The product was purified by column chromatography (silica gel, 0 to 30% methanol/ethyl acetate) to give the title compound (1.3 g) as a light yellow oil. MS: m/e=312.1 [M+H]$^+$.

d) 8-Hydroxy-6-(2-((2-(1-methylpiperidin-4-yl)ethoxy)methyl)phenyl)quinazolin-4(3H)-one The title compound (0.01 g) was obtained as a colorless oil in analogy to example 80 from 4-((2-(2-bromobenzyloxy)ethyl)-1-methylpiperidine using dioxane instead of dimethylformamide in the first step. MS: m/e=394.3 [M+H]$^+$.

The invention claimed is:
1. A compound of formula

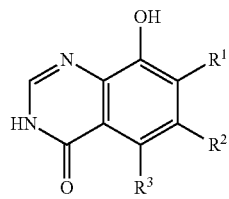

I wherein
R$^1$ is hydrogen;
R$^2$ is heteroaryl, selected from the group consisting of pyrazolyl, thiazolyl, pyridinyl, pyrimidinyl, imidazolyl, isoxazolyl, isothiazolyl, thiophenyl, 1-thia-3,4-diazolyl, imidazo[1,2-a]pyridinyl, indazolyl, quinolinyl or isoquinolinyl, and which groups are optionally substituted by R$^5$, or is C(O)-heteroaryl, selected from pyridinyl or thiophenyl, wherein the heteroaryl groups are optionally substituted by lower alkyl;
R$^5$ is halogen, lower alkyl, lower alkoxy, lower alkyl substituted by halogen, lower alkoxy substituted by halogen, hydroxy, (CH$_2$)$_{1,2}$-lower alkoxy, CH$_2$-di-lower alkyl amino, di-lower alkyl amino, morpholinyl, piperazinyl, pyrrolidin-1-yl, C(O)-piperidinyl, C(O)-4-methyl-piperazinyl, phenyl optionally substituted by halogen, pyridinyl, S(O)$_2$N(CH$_3$)$_2$, C(O)O-lower alkyl, NHC(O)-lower alkyl,
or is C(O)-heteroaryl, selected from pyridinyl or thiophenyl, wherein the heteroaryl groups are optionally substituted by lower alkyl,
R$^3$ is hydrogen;
and pharmaceutically acceptable salts thereof.
2. A compound selected from the group consisting of:
8-Hydroxy-6-(1-(2-methoxyethyl)-1H-pyrazol-5-yl)quinazolin-4(3H)-one;
8-Hydroxy-6-(4-(methoxymethyl)-2-methylthiazol-5-yl)quinazolin-4(3H)-one;
8-Hydroxy-6-(1-(2-methoxyethyl)-1H-pyrazol-4-yl)quinazolin-4(3H)-one;
6-(6-(Dimethylamino)pyridin-3-yl)-8-hydroxyquinazolin-4(3H)-one;
8-Hydroxy-6-(6-morpholinopyridin-2-yl)quinazolin-4(3H)-one;
8-Hydroxy-6-(6-(pyrrolidin-1-yl)pyridin-2-yl)quinazolin-4(3H)-one;
8-Hydroxy-6-(5-methylthiazol-2-yl)quinazolin-4(3H)-one;
8-Hydroxy-6-(1-methyl-1H-imidazol-2-yl)quinazolin-4(3H)-one;
8-Hydroxy-6-nicotinoylquinazolin-4(3H)-one;
8-Hydroxy-6-(1-methyl-1H-imidazol-4-yl)quinazolin-4(3H)-one;
8-Hydroxy-6-(5-methyl-3-phenylisoxazol-4-yl)quinazolin-4(3H)-one;
4-(8-Hydroxy-4-oxo-3,4-dihydroquinazolin-6-yl)-N,N-dimethyl-1H-imidazole-1-sulfonamide;
6-(3,5-Dimethylisoxazol-4-yl)-8-hydroxyquinazolin-4(3H)-one;
8-Hydroxy-6-(1-methyl-1H-imidazol-5-yl)quinazolin-4(3H)-one;
Ethyl 2-(8-hydroxy-4-oxo-3,4-dihydroquinazolin-6-yl)-4-methyl-1H-imidazole-5-carboxylate;
Methyl 5-(8-hydroxy-4-oxo-3,4-dihydroquinazolin-6-yl)-4-methylthiophene-2-carboxylate;
8-Hydroxy-6-(1-methyl-3-(trifluoromethyl)-1H-pyrazol-4-yl)quinazolin-4(3H)-one;
8-Hydroxy-6-(5-methyl-1,3,4-thiadiazol-2-yl)quinazolin-4(3H)-one;
Methyl 2-(8-hydroxy-4-oxo-3,4-dihydroquinazolin-6-yl)thiazole-4-carboxylate;
8-Hydroxy-6-(2-methylthiazol-4-yl)quinazolin-4(3H)-one;
8-Hydroxy-6-(imidazo[1,2-a]pyridin-3-yl)quinazolin-4(3H)-one;
6-(1,2-Dimethyl-1H-imidazol-5-yl)-8-hydroxyquinazolin-4(3H)-one;
Methyl 4-(8-hydroxy-4-oxo-3,4-dihydroquinazolin-6-yl)-1-methyl-1H-pyrazole-3-carboxylate;
8-Hydroxy-6-(5-(pyridin-2-yl)thiophen-2-yl)quinazolin-4(3H)-one;
8-Hydroxy-6-(thiazol-5-yl)quinazolin-4(3H)-one;
8-Hydroxy-6-(thiazol-4-yl)quinazolin-4(3H)-one;
8-Hydroxy-6-(isothiazol-4-yl)quinazolin-4(3H)-one;
8-Hydroxy-6-isonicotinoylquinazolin-4(3H)-one;
8-Hydroxy-6-(5-methylthiophene-2-carbonyl)quinazolin-4(3H)-one;
6-(1,5-Dimethyl-3-(trifluoromethyl)-1H-pyrazol-4-yl)-8-hydroxyquinazolin-4(3H)-one;
8-Hydroxy-6-(1-methyl-1H-indazol-5-yl)quinazolin-4(3H)-one;
8-Hydroxy-6-(3-methyl-5-(piperidine-1-carbonyl)thiophen-2-yl)quinazolin-4(3H)-one;
8-Hydroxy-6-[3-methyl-5-(4-methyl-piperazine-1-carbonyl)-thiophen-2-yl]-3H-quinazolin-4-one;
N-(5-(8-Hydroxy-4-oxo-3,4-dihydroquinazolin-6-yl)-6-(methoxymethyl)pyridin-2-yl)pivalamide;
8-Hydroxy-6-(2-(methoxymethyl)pyridin-3-yl)quinazolin-4(3H)-one bis(2,2,2-trifluoroacetate);
8-Hydroxy-6-(2-methylpyridin-4-yl)quinazolin-4(3H)-one;
8-Hydroxy-6-(2-methylpyridin-3-yl)quinazolin-4(3H)-one;
6-(6-Bromo-pyridin-3-yl)-8-hydroxy-3H-quinazolin-4-one;
6-(2,5-Dimethyl-2H-pyrazol-3-yl)-8-hydroxy-3H-quinazolin-4-one;
6-[1-(4-Fluoro-phenyl)-1H-pyrazol-4-yl]-8-hydroxy-3H-quinazolin-4-one;

8-Hydroxy-6-(pyrimidin-5-yl)quinazolin-4(3H)-one 2,2,2-trifluoroacetate;
8-Hydroxy-6-(2-methyl-5-trifluoromethyl-2H-pyrazol-3-yl)-3H-quinazolin-4-one;
6-(2-((Dimethylamino)methyl)phenyl)-8-hydroxyquinazolin-4(3H)-one;
8-Hydroxy-6-(1-methyl-1H-indazol-4-yl)quinazolin-4(3H)-one;
6-(2,4-Dimethoxypyrimidin-5-yl)-8-hydroxyquinazolin-4(3H)-one;
8-Hydroxy-6-(2-methoxypyridin-3-yl)quinazolin-4(3H)-one;
8-Hydroxy-6-(6-methoxypyridin-3-yl)quinazolin-4(3H)-one;
8-Hydroxy-6-(4-methylthiophen-3-yl)quinazolin-4(3H)-one;
6-(2,5-Dimethylthiophen-3-yl)-8-hydroxyquinazolin-4(3H)-one;
8-Hydroxy-6-(6-methylpyridin-3-yl)quinazolin-4(3H)-one;
8-Hydroxy-6-(quinolin-8-yl)quinazolin-4(3H)-one;
8-Hydroxy-6-(isoquinolin-4-yl)quinazolin-4(3H)-one;
6-(2,4-Dimethylthiazol-5-yl)-8-hydroxyquinazolin-4(3H)-one;
8-Hydroxy-6-(1-methyl-1H-pyrazol-4-yl)quinazolin-4(3H)-one;
8-Hydroxy-6-(2-hydroxypyridin-3-yl)quinazolin-4(3H)-one;
8-Hydroxy-6-(1-methyl-1H-pyrazol-5-yl)quinazolin-4(3H)-one;
8-Hydroxy-6-(6-morpholinopyridin-3-yl)quinazolin-4(3H)-one;
6-(6-(Dimethylamino)pyridin-2-yl)-8-hydroxyquinazolin-4(3H)-one;
8-Hydroxy-6-(6-(piperazin-1-yl)pyridin-3-yl)quinazolin-4(3H)-one;
8-Hydroxy-6-(2-(piperazin-1-yl)pyridin-4-yl)quinazolin-4(3H)-one;
6-(1,4-Dimethyl-1H-imidazol-2-yl)-8-hydroxyquinazolin-4(3H)-one;
6-(2,6-Dimethyl-pyridin-3-yl)-8-hydroxy-3H-quinazolin-4-one;
8-Hydroxy-6-(4-methyl-2-phenylthiazol-5-yl)quinazolin-4(3H)-one;
8-Hydroxy-6-(5-methyl-1-phenyl-1H-pyrazol-4-yl)quinazolin-4(3H)-one;
8-Hydroxy-6-(3-methyl-1H-pyrazol-4-yl)quinazolin-4(3H)-one;
6-(1,5-Dimethyl-1H-pyrazol-4-yl)-8-hydroxyquinazolin-4(3H)-one;
8-Hydroxy-6-(2-(2,2,2-trifluoroethoxy)pyridin-3-yl)quinazolin-4(3H)-one;
8-Hydroxy-6-(3-methylpyridin-4-yl)quinazolin-4(3H)-one; and
8-Hydroxy-6-(1-methyl-3-(4-methylpiperazine-1-carbonyl)-1H-pyrazol-5-yl)quinazolin-4(3H)-one.

3. A Pharmaceutical composition comprising a compound according to claim 1 and a pharmaceutical acceptable carrier and/or adjuvant.

* * * * *